(12) United States Patent
Ito et al.

(10) Patent No.: US 8,299,073 B2
(45) Date of Patent: *Oct. 30, 2012

(54) P38 MAP KINASE INHIBITORS

(75) Inventors: Kazuhiro Ito, London (GB); Peter Strong, London (GB); William Garth Rapeport, London (GB); Peter John Murray, London (GB); John King-Underwood, Pendock (GB); Jonathan Gareth Williams, Nottingham (GB); Stuart Thomas Onions, Nottingham (GB); Simon Christopher Hirst, Nottingham (GB); David Michel Adrien Taddei, Nottingham (GB); Catherine Elisabeth Charron, London (GB)

(73) Assignee: Respivert Ltd. (GB)

( * ) Notice: Subject to any disclaimer, the term of this patent is extended or adjusted under 35 U.S.C. 154(b) by 0 days.

This patent is subject to a terminal disclaimer.

(21) Appl. No.: 13/133,998

(22) PCT Filed: Dec. 11, 2009

(86) PCT No.: PCT/GB2009/051703
§ 371 (c)(1),
(2), (4) Date: Aug. 9, 2011

(87) PCT Pub. No.: WO2010/067131
PCT Pub. Date: Jul. 17, 2010

(65) Prior Publication Data
US 2011/0294812 A1    Dec. 1, 2011

Related U.S. Application Data

(60) Provisional application No. 61/166,594, filed on Apr. 3, 2009.

(30) Foreign Application Priority Data

Dec. 11, 2008 (GB) .................................. 0822609.4
Jul. 17, 2009 (GB) .................................. 0912470.2

(51) Int. Cl.
A61K 31/5377 (2006.01)
A61K 31/505 (2006.01)
A61K 31/445 (2006.01)
A61K 31/4427 (2006.01)
A61K 31/496 (2006.01)
C07D 413/14 (2006.01)
C07D 403/02 (2006.01)
C07D 213/02 (2006.01)
C07D 211/06 (2006.01)
C07D 401/02 (2006.01)
C07D 401/14 (2006.01)

(52) U.S. Cl. ..................... 514/236.5; 514/269; 514/333; 514/340; 514/253.09; 544/111; 544/333; 546/193; 546/275.4

(58) Field of Classification Search ................ 514/236.5, 514/253.09, 269, 333, 340; 544/111, 333; 546/193, 275.4
See application file for complete search history.

(56) References Cited

U.S. PATENT DOCUMENTS

| | | | |
|---|---|---|---|
| 6,525,046 B1 | 2/2003 | Cirillo et al. | |
| 6,916,814 B2 | 7/2005 | Moss et al. | |
| 7,329,670 B1 | 2/2008 | Dumas et al. | |
| 7,625,915 B2 | 12/2009 | Dumas et al. | |
| 2004/0180906 A1 | 9/2004 | Flynn et al. | |
| 2004/0192653 A1 | 9/2004 | Munson et al. | |
| 2007/0010529 A1 | 1/2007 | Takahashi et al. | |
| 2008/0113967 A1 | 5/2008 | Flynn et al. | |
| 2008/0207699 A1 | 8/2008 | Hoelzemann et al. | |
| 2008/0300281 A1 | 12/2008 | Dumas et al. | |
| 2011/0212962 A1 | 9/2011 | Ito et al. | |

FOREIGN PATENT DOCUMENTS

| | | |
|---|---|---|
| WO | WO 99-23091 | 5/1999 |
| WO | WO 99/32110 | 7/1999 |
| WO | WO 99/32111 | 7/1999 |
| WO | WO 99/32455 | 7/1999 |
| WO | WO 99/47529 | 9/1999 |

(Continued)

OTHER PUBLICATIONS

Friedenreich, Christine M. State of the epidemiological evidence on physical activity and cancer prevention. European Journal of Cancer, 46, (2010), 2593-2604.*

(Continued)

*Primary Examiner* — Joseph K. McKane
*Assistant Examiner* — Samantha Shterengarts
(74) *Attorney, Agent, or Firm* — Mary A. Appollina

(57) ABSTRACT

The invention relates to compounds of formula (I):

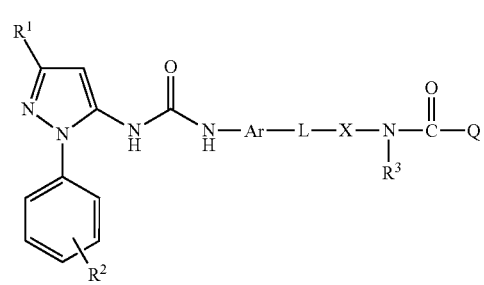

or a pharmaceutically acceptable salt thereof, including all stereoisomers, tautomers and isotopic derivatives thereof, which are inhibitors of p38 mitogen-activated protein kinase enzymes (referred to herein as p38 MAP kinase inhibitors), particularly the alpha and gamma kinase sub-types thereof, and their use in therapy, including in pharmaceutical combinations, especially in the treatment of inflammatory diseases, including inflammatory diseases of the lung, such as COPD.

19 Claims, 3 Drawing Sheets

FOREIGN PATENT DOCUMENTS

| | | |
|---|---|---|
| WO | WO 00/43384 | 7/2000 |
| WO | WO 01/04115 | 1/2001 |
| WO | WO 02/066442 | 8/2002 |
| WO | WO 02/092576 | 11/2002 |
| WO | WO 03/005999 | 1/2003 |
| WO | WO 03/068228 | 8/2003 |
| WO | WO 03/072569 | 9/2003 |
| WO | WO 03/084503 | 10/2003 |
| WO | WO 2004/014387 | 2/2004 |
| WO | WO 2004/021988 | 3/2004 |
| WO | WO 2004/060306 | 7/2004 |
| WO | WO 2004/078746 | 9/2004 |
| WO | WO 2004/089929 | 10/2004 |
| WO | WO 2004/100946 | 11/2004 |
| WO | WO 2005/018624 | 3/2005 |
| WO | WO 2005/048948 | 6/2005 |
| WO | WO 2005/110994 | 11/2005 |
| WO | WO 2005/113511 | 12/2005 |
| WO | WO 2006/009741 | 1/2006 |
| WO | WO 2006/014290 | 2/2006 |
| WO | WO 2006/015775 | 2/2006 |
| WO | WO 2006/028524 | 3/2006 |
| WO | WO 2006/043090 | 4/2006 |
| WO | WO 2006/062984 | 6/2006 |
| WO | WO 2006/068591 | 6/2006 |
| WO | WO 2006/072589 | 7/2006 |
| WO | WO 2006/081034 | 8/2006 |
| WO | WO 2007/002635 | 1/2007 |
| WO | WO 2007/017083 | 2/2007 |
| WO | WO 2007/038425 | 4/2007 |
| WO | WO 2007/059202 | 5/2007 |
| WO | WO 2007/064872 | 6/2007 |
| WO | WO 2008/016192 | 2/2008 |

OTHER PUBLICATIONS

ISR PCT/GB2009/051703, Dated, Apr. 15, 2010.
U.S. Appl. No. 13/121,445, filed Mar. 29, 2011, Ito et al.
U.S. Appl. No. 13/139,010, filed Aug. 9, 2011, Ito et al.
U.S. Appl. No. 13/262,266, filed Sep. 30, 2011, Ito et al.
Dumas et al., "Synthesis and Pharmacological Characterization of a Potent, Orally Active p38 Kinase Inhibitor", Bioorganic & Medicinal Chemistry Letters 12 (2002) 1559-1562.

* cited by examiner

The Effect of pre-dose time for the compound of Example 1 against neutrophil number in BALF in LPS-induced neutrophil accumulation in the mouse.

The Effect of pre-dose time for the compound of Example 1 against % inhibition of neutrophilia in the LPS-induced neutrophil accumulation in the mouse Figure 3: MOMA2⁺-Macrophage Accumulation in BALF

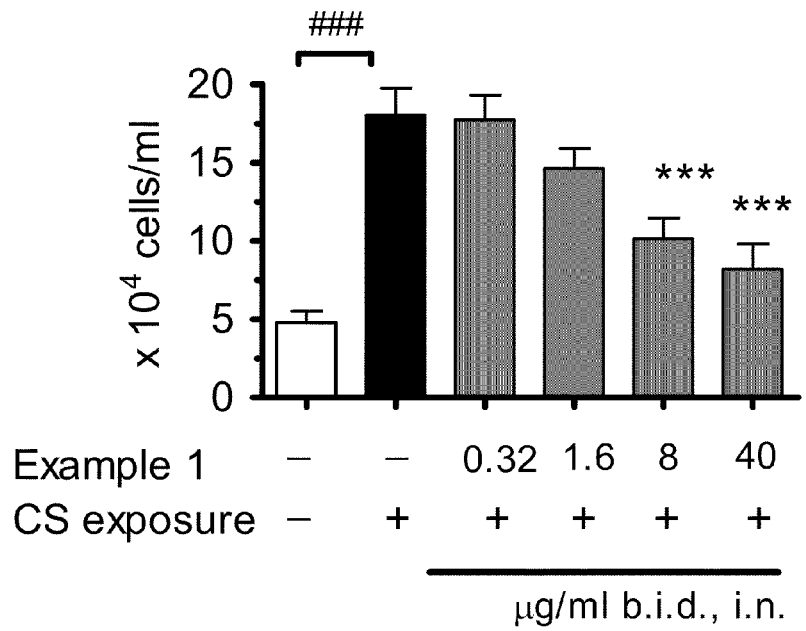

Significant difference between air exposure and cigarette smoke exposure.
***$P<0.001$ vs. cigarette smoke (CS) control (ANNOVA, Dunnett,s multiple comparison), n=6-11

Figure 4: Neutrophil Accumulation in BALF

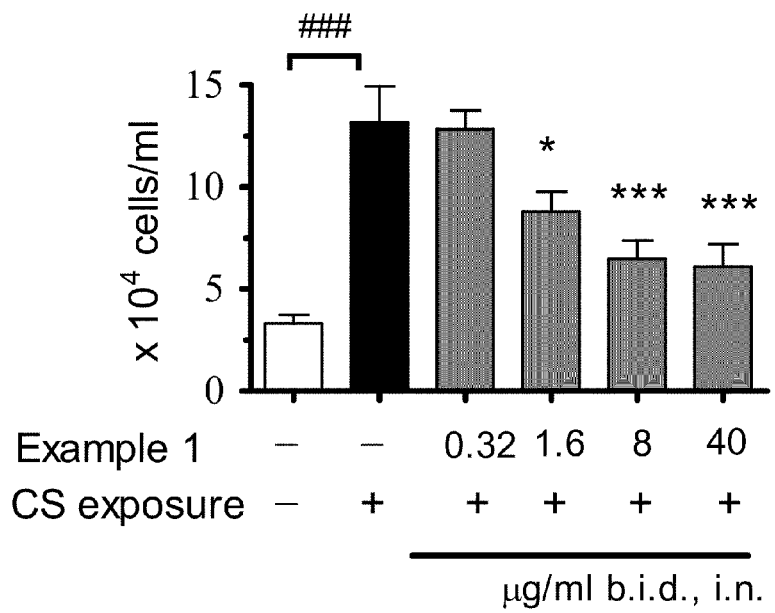

Significant difference between air exposure and cigarette smoke exposure.
*$P<0.05$ or ***$P<0.001$ vs. cigarette smoke (CS) control (ANNOVA, Dunnett,s multiple comparison), n=6-11

Change of sGaw values after OVA exposure in OVA sensitized PIV3 infected guinea pigs

Data are shown as the mean of 6 observations;
(●) PIV3 + vehicle treatment;
(■) PIV3 + fluticasone propionate treatment;
(▲) PIV3 + Example 1 treatment

P38 MAP KINASE INHIBITORS

This application is a National Stage application under 35 U.S.C. 371 of PCT International Application No. PCT/GB2009/051703, filed Dec. 11, 2009, which claims priority from Great Britain patent applications numbers GB 0822609.4, filed Dec. 11, 2008 and GB 0912470.2, filed Jul. 17, 2009, and U.S. provisional patent application Ser. No. 61/166,594, filed Apr. 3, 2009, the contents of all of which are hereby incorporated by reference in their entirety.

FIELD OF THE INVENTION

The invention relates to compounds which are inhibitors of p38 mitogen-activated protein kinase enzymes (referred to herein as p38 MAP kinase inhibitors), particularly the alpha and gamma kinase sub-types thereof, and their use in therapy, including in pharmaceutical combinations, especially in the treatment of inflammatory diseases, including inflammatory diseases of the lung, such as COPD.

BACKGROUND OF THE INVENTION

Four p38 MAPK isoforms (alpha, beta, gamma and delta respectively) have been identified, each displaying a tissue-specific expression pattern. The p38 MAPK alpha and beta isoforms are ubiquitously expressed throughout the body and are found in many different cell types. The p38 MAPK alpha and beta isoforms are inhibited by certain known small molecule p38 MAPK inhibitors. Earlier generations of compounds were highly toxic due to the ubiquitous expression pattern of these isoforms and off-target effects of the compounds. More recent inhibitors are improved to be highly selective for p38 MAPK alpha and beta isoforms and have a wider safety margin.

Less is known about the p38 MAPK gamma and delta isoforms. These isoforms are expressed in specific tissues/cells (unlike the p38 alpha and p38 beta isoforms). The p38 MAPK-delta isoform is expressed more in the pancreas, testes, lung, small intestine and kidney. It is also abundant in macrophages (Smith, S. J. (2006) *Br. J. Pharmacol.* 149:393-404) and detectable in neutrophils, CD4+ T cells and endothelial cells (www.genecard.org, Karin, K. (1999) *J. Immunol.*). Very little is known about the expression of p38 MAPK gamma but it is expressed more in brain, skeletal muscle and heart, as well as in lymphocytes and macrophages (www.genecard.org).

Selective small molecule inhibitors of p38 MAPK-gamma and -delta are not currently available, but one existing compound, BIRB 796, is known to have pan-isoform inhibitory activity. The p38 gamma and p38 delta inhibition is observed at higher concentrations of the compound than those required to inhibit p38 alpha and p38 beta (Kuma, Y. (2005) *J. Biol. Chem.* 280:19472-19479). BIRB 796 also impaired the phosphorylation of p38 MAPKs or JNKs by the upstream kinase MKK6 or MKK4. Kuma discussed the possibility that the conformational change caused by the binding of the inhibitor to the MAPK may affect the structure of both its phosphorylation site and the docking site for the upstream activator, therefore impairing the phosphorylation of p38 MAPKs or JNKs.

p38 MAP kinase is believed to play a pivotal role in many of the signalling pathways that are involved in initiating and maintaining chronic, persistent inflammation in human disease, for example, in severe asthma and COPD. There is now an abundant literature which demonstrates that p38 MAP kinase is activated by a range of pro-inflammatory cytokines and that its activation results in the recruitment and release of further pro-inflammatory cytokines. Indeed, data from some clinical studies demonstrate beneficial changes in disease activity in patients during treatment with p38 MAP kinase inhibitors. For instance Smith, S. J. (2006) *Br. J. Pharmacol.* 149:393-404 describes the inhibitory effect of p38 MAP kinase inhibitors on TNFα (but not IL-8) release from human PBMCs. Use of inhibitors of p38 MAP kinase in the treatment of chronic obstructive pulmonary disease (COPD) is proposed. Small molecule inhibitors targeted to p38 MAPKα/β have proved to be effective in reducing various parameters of inflammation in cells and tissues obtained from patients with COPD, who are generally corticosteroid insensitive, (Smith, S. J. (2006) *Br. J. Pharmacol.* 149:393-404) and in vivo animal models (Underwood, D. C. et al. *Am. J. Physiol.* (2000) 279:L895-902; Nath, P. et al. (2006) *Eur. J. Pharmacol.* 544:160-167). Irusen and colleagues also suggested the possibility of involvement of p38 MAPKα/β on corticosteroid insensitivity via reduction of binding affinity of glucocorticoid receptor (GR) in nuclei (Irusen, E. et al., (2002) *J. Allergy Clin. Immunol.*, 109:649-657). Clinical experience with a range of p38 MAP kinase inhibitors, including AMG548, BIRB 796, VX702, SCIO469 and SCIO323 is described in Lee et al. (2005) *Current Med. Chem.* 12:2979-2994.

COPD is a condition in which the underlying inflammation is reported to be substantially resistant to the anti-inflammatory effects of inhaled corticosteroids. Consequently, a superior strategy for treating COPD would be to develop an intervention which has both inherent anti-inflammatory effects and the ability to increase the sensitivity of the lung tissues of COPD patients to inhaled corticosteroids. The recent publication of Mercado et al (2007; *American Thoracic Society Abstract A56*) demonstrates that silencing p38 gamma has the potential to restore sensitivity to corticosteroids. Thus there may be a "two pronged" benefit to the use of a p38 MAP kinase inhibitor for the treatment of COPD and severe asthma.

However, the major obstacle hindering the utility of p38 MAP kinase inhibitors in the treatment of human chronic inflammatory diseases has been the toxicity observed in patients. This has been sufficiently severe to result in the withdrawal from clinical development of many of the compounds progressed, including all those specially mentioned above.

There remains a need to identify and develop new compounds therapeutically useful as p38 MAP kinase inhibitors which have improved therapeutic potential, in particular which are more efficacious, longer acting and/or less toxic at the relevant therapeutic dose. An objective of the present invention is to provide compounds which inhibit p38 MAP kinase with certain sub-type specificity, which show good anti-inflammatory potential, in particular suitable for use in therapy.

SUMMARY OF THE INVENTION

According to the invention, there is provided a compound of formula (I):

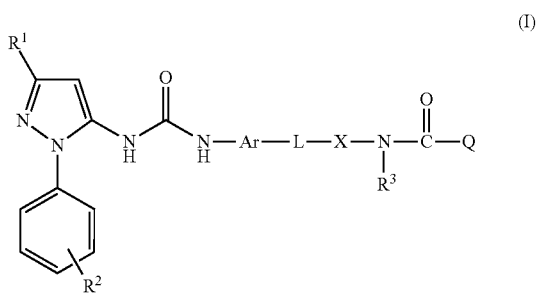

wherein $R^1$ is $C_{1-6}$ alkyl optionally substituted by a hydroxyl group;
$R^2$ is H or $C_{1-6}$ alkyl optionally substituted by a hydroxyl group;
$R^3$ is H, $C_{1-6}$ alkyl or $C_{0-3}$ alkyl$C_{3-6}$ cycloalkyl;
Ar is a naphthyl or a phenyl ring either of which may be optionally substituted by one or more groups (for example 1 to 3, such as 1, 2 or 3 groups) independently selected from $C_{1-6}$ alkyl, $C_{1-6}$ alkoxy, amino, $C_{1-4}$ mono or di-alkyl amino;
L is a saturated or unsaturated branched or unbranched $C_{1-8}$ alkylene chain, wherein one or more carbons (for example 1 to 3, such as 1, 2 or 3 carbons) are optionally replaced by —O— and the chain is optionally substituted by one or more halogen atoms (for example 1 to 6);
X is 5 or 6 membered heteroaryl group containing at least one nitrogen atom and optionally including 1 or 2 further heteroatoms selected from O, S and N;
Q is selected from:
a) a saturated or unsaturated, branched or unbranched $C_{1-10}$ alkyl chain, wherein at least one carbon (for example 1, 2 or 3 carbons, suitably 1 or 2, in particular 1 carbon) is replaced by a heteroatom selected from O, N, $S(O)_p$, wherein said chain is optionally, substituted by one or more groups (for example 1, 2 or 3 groups) independently selected from oxo, halogen, an aryl group, a heteroaryl group, a heterocyclyl group or a $C_{3-8}$ cycloalkyl group,
 each aryl, heteroaryl, heterocyclyl or $C_{3-8}$ cycloalkyl group bearing 0 to 3 substituents selected from halogen, hydroxyl, $C_{1-6}$ alkyl, $C_{1-6}$ alkoxy, $C_{1-6}$ haloalkyl, amino, $C_{1-4}$ mono or di-alkyl amino, $C_{1-4}$ mono or di-acyl amino, $S(O)_q C_{1-6}$ alkyl, $C_{0-6}$ alkylC(O)$C_{1-6}$ alkyl or $C_{0-6}$ alkylC(O)$C_{1-6}$ heteroalkyl,
 with the proviso that the atom linked directly to the carbonyl in —$NR^3C(O)$— is not an oxygen or a sulfur atom; and
b) a $C_{0-8}$ alkyl-heterocycle said heterocyclyl group comprising at least one heteroatom (for example 1, 2 or 3, suitably 1 or 2, in particular 1 heteroatom) selected from O, N, and S, and which is optionally substituted by one, two or three groups independently selected from halogen, hydroxyl, $C_{1-6}$ alkyl, $C_{1-6}$ alkoxy, $C_{1-6}$ haloalkyl, amino, $C_{1-4}$ mono and di-alkyl amino, $C_{1-4}$ mono or di-acyl amino, $S(O)_q C_{1-6}$ alkyl, $C_{0-6}$ alkylC(O)$C_{1-6}$ alkyl, $C_{0-6}$ alkylC(O)N$C_{0-6}$ alkyl $C_{0-6}$ alkyl or $C_{0-6}$ alkylC(O)$C_{0-6}$ heteroalkyl; and
p is 0, 1 or 2;
q is 0, 1 or 2; or
a pharmaceutically acceptable salt thereof, including all stereoisomers, tautomers and isotopic derivatives thereof.
In one embodiment Q is selected from:
a) a saturated or unsaturated, branched or unbranched $C_{1-10}$ alkyl chain, wherein at least one carbon (for example 1, 2 or 3 carbons, suitably 1 or 2, in particular 1) is replaced by a heteroatom selected from O, N, $S(O)_p$, wherein said chain is optionally, substituted by one or more groups independently selected from oxo, halogen, an aryl group, a heteroaryl group or a heterocyclyl group,
 each aryl, heteroaryl or heterocyclyl group bearing 0 to 3 substituents selected from halogen, $C_{1-6}$ alkyl, $C_{1-6}$ alkoxy, $C_{1-6}$ haloalkyl, amino, $C_{1-4}$ mono or di-alkyl amino, $C_{1-4}$ mono or di-acyl amino,
 with the proviso that the atom linked directly to the carbonyl in —$NR^3C(O)$— is not an oxygen or a sulfur atom; and
b) a $C_{0-8}$ alkyl$C_{5-6}$ heterocycle said heterocyclyl group comprising at least one heteroatom (for example 1, 2 or 3, suitably 1 or 2, in particular 1 heteroatom) selected from O, N and S, and is optionally substituted by one or two or three groups independently selected from halogen, $C_{1-6}$ alkyl, $C_{1-6}$ alkoxy, $C_{1-6}$ haloalkyl, amino, $C_{1-4}$ mono and di-alkyl amino $C_{1-4}$ mono or di-acyl amino.
For example, Q is selected from:
a) a saturated or unsaturated, branched or unbranched $C_{1-10}$ alkyl chain, wherein at least one carbon (for example 1, 2 or 3 carbons) is replaced by a heteroatom selected from O, N, $S(O)_p$, wherein said chain is optionally, substituted by one or more groups independently selected from oxo, halogen, an aryl group, a heteroaryl group or a heterocyclyl group,
 each aryl, heteroaryl or heterocyclyl group bearing 0 to 3 substituents selected from halogen, $C_{1-6}$ alkyl, $C_{1-6}$ alkoxy, $C_{1-6}$ haloalkyl, amino, and $C_{1-4}$ mono or di-alkyl amino,
 with the proviso that the atom linked directly to the carbonyl in —$NR^3C(O)$— is not an oxygen or a sulfur atom; and
b) a $C_{0-8}$ alkyl$C_{5-6}$ heterocycle said heterocyclyl group comprising at least one heteroatom (for example 1, 2 or 3, suitably 1 or 2, in particular 1 heteroatom) selected from O, N and S, and is optionally substituted by one or two or three groups independently selected from halogen, $C_{1-6}$ alkyl, $C_{1-6}$ alkoxy, $C_{1-6}$ haloalkyl, amino, and $C_{1-4}$ mono or di-alkyl amino.

BRIEF DESCRIPTION OF THE FIGURES

FIG. 3 shows the effects of dose for the compound of Example 1 on the numbers of activated macrophages in the BAL of mice exposed to cigarette smoke.

FIG. 4 shows the effects of dose for the compound of Example 1 on numbers of neutrophils in the BAL of mice exposed to cigarette smoke.

DETAILED DESCRIPTION OF THE INVENTION

Figure 1:
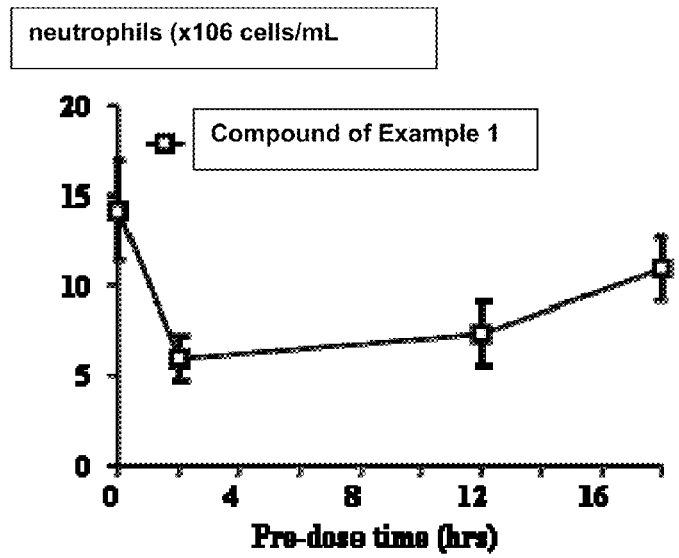
FIG. 1 shows a plot of the pre-dose time for the administration of the compound of Example 1 against the resulting neutrophil number in BALF in the LPS-induced neutrophil accumulation test.

In one embodiment Q is:
a) a saturated or unsaturated, branched or unbranched $C_{1-10}$ alkyl chain, wherein at least one carbon (for example 1, 2 or 3 carbons, suitably 1 or 2, in particular 1) is replaced by a heteroatom selected from O, N, $S(O)_p$, wherein said chain is optionally, substituted by one or more groups (for example 1, 2 or 3) independently selected from oxo, halogen, an aryl group, a heteroaryl group, a heterocyclyl group or a $C_{3-8}$ cycloalkyl,
 at least one of said aryl, heteroaryl or heterocyclyl groups (such as each group) bears a substituents $C_{1-4}$ mono or di-acyl amino and optionally 1 or 2 further substituents independently selected from the relevant list of substituents above for compounds of formula (I); or
b) a $C_{0-8}$ alkyl$C_{5-6}$ heterocycle said heterocyclyl group comprising at least one heteroatom (for example 1, 2 or 3, suitably 1 or 2, in particular 1 heteroatom) selected from O, N, and S, substituted by a $C_{1-4}$ mono or di-acyl amino and optionally 1 or 2 further substituents independently selected from the relevant list of substituents above for compounds of formula (I).

Alkyl as used herein refers to straight chain or branched chain alkyl, such as, without limitation, methyl, ethyl, n-propyl, iso-propyl, butyl, n-butyl and tert-butyl. In one embodiment alkyl refers to straight chain alkyl.

Alkoxy as used herein refers to straight or branched chain alkoxy, for example methoxy, ethoxy, propoxy, butoxy. Alkoxy as employed herein also extends to embodiments in which the oxygen atom is located within the alkyl chain, for example —$C_{1-3}$ alkylO$C_{1-3}$ alkyl, such as —$CH_2CH_2OCH_3$ or —$CH_2OCH_3$. Thus in one embodiment the alkoxy is linked through carbon to the remainder of the molecule. In one embodiment the alkoxy is linked through oxygen to the remainder of the molecule, for example —$C_0$ alkylO$C_{1-6}$ alkyl. In one embodiment the disclosure relates to straight chain alkoxy.

Heteroalkyl as employed herein is intended to refer to a branched or straight chain alkyl wherein one or more, such as 1, 2 or 3 carbons are replaced by a heteroatom, selected from N, O or $S(O)_q$, wherein q represents 0, 1 or 2. The heteroatom may replace a primary, secondary or tertiary carbon, that is, for example, SH, OH or $NH_2$ for $CH_3$, or NH or O or $SO_2$ for —$CH_2$— or N for a —CH— or a branched carbon group, as technically appropriate.

Haloalkyl as employed herein refers to alkyl groups having 1 to 6 halogen atoms, for example 1 to 5 halogens, such as per haloalkyl, in particular perfluoroalkyl, more specifically —$CF_2CF_3$ or $CF_3$.

$C_{1-4}$ mono or di-acyl amino is intended to refer to —NHC(O)$C_{1-3}$ alkyl and to (—NC(O)$C_{1-3}$ alkyl) C(O)$C_{1-3}$ alkyl) respectively.

$C_{1-4}$ mono or di-alkyl amino is intended to refer to —NH$C_{1-4}$ alkyl and —N($C_{1-4}$ alkyl) ($C_{1-4}$ alkyl) respectively.

Aryl as used herein refers to, for example $C_{6-14}$ mono or polycyclic groups having from 1 to 3 rings wherein at least one ring is aromatic including phenyl, naphthyl, anthracenyl, 1,2,3,4-tetrahydronaphthyl and the like, such as phenyl and naphthyl.

Heteroaryl is a 6 to 10 membered aromatic monocylic ring or bicyclic ring system wherein at least one ring is an aromatic nucleus comprising one or more, for example 1, 2, 3 or 4 heteroatoms independently selected from O, N and S. Examples of heteroaryls include: pyrrole, oxazole, thiazole, isothiazole, imidazole, pyrazole, isoxazole, pyridine, pyridazine, pyrimidine, pyrazine, benzothiophene, benzofuran, or 1, 2, 3 and 1, 2, 4 triazole.

Heterocyclyl as employed herein refers to a 5 to 6 membered saturated or partially unsaturated non-aromatic ring comprising one or more, for example 1, 2, 3 or 4 heteroatoms independently selected from O, N and S optionally one or two carbons in the ring may bear an oxo substituent. The definition of $C_{5-6}$ heterocycle as employed herein refers to a is a 5 to 6 membered saturated or partially unsaturated non-aromatic carbocyclic ring comprising one or more, for example 1, 2, 3 or 4 heteroatoms independently selected from O, N and S, wherein each heteroatom replaces a carbon atom and optionally one or two carbons may bear an oxo substitutent. Clearly any valancies of a heteroatom not employed in forming or retaining the ring structure may be filled by hydrogen or a substituent, as appropriate. Thus substituents on heterocycles may be on carbon or on a heteroatom, such as N as appropriate. Examples of heterocycles and $C_{5-6}$ heterocycles include pyrroline, pyrrolidine, tetrahydrofuran, tetrahydrothiophene, pyrazoline, imidazoline, pyrazolidine, imidazolidine, oxoimidazolidine, dioxolane, thiazolidine, isoxazolidine, pyran, dihydropyran, piperidine, piperazine, morpholine, dioxane, thiomorpholine and oxathiane.

Halogen includes fluoro, chloro, bromo or iodo, in particular fluoro, chloro or bromo, especially fluoro or chloro.

Oxo as used herein refers to C=O and will usually be represented as C(O).

$C_{3-8}$ cycloalkyl as employed herein is intended to refer to a saturated or partially unsaturated non-aromatic ring containing 3 to 8 carbon atoms.

$C_{1-10}$ alkyl includes $C_2, C_3, C_4, C_5, C_6, C_7, C_8$ or $C_9$ as well as $C_1$ and $C_{10}$ $C_{0-8}$ alkyl includes $C_1, C_2, C_3, C_4, C_5, C_6$, or $C_1$ as well as $C_0$ and $C_8$.

In relation to a saturated or unsaturated, branched or unbranched $C_{1-10}$ alkyl chain, wherein at least one carbon (for example 1, 2 or 3 carbons, suitably 1 or 2, in particular 1) is replaced by a heteroatom selected from O, N, $S(O)_p$, wherein said chain is optionally, substituted by one or more groups independently selected from oxo, halogen, an aryl group, a heteroaryl group or a heterocyclyl group, it will be clear to persons skilled in the art that the heteroatom may replace a primary, secondary or tertiary carbon, that is $CH_3$, —$CH_2$— or a —CH— or a branched carbon group, as technically appropriate.

In one embodiment of the disclosure there is provided compounds of formula (I), wherein $R^1$ is methyl, ethyl, propyl, iso-propyl, butyl or tert-butyl, in particular tert-butyl.

In one embodiment $R^1$ is —$C(CH_3)_2CH_2OH$.

In one embodiment $R^2$ is methyl, ethyl, n-propyl, iso-propyl, n-butyl or tert-butyl, in particular methyl.

In one embodiment $R^2$ is —$CH_2OH$.

In one embodiment $R^2$ is in the 2, 3, or 4 position (i.e. ortho, meta or para position), in particular the para (4) position.

In one embodiment Ar is naphthyl.

In one embodiment Ar is not substituted with optional substituents.

In one embodiment Ar is substituted with 1 or 2 groups.

In one embodiment Ar is phenyl optionally substituted by 1 or 2 substituents independently selected from $C_{1-3}$ alkyl or $C_{1-3}$ alkoxy, for example tolyl, xylyl, anisoyl, di-methoxybenzene or methoxy-methylbenzene. The phenyl ring may, for example, be linked to the nitrogen of the urea through carbon 1 and to the group L through carbon 4. In such a case the optional one or two substituents selected from $C_{1-3}$ alkyl or $C_{1-3}$ alkoxy may be located in any of the unoccupied positions in the aromatic ring, for example in position 2 or in position 3 or in positions 2 and 3 or in positions 2 and 6 or in positions 3 and 5. Embodiments encompassing other possible regioisomers also form an aspect of the present disclosure.

In one embodiment L is a straight chain linker, for example:

—$(CH_2)_n$— wherein n is 1, 2, 3, 4, 5, 6, 7 or 8; or

—$(CH_2)_nO(CH_2)_m$— wherein n and m are independently 0, 1, 2, 3, 4, 5, 6 or 7, with the proviso that n+m is zero or an integer from 1 to 7, for example where n is 0 and m is 1 or 2 or alternatively, for example, where n is 1 or 2 and m is 0.

In one embodiment L is —$OCH_2$—, —$OCH_2CH_2$—, —$CH_2O$— or —$CH_2CH_2O$—.

In one embodiment L is a branched chain linker $R^aO(CH_2)_m$ wherein m is zero or an integer 1, 2, 3, 4 or 5 and $R^a$ is a $C_{2-7}$ branched alkyl, with the proviso that the number of carbons in $R^a$+m is an integer from 2 to 7, especially where m is zero, such as —$CH(CH_3)O$—, —$C(CH_3)_2O$—, —$CH_2CH(CH_3)O$—, —$CH(CH_3)CH_2O$—, —$C(CH_3)_2CH_2O$— or —$CH_2C(CH_3)_2O$, in particular —$CH(CH_3)O$—.

In one embodiment L is a branched chain linker $(CH_2)_nOR^b$ wherein n is zero or an integer 1, 2, 3, 4 or 5 and $R^b$ is a $C_{2-7}$ branched alkyl, with the proviso that the number of carbons in $R^b$+n is an integer from 2 to 7, for example n is zero, such as —OCH(CH$_3$)—, —OC(CH$_3$)$_2$—, —OCH$_2$CH(CH$_3$)—, —OCH(CH$_3$)CH$_2$—, —OC(CH$_3$)$_2$CH$_2$— or —OCH$_2$C(CH$_3$)$_2$ in particular —OCH(CH$_3$)— or —OC(CH$_3$)$_2$CH$_2$—.

In one embodiment L is a branched chain linker R$^a$OR$^b$ wherein R$^a$ and R$^b$ are independently selected from a C$_{2-7}$ branched alkylene with the proviso that the number of carbons in R$^a$+R$^b$ is an integer from 4 to 7.

In one embodiment L is a saturated unbranched C$_1$-C$_8$ alkylene chain or a saturated branched or unbranched C$_{2-8}$ alkylene chain.

In one embodiment at least one carbon in L is replaced by —O—.

In one embodiment L is —O—.

Alkylene as employed herein refers to branched or unbranched carbon radicals, such as methylene (—CH$_2$—) or chains thereof. In the context of the present specification where alkyl is a linker then the latter is used interchangeably with the term alkylene.

In one embodiment the chain L includes 1, 2 or 3 halogen atom substituents, independently selected from fluoro, chloro, and bromo, for example an alkylene carbon may incorporate one or two chlorine atoms or one or two fluorine atoms and a terminal carbon atom, for example of a branch of an alkylene chain, may be bonded to one, two or three fluorine atoms or one, two or three chlorine atoms to provide a radical such as a trifluoromethyl or a trichloromethyl group.

In one embodiment the chain L does not include a halogen atom or atoms.

In one embodiment R$^3$ is H.

In one embodiment R$^3$ is methyl, ethyl, n-propyl or isopropyl.

In one embodiment R$^3$ is cyclopropyl.

In one embodiment X is selected from, pyrrole, oxazole, thiazole, isothiazole, imidazole, pyrazole, isoxazole, oxadiazole, pyridazine, pyrimidine, pyrazine, or 1,2,3 and 1,2,4 triazole, such as pyrazole, isoxazole, oxadiazole, pyridine, pyridazine, pyrimidine, pyrazine, or 1,2,3 and 1,2,4 triazole, in particular, pyrimidine, imidazole or pyridine, and especially pyridine or pyrimidine, more specifically pyridine.

In one embodiment 1, 2, 3 or 4 carbon atoms are replaced in the alkyl chain of Q by heteroatoms independently selected from O, N, S(O)$_p$.

In one embodiment the heteroatom(s) replacing carbon(s) in the alkyl chain fragment of Q are selected from N and O.

In one embodiment Q is a saturated or unsaturated, branched or unbranched C$_{1-8}$ alkyl chain or a C$_{1-6}$ alkyl chain, wherein at least one carbon is replaced by a heteroatom selected from —O, —N, S(O)$_p$. Alternatively, in this embodiment the alkyl chain may be a C$_{2-8}$ alkyl or a C$_{3-6}$ alkyl group, such as a C$_4$ alkyl or a C$_5$ alkyl group.

In one embodiment a nitrogen atom in the alkyl chain is directly bonded to the carbonyl of the fragment —NR$^3$C(O) and additionally may, for example, be a terminal amino group.

In one embodiment Q represents C$_{1-6}$ alkylNH$_2$ or NH$_2$.

In one embodiment Q represents —NHC$_{1-6}$ alkyl such as —NHCH$_3$ or —NHCH$_2$CH$_3$ or —NHCH(CH$_3$)$_2$.

In one embodiment the fragment Q is a saturated or unsaturated, branched or unbranched C$_{1-10}$ alkyl chain wherein at least one carbon (for example 1, 2, 3 or 4 carbons, in particular 1 or 2 carbons) is replaced by a heteroatom selected from O, N, S(O)$_p$, for example in such a manner as to provide a stable N-acyl group, NR$^3$C(O)Q, wherein said chain is optionally substituted by one or more groups selected from oxo, halogen, an aryl group, a heteroaryl group, a heterocyclyl group, or C$_{3-8}$ cycloalkyl each aryl, heteroaryl or heterocyclyl or C$_{3-8}$ cycloalkyl group bearing 0 to 3 substituents independently selected from a relevant substituent listed above for compounds of formula (I).

In one embodiment the fragment Q is a saturated or unsaturated, branched or unbranched C$_{1-10}$ alkyl chain wherein at least one carbon (for example 1, 2, 3 or 4 carbons, in particular 1 or 2 carbons) is replaced by a heteroatom selected from O, N, S(O)$_p$, for example in such a manner as to provide a stable N-acyl group, NR$^3$C(O)Q, wherein said chain is optionally substituted by one or more groups selected from oxo, halogen, an aryl group, a heteroaryl group or a heterocyclyl group, each aryl, heteroaryl or heterocyclyl group bearing 0 to 3 substituents independently selected from a relevant substituent listed above for compounds of formula (I), for example halogen, C$_{1-6}$ alkyl, C$_{1-6}$ alkoxy, C$_{1-6}$ haloalkyl, amino, C$_{1-4}$ mono or di-alkyl amino and C$_{1-4}$ mono or di-acyl amino.

In one embodiment the latter chain is optionally substituted by one or more groups selected from oxo, halogen, an aryl group, a heteroaryl group or a heterocyclyl group, each aryl, heteroaryl or heterocyclyl group bearing 0 to 3 substituents selected from halogen, C$_{1-6}$ alkyl, C$_{1-6}$ alkoxy, C$_{1-6}$ haloalkyl, amino, and C$_{1-4}$ mono or di-alkyl amino.

In one embodiment Q is C$_{1-4}$alkyl-V—R$^4$, such as C$_{1-3}$alkyl-V—R$^4$ wherein:
V is a heteroatom selected from NR$^V$, O or S(O)$_p$;
R$^V$ represents H or C$_{1-3}$ alkyl;
R$^4$ is H or —C$_{1-3}$ alkyl, and p is as defined above,
with the proviso that the total alkyl chain length is not more than 10 carbon atoms, including replacement heteroatoms and that the resulting radical Q is a stable group, for example —CH$_2$SCH$_3$, —CH$_2$SO$_2$CH$_3$, —CH$_2$NHCH$_3$, —CH$_2$N(CH$_3$)$_2$—C(CH$_3$)$_2$NHCH$_3$, —CH(CH$_3$)N(CH$_3$)$_2$, —(CH$_2$)$_3$CHNHCH$_3$, —(CH$_2$)$_3$N(CH$_3$)$_2$, —CH$_2$OH, —CH$_2$OCH$_3$, —CH(CH$_3$)OCH$_3$, or —(CH$_2$)$_2$OCH$_3$.

In one embodiment Q is C$_{1-3}$ alkyl-V—(C$_{1-3}$ alkyl-Z—R$^5$)$_k$ such as C$_{1-3}$ alkyl-V—(C$_{2-3}$ alkyl-Z—R$^5$)$_k$ wherein:
V is a heteroatom selected from N, NH, O or S(O)$_p$, such as N or NH
(V is N in the case where k=2, or will be selected from NH, O or S(O)$_p$, in the case where k=1, in particular NH);
Z is independently selected from NH, O or S(O)$_p$;
R$^5$ is H or —C$_{1-3}$alkyl;
k is an integer 1 or 2 (such as 1); and
p is as defined above,
with the proviso that the total alkyl chain length is not more than 10 carbon atoms, including replacement heteroatoms and that the resulting radical Q is a stable group. Suitably Q is C$_{1-3}$alkyl-V—C$_{1-3}$alkyl-OCH$_3$ for example C$_{1-3}$alkyl-V—C$_{2-3}$alkyl-OCH$_3$ such as C$_{1-3}$alkyl-V—(CH$_2$)$_2$OCH$_3$, in particular —CH$_2$O(CH$_2$)$_2$OCH$_3$ and CH$_2$S(CH$_2$)$_2$OCH$_3$, or —CH$_2$NH(CH$_2$)$_2$OCH$_3$, C$_{1-3}$alkyl-V—(C$_{1-3}$alkyl-OCH$_3$)$_k$ wherein k represents 2, for example C$_{1-3}$alkyl-V—(C$_{2-3}$alkyl-OCH$_3$)$_k$ such as —CH$_2$N[(CH$_2$)$_2$OCH$_3$]$_2$.

In one embodiment Q is C$_{1-3}$ alkyl-V—C$_{1-2}$ alkyl-Z—C$_{1-2}$ alkyl-Y—R$^6$, or C$_{1-3}$alkyl-V—C$_{2-3}$ alkyl-Z—C$_{2-3}$ alkyl-Y—R$^6$, wherein V, Z and Y are independently a heteroatom selected from NH, O or S(O)$_p$,
R$^6$ is H or methyl, and
p is as defined above,
with the proviso that the total alkyl chain length is not more than 10 carbon atoms, including replacement heteroatoms and that the resulting radical Q is a stable group. Suitably Q is —CH$_2$V(CH$_2$)$_2$O(CH$_2$)$_2$OCH$_3$, such as —CH$_2$O(CH$_2$)$_2$O(CH$_2$)$_2$OCH$_3$, —CH$_2$NH(CH$_2$)$_2$O(CH$_2$)$_2$OCH$_3$, or —CH$_2$S(CH$_2$)$_2$O(CH$_2$)$_2$OCH$_3$.

In one embodiment Q represents —NR$^7$R$^8$ and —NR$^3$C(O)Q forms a urea, where R$^7$ and R$^8$ independently represent hydrogen or a C$_{1-9}$ saturated or unsaturated, branched or unbranched alkyl chain, wherein one or more carbons, such as 1, 2 or 3 are optionally replaced by a heteroatom selected from O, N or S(O)$_p$. Said chain is optionally substituted by one or more groups independently selected from oxo, halogen, an aryl group, a heteroaryl group, a heterocyclyl or C$_{3-8}$ cycloalkyl group, each aryl, heteroaryl or heterocyclyl group bearing 0 to 3 substituents independently selected from the relevant substituents listed above for compounds of formula (I), for example halogen, C$_{1-6}$ alkyl, C$_{1-6}$ alkoxy, C$_{1-6}$ haloalkyl, amino, C$_{1-4}$ mono or di-alkyl amino and C$_{1-4}$ mono or di-acyl amino with the proviso that the total alkyl chain length is not more than 10 carbon atoms, including replacement heteroatoms and that the resulting radical Q is a stable group.

In one embodiment Q represents —NR$^7$R$^8$ and —NR$^3$C(O)Q forms a urea, where R$^7$ and R$^8$ independently represent hydrogen or a C$_{1-9}$ saturated or unsaturated, branched or unbranched alkyl chain, wherein one or more carbons, such as 1, 2 or 3 are optionally replaced by a heteroatom selected from O, N or S(O)$_p$. Said chain is optionally substituted by one or more groups independently selected from oxo, halogen, an aryl group, a heteroaryl group or a heterocyclyl group, each aryl, heteroaryl or heterocyclyl group bearing 0 to 3 substituents independently selected from the relevant substituents listed above for compounds of formula (I), for example halogen, C$_{1-6}$ alkyl, C$_{1-6}$ alkoxy, C$_{1-6}$ haloalkyl, amino, C$_{1-4}$ mono or di-alkyl amino and C$_{1-4}$ mono or di-acyl amino with the proviso that the total alkyl chain length is not more than 10 carbon atoms, including replacement heteroatoms and that the resulting radical Q is a stable group.

In this urea embodiment in one sub-embodiment R$^7$ represents hydrogen.

Examples of ureas include those in which R$^7$ and R$^8$ are both hydrogen and Q is —NH$_2$, or where Q is —NHCH$_3$ or —N(CH$_3$)$_2$ to provide, for example, a fragment —NR$^3$C(O)NH$_2$ or —NR$^3$C(O)NHCH$_3$ or —NR$^3$C(O)N(CH$_3$)$_2$.

Examples of ureas containing a heteroatom in the alkyl chain include those in which Q is —NH(CH$_2$)$_2$OCH$_3$ or —N[(CH$_2$)$_2$OCH$_3$]$_2$. In one embodiment Q represents —NHC$_{2-6}$alkylOC$_{1-3}$alkyl, such as —NHCH$_2$CH$_2$OCH$_3$.

Examples of ureas containing an oxo substituent include those in which Q is —NHCH$_2$C(O)NH—C$_{2-3}$alkyl-X$^1$—C$_{1-3}$ alkyl, wherein X$^1$ is a heteroatom selected from N, O or S(O)$_p$ and p is defined as above. Examples of the latter include those wherein Q is —NHCH$_2$C(O)NHCH$_2$CH$_2$OCH$_3$. Thus in one embodiment Q represents —NHC$_{1-4}$ alkylC(O)NHC$_2$alkylOCH$_3$ such as —NHCH$_2$C(O)NHCH$_2$CH$_2$OCH$_3$.

In one embodiment Q represents —NHC$_{1-4}$alkylC(O)R$^Q$ wherein R$^Q$ is selected from OH or —NR'R" where R' is hydrogen or C$_{1-3}$ alkyl and R" is hydrogen or C$_{1-3}$ alkyl, for example —NHCH$_2$C(O)OH, —NHCH$_2$C(O)NH$_2$ or —NHCH$_2$C(O)NHCH$_3$ such as —NHCH$_2$C(O)OH or —NHCH$_2$C(O)NHCH$_3$.

In one embodiment Q represents —NHC$_{1-4}$alkylC(O)OC$_{1-3}$alkyl, such as —NHCH$_2$C(O)OCH$_2$CH$_3$.

In a further urea sub-embodiment Q represents —N—R$^9$C$_{1-3}$ alkyl-V—(C$_{1-3}$ alkyl-Z—R$^{10}$)$_k$ for example —N—R$^9$C$_{2-3}$ alkyl-V—(C$_{2-3}$alkyl-Z—R$^{10}$)$_k$ wherein:

V represents N, NH, O, S(O)$_p$;
Z represents NH, O, S(O)$_p$;
k is an integer 1 or 2;
p is an integer 0, 1 or 2

R$^9$ represents H or C$_{1-3}$ alkyl-V—(C$_{1-3}$ alkyl-Z—R$^{10}$)$_k$ such as C$_{2-3}$ alkyl-V—(C$_{2-3}$ alkyl-Z—R$^{10}$)$_k$; and R$^{10}$ is H or C$_{1-3}$ alkyl such as C$_{1-3}$ alkyl;

with the proviso that the total alkyl chain length is not more than 10 carbon atoms, including replacement heteroatoms and that the resulting radical Q is a stable group.

In one embodiment Q is a saturated or unsaturated, branched or unbranched C$_{1-10}$ alkyl chain, wherein at least one carbon is replaced by a heteroatom selected from O, N, and S(O)$_p$, wherein said chain is substituted by an aryl group bearing 0 to 3 substituents, for example 1, 2 or 3, such as 1 or 2 substituents independently selected from the relevant substituents listed above for compounds of formula (I), for example from halogen, C$_{1-6}$ alkyl, C$_{1-6}$ alkoxy, C$_{1-6}$ haloalkyl, amino and C$_{1-4}$ mono or di-alkyl amino and C$_{1-4}$ mono or di-acyl amino, such as a saturated or unsaturated, branched or unbranched C$_{1-10}$ alkyl chain, wherein at least one carbon is replaced by a heteroatom selected from O, N, and S(O)$_p$, wherein said chain is substituted by an aryl group bearing 0 to 3 substituents, for example 1, 2 or 3, such as 1 or 2 substituents independently selected from halogen, C$_{1-6}$ alkyl, C$_{1-6}$ alkoxy, C$_{1-6}$ haloalkyl, amino and C$_{1-4}$ mono or di-alkyl amino. In one embodiment the said aryl group is phenyl, for example substituted phenyl or unsubstituted phenyl.

In one embodiment Q represents —NHC$_{0-6}$ alkylphenyl, such as —NHphenyl or NHbenzyl.

Examples of the fragment —NR$^3$C(O)Q wherein Q comprises substituted benzyl include: —NR$^3$C(O)CH$_2$NHCH$_2$C$_6$H$_4$(OCH$_3$) such as —NHC(O)CH$_2$NHCH$_2$C$_6$H$_4$(OCH$_3$), for example where the methoxy substituent is in the ortho, meta or para position, such as the para position.

In one embodiment Q is a saturated or unsaturated, branched or unbranched C$_{1-10}$ alkyl chain, wherein at least one carbon is replaced by a heteroatom selected from O, N, and S(O)$_p$, wherein said chain is substituted by a heteroaryl group bearing 0 to 3 substituents (for example 1, 2 or 3, such as 1 or 2 substituents) independently selected from the relevant substituents listed above for compounds of formula (I), for example halogen, C$_{1-6}$ alkyl, C$_{1-6}$ alkoxy, C$_{1-6}$ alkyl amino, C$_{1-4}$ mono or di-alkyl amino and C$_{1-4}$ mono or di-acyl amino, such as a saturated or unsaturated, branched or unbranched C$_{1-10}$ alkyl chain, wherein at least one carbon is replaced by a heteroatom selected from O, N, and S(O)$_p$, wherein said chain is substituted by a heteroaryl group bearing 0 to 3 substituents for example 1, 2 or 3, such as 1 or 2 substituents selected from halogen, C$_{1-6}$ alkyl, C$_{1-6}$ alkoxy, C$_{1-6}$ alkyl amino, C$_{1-4}$ mono or di-alkyl amino. In one embodiment the said heteroaryl group is selected from, thiophene, oxazole, thiazole, isothiazole, imidazole, pyrazole, isoxazole, isothiazole, oxadiazole, 1,2,3 or 1,2,4 triazole, pyridine, pyridazine, pyrimidine, pyrazine and, in particular pyridine and pyrimidine, especially pyridine.

In one embodiment Q represents —NHC$_{1-6}$ alkylheteroaryl, for example —NH(CH$_2$)$_3$imidazolyl or —NHCH$_2$ isoxazole wherein the isoxazole is optionally substituted such as —NHCH$_2$ isoxazole(CH$_3$).

In one embodiment Q represents —NHC$_{1-4}$ alkylC(O)NHC$_{1-3}$alkylheteroaryl, for example a nitrogen containing heteroaryl group or a nitrogen and oxygen containing heteroaryl, more specifically —NHCH$_2$C(O)NHCH$_2$CH$_2$pyridinyl, in particular where pyridinyl is linked through carbon, for example pyridin-4-yl or —NHCH$_2$C(O)NHCH$_2$CH$_2$CH$_2$imidazolyl, in particular where imidazolyl is linked through nitrogen.

In one embodiment Q is a saturated or unsaturated, branched or unbranched $C_{1-10}$ alkyl chain, wherein at least one carbon is replaced by a heteroatom selected from O, N and $S(O)_p$ wherein said chain is substituted by a heterocyclyl group bearing 0 to 3 substituents (for example 1, 2 or 3, such as 1 or 2 substituents) independently selected from the relevant substituents listed above for compounds of formula (I), for example halogen, $C_{1-6}$ alkyl, $C_{1-6}$ alkoxy, $C_{1-6}$ haloalkyl amino, $C_{1-4}$ mono or di-alkyl amino and $C_{1-4}$ mono or di-acyl amino, such as a saturated or unsaturated, branched or unbranched $C_{1-10}$ alkyl chain, wherein at least one carbon is replaced by a heteroatom selected from O, N and $S(O)_p$ wherein said chain is substituted by a heterocyclyl group bearing 0 to 3 substituents, for example 1, 2 or 3, such as 1 or 2 substituents selected from halogen, $C_{1-6}$ alkyl, $C_{1-6}$ alkoxy, $C_{1-6}$ haloalkyl amino, $C_{1-4}$ mono or di-alkyl amino.

In one embodiment said heterocyclyl is selected, from a 5 or 6 membered saturated or partially unsaturated ring system comprising one or more (for example 1, 2 or 3 in particular 1 or 2) heteroatoms independently selected from O, N and S, for example pyrrolidine, tetrahydrofuran, tetrahydrothiophene, piperidine, piperazine, morpholine, 1,4-dioxane, pyrrolidine and oxoimidazolidine such as pyrrolidine, tetrahydrofuran, tetrahydrothiophene, piperidine, piperazine, morpholine, and 1,4-dioxane, in particular piperidine, piperazine, and morpholine.

A heterocyclic group may be linked to the alkyl chain of Q or to the carbonyl of —$NR^3C(O)$— through carbon or nitrogen, in particular a nitrogen atom.

In one embodiment Q is —$C_{0-3}$alkylheterocycle (for example —$C_{0-1}$alkylheterocycle) said heterocyclyl group comprising at least one heteroatom (for example 1, 2 or 3, in particular 1 or 2, heteroatoms) selected from O, N and S, and is optionally substituted by one or two or three groups independently selected from the relevant substituents listed above for compounds of formula (I), for example halogen, $C_{1-6}$ alkyl, $C_{1-6}$ alkoxy, $C_{1-6}$ haloalkyl, amino, $C_{1-4}$ mono and di-alkyl amino and $C_{1-4}$ mono or di-acyl amino.

In one embodiment Q is —$C_0$alkylheterocycle, for example a tetrahydropyranyl or a pyrrolidinyl or a morpholinyl or a piperazinyl or an oxoimidazolinyl group, such as 2-oxoimidazolidinyl group.

In one embodiment in which Q is —$C_0$alkylheterocycle, the heterocycle is linked through carbon, and is, for example, a C-linked tetrahydropyran or a C-linked piperidine or a C-linked morpholine or a C-linked piperazine.

In one embodiment in which Q is —$C_0$alkylheterocycle, the heterocyclic group containing one or more N atoms is linked through N. This embodiment provides for ureas in which one of the urea nitrogens is embedded within a heterocyclic ring. Examples of this embodiment include, but are not limited to, an N-linked morpholine or an N-linked piperidine or an N-linked piperazine, said N-linked piperizinyl group optionally bearing an additional C- or N-substituent (such as an N-methyl group or N—$CH_2CH_2OCH_3$ group. In one embodiment Q is a heterocyclyl linked through nitrogen such as piperidinyl, in particular 4-hydroxypiperidinyl or piperazinyl, such as 4-methyl piperazinyl.

In one embodiment Q represents a heterocyclyl group, for example a nitrogen containing heterocyclyl group, in particular linked through N, such as morpholinyl or piperazinyl optionally substituted by methyl, especially 4-methyl, or piperidinyl.

In one embodiment Q is a —$C_1$alkylheterocycle, for example tetrahydropyranylmethyl or a C- or N-linked piperazinylmethyl optionally bearing a substituent (for example a $C_{1-6}$ alkyl substituent such as methyl or a $C_{1-6}$ alkoxy substituent such as —$CH_2CH_2OCH_3$). Additional examples include a C- or N-linked pyrrolidinylmethyl, or a C- or N-linked oxoimidazolinylmethyl (such as 2-oxoimidazolidinylmethyl, said heterocycle optionally bearing a substitutent (such as N-methyl or N—$SO_2CH_3$).

In one embodiment Q represents —NHheterocyclyl (wherein the heterocyclyl bears 0 to 3 substituents selected from the relevant list of substituents listed above for compounds of formula (I), for example halogen, hydroxy, $C_{1-6}$ alkyl, $C_{1-6}$ alkoxy, $C_{1-6}$ haloalkyl, amino, $C_{1-4}$ mono or di-alkyl amino, —$S(O)_qC_{1-6}$ alkyl, $C_{1-4}$ mono or di-acyl amino, $C_{0-6}$ alkylC(O)$C_{1-6}$ alkyl or $C_{0-6}$ alkylC(O)$C_{1-6}$ heteroalkyl), such as where the ring is linked through carbon, for example 2-piperidinyl or 3-piperidinyl or 4-piperidinyl, in particular 1-acetylpiperidin-4-yl, 1-methylpiperidin-4-yl, 1-(methylsulfonyl)piperidin-4-yl or 1-(2-(2-methoxyethoxy)acetyl)piperidin-4-yl In one embodiment Q represents —$NHC_{1-6}$ alkylheterocyclyl for example a nitrogen containing heterocyclyl group, in particular one linked through nitrogen, such as —$NHCH_2CH_2$morpholine, —$NH(CH_2)_3$morpholine or —$NH(CH_2)_4$morpholine.

In one embodiment Q represents —$NHC_{1-6}$ alkylC(O)heterocyclyl (wherein the heterocyclyl bears 0 to 3 substituents selected from the relevant list of substituents listed above for compounds of formula (I), for example halogen, hydroxy, $C_{1-6}$ alkyl, $C_{1-6}$ alkoxy, $C_{1-6}$ haloalkyl, amino, $C_{1-4}$ mono or di-alkyl amino, $C_{1-4}$ mono or di-acyl amino, $C_{0-6}$ alkylC(O)$C_{1-6}$ alkyl or $C_{0-6}$ alkylC(O)$C_{1-6}$ heteroalkyl) for example a nitrogen containing heterocyclyl group, in particular one linked through nitrogen, such as —$NHCH_2C(O)$-1-pyrrolindinyl, —$NHCH_2C(O)$-1-piperidinyl, —$NHCH_2C(O)$-4-morpholinyl or —$NHCH_2C(O)$piperazinyl such as —$NHCH_2C(O)$-4-methyl-1-piperazinyl.

In one embodiment Q represents —$NHC_{1-4}$ alkylC(O)$NHC_{1-3}$alkylheterocyclyl for example a nitrogen containing heterocyclyl group or a nitrogen and/or oxygen containing heterocyclyl, such as —$NHCH_2C(O)$$NHCH_2CH_2$morpholinyl, in particular where morpholinyl is linked through nitrogen.

In one embodiment Q represents —N($C_{1-3}$ alkyl)$C_{1-6}$ alkylheterocyclyl, for example a nitrogen containing heterocyclyl group, in particular linked through nitrogen, such as —$N(CH_3)CH_2CH_2$morpholine, —$N(CH_3)(CH_2)_3$morpholine or —$N(CH_3)(CH_2)_4$morpholine.

In one embodiment Q is —$C_{1-3}$alkyl-G-$C_{1-3}$alkylheterocycle wherein G is a heteroatom selected from NH, O or $S(O)_p$ said heterocyclyl group comprising at least one heteroatom (for example 1, 2 or 3, in particular 1 or 2, heteroatoms) selected from O, N, and S, and is optionally substituted by one or two or three groups independently selected from relevant substituents listed above for compounds of formula (I), for example halogen, $C_{1-6}$ alkyl, $C_{1-6}$ alkoxy, $C_{1-6}$ haloalkyl, amino, $C_{1-4}$ mono and di-alkyl amino and $C_{1-4}$ mono or di-acyl amino such as one or two or three groups halogen, $C_{1-6}$ alkyl, $C_{1-6}$ alkoxy, $C_{1-6}$ haloalkyl, amino, $C_{1-4}$ mono and di-alkyl amino. Suitably Q is —$CH_2G(CH_2)_2$heterocycle for example —$CH_2G(CH_2)_2$tetrahydropyranyl; or —$CH_2G(CH_2)_2$morpholinyl in which the heterocyclyl is linked through nitrogen or carbon; or $CH_2G(CH_2)_2$piperazinyl in which the heterocyclyl is linked through nitrogen or carbon and optionally bearing a further C- or N-substituent (for example a $C_{1-6}$ alkyl substitutent such as methyl or a $C_{1-6}$ alkoxy substituent such as —$CH_2CH_2OCH_3$); or —$CH_2G(CH_2)_2$pyrrolidinyl, in which the heterocyclyl is linked through nitrogen or carbon, for example linked through nitrogen; or —$CH_2G(CH_2)_2$oxoimidazolinyl (such as 2-oxoimidazolidinyl) for example linked through N and optionally bearing an additional C- or N-substituent (such as N-methyl or N—SO$_2$CH$_3$), and in which G is O or NH.

In one embodiment G is O.

In one embodiment G is NH.

In one embodiment Q is a saturated or unsaturated C$_{1-10}$ alkyl chain wherein at least one carbon (for example 1, 2 or 3 carbons) is replaced by a heteroatom selected from O, N, S(O)$_p$ wherein said chain is substituted by a C$_{3-8}$ carbocyclyl group and said alkyl chain is optionally substituted by one or more (for example 1 or 2) groups selected from oxo and halogen. In one embodiment said C$_{3-8}$ carbocyclyl group bears one or more groups (for example 1, 2 or 3 groups) independently selected from halogen, hydroxyl, C$_{1-6}$ alkyl, C$_{1-6}$ alkoxy, C$_{1-6}$ haloalkyl, amino, C$_{1-4}$ mono or di-alkyl amino, C$_{1-4}$ mono or di-acyl amino, S(O)$_q$C$_{1-6}$ alkyl, C$_{0-6}$ alkylC(O)C$_{1-6}$ alkyl or C$_{0-6}$ alkylC(O)C$_{1-6}$ heteroalkyl.

In one embodiment Q represents —NHC$_{3-6}$ cycloalkyl, such as —NHcyclopropyl, —NHcyclopentyl or —NHcyclohexyl.

In one embodiment the aryl, heteroaryl or heterocyclyl group bears at least one —S(O)$_q$C$_{1-6}$ alkyl substituent and optionally bears one or two further relevant substituents independently selected from the list of substituents defined above for compounds of formula (I).

In one embodiment the C$_{5-6}$ heterocycle bears at least one —S(O)$_q$C$_{1-6}$ alkyl substituent and optionally bears one or two further substituents independently selected from the relevant list of substituents defined above for compounds of formula (I).

In one embodiment the aryl, heteroaryl or heterocyclyl group bears at least one hydroxyl substituent and optionally bears one or two further substituents independently selected from the relevant list of substituents defined above for compounds of formula (I).

In one embodiment the C$_{5-6}$heterocycle bears at least one hydroxyl substituent and optionally bears one or two further substituents independently selected from the relevant list of substituents defined above for compounds of formula (I).

In one embodiment the aryl, heteroaryl or heterocyclyl group bears at least one C$_{1-4}$ mono and/or di-acyl amino substituent and optionally bears one or two further substituents independently selected from the relevant list defined above for compounds of formula (I).

In one embodiment the C$_{5-6}$heterocycle bears at least one C$_{1-4}$ mono and/or di-acyl amino substituent and optionally bears one or two further substituents independently selected from the relevant list defined above for compounds of formula (I).

In one embodiment the aryl, heteroaryl or heterocyclyl group bears at least one C$_{0-6}$ alkylC(O)C$_{1-6}$ heteroalkyl substituent and optionally bears one or two further substituents independently selected from the relevant list defined above for compounds of formula (I).

In one embodiment the C$_{5-6}$heterocycle bears at least one C$_{0-6}$ alkylC(O)C$_{1-6}$ heteroalkyl substituent and optionally bears one or two further substituents independently selected from the relevant list defined above for compounds of formula (I).

In one embodiment the aryl, heteroaryl or heterocyclyl group bears at least one C$_{0-6}$ alkylC(O)C$_{1-6}$ alkyl substituent and optionally bears one or two further substituents independently selected from the relevant list defined above for compounds of formula (I).

In one embodiment the C$_{5-6}$heterocycle bears at least one C$_{0-6}$ alkylC(O)C$_{1-6}$ alkyl substituent and optionally bears one or two further substituents independently selected from the relevant substituents defined above for compounds of formula (I).

In one embodiment Q represents tetrahydrofuranyl, morpholinyl, piperidinyl such as piperidinyl bearing one hydroxyl substituent, piperazinyl such as piperazinyl bearing one methyl substituent or pyrrolidinyl such a pyrrolidinyl bearing one di-methyl amino substituent. The ring may be linked through the heteroatom, such as nitrogen. Alternatively, the ring may be linked through carbon. The substituent may, for example be para relative to the atom through which the ring is linked to the remainder of the molecule.

In one embodiment the alkyl chain fragment of Q does not bear any optional substituents.

In one embodiment the alkyl chain is saturated.

In one embodiment the alkyl chain is unbranched.

In one embodiment the alkyl chain fragment of Q bears 1, 2, or 3, for example 1 or 2, in particular 1 optional substituent.

It will be clear to persons skilled in the art that the heteroatom may replace a primary, secondary or tertiary carbon, that is a CH$_3$, —CH$_2$— or a —CH—, group, as technically appropriate.

In one embodiment p is 0 or 2.

In one embodiment p is 1.

In one embodiment compounds of the disclosure include those in which the fragment Q is:
- —CH$_2$OH;
- —CH$_2$OC$_{1-6}$ alkyl, in particular —CH$_2$OCH$_3$;
- —CH$_2$CH$_2$OCH$_3$;
- —CH$_2$O(CH$_2$)$_2$OCH$_3$;
- —CH(CH$_3$)OCH$_3$;
- —CH$_2$NHCH$_3$ or —CH$_2$N(CH$_3$)$_2$
- —CH$_2$NHCH$_2$CH$_2$OCH$_3$ or —CH$_2$NHC(O)CH$_2$OCH$_3$;
- —CH$_2$SCH$_3$, —CH$_2$S(O)$_2$CH$_3$ or —CH$_2$NHC(O)CH$_2$S(O)$_2$CH$_3$; or
- —CH$_2$NHC(O)CH$_2$.

In one embodiment compounds of the disclosure include those in which the fragment —NR$^3$C(O)Q in formula (I) is represented by:
- —NR$^3$C(O)CH$_2$OH, in particular —NHC(O)CH$_2$OH;
- —NR$^3$C(O)CH$_2$OC$_{1-6}$ alkyl, in particular —NR$^3$C(O)CH$_2$OCH$_3$, especially —NHC(O)CH$_2$OCH$_3$;
- —NR$^3$C(O)CH$_2$O(CH$_2$)$_2$OCH$_3$, in particular —NHC(O)CH$_2$O(CH$_2$)$_2$OCH$_3$;
- —NR$^3$C(O)CH(CH$_3$)OCH$_3$ in particular —NHC(O)CH(CH$_3$)OCH$_3$;
- —NR$^3$C(O)CH(CH$_3$)NHC$_{1-3}$alkyl in particular —NHC(O)CH(CH$_3$)NHCH$_3$;
- —NR$^3$C(O)CH(CH$_3$)N(C$_{1-3}$alkyl)$_2$ in particular —NHC(O)CH(CH$_3$)N(CH$_3$)$_2$;
- —NR$^3$C(O)C(CH$_3$)$_2$NHCH$_3$ in particular —NHC(O)C(CH$_3$)$_2$NHCH$_3$;
- —NR$^3$C(O)(CH$_2$)$_2$OC$_{1-6}$alkyl, such as —NR$^3$C(O)(CH$_2$)$_2$OCH$_3$, in particular —NHC(O)(CH$_2$)$_2$OCH$_3$;
- —NR$^3$C(O)(CH$_2$)$_3$NHC$_{1-3}$alkyl in particular —NHC(O)(CH$_2$)$_3$NHCH$_3$;
- —NR$^3$C(O)(CH$_2$)$_3$N(C$_{1-3}$alkyl)$_2$ in particular —NHC(O)(CH$_2$)$_3$N(CH$_3$)$_2$;
- —NR$^3$C(O)CH$_2$NHC$_{1-3}$alkyl in particular —NHC(O)CH$_2$NHCH$_3$;
- —NR$^3$C(O)CH$_2$NH(CH$_2$)$_2$OCH$_3$ in particular —NHC(O)CH$_2$NH(CH$_2$)$_2$OCH$_3$;
- —NR$^3$C(O)CH$_2$SCH$_3$, in particular —NHC(O)CH$_2$SCH$_3$;
- —NR$^3$C(O)CH$_2$S(CH$_2$)$_2$OCH$_3$, in particular —NHC(O)CH$_2$S(CH$_2$)$_2$OCH$_3$;
- —NR$^3$C(O)CH$_2$S(CH$_2$)$_2$O(CH$_2$)$_2$OCH$_3$, in particular —NHC(O)CH$_2$S(CH$_2$)$_2$O(CH$_2$)$_2$OCH$_3$;

—NR³C(O)CH₂SOCH₃, in particular —NHC(O)CH₂SOCH₃;

—NR³C(O)CH₂S(O)₂CH₃, in particular —NHC(O)CH₂S(O)₂CH₃;

—NR³C(O)CH₂N[(CH₂)₂OCH₃]₂ in particular —NHC(O)CH₂N[(CH₂)₂OCH₃]₂;

—NR³C(O)NH₂ in particular —NHC(O)NH₂;

—NR³C(O)NHC$_{1-9}$ alkyl, such as NR³C(O)NHC$_{1-7}$ alkyl, in particular —NHC(O)NHCH₃

—NR³C(O)N(C$_{1-4}$ alkyl)C$_{1-5}$ alkyl in particular —NHC(O)N(CH₃)₂; or

—NR³C(O)NHCH₂CONH(CH₂)₂OCH₃ in particular —NHC(O)NHCH₂CONH(CH₂)₂OCH₃.

In one embodiment compounds of the disclosure include compounds of formula (I) in which the fragment —NR³C(O)C$_{0-8}$alkylheterocyclyl is represented by:

—NHC(O)-(tetrahydropyranyl), such as —NHC(O)-(tetrahydro-2H-pyran-4-yl):

—NHC(O)-(morpholinyl) such as —NHC(O)-(4-morpholinyl) or —NHC(O)-(3-morpholinyl);

—NHC(O)-(pyrrolidinyl), such as —NHC(O)-(pyrrolidin-1-yl);

—NHC(O)-(piperazinyl), such as —NHC(O)-(piperazin-1-yl);

—NHC(O)-(methylpiperazinyl), such as —NHC(O)-(4-methylpiperazin-1-yl);

—NHC(O)-[(methoxyethyl)piperazinyl], such as —NHC(O)$_{44}$-(2-methoxyethyl)piperazin-1-yl);

—NHC(O)-(oxoimidazolidinyl) such as —NHC(O)-(2-oxoimidazolidinyl), in particular —NHC(O)-(2-oxoimidazolidin-1-yl);

—NHC(O)CH₂-(tetrahydropyranyl), such as —NHC(O)CH₂-(tetrahydro-2H-pyran-4-yl);

—NHC(O)CH₂-(morpholinyl), such as —NHC(O)CH₂-(4-morpholinyl);

—NHC(O)CH₂-(pyrrolidinyl), such as —NHC(O)CH₂-(pyrrolidin-1-yl);

—NHC(O)CH₂-(piperazinyl), such as —NHC(O)CH₂-(piperazin-1-yl);

—NHC(O)CH₂-(methylpiperazinyl), such as —NHC(O)CH₂-(4-methylpiperazin-1-yl);

—NHC(O)CH₂—[(methoxyethyl)piperazinyl], such as —NHC(O)CH₂-[4-(2-methoxyethyl)piperazin-1-yl];

—NHC(O)CH₂SCH₂CH₂-(morpholinyl), such as —NHC(O)CH₂SCH₂CH₂-(4-morpholinyl), or

—NHC(O)CH₂SCH₂CH₂-(3-morpholinyl); and

—NHC(O)CH₂SO₂CH₂CH₂-(morpholinyl), such as —NHC(O)CH₂SO₂CH₂CH₂-(4-morpholinyl), or —NHC(O)CH₂SO₂CH₂CH₂-(3-morpholinyl).

In one embodiment of the fragment Q, the saturated or unsaturated, branched or unbranched C$_{1-10}$ alkyl chain, wherein at least one carbon is replaced by a heteroatom selected from —O, —N, S(O)$_p$ is a linker selected from: —CH₂OCH₂—, —CH₂NHCH₂—, —CH₂NH— and —CH₂OCH₂CH₂—. These fragments may optionally terminate in an aryl group, a heteroaryl group a heterocyclyl group or C$_{3-8}$ cycloalkyl group, such as an aryl group, a heteroaryl group a heterocyclyl group as defined for fragment Q above.

In one embodiment the disclosure relates to compounds of formula (IA):

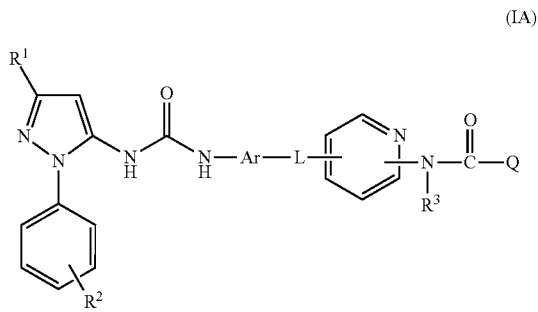

(IA)

wherein R¹, R², Ar, L, R³ and Q are as defined above.

In one embodiment of the compounds of formula (IA) the substituent —NR³C(O)Q is in the 2 or 3 position.

In a further embodiment the disclosure relates to compounds of formula (IB):

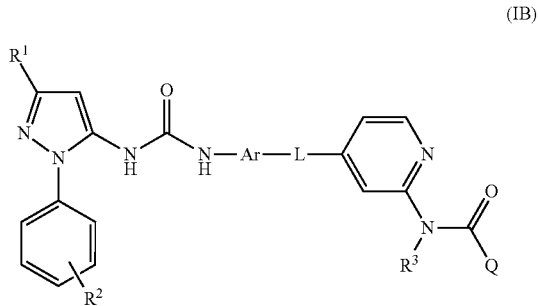

(IB)

wherein R¹, R², Ar, L, R³ and Q are as defined above.

In yet another embodiment the disclosure relates to compounds of formula (IC):

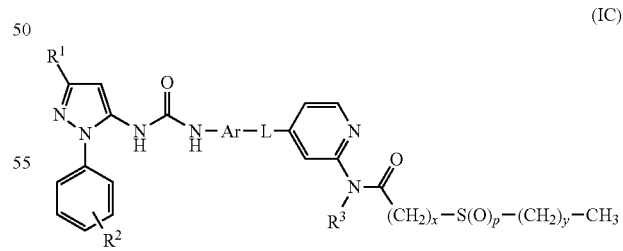

(IC)

wherein R¹, R², Ar, L and R³ are as defined above and p is 0, 1 or 2, in particular 0 or 2, and x is an integer from 1 to 6 (including 2, 3, 4 and 5) and y is zero or an integer from 1 to 5 (including 2, 3 and 4) with the proviso that x+y is an integer from 1 to 8 such as 1 to 6, for example x is 1 and y is 1.

In one embodiment the disclosure relates to compounds of formula (ID):

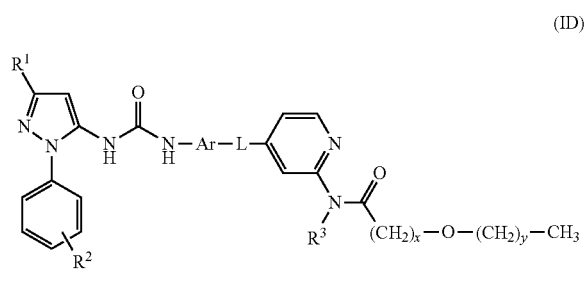

(ID)

wherein $R^1$, $R^2$, Ar, L and $R^3$ are as defined above x is an integer from 1 to 6 (including 2, 3, 4 and 5) and y is zero or an integer from 1 to 5 (including 2, 3 and 4), with the proviso that x+y is an integer from 1 to 6, for example x is 1 and y is 0.

In one embodiment of the compounds of formula (ID) the fragment represented by —NR$^3$C(O)(CH$_2$)$_x$O(CH$_2$)$_y$CH$_3$ is: —NR$^3$C(O)CH$_2$OCH$_3$, especially —NHC(O)CH$_2$OCH$_3$.

In one embodiment the disclosure relates to compounds of formula (IE):

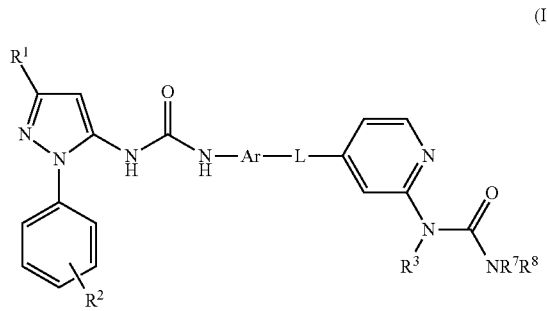

(IE)

wherein $R^1$, $R^2$, Ar, L, $R^3$, $R^7$ and $R^8$ are as defined above.

In one embodiment the disclosure relates to compounds of formula (IF):

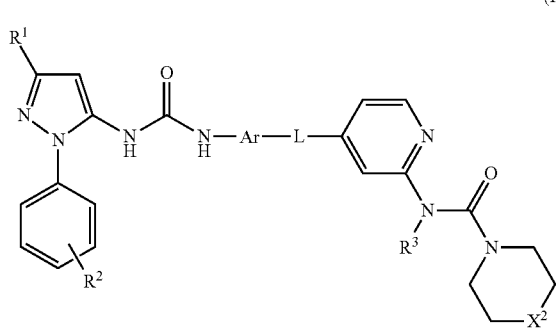

(IF)

wherein $R^1$, $R^2$, Ar, L and $R^3$ are as defined above and $X^2$ represents O, CH$_2$, NH, NCH$_3$ or NCH$_2$CH$_2$OCH$_3$.

In one aspect there is provided a compound of formula (IG):

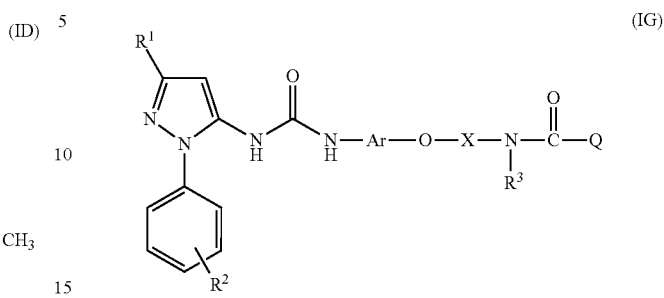

(IG)

wherein $R^1$ is $C_{1-6}$ alkyl optionally substituted by a hydroxyl group;

$R^2$ is H or $C_{1-6}$ alkyl optionally substituted by a hydroxyl group;

$R^3$ is H, $C_{1-6}$ alkyl or $C_{0-3}$ alkyl$C_{3-6}$ cycloalkyl;

Ar is a naphthyl or a phenyl ring either of which may be optionally substituted by one or more groups independently selected from $C_{1-6}$ alkyl, $C_{1-6}$ alkoxy, amino, $C_{1-4}$ mono or di-alkyl amino;

X is 5 or 6 membered heteroaryl group containing at least one nitrogen atom and optionally including 1 or 2 further heteroatoms selected from O, S and N;

Q is selected from:

a) a saturated or unsaturated, branched or unbranched $C_{1-10}$ alkyl chain, wherein at least one carbon (for example 1, 2 or 3 carbons, suitably 1 or 2, in particular 1) is replaced by a heteroatom selected from O, N, S(O)$_p$, wherein said chain is optionally, substituted by one or more groups (for example 1, 2 or 3) independently selected from oxo, halogen, an aryl group, a heteroaryl group, a heterocyclyl group or a $C_{3-8}$ cycloalkyl, each aryl, heteroaryl or heterocyclyl group bearing 0 to 3 substituents selected from halogen, hydroxyl, $C_{1-6}$ alkyl, $C_{1-6}$ alkoxy, $C_{1-6}$ haloalkyl, amino, $C_{1-4}$ mono or di-alkyl amino, $C_{1-4}$ mono or di-acyl amino, $S(O)_q C_{1-6}$ alkyl, $C_{0-6}$ alkylC(O)$C_{1-6}$ alkyl or $C_{0-6}$ alkylC(O)$C_{1-6}$ heteroalkyl, with the proviso that the atom linked directly to the carbonyl in —NR$^3$C(O)— is not an oxygen or a sulfur atom; and b) a $C_{0-8}$ alkyl$C_{5-6}$ heterocycle or said heterocyclyl group comprising at least one heteroatom (for example 1, 2 or 3, suitably 1 or 2, in particular 1 heteroatom) selected from O, N, and S, and is optionally substituted by one, two or three groups independently selected from halogen, hydroxyl, $C_{1-6}$ alkyl, $C_{1-6}$ alkoxy, $C_{1-6}$ haloalkyl, amino, $C_{1-4}$ mono and di-alkyl amino, $C_{1-4}$ mono or di-acyl amino, $S(O)_q C_{1-6}$ alkyl, $C_{0-6}$ alkylC(O)$C_{1-6}$ alkyl or $C_{0-6}$ alkylC(O)$C_{1-6}$ heteroalkyl; and is 0, 1 or 2;

or a pharmaceutically acceptable salt thereof, including all stereoisomers, tautomers and isotopic derivatives thereof.

In one embodiment the disclosure relates to compounds of formula (IH):

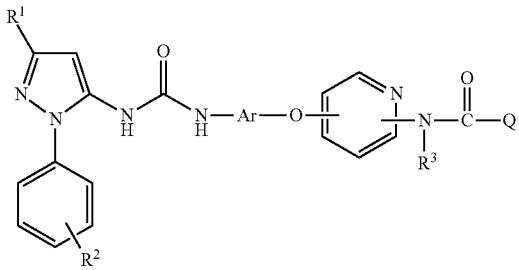

(IH)

wherein $R^1$, $R^2$, Ar, $R^3$ and Q are as defined above.

In a further embodiment the disclosure relates to compounds of formula (IJ):

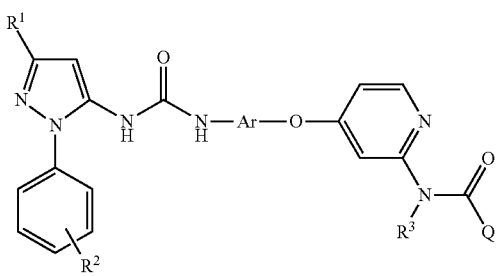

(IJ)

wherein $R^1$, $R^2$, Ar, $R^3$ and Q are as defined above.

In yet another embodiment the disclosure relates to compounds of formula (IK):

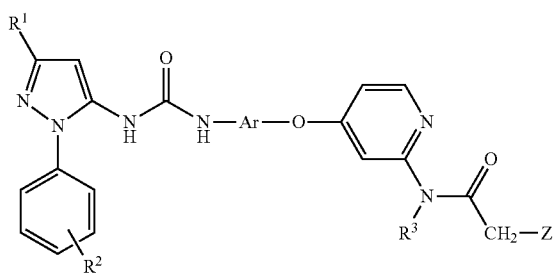

(IK)

wherein $R^1$, $R^2$, Ar and $R^3$ are as defined above and

Z represents a saturated or unsaturated, branched or unbranched $C_{1-9}$ alkyl chain, wherein at least one carbon (for example 1, 2 or 3 carbons, suitably 1 or 2, in particular 1) is replaced by a heteroatom selected from O, N, $S(O)_p$, or a $C_{0-7}$ alkyl$C_{5-6}$ heterocycle said heterocyclyl group comprising at least one heteroatom (for example 1, 2 or 3, suitably 1 or 2, in particular 1 heteroatom) selected from O, N and S, and is optionally substituted by one or two or three groups independently selected from the relevant substituents listed above for compounds of formula (I), for example halogen, $C_{1-6}$ alkyl, $C_{1-6}$ alkoxy, $C_{1-6}$ haloalkyl, amino, $C_{1-4}$ mono and di-alkyl amino.

In one embodiment of formula (IK) Z is —$OCH_3$ or —$OCH_2CH_2OCH_3$.

In one embodiment of formula (IK) Z is —$SO_2CH_3$.

In one embodiment of formula (IK) Z is —$NR^A R^B$ wherein $R^A$ and $R^B$ are independently selected from hydrogen, $C_{1-6}$ alkyl, and $C_{3-6}$ alkoxy such that for example Z represents —$NH_2$, —$NHCH_3$, —$N(CH_3)_2$ or —$NHCH_2CH_2OCH_3$.

In one embodiment of formula (IK) Z is —$S(O)_q CH_3$ wherein n is 0, 1 or 2, such as 0 or 2.

In one embodiment of formula (IK) Z represents a —$C_{5-6}$ heterocycle said heterocyclyl group comprising at least one heteroatom (for example 1, 2 or 3, suitably 1 or 2, in particular 1 heteroatom) selected from O, N and S, and is optionally substituted by one, two or three groups independently selected from the relevant substituents listed above for compounds of formula (I) for example halogen, $C_{1-6}$ alkyl, $C_{1-6}$ alkoxy, $C_{1-6}$ haloalkyl, amino, $C_{1-4}$ mono and di-alkyl amino, for example:

morpholinyl (in particular linked through nitrogen) or tetrahydropyranyl, or piperazinyl (in particular linked through nitrogen) optionally substituted on the second nitrogen by —$CH_3$ or —$CH_2CH_2OCH_3$.

In one embodiment the disclosure relates to compounds of formula (IL):

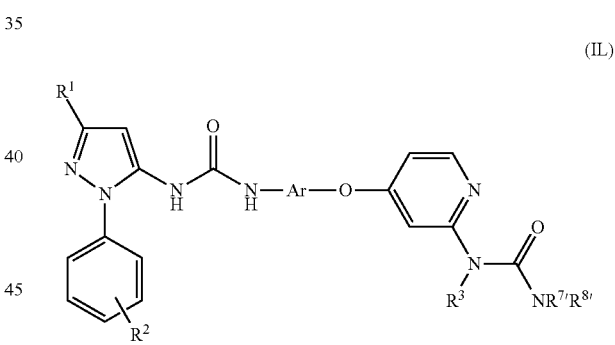

(IL)

wherein $R^1$, $R^2$, Ar and $R^3$ are as defined above and $R^{7'}$ and $R^{8'}$ independently represent hydrogen, $C_{1-6}$ alkyl, or $R^{7'}$ and $R^{8'}$ together with the nitrogen to which they are attached represent a 5 or 6 membered heterocycle optionally comprising a further heteroatom selected from O, N and S, wherein said heterocycle is optionally substituted by one or two or three groups independently selected from the relevant substituents listed above for compounds of formula (I), for example halogen, $C_{1-6}$ alkyl, $C_{1-6}$ alkoxy, $C_{1-6}$ haloalkyl, amino, $C_{1-4}$ mono and di-alkyl amino.

In one embodiment of compounds of formula (IL) the group —$NR^{7'}R^{8'}$ represents —$NH_2$, —$NHCH_3$ or $NHCH_2CH_3$.

In one embodiment of compounds of formula (IL) —$NR^{7'}R^{8'}$ represents morpholinyl or piperazinyl.

In an alternative embodiment the disclosure relates to compounds of formula (IM):

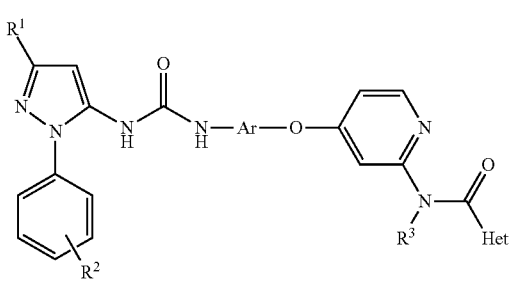

wherein R¹, R², Ar and R³ are as defined above and
Het represents a $C_{5-6}$ heterocycle said heterocyclyl group comprising at least one heteroatom (for example 1, 2 or 3, suitably 1 or 2, in particular 1 heteroatom) selected from O, N and S, and is optionally substituted by one or two or three groups independently selected from the relevant substituents listed above for compounds of formula (I) for example halogen, $C_{1-6}$ alkyl, $C_{1-6}$ alkoxy, $C_{1-6}$ haloalkyl, amino, $C_{1-4}$ mono and di-alkyl amino.

In one embodiment of compounds of formula (IM) Het is morpholinyl or tetrahydropyranyl.

In one embodiment the compound is not: N-(4-((4-(3-(3-tert-Butyl-1-p-tolyl-1H-pyrazol-5-yl)ureido)naphthalen-1-yloxy)methyl)pyridin-2-yl)-2-methoxyacetamide.

In one embodiment the compound is:
Methyl 4-((4-(3-(3-tert-butyl-1-p-tolyl-1H-pyrazol-5-yl)ureido)naphthalen-1-yloxy)methyl)pyridin-2-ylurea;
N-(4-((4-(3-(3-tert-Butyl-1-p-tolyl-1H-pyrazol-5-yl)ureido)naphthalen-1-yloxy)methyl)pyridin-2-yl)tetrahydro-2H-pyran-4-carboxamide;
(S)-N-(4-((4-(3-(3-tert-Butyl-1-p-tolyl-1H-pyrazol-5-yl)ureido)naphthalen-1-yloxy)methyl)pyridin-2-yl)-2-methoxypropanamide;
(R)-N-(4-((4-(3-(3-tert-Butyl-1-p-tolyl-1H-pyrazol-5-yl)ureido)naphthalen-1-yloxy)methyl)pyridin-2-yl)-2-methoxypropanamide;
N-(4-((4-(3-(3-tert-Butyl-1-p-tolyl-1H-pyrazol-5-yl)ureido)naphthalen-1-yloxy)methyl)pyridin-2-yl)-2-(methylthio)acetamide;
N-(4-((4-(3-(3-tert-Butyl-1-p-tolyl-1H-pyrazol-5-yl)ureido)naphthalen-1-yloxy)methyl)pyridin-2-yl)-2-morpholinoacetamide;
N-(4-((4-(3-(3-tert-Butyl-1-p-tolyl-1H-pyrazol-5-yl)ureido)naphthalen-1-yloxy)methyl)pyridin-2-yl)-2-(pyrrolidin-1-yl)acetamide;
N-(4-((4-(3-(3-tert-Butyl-1-p-tolyl-1H-pyrazol-5-yl)ureido)naphthalen-1-yloxy)methyl)pyridin-2-yl)-2-(4-methylpiperazin-1-yl)acetamide;
N-(4-((4-(3-(3-tert-Butyl-1-p-tolyl-1H-pyrazol-5-yl)ureido)naphthalen-1-yloxy)methyl)pyridin-2-yl)-2-(4-(2-methoxyethyl)piperazin-1-yl)acetamide;
N-(4-((4-(3-(3-tert-Butyl-1-p-tolyl-1H-pyrazol-5-yl)ureido)naphthalen-1-yloxy)methyl)pyridin-2-yl)-2-(2-methoxyethylamino)acetamide;
N-(4-((4-(3-(3-tert-Butyl-1-p-tolyl-1H-pyrazol-5-yl)ureido)naphthalen-1-yloxy)methyl)pyridin-2-yl)-2-(dimethylamino)acetamide;
N-(4-((4-(3-(3-tert-Butyl-1-p-tolyl-1H-pyrazol-5-yl)ureido)naphthalen-1-yloxy)methyl)pyridin-2-yl)-2-(methylamino)acetamide;
N-(4-((4-(3-(3-tert-Butyl-1-p-tolyl-1H-pyrazol-5-yl)ureido)naphthalen-1-yloxy)methyl)pyridin-2-yl)-2-((4-methoxybenzyl)(methyl)amino)acetamide;
1-(4-((3-Methylureidopyridin-4-yl)methoxy)naphthalen-1-yl)-3-(3-tert-butyl-1-p-tolyl-1H-pyrazol-5-yl)urea;
N-(4-((4-(3-(3-tert-Butyl-1-p-tolyl-1H-pyrazol-5-yl)ureido)naphthalen-1-yloxy)methyl)pyridin-3-yl)-2-methoxyacetamide;
N-(4-((4-(3-(3-tert-Butyl-1-p-tolyl-1H-pyrazol-5-yl)ureido)naphthalen-1-yloxy)methyl)pyridin-3-yl)-2-(2-methoxyethoxy)acetamide;
N-(4-(2-(4-(3-(3-tert-Butyl-1-p-tolyl-1H-pyrazol-5-yl)ureido)naphthalen-1-yloxy)ethyl)pyridin-2-yl)-2-methoxyacetamide;
N-(4-(2-(4-(3-(3-tert-Butyl-1-p-tolyl-1H-pyrazol-5-yl)ureido)naphthalen-1-yloxy)ethyl)pyridin-2-yl)-2-(2-methoxyethoxy)acetamide;
4-(2-(4-(3-(3-tert-Butyl-1-p-tolyl-1H-pyrazol-5-yl)ureido)naphthalen-1-yloxy)ethyl)-1-methyl-3-(pyridin-2-yl)urea;
4-(2-(4-(3-(3-tert-Butyl-1-p-tolyl-1H-pyrazol-5-yl)ureido)naphthalen-1-yloxy)ethyl)-3-(pyridin-2-yl)urea;
N-(4-(2-(4-(3-(3-tert-Butyl-1-p-tolyl-1H-pyrazol-5-yl)ureido)naphthalen-1-yloxy)ethyl)pyridin-3-yl)-2-(2-methoxyethoxy)acetamide;
N-(4-((4-(3-(3-tert-Butyl-1-p-tolyl-1H-pyrazol-5-yl)ureido)naphthalen-1-yloxy)methyl)pyrimidin-2-yl)-2-methoxyacetamide;
N-(1-(2-(4-(3-(3-tert-butyl-1-p-tolyl-1H-pyrazol-5-yl)ureido)naphthalen-1-yloxy)ethyl)-1H-imidazol-4-yl)-2-methoxyacetamide;
N-(4-((4-(3-(3-tert-Butyl-1-p-tolyl-1H-pyrazol-5-yl)ureido)naphthalen-1-yloxy)methyl)pyridin-2-yl)-2-(methylsulfonyl)acetamide;
N-(4-((4-(3-(3-tert-Butyl-1-p-tolyl-1H-pyrazol-5-yl)ureido)naphthalen-1-yloxy)methyl)pyridin-2-yl)-2-hydroxyacetamide;
N-(4-((4-(3-(3-tert-Butyl-1-p-tolyl-1H-pyrazol-5-yl)ureido)naphthalen-1-yloxy)methyl)pyridin-2-yl)-2-methyl-2-(methylamino)propanamide;
(S)-N-(4-((4-(3-(3-tert-Butyl-1-p-tolyl-1H-pyrazol-5-yl)ureido)naphthalen-1-yloxy)methyl)pyridin-2-yl)-2-(methylamino)propanamide;
(R)-N-(4-((4-(3-(3-tert-Butyl-1-p-tolyl-1H-pyrazol-5-yl)ureido)naphthalen-1-yloxy)methyl)pyridin-2-yl)morpholine-3-carboxamide;
(S)-N-(4-((4-(3-(3-tert-Butyl-1-p-tolyl-1H-pyrazol-5-yl)ureido)naphthalen-1-yloxy)methyl)pyridin-2-yl)morpholine-3-carboxamide;
N-(4-((4-(3-(3-tert-Butyl-1-p-tolyl-1H-pyrazol-5-yl)ureido)naphthalen-1-yloxy)methyl)pyridin-2-yl)-4-methylpiperazine-1-carboxamide;
N-(4-((4-(3-(3-tert-Butyl-1-p-tolyl-1H-pyrazol-5-yl)ureido)naphthalen-1-yloxy)methyl)pyridin-2-yl)morpholine-4-carboxamide;
N-(4-((4-(3-(3-tert-Butyl-1-p-tolyl-1H-pyrazol-5-yl)ureido)naphthalen-1-yloxy)methyl)pyridin-2-yl)-3-methoxypropanamide;
2-(3-(4-((4-(3-(3-tert-Butyl-1-p-tolyl-1H-pyrazol-5-yl)ureido)naphthalen-1-yloxy)methyl)pyridin-2-yl)ureido)-N-(2-methoxyethyl)acetamide;
N-(4-((4-(3-(3-tert-Butyl-1-p-tolyl-1H-pyrazol-5-yl)ureido)naphthalen-1-yloxy)methyl)pyridin-2-yl)-4-(dimethylamino)butanamide;
N-(4-((4-(3-(3-tert-Butyl-1-p-tolyl-1H-pyrazol-5-yl)ureido)naphthalen-1-yloxy)methyl)pyridin-2-yl)-3-(methylsulfonyl)propanamide;

N-(4-((4-(3-(3-tert-Butyl-1-p-tolyl-1H-pyrazol-5-yl)ureido)naphthalen-1-yloxy)methyl)pyridin-2-yl)-3-(methylsulfonyl)-2-oxoimidazolidine-1-carboxamide;

N-(4-((4-(3-(3-tert-Butyl-1-p-tolyl-1H-pyrazol-5-yl)ureido)naphthalen-1-yloxy)methyl)pyridin-2-yl)-2-(methylsulfinyl)acetamide;

N-(4-((4-(3-(3-tert-Butyl-1-p-tolyl-1H-pyrazol-5-yl)ureido)naphthalen-1-yloxy)methyl)pyridin-2-yl)-2-(2-methoxyethylthio)acetamide;

N-(4-((4-(3-(3-tert-Butyl-1-p-tolyl-1H-pyrazol-5-yl)ureido)naphthalen-1-yloxy)methyl)pyridin-2-yl)-2-(2-(2-methoxyethoxy)ethylthio)acetamide;

N-(4-((4-(3-(3-tert-Butyl-1-p-tolyl-1H-pyrazol-5-yl)ureido)naphthalen-1-yloxy)methyl)pyridin-2-yl)-2-(2-morpholinoethylthio)acetamide;

N-(4-((4-(3-(3-tert-Butyl-1-p-tolyl-1H-pyrazol-5-yl)ureido)naphthalen-1-yloxy)methyl)pyridin-2-yl)-2-(2-morpholinoethylsulfonyl)acetamide;

2-(Bis(2-methoxyethyl)amino)-N-(4-((4-(3-(3-tert-butyl-1-p-tolyl-1H-pyrazol-5-yl)ureido)naphthalen-1-yloxy)methyl)pyridin-2-yl)acetamide;

N-(4-(2-(4-(3-(3-tert-Butyl-1-p-tolyl-1H-pyrazol-5-yl)ureido)naphthalen-1-yloxy)ethyl)pyridin-3-yl)-2-methoxyacetamide;

N-(4-(2-(4-(3-(3-tert-butyl-1-p-tolyl-1H-pyrazol-5-yl)ureido)naphthalen-1-yl)ethoxy)pyridin-2-yl)-2-methoxyacetamide;

N-(4-(1-(4-(3-(3-tert-Butyl-1-p-tolyl-1H-pyrazol-5-yl)ureido)naphthalen-1-yloxy)ethyl)pyridin-2-yl)-2-methoxyacetamide;

N-(4-(2-(4-(3-(3-tert-Butyl-1-p-tolyl-1H-pyrazol-5-yl)ureido)naphthalen-1-yloxy)-2-methylpropyl)pyridin-2-yl)-2-methoxyacetamide;

N-(4-(2-(4-(3-(3-tert-Butyl-1-p-tolyl-1H-pyrazol-5-yl)ureido)naphthalen-1-yloxy)propyl)pyridin-2-yl)-2-methoxyacetamide;

N-(4-(1-(4-(3-(3-tert-Butyl-1-p-tolyl-1H-pyrazol-5-yl)ureido)naphthalen-1-yloxy)propan-2-yl)pyridin-2-yl)-2-methoxyacetamide;

N-(4-(1-(4-(3-(3-tert-Butyl-1-p-tolyl-1-pyrazol-5-yl)ureido)naphthalen-1-yloxy)-2-methylpropan-2-yl)pyridin-2-yl)-2-methoxyacetamide;

N-(4-((4-(3-(3-tert-Butyl-1-(4-(hydroxymethyl)phenyl)-1H-pyrazol-5-yl)ureido)naphthalen-1-yloxy)methyl)pyridin-2-yl)-2-methoxyacetamide;

N-(4-(4-(3-(3-tert-Butyl-1-p-tolyl-1H-pyrazol-5-yl)ureido)naphthalen-1-yloxy)pyridin-2-yl)-2-(methylsulfonyl)acetamide or a pharmaceutically acceptable salt thereof, including all stereoisomers, tautomers and isotopic derivatives thereof.

In one embodiment the compound according to the disclosure is:

Methyl 4-((4-(3-(3-tert-butyl-1-p-tolyl-1H-pyrazol-5-yl)ureido)naphthalen-1-yloxy)methyl)pyridin-2-ylurea;

N-(4-((4-(3-(3-tert-Butyl-1-p-tolyl-1H-pyrazol-5-yl)ureido)naphthalen-1-yloxy)methyl)pyridin-2-yl)tetrahydro-2H-pyran-4-carboxamide;

(S)-N-(4-((4-(3-(3-tert-Butyl-1-p-tolyl-1H-pyrazol-5-yl)ureido)naphthalen-1-yloxy)methyl)pyridin-2-yl)-2-methoxypropanamide;

(R)-N-(4-((4-(3-(3-tert-Butyl-1-p-tolyl-1H-pyrazol-5-yl)ureido)naphthalen-1-yloxy)methyl)pyridin-2-yl)-2-methoxypropanamide;

Example 6

N-(4-((4-(3-(3-tert-Butyl-1-p-tolyl-1H-pyrazol-5-yl)ureido)naphthalen-1-yloxy)methyl)pyridin-2-yl)-2-(methylsulfonyl)acetamide N-(4-((4-(3-(3-tert-Butyl-1-p-tolyl-1H-pyrazol-5-yl)ureido)naphthalen-1-yloxy)methyl)pyridin-2-yl)-2-hydroxyacetamide;

N-(4-((4-(3-(3-tert-Butyl-1-p-tolyl-1H-pyrazol-5-yl)ureido)naphthalen-1-yloxy)methyl)pyridin-2-yl)-2-methyl-2-(methylamino)propanamide;

(S)-N-(4-((4-(3-(3-tert-Butyl-1-p-tolyl-1H-pyrazol-5-yl)ureido)naphthalen-1-yloxy)methyl)pyridin-2-yl)-2-(methylamino)propanamide;

(R)-N-(4-((4-(3-(3-tert-Butyl-1-p-tolyl-1H-pyrazol-5-yl)ureido)naphthalen-1-yloxy)methyl)pyridin-2-yl)morpholine-3-carboxamide;

(S)-N-(4-((4-(3-(3-tert-Butyl-1-p-tolyl-1H-pyrazol-5-yl)ureido)naphthalen-1-yloxy)methyl)pyridin-2-yl)morpholine-3-carboxamide;

N-(4-((4-(3-(3-tert-Butyl-1-p-tolyl-1H-pyrazol-5-yl)ureido)naphthalen-1-yloxy)methyl)pyridin-2-yl)-4-methylpiperazine-1-carboxamide;

N-(4-((4-(3-(3-tert-Butyl-1-p-tolyl-1H-pyrazol-5-yl)ureido)naphthalen-1-yloxy)methyl)pyridin-2-yl)morpholine-4-carboxamide;

N-(4-((4-(3-(3-tert-Butyl-1-p-tolyl-1H-pyrazol-5-yl)ureido)naphthalen-1-yloxy)methyl)pyridin-2-yl)-3-methoxypropanamide;

2-(3-(4-((4-(3-(3-tert-Butyl-1-p-tolyl-1H-pyrazol-5-yl)ureido)naphthalen-1-yloxy)methyl)pyridin-2-yl)ureido)-N-(2-methoxyethyl)acetamide;

N-(4-((4-(3-(3-tert-Butyl-1-p-tolyl-1H-pyrazol-5-yl)ureido)naphthalen-1-yloxy)methyl)pyridin-2-yl)-4-(dimethylamino)butanamide;

N-(4-((4-(3-(3-tert-Butyl-1-p-tolyl-1H-pyrazol-5-yl)ureido)naphthalen-1-yloxy)methyl)pyridin-2-yl)-3-(methylsulfonyl)propanamide;

N-(4-((4-(3-(3-tert-Butyl-1-p-tolyl-1H-pyrazol-5-yl)ureido)naphthalen-1-yloxy)methyl)pyridin-2-yl)-3-(methylsulfonyl)-2-oxoimidazolidine-1-carboxamide;

N-(4-((4-(3-(3-tert-Butyl-1-p-tolyl-1H-pyrazol-5-yl)ureido)naphthalen-1-yloxy)methyl)pyridin-2-yl)-2-(methylthio)acetamide;

N-(4-((4-(3-(3-tert-Butyl-1-p-tolyl-1H-pyrazol-5-yl)ureido)naphthalen-1-yloxy)methyl)pyridin-2-yl)-2-(methylsulfinyl)acetamide;

N-(4-((4-(3-(3-tert-Butyl-1-p-tolyl-1H-pyrazol-5-yl)ureido)naphthalen-1-yloxy)methyl)pyridin-2-yl)-2-morpholinoacetamide;

N-(4-((4-(3-(3-tert-Butyl-1-p-tolyl-1H-pyrazol-5-yl)ureido)naphthalen-1-yloxy)methyl)pyridin-2-yl)-2-(pyrrolidin-1-yl)acetamide;

N-(4-((4-(3-(3-tert-Butyl-1-p-tolyl-1H-pyrazol-5-yl)ureido)naphthalen-1-yloxy)methyl)pyridin-2-yl)-2-(4-methylpiperazin-1-yl)acetamide;

N-(4-((4-(3-(3-tert-Butyl-1-p-tolyl-1H-pyrazol-5-yl)ureido)naphthalen-1-yloxy)methyl)pyridin-2-yl)-2-(4-(2-methoxyethyl)piperazin-1-yl)acetamide;

N-(4-((4-(3-(3-tert-Butyl-1-p-tolyl-1H-pyrazol-5-yl)ureido)naphthalen-1-yloxy)methyl)pyridin-2-yl)-2-(2-methoxyethylamino)acetamide;

N-(4-((4-(3-(3-tert-Butyl-1-p-tolyl-1H-pyrazol-5-yl)ureido)naphthalen-1-yloxy)methyl)pyridin-2-yl)-2-(dimethylamino)acetamide;

N-(4-((4-(3-(3-tert-Butyl-1-p-tolyl-1H-pyrazol-5-yl)ureido)naphthalen-1-yloxy)methyl)pyridin-2-yl)-2-(methylamino)acetamide;

N-(4-((4-(3-(3-tert-Butyl-1-p-tolyl-1H-pyrazol-5-yl)ureido)naphthalen-1-yloxy)methyl)pyridin-2-yl)-2-((4-methoxybenzyl)(methyl)amino)acetamide;

N-(4-((4-(3-(3-tert-Butyl-1-p-tolyl-1H-pyrazol-5-yl)ureido) naphthalen-1-yloxy)methyl)pyridin-2-yl)-2-(2-methoxyethylthio)acetamide;

N-(4-((4-(3-(3-tert-Butyl-1-p-tolyl-1H-pyrazol-5-yl)ureido) naphthalen-1-yloxy)methyl)pyridin-2-yl)-2-(2-(2-methoxyethoxy)ethylthio)acetamide;

N-(4-((4-(3-(3-tert-Butyl-1-p-tolyl-1H-pyrazol-5-yl)ureido) naphthalen-1-yloxy)methyl)pyridin-2-yl)-2-(2-morpholinoethylthio)acetamide;

N-(4-((4-(3-(3-tert-Butyl-1-p-tolyl-1H-pyrazol-5-yl)ureido) naphthalen-1-yloxy)methyl)pyridin-2-yl)-2-(2-morpholinoethylsulfonyl)acetamide;

2-(Bis(2-methoxyethyl)amino)-N-(4-((4-(3-(3-tert-butyl-1-p-tolyl-1H-pyrazol-5-yl)ureido) naphthalen-1-yloxy)methyl)pyridin-2-yl)acetamide;

1-(4-((3-Methylureidopyridin-4-yl)methoxy)naphthalen-1-yl)-3-(3-tert-butyl-1-p-tolyl-1H-pyrazol-5-yl)urea;

N-(4-((4-(3-(3-tert-Butyl-1-p-tolyl-1H-pyrazol-5-yl)ureido) naphthalen-1-yloxy)methyl)pyridin-3-yl)-2-methoxyacetamide;

N-(4-((4-(3-(3-tert-Butyl-1-p-tolyl-1H-pyrazol-5-yl)ureido) naphthalen-1-yloxy)methyl)pyridin-3-yl)-2-(2-methoxyethoxy)acetamide;

N-(4-(2-(4-(3-(3-tert-Butyl-1-p-tolyl-1H-pyrazol-5-yl)ureido)naphthalen-1-yloxy)ethyl)pyridin-2-yl)-2-methoxyacetamide;

N-(4-(2-(4-(3-(3-tert-Butyl-1-p-tolyl-1H-pyrazol-5-yl)ureido)naphthalen-1-yloxy)ethyl)pyridin-2-yl)-2-(2-methoxyethoxy)acetamide;

4-(2-(4-(3-(3-tert-Butyl-1-p-tolyl-1H-pyrazol-5-yl)ureido)naphthalen-1-yloxy)ethyl)-1-methyl-3-(pyridin-2-yl)urea;

4-(2-(4-(3-(3-tert-Butyl-1-p-tolyl-1H-pyrazol-5-yl)ureido)naphthalen-1-yloxy)ethyl)-3-(pyridin-2-yl)urea;

N-(4-(2-(4-(3-(3-tert-Butyl-1-p-tolyl-1H-pyrazol-5-yl)ureido)naphthalen-1-yloxy)ethyl)pyridin-3-yl)-2-methoxyacetamide;

N-(4-(2-(4-(3-(3-tert-Butyl-1-p-tolyl-1H-pyrazol-5-yl)ureido)naphthalen-1-yloxy)ethyl)pyridin-3-yl)-2-(2-methoxyethoxy)acetamide;

N-(4-(2-(4-(3-(3-tert-butyl-1-p-tolyl-1H-pyrazol-5-yl)ureido)naphthalen-1-yl)ethoxy)pyridin-2-yl)-2-methoxyacetamide;

N-(4-(1-(4-(3-(3-tert-Butyl-1-p-tolyl-1H-pyrazol-5-yl)ureido)naphthalen-1-yloxy)ethyl)pyridin-2-yl)-2-methoxyacetamide;

N-(4-(2-(4-(3-(3-tert-Butyl-1-p-tolyl-1H-pyrazol-5-yl)ureido)naphthalen-1-yloxy)-2-methylpropyl)pyridin-2-yl)-2-methoxyacetamide;

N-(4-(2-(4-(3-(3-tert-Butyl-1-p-tolyl-1H-pyrazol-5-yl)ureido)naphthalen-1-yloxy)propyl)pyridin-2-yl)-2-methoxyacetamide;

N-(4-(1-(4-(3-(3-tert-Butyl-1-p-tolyl-1H-pyrazol-5-yl)ureido)naphthalen-1-yloxy)propan-2-yl)pyridin-2-yl)-2-methoxyacetamide;

N-(4-(1-(4-(3-(3-tert-Butyl-1-p-tolyl-1-pyrazol-5-yl)ureido)naphthalen-1-yloxy)-2-methylpropan-2-yl)pyridin-2-yl)-2-methoxyacetamide;

N-(4-((4-(3-(3-tert-Butyl-1-(4-(hydroxymethyl)phenyl)-1H-pyrazol-5-yl)ureido)naphthalen-1-yloxy)methyl)pyridin-2-yl)-2-methoxyacetamide;

N-(4-((4-(3-(3-tert-Butyl-1-p-tolyl-1H-pyrazol-5-yl)ureido)naphthalen-1-yloxy)methyl)pyrimidin-2-yl)-2-methoxyacetamide;

N-(4-(4-(3-(3-tert-Butyl-1-p-tolyl-1H-pyrazol-5-yl)ureido)naphthalen-1-yloxy)pyridin-2-yl)-2-(methylsulfonyl)acetamide;

N-(4-(4-(3-(3-tert-Butyl-1-p-tolyl-1H-pyrazol-5-yl)ureido) naphthalen-1-yloxy)pyridin-2-yl)-2-methoxyacetamide;

N-(4-(4-(3-(3-tert-Butyl-1-p-tolyl-1H-pyrazol-5-yl)ureido) naphthalen-1-yloxy)pyridin-2-yl)-2-(2-methoxyethoxy)acetamide;

N-(4-(4-(3-(3-tert-Butyl-1-p-tolyl-1H-pyrazol-5-yl)ureido) naphthalen-1-yloxy)pyridin-2-yl)tetrahydro-2H-pyran-4-carboxamide;

N-(4-(4-(3-(3-tert-Butyl-1-p-tolyl-1H-pyrazol-5-yl)ureido) naphthalen-1-yloxy)pyridin-2-yl)-2-(methylthio)acetamide;

N-(4-(4-(3-(3-tert-Butyl-1-p-tolyl-1H-pyrazol-5-yl)ureido) naphthalen-1-yloxy)pyridin-2-yl)-3-methoxypropanamide;

N-(4-(4-(3-(3-tert-Butyl-1-p-tolyl-1H-pyrazol-5-yl)ureido) naphthalen-1-yloxy)pyridin-2-yl)-2-hydroxyacetamide;

N-(4-(4-(3-(3-Isopropyl-1-p-tolyl-1H-pyrazol-5-yl)ureido) naphthalen-1-yloxy)pyridin-2-yl)-2-methoxyacetamide;

N-(4-(4-(3-(3-Ethyl-1-p-tolyl-1H-pyrazol-5-yl)ureido) naphthalen-1-yloxy)pyridin-2-yl)-2-methoxyacetamide;

N-(4-(4-(3-(3-tert-Butyl-1-p-tolyl-1H-pyrazol-5-yl)ureido) naphthalen-1-yloxy)pyridin-2-yl)-2-methoxyacetamide;

N-(4-(4-(3-(1-Hydroxy-2-methylpropan-2-yl)-1-p-tolyl-1H-pyrazol-5-yl)ureido)naphthalen-1-yloxy)pyridin-2-yl)-2-methoxyacetamide;

N-(4-(4-(3-(3-tert-butyl-1-(2,3,5,6-tetradeutero-4-(trideuteromethyl)phenyl)-1H-pyrazol-5-yl)ureido)naphthalen-1-yloxy)pyridin-2-yl)-2-methoxyacetamide;

N-(4-(4-(3-(3-tert-Butyl-1-p-tolyl-1H-pyrazol-5-yl)ureido) naphthalen-1-yloxy)pyridin-2-yl)-2-morpholinoacetamide;

N-(4-(4-(3-(3-tert-Butyl-1-p-tolyl-1H-pyrazol-5-yl)ureido) naphthalen-1-yloxy)pyridin-2-yl)-(dimethylamino)acetamide;

N-(4-(4-(3-(3-tert-Butyl-1-p-tolyl-1H-pyrazol-5-yl)ureido) naphthalen-1-yloxy)pyridin-2-yl)-2-(2-methoxyethylamino)acetamide;

N-(4-(4-(3-(3-tert-Butyl-1-p-tolyl-1H-pyrazol-5-yl)ureido) naphthalen-1-yloxy)pyridin-2-yl)-2-ureidoacetamide;

N-(4-(4-(3-(3-tert-Butyl-1-p-tolyl-1H-pyrazol-5-yl)ureido) naphthalen-1-yloxy)pyridin-2-yl)-2-(2-methoxyacetamido)acetamide;

N-(2-(4-(4-(3-(3-tert-Butyl-1-p-tolyl-1H-pyrazol-5-yl)ureido)naphthalen-1-yloxy)pyridin-2-ylamino)-2-oxoethyl)tetrahydro-2H-pyran-4-carboxamide;

N-(2-(4-(4-(3-(3-tert-Butyl-1-p-tolyl-1H-pyrazol-5-yl)ureido)naphthalen-1-yloxy)pyridin-2-ylamino)-2-oxoethyl)isonicotinamide;

N-(4-(4-(3-(3-tert-Butyl-1-p-tolyl-1H-pyrazol-5-yl)ureido) naphthalen-1-yloxy)pyridin-2-yl)-2-(2-(methylsulfonyl)acetamido)acetamide;

N-(2-(4-(4-(3-(3-tert-Butyl-1-p-tolyl-1H-pyrazol-5-yl)ureido)naphthalen-1-yloxy)pyridin-2-ylamino)-2-oxoethyl)-3-morpholinopropanamide;

N-(2-(4-(4-(3-(3-tert-Butyl-1-p-tolyl-1H-pyrazol-5-yl)ureido)naphthalen-1-yloxy)pyridin-2-ylamino)-2-oxoethyl)morpholine-4-carboxamide;

N-(2-(4-(4-(3-(3-tert-Butyl-1-p-tolyl-1H-pyrazol-5-yl)ureido)naphthalen-1-yloxy)pyridin-2-ylamino)-2-oxoethyl)-2,6-difluoro-3-(2-(2-methoxyethoxy)ethoxy)benzamide;

N-(4-(4-(3-(3-tert-Butyl-1-p-tolyl-1H-pyrazol-5-yl)ureido) phenoxy)pyridin-2-yl)-2-methoxyacetamide;

N-(4-(4-(3-(3-tert-Butyl-1-p-tolyl-1H-pyrazol-5-yl)ureido)-2-methylphenoxy)pyridin-2-yl)-2-methoxyacetamide;

N-(4-(4-(3-(3-tert-Butyl-1-p-tolyl-1H-pyrazol-5-yl)ureido)-3-methylphenoxy)pyridin-2-yl)-2-methoxyacetamide;

N-(4-(4-(3-(3-tert-Butyl-1-p-tolyl-1H-pyrazol-5-yl)ureido)-2-methoxyphenoxy)pyridin-2-yl)-2-methoxyacetamide;

N-(4-(4-(3-(3-tert-Butyl-1-p-tolyl-1H-pyrazol-5-yl)ureido)-2,3-dimethylphenoxy)pyridin-2-yl)-2-methoxyacetamide;

N-(4-(4-(3-(3-tert-Butyl-1-p-tolyl-1H-pyrazol-5-yl)ureido)-3-methoxyphenoxy)pyridin-2-yl)-2-methoxyacetamide;

N-Ethyl-N'-4-(4-(3-(3-tert-butyl-1-p-tolyl-1H-pyrazol-5-yl)ureido) naphthalen-1-yloxy)pyridin-2-ylurea;

4-(4-(3-(3-tert-Butyl-1-p-tolyl-1H-pyrazol-5-yl)ureido) naphthalen-1-yloxy)pyridin-2-ylurea;

N-Propan-2-yl-N=4-(4-(3-(3-tert-butyl-1-p-tolyl-1H-pyrazol-5-yl)ureido)naphthalen-1-yloxy)pyridin-2-ylurea;

1-(3-(tert-Butyl)-1-(p-tolyl)-1H-pyrazol-5-yl)-3-(4-((2-(3-phenylureido)pyridin-4-yl)oxy)naphthalen-1-yl)urea;

1-(4-((2-(3-Benzylureido)pyridin-4-yl)oxy)naphthalen-1-yl)-3-(3-(tert-butyl)-1-(p-tolyl)-1H-pyrazol-5-yl)urea;

1-(4-((2-(3-Cyclopropylureido)pyridin-4-yl)oxy)naphthalen-1-yl)-3-(3-(tert-butyl)-1-(p-tolyl)-1H-pyrazol-5-yl)urea;

1-(3-(tert-Butyl)-1-(p-tolyl)-1H-pyrazol-5-yl)-3-(4-((2-(3-(2-methoxyethyl)ureido)pyridin-4-yl)oxy)naphthalen-1-yl)urea;

1-(3-(tert-Butyl)-1-(p-tolyl)-1H-pyrazol-5-yl)-3-(4-((2-(3-cyclopentyl)ureido)pyridin-4-yl)oxy)naphthalen-1-yl)urea;

1-(3-(tert-Butyl)-1-(p-tolyl)-1H-pyrazol-5-yl)-3-(4-((2-(3-methyl)ureido)pyridin-4-yl)oxy)naphthalen-1-yl)urea;

Ethyl 2-(3-(4-((4-(3-(3-(tert-butyl)-1-(p-tolyl)-1H-pyrazol-5-yl)ureido)naphthalen-1-yl)oxy)pyridin-2-yl)ureido)acetate;

4-(3-(4-(4-(3-(3-tert-Butyl-1-p-tolyl-1H-pyrazol-5-yl)ureido)naphthalen-1-yloxy)pyridin-2-yl)ureido)piperidine;

N-Acetyl 4-(3-(4-(4-(3-(3-tert-butyl-1-p-tolyl-1H-pyrazol-5-yl)ureido) naphthalen-1-yloxy)pyridin-2-yl)ureido)piperidine;

2-(2-Methoxyethoxy)-1-(4-(3-(4-(4-(3-(3-tert-butyl-1-p-tolyl-1H-pyrazol-5-yl)ureido)naphthalen-1-yloxy)pyridin-2-yl)ureido)piperidin-1-yl)ethanone;

N-Methylsulfonyl-4-(3-(4-(4-(3-(3-tert-butyl-1-p-tolyl-1H-pyrazol-5-yl)ureido)naphthalen-1-yloxy)pyridin-2-yl)ureido)piperidine;

N-(4-(4-(3-(3-tert-Butyl-1-p-tolyl-1H-pyrazol-5-yl)ureido)naphthalen-1-yloxy)pyridin-2-yl)morpholine-4-carboxamide;

N-(4-((4-(3-(3-(tert-butyl)-1-(p-tolyl)-1H-pyrazol-5-yl)ureido)naphthalen-1-yl)oxy)pyridin-2-yl)-4-methylpiperazine-1-carboxamide;

3-(4-((4-(3-(3-(tert-butyl)-1-(p-tolyl)-1H-pyrazol-5-yl)ureido)naphthalen-1-yl)oxy)pyridin-2-yl)-1,1-dimethylurea;

N-(4-((4-(3-(3-(tert-Butyl)-1-(p-tolyl)-1H-pyrazol-5-yl)ureido)naphthalen-1-yl)oxy)pyridin-2-yl)piperidine-1-carboxamide;

N-Methyl-N-(2-(morpholin-4-yl)ethyl)-N'-4-(4-(3-(3-tert-butyl-1-p-tolyl-1H-pyrazol-5-yl)ureido)naphthalen-1-yloxy)pyridin-2-ylurea;

N-(4-(morpholin-4-yl)butyl)-N'-4-(4-(3-(3-tert-butyl-1-p-tolyl-1H-pyrazol-5-yl)ureido)naphthalen-1-yloxy)pyridin-2-ylurea;

N-(2-(morpholin-4-yl)ethyl)-N'-4-(4-(3-(3-tert-butyl-1-p-tolyl-1H-pyrazol-5-yl)ureido)naphthalen-1-yloxy)pyridin-2-ylurea;

N-(3-methylisoxazol-5-yl)methyl-N'-4-(4-(3-(3-tert-butyl-1-p-tolyl-1H-pyrazol-5-yl)ureido) naphthalen-1-yloxy)pyridin-2-ylurea;

N-(1-methyl)piperidin-4-yl-N'-4-(4-(3-(3-tert-butyl-1-p-tolyl-1H-pyrazol-5-yl)ureido)naphthalen-1-yloxy)pyridin-2-ylurea;

N-(4-(4-(3-(3-tert-Butyl-1-p-tolyl-1H-pyrazol-5-yl)ureido) naphthalen-1-yloxy)pyridin-2-yl)-4-hydroxypiperidine-1-carboxamide;

N-(3-(imidazol-1-yl)propyl)-N'-4-(4-(3-(3-tert-butyl-1-p-tolyl-1H-pyrazol-5-yl)ureido)naphthalen-1-yloxy)pyridin-2-ylurea;

N-(2-(3-(4-(4-(3-(3-tert-Butyl-1-p-tolyl-1H-pyrazol-5-yl)ureido)naphthalen-1-yloxy)pyridin-2-yl)ureido)acetyl)pyrrolidine;

(R)-N-(4-(4-(3-(3-tert-Butyl-1-p-tolyl-1H-pyrazol-5-yl)ureido)naphthalen-1-yloxy)pyridin-2-yl)-3-(dimethylamino)pyrrolidine-1-carboxamide;

N-(4-(4-(3-(3-tert-Butyl-1-p-tolyl-1H-pyrazol-5-yl)ureido) naphthalen-1-yloxy)pyridin-2-yl)pyrrolidine-1-carboxamide;

2-(3-(4-(4-(3-(3-tert-Butyl-1-p-tolyl-1H-pyrazol-5-yl)ureido)naphthalen-1-yloxy)pyridin-2-yl)ureido)-N-methylacetamide;

2-(3-(4-(4-(3-(3-tert-Butyl-1-p-tolyl-1H-pyrazol-5-yl)ureido)naphthalen-1-yloxy)pyridin-2-yl)ureido)-N-(2-morpholinoethyl)acetamide;

2-(3-(4-(4-(3-(3-tert-Butyl-1-p-tolyl-1H-pyrazol-5-yl)ureido)naphthalen-1-yloxy)pyridin-2-yl)ureido)acetyl morpholine;

2-(3-(4-(4-(3-(3-tert-Butyl-1-p-tolyl-1H-pyrazol-5-yl)ureido)naphthalen-1-yloxy)pyridin-2-yl)ureido)-N-(2-(pyridin-4-yl)ethyl)acetamide;

N-(3-(1H-Imidazol-1-yl)propyl)-2-(3-(4-(4-(3-(3-tert-butyl-1-p-tolyl-1H-pyrazol-5-yl)ureido)naphthalen-1-yloxy) pyridin-2-yl)ureido)acetamide;

1-(2-(3-(4-(4-(3-(3-tert-Butyl-1-p-tolyl-1H-pyrazol-5-yl)ureido)naphthalen-1-yloxy)pyridin-2-yl)ureido)acetyl)-4-methylpiperazine;

N-(3-(1H-Imidazol-1-yl)propyl)-2-(3-(4-(4-(3-(3-tert-butyl-1-p-tolyl-1H-pyrazol-5-yl)ureido)naphthalen-1-yloxy) pyridin-2-yl)ureido)acetamide;

N-(6-(4-(3-(3-tert-Butyl-1-p-tolyl-1H-pyrazol-5-yl)ureido) naphthalen-1-yloxy)pyrimidin-4-yl)-2-methoxyacetamide;

N-(6-(4-(3-(3-tert-Butyl-1-p-tolyl-1H-pyrazol-5-yl)ureido) phenoxy)pyrimidin-4-yl)-2-methoxyacetamide;

N-(4-(4-(3-(3-tert-Butyl-1-p-tolyl-1H-pyrazol-5-yl)ureido) naphthalen-1-yloxy)pyrimidin-2-yl)-2-methoxyacetamide;

3-(4-(4-(3-(3-tert-Butyl-1-p-tolyl-1H-pyrazol-5-yl)ureido) naphthalen-1-yloxy)pyrimidin-2-yl)urea;

1-Methyl-3-(4-(4-(3-(3-tert-butyl-1-p-tolyl-1H-pyrazol-5-yl)ureido)naphthalen-1-yloxy)pyrimidin-2-yl)urea;

1,1-Dimethyl-3-(4-(4-(3-(3-tert-butyl-1-p-tolyl-1H-pyrazol-5-yl)ureido)naphthalen-1-yloxy)pyrimidin-2-yl)urea;

1-Cyclopropyl-3-(4-(4-(3-(3-tert-butyl-1-p-tolyl-1H-pyrazol-5-yl)ureido)naphthalen-1-yloxy)pyrimidin-2-yl)urea;

(4-(4-(3-(3-tert-butyl-1-p-tolyl-1H-pyrazol-5-yl)ureido) naphthalen-1-yloxy)pyrimidin-2-yl)morpholine-4-carboxamide;

3-(6-(4-(3-(3-tert-Butyl-1-p-tolyl-1H-pyrazol-5-yl)ureido) naphthalen-1-yloxy)pyrimidin-4-yl)urea;

2-(3-(4-(4-(3-(3-tert-Butyl-1-p-tolyl-1H-pyrazol-5-yl)ureido)naphthalen-1-yloxy)pyridin-2-yl)ureido)acetic acid.

or a pharmaceutically acceptable salt thereof, including all stereoisomers, tautomers and isotopic derivatives thereof.

Examples of salts of compound (I) include all pharmaceutically acceptable salts, such as, without limitation, acid addition salts of mineral acids such as HCl and HBr salts and addition salts of organic acids such as a methansulfonic acid salt.

The disclosure herein extends to solvates of compounds of formula (I). Examples of solvates include hydrates.

The compounds of the disclosure include those where the atom specified is a naturally occurring or non-naturally occurring isotope. In one embodiment the isotope is a stable isotope. Thus the compounds of the disclosure include, for example deuterium containing compounds and the like.

The compounds described herein may include one or more chiral centres, and the disclosure extends to include racemates, both enantiomers (for example each substantially free of the other enantiomer) and all stereoisomers resulting therefrom. In one embodiment one enantiomeric form is present in a substantially purified form that is substantially free of the corresponding entaniomeric form.

The disclosure also extends to all polymorphic forms of the compounds herein defined.

Compounds of formula (I) can be prepared by a process comprising reacting compounds of formula (II):

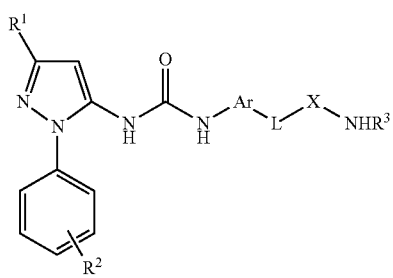

where Ar, X, $R^1$, $R^2$ and $R^3$ are as defined above for compounds of formula (I)

wherein Q is not —NHR* (wherein R* is the remainder of the Q fragment) with a compound of formula (IIIa):

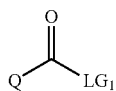

where $LG_1$ is a leaving group for example halogen, such as chloro.

When $NR^3C(O)Q$ is $NR^3C(O)NHR^*$ compounds of formula (I) can be prepared by reacting compounds of formula (II) with a compound of formula (IIIb):

The reaction is suitably carried out in the presence of a base (e.g. DIPEA). The reaction is suitably carried out in an aprotic solvent or solvent mixture, e.g. DCM and DMF.

Compounds of formula (II) can be prepared by reacting a compound of formula (IV):

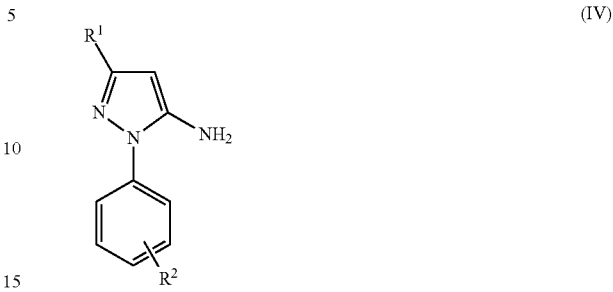

where $R^1$ and $R^2$ are as defined above for compounds of formula (I), with a compound of formula (VI):

wherein $LG_2$ and $LG_3$ each independently represent leaving groups (e.g. $LG_2$ and $LG_3$ both represent imidazolyl followed by reaction with a compound of formula (V):

wherein Ar, L, X and $R^3$ are defined above for compounds of formula (I)

The reaction is suitably carried out in an aprotic solvent (e.g. dichloromethane), using appropriate protecting groups for chemically sensitive groups and a base, for example DIPEA.

Specifically compounds of formula (II) can be prepared by reacting a compound of formula (IVa):

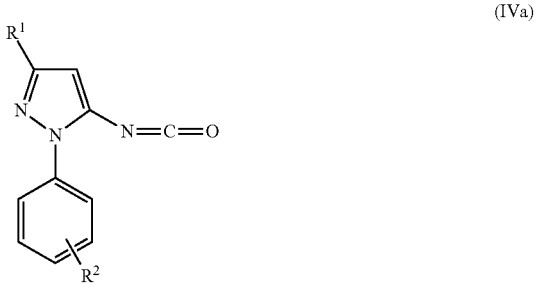

where $R^1$ and $R^2$ are as defined above for compounds of formula (I), with a compound of formula (V).

The reaction may be performed in the presence of a sterically hindered base such as DIPEA, in a suitable inert solvent such as dichloromethane.

Compounds of formula (I) wherein $R^2$ is a hydroxyalkyl may be prepared by reacting a (hydrazinylphenyl)alkanoic acid with an alkanoyl acetonitrile such as $R^1C(O)CH_2CN$, for example. The coupling may be effected in presence of an alcohol solvent such as ethanol and a mineral acid, such as HCl followed by treatment with a lithium hydroxide in a solvent such as THF. The substituent $R^2$ comprising a hydroxyalkyl may be revealed by a reduction employing borane in a suitable solvent, for example THF to afford a compound of formula (IV) where $R^2$ is hydroxylated alkyl. The hydroxyl may then be protected, for example as a silyl ether and (IV) carried through one of the routes described elsewhere in this section to generate a compound of formula (I) in which $R^2$ is a protected hydroxyalkyl group. The hydroxyl can be revealed by cleavage of the sillyl group, for example with tetrabutylammonium fluoride.

Compounds of formula (I) wherein $R^1$ is a hydroxylated alkyl species may be prepared by reacting protected benzyloxyalkanoyl acetonitrile an aryl hydrazine employing analogous conditions to those described directly above.

A compound of formula (IVa) can be prepared by reacting a compound of formula (IV) with phosgene or a phosgene equivalent such as diphosgene or triphosgene in the presence of a base such DIPEA. It will be understood by persons skilled in the art that the compound of formula (IVa) is generally a reactive intermediate, and may be isolated and used directly in subsequent transformations or may be a transient intermediate, that is generated in situ and used without isolation.

More specifically compounds of formula (II) may be prepared by reacting a compound of formula (IVb):

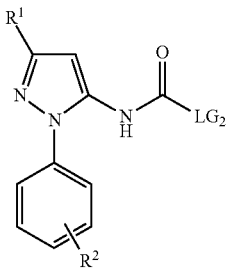

(IVb)

where $LG_2$ is as defined above with a compound of formula (VI).

The reaction may be performed in the presence of a sterically hindered base such as DIPEA, in a suitable inert solvent such as dichloromethane.

A compound of (IVb) can be prepared by reacting a compound of formula (IV) with a compound of formula (VI) in the presence of a base such as DIPEA. It will be understood by persons skilled in the art that the compound of formula (IVb) may be an intermediate, including a transient intermediate, that is not isolated.

A compound of formula (V) may be prepared by reduction of a compound of formula (VII):

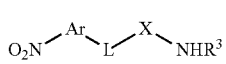

(VII)

wherein Ar, L, X and $R^3$ are as defined above for compounds of formula (I), for example by hydrogenation in the presence of a catalyst such as platinum supported on carbon.

The reaction is suitably carried out in polar protic solvent or mixture of solvents (e.g. methanol and acetic acid).

Alternatively, a compound of formula (V) where L is O may be prepared by deprotecting a compound of formula (VIIa):

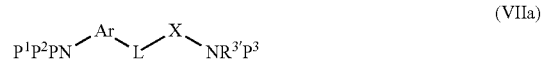

(VIIa)

wherein $P^1$, $P^2$ and $P^3$ are protecting groups and $R^{3'}$ is a protecting group, for example acetyl such as —C(O)CH$_2$OCH$_3$ or $R^3$ as defined above for compounds of formula (I).

A compound of formula (VII) wherein L represents —(CH$_2$)$_n$O(CH$_2$)$_m$ or (CH$_2$)$_n$OR$^b$, as defined above, wherein n is zero and the linker L contains at least one —CH$_2$— may be prepared by reaction of a compound of formula (VIIIa) or (VIIIb):

(VIIIa)

(VIIIb)

or analogues thereof and wherein m, X and $R^b$ are as defined above for compounds of formula
(I) and $R^{3'}$ is a protecting group or $R^3$ as defined above for compounds of formula (I) with a compound of formula (IX) or (X):

(IX)

(X)

wherein compounds (IX) and (X) may bear optional substitutents as defined above for compounds of formula (I).

The reaction may be performed under Mitsunobu conditions, such as in the presence of triphenylphosphine and diisopropylazodicarboxylate. The reaction is suitably carried out in a polar aprotic solvent (e.g. tetrahydrofuran, in particular anhydrous tetrahydrofuran).

In an alternative process, certain compounds of formula (V), wherein Ar, L and X are as defined above for compounds of formula (I) may be prepared by reacting a compound of formula (XI):

(XI)

or a protected derivative thereof, such as a carbamate, wherein Ar, L and X are as defined above and $LG_4$ represents a leaving group such as chloro (in particular where L represents O) with an amidation reagent, for example with the carbamate (XII):

(XII)

wherein P³ and R³ are as defined above in the presence of an dry inert solvent such as THF and a suitable palladium catalyst, for example under a nitrogen atmosphere, followed by deprotection of both the original and newly introduced protected amines, for example employing dichloromethane and TFA.

In one embodiment the compound formula (XII) is:

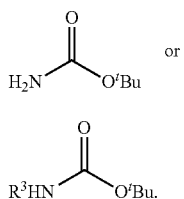

Compounds of formula (XI), where L is linked to X through O, for example, wherein L represents —(CH₂)ₙO (CH₂)ₘ or R^aO(CH₂)ₘ, as defined above, wherein m is zero, may be prepared by reacting a compound of formula (XIII):

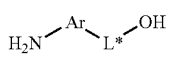

or a protected derivative thereof, for example where the free amine is protected as a carbamate, wherein Ar is as defined above and L* and OH taken together represent L (in particular L* represents alkylene or a bond), with a compound of formula (XIV):

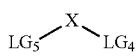

wherein X is as defined above and LG₄ represents a leaving group such as chloro and LG₅ represents a leaving group such a fluoro.

The reaction may be performed in the presence of a strong base such as sodium hydride in a polar aprotic solvent such as DMF.

Compounds of formula (XIII) may be prepared from compounds of formula (XV):

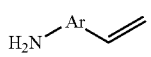

wherein the free amine is suitably protected, for example as a carbamate, and Ar is as defined above, and wherein L represents —(CH₂)ₙO(CH₂)ₘ, as defined above, wherein n is 2 and m is zero by hydroboration with a reagent such as 9-BBN followed by oxidation using hydrogen peroxide in the present of a base such as sodium hydroxide.

Compounds of formula (XV) may be prepared in a two step transformation from compounds of formula (XVI) via compounds of formula (XVII), wherein Ar is as defined above and the free amine is suitably protected, for example as a carbamate:

Treatment of a compound of formula (XVI) with a base such as n-butyl lithium in an inert solvent such as THF followed by the addition of DMF provides compounds of formula (XVII). Compounds of formula (XVII) may be transformed into compounds of formula (XV) by an olefination step such as by reaction with a Wittig reagent generated in situ, such as the ylid generated from methyltriphenylphosphonium bromide in the presence of a base such potassium tert-butoxide. Generally the reaction will be performed in an inert solvent, for example THF, and under an inert atmosphere such as nitrogen at a low temperature, such a –78° C.

Compounds of formula (I) wherein Q is linked to —NR³C(O) by —CH₂V', wherein V' is a heteroatom selected from N, O, or S, can be prepared by the process comprising of a nucleophilic displacement reaction on a compound of formula (IIa):

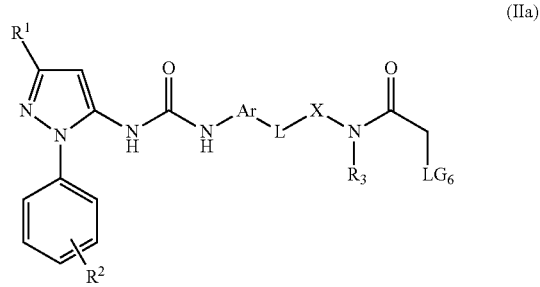

wherein R¹, R², Ar, L, X, NR³ are as defined above for compounds of formula (I) and LG₆ represents a leaving group, for example halogen such as chloro, with a compound of formula (XVIII):

wherein H represents hydrogen, V' represents a heteroatom selected from N, NH, O, or S and q represents the residual portion of Q (i.e. —CH₂V'-q=Q).

The reaction may, be performed in the presence of a sterically hindered base, for example DIPEA, in an inert solvent, for example dichloromethane.

Compounds of formula (IIa) may be prepared by reacting a compound of formula (II) with a compound of formula (XVI):

wherein LG₆ is defined above for compounds of formula (IIa), and LG₇ is a leaving group, for example a halogen such as chloro.

The reaction may, for example be performed in the presence of a sterically hindered base, for example DIPEA, in an inert solvent, for example dichloromethane.

Compounds of formula (I) wherein Q is NH—$(CH_2)_d$—C(O)$NHR^8$, can be prepared by the process comprising of an amide coupling between (IIb):

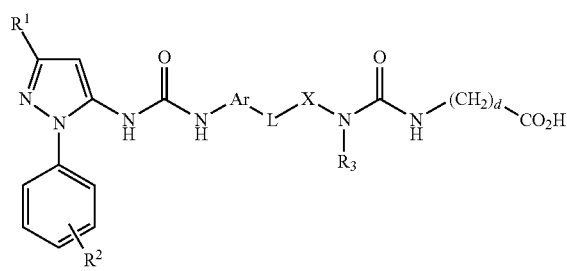

(IIb)

wherein $R^1$, $R^2$, Ar, L, X and $R^{3\ 9}$ are as defined above for compounds of formula (I) and d is an integer 1 to 5 (such as 1 to 4), and an amine $R^dNH_2$ using a coupling reagent such as EDC (wherein $R^d$ is a fragment of Q).

Compounds of formula (IIb) can be synthesisized by reaction of Compound (II) with an isocyanate of formula (IIIb) in which Q is N—$(CH_2)_p$—$CO_2Et$, followed by hydrolysis of the resulting ethyl ester product using, for example, aqueous lithium hydroxide in THF.

Compounds of formula (I) wherein Q is $NR^7R^8$ can be prepared by the process comprising of reaction between an amine $R^7R^8NH$ and a compound of formula (IIc):

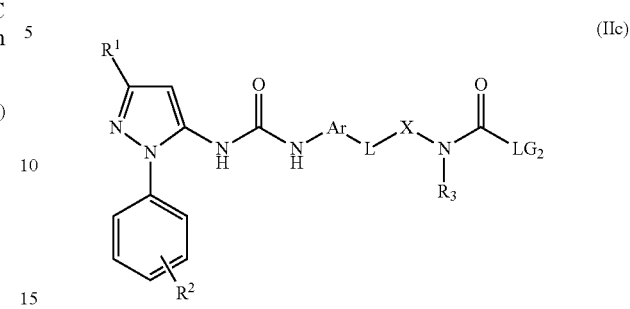

(IIc)

wherein $R^1$, $R^2$, Ar, X and $R^3$ are as defined above for compounds of formula (I) and $LG_2$ is a leaving group such as 2-isopropenyloxy.

Compounds of formula (IIc) can be synthesized by reaction of Compound (II) with a compound of formula (VI), such as isopropenylchloroformate in the presence of a hindered base such as DIPEA.

The reaction may, be performed in the presence of a sterically hindered base, for example DIPEA, in an inert solvent, for example dichloromethane.

A scheme summarising routes for preparing compounds of formula (I) wherein Ar is naphthyl and X is pyridine and Q is linked through an amide is provided in Scheme 1:

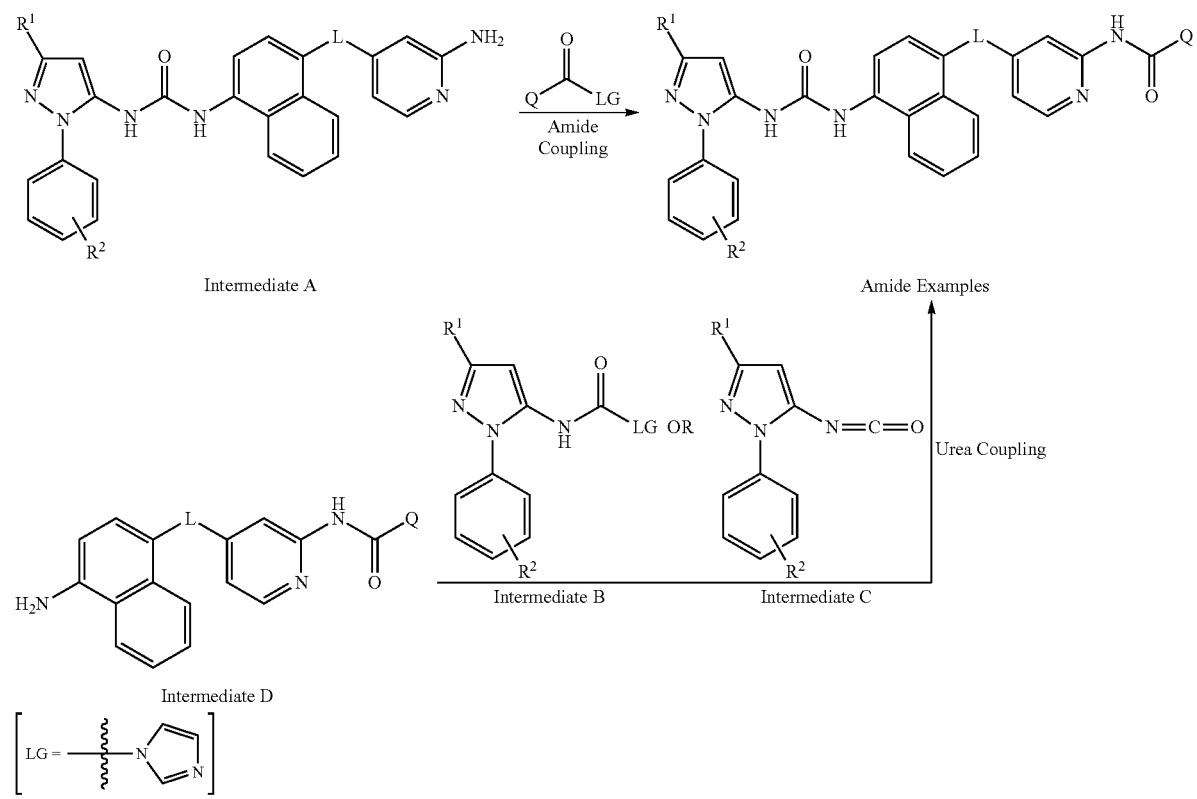

The reaction may, be performed in the presence of a sterically hindered base, for example DIPEA, in an inert solvent, for example dichloromethane.

Similar methods may be used to prepare compounds of formula (I) wherein Ar represents phenyl and X is as defined above for compounds of formula (I).

A scheme summarising routes for preparing compounds of formula (I) wherein Ar is naphthyl and X is pyridinyl and Q is a glycinamide derivative is provided in Scheme 2:

Scheme 2

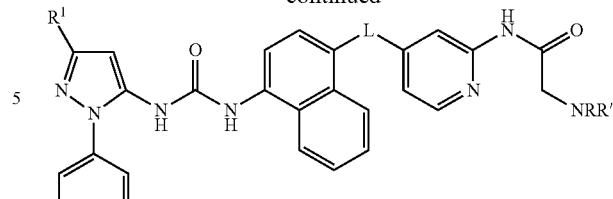

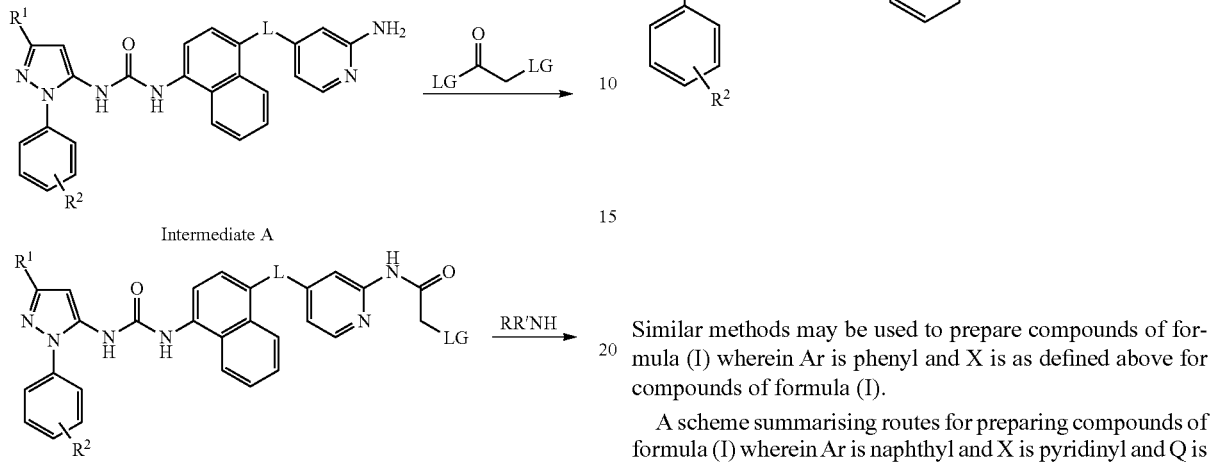

Similar methods may be used to prepare compounds of formula (I) wherein Ar is phenyl and X is as defined above for compounds of formula (I).

A scheme summarising routes for preparing compounds of formula (I) wherein Ar is naphthyl and X is pyridinyl and Q is an N-acyl glycinamide derivative is provided in Scheme 3:

Scheme 3

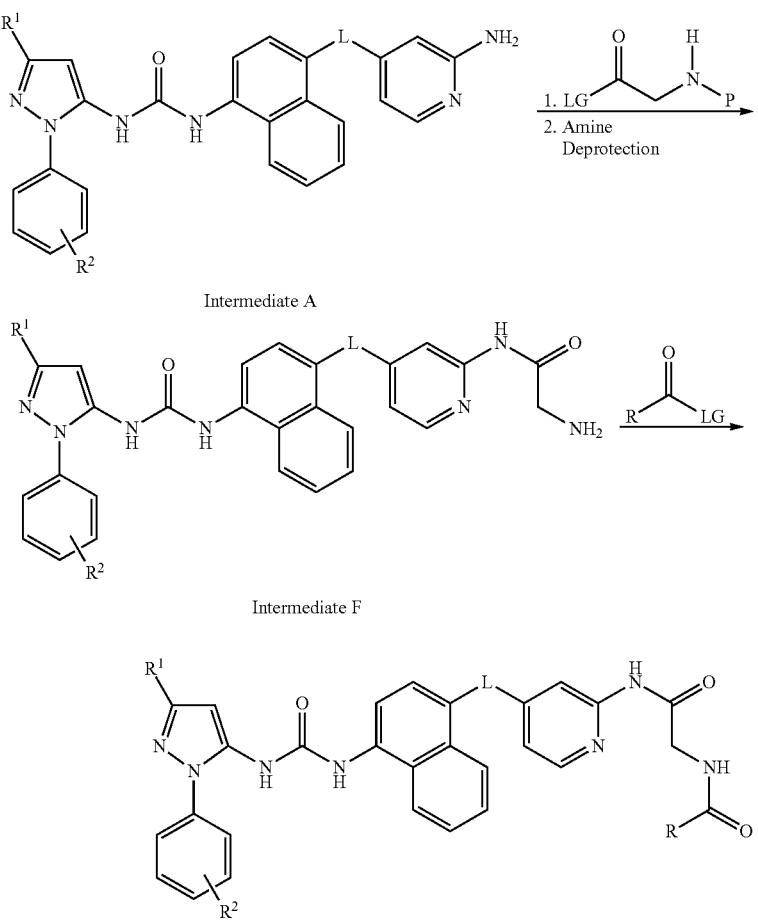

where P is a protecting group and LG is a leaving group and $RC(O)NHCH_2$ is Q.

Similar methods may be used to prepare compounds of formula (I) wherein Ar is phenyl and X is as defined above for compounds of formula (I).

A scheme summarising routes for preparing compounds of formula (I) wherein Ar is napthyl and X is pyridinyl and Q together with NHC(O) forms a urea is provided in Scheme 4:

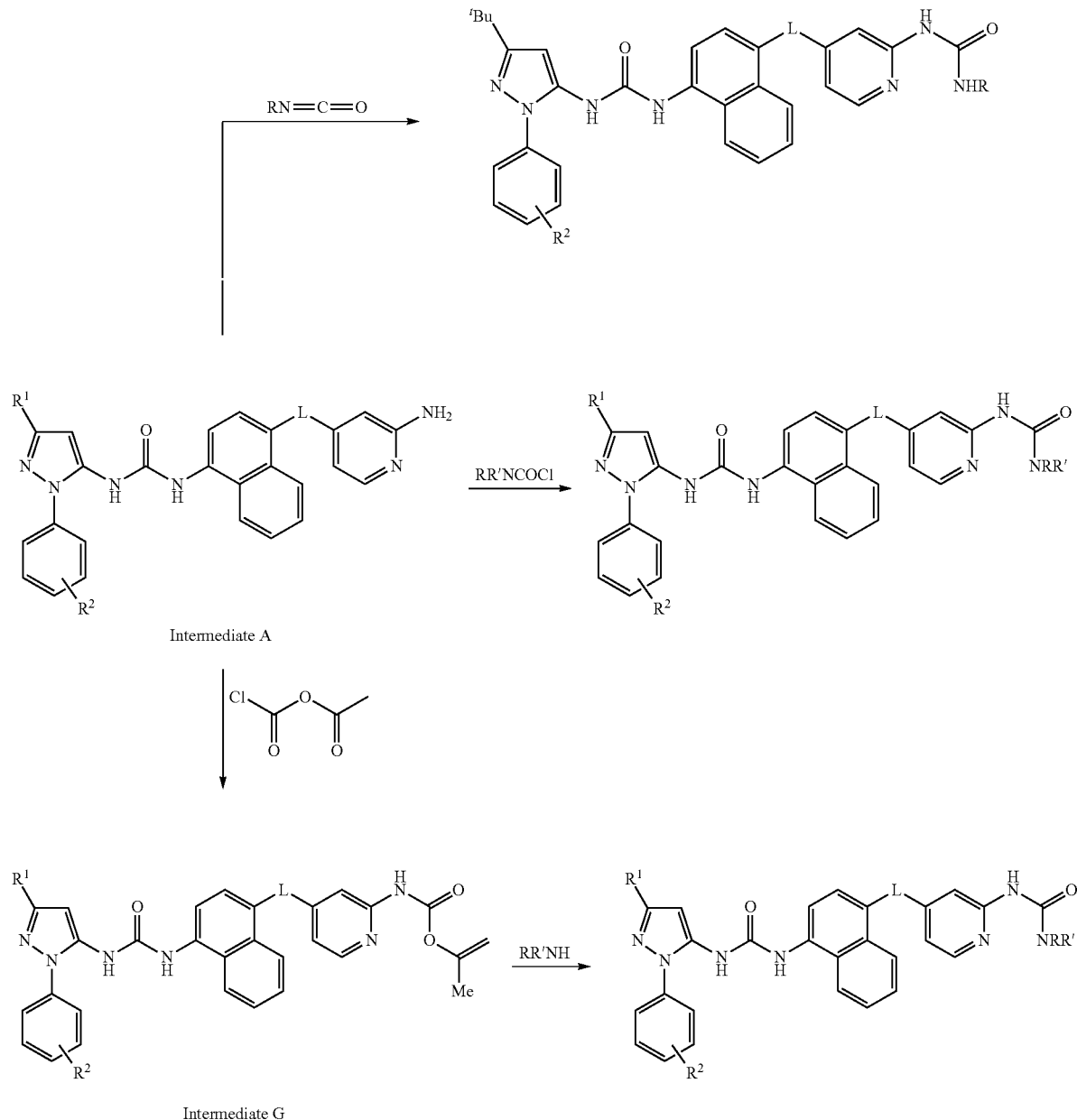

where N, R and R' together represent Q.

Similar methods may be used to prepare compounds of formula (I) wherein Ar is phenyl and X is as defined above for compounds of formula (I).

A scheme summarising routes for preparing compounds of formula (I) wherein Ar is naphthyl and X is pyridinyl and Q together with NHC(O) forms a urea is provided in Scheme 5:

Scheme 5

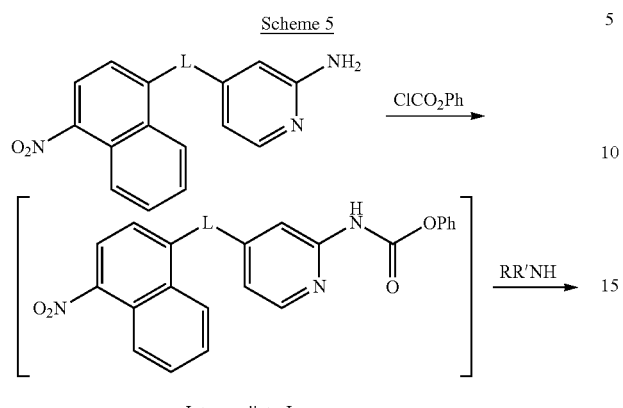

Intermediate J

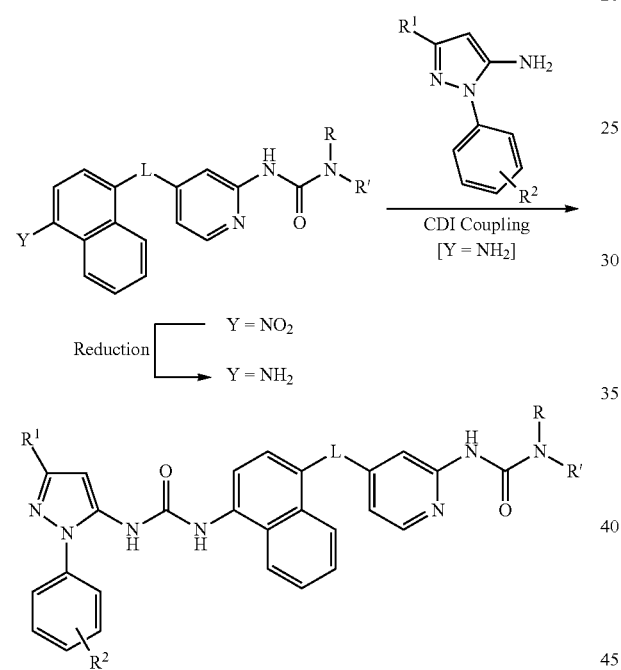

where N, R and R' together represent Q.

A scheme summarising the preparation of Intermediate A, as per Schemes 1 to 5 above, is shown in Scheme 6:

Scheme 6

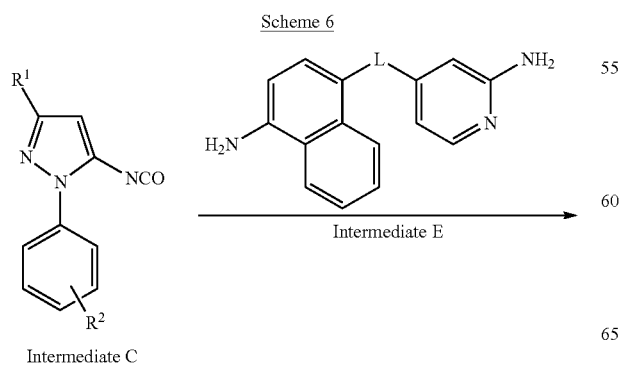

Intermediate C

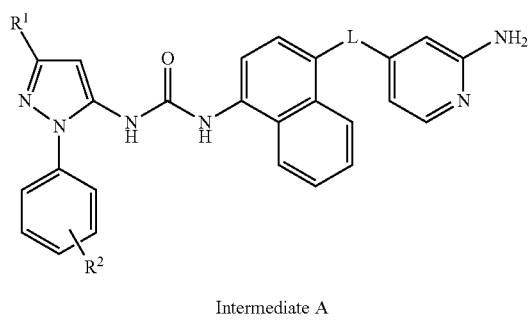

Intermediate A

A scheme showing the preparation for intermediate B and C is shown below in Scheme 7:

Scheme 7

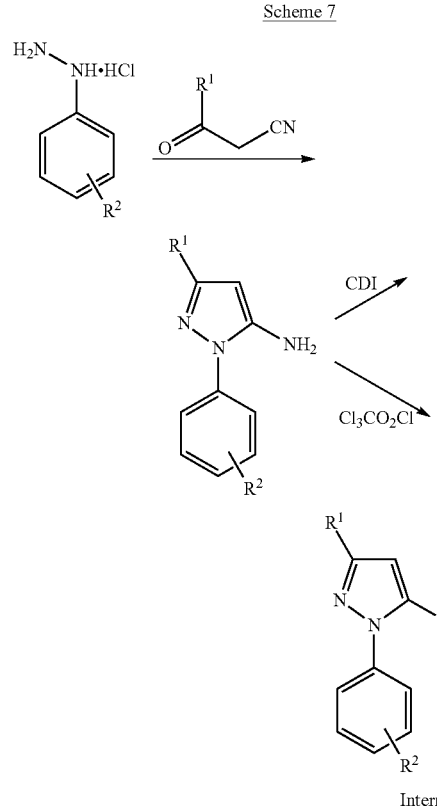

Intermediate B

Intermediate C

A scheme showing compounds the preparation of intermediate D and E where L therein does not represent O is shown in Scheme 8 below:

Scheme 8
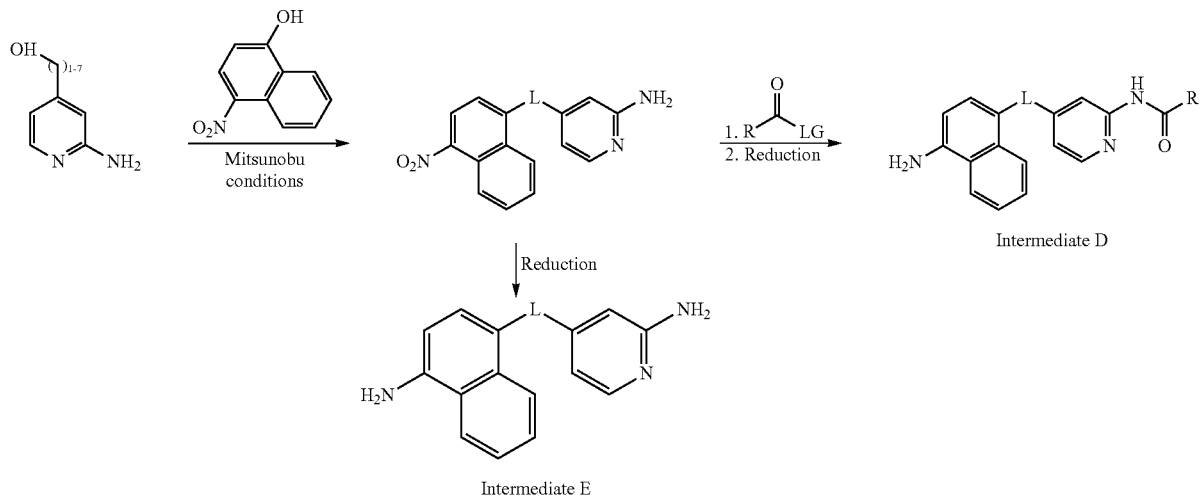
A scheme showing compounds the preparation of intermediate D and E where L therein represents O is shown in scheme 9 below:
Scheme 9
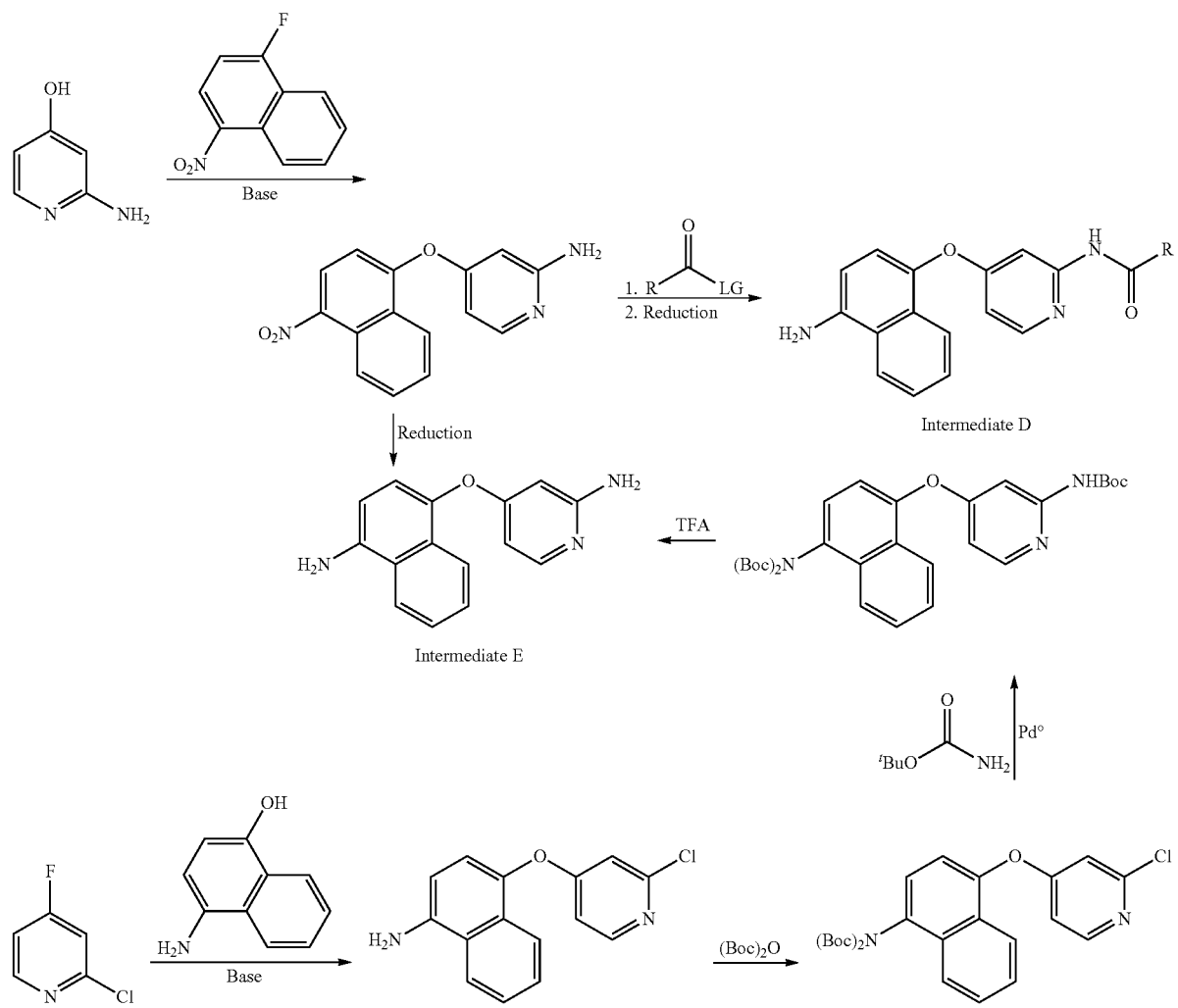

Compounds of formula (I) wherein XNR³(CO)Q represents N-acyl-2-aminopyrimidinyl or N-acyl-4-aminopyrimidinyl may be prepared as summarised in scheme 10 below:

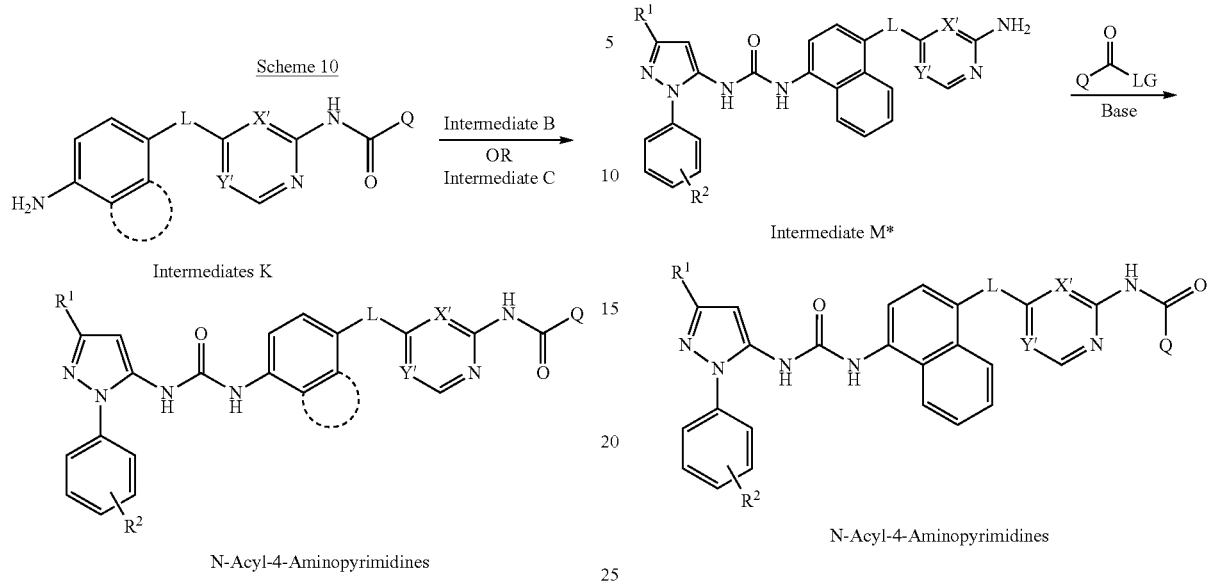

where each X' and Y' independently represents CH or N.

Compounds of formula (I) wherein Ar represents naphthyl and XNR³C(O)Q represents N-acyl-2-aminopyrimidinyl may be prepared as summarised in Scheme 11 below:

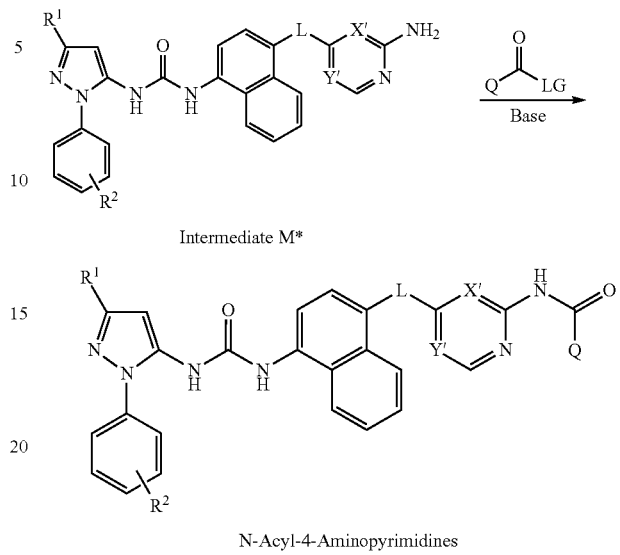

where X' and Y' independently represents CH or N.

Compounds of formula (I) wherein XNHR³ represents 2-aminopyrimidinyl or 4-aminopyrimidinyl and NR³(CO)Q is a urea may be prepared as summarised below in Scheme 12:

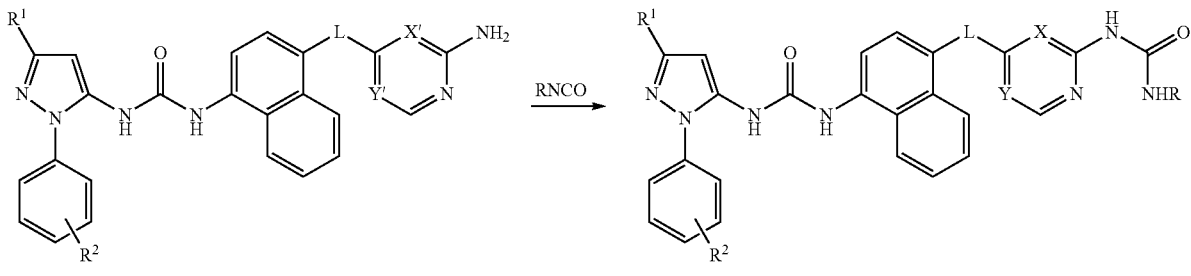

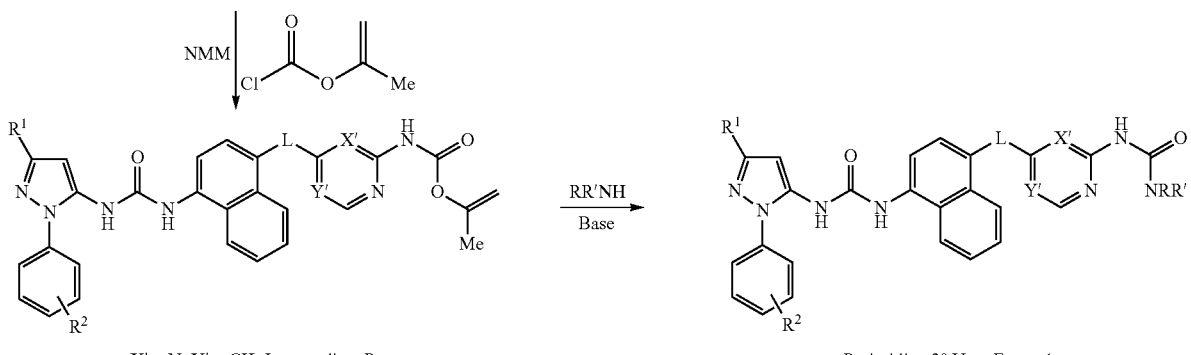

where X' and Y' independently represents CH or N.

Scheme 13 below summarises the preparation of additional compounds of formula (I) wherein Ar is naphthyl and XNHR³ represents 2-aminopyrimidinyl or 4-aminopyrimidinyl:

Scheme 13

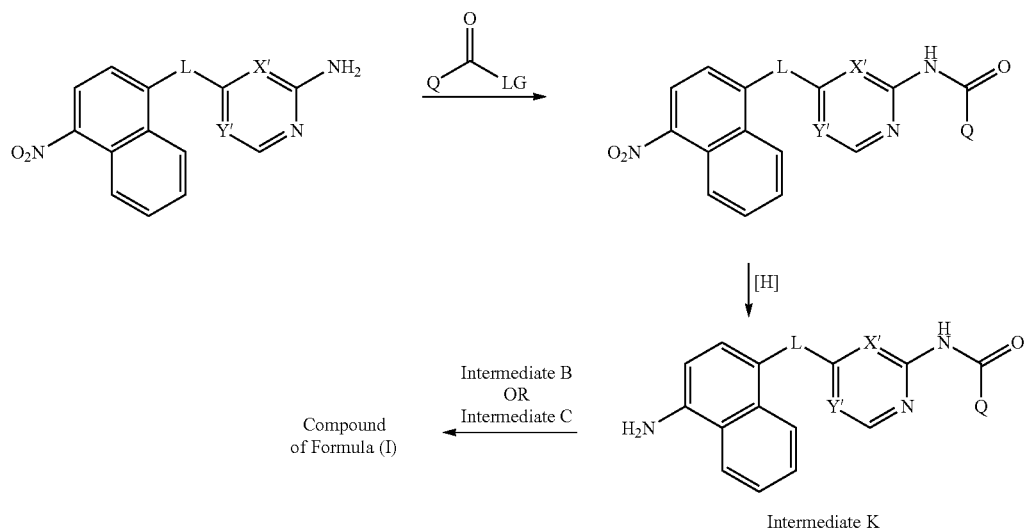

The starting material where L is O for use in scheme 13 for the preparation of 4-amino pyrimidines may be prepared as summarised in the scheme 14 below:

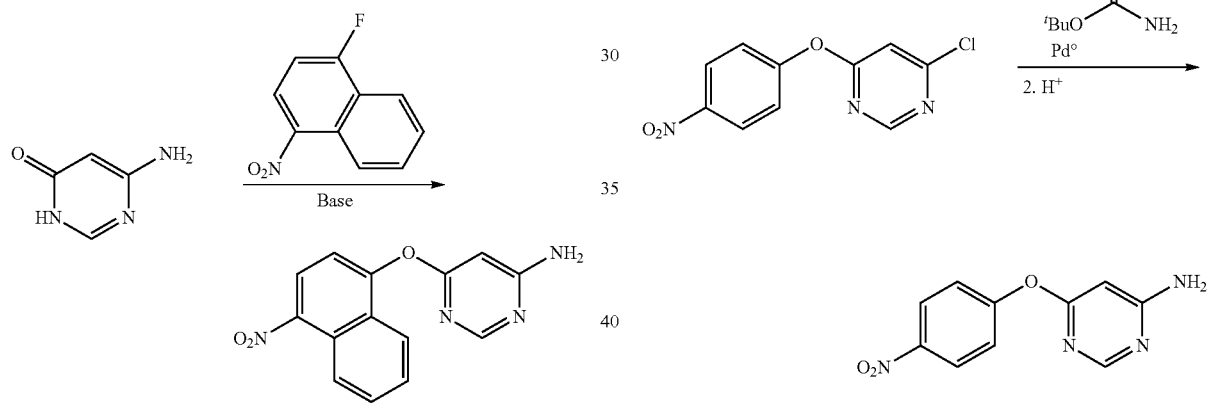

or as shown in scheme 15:

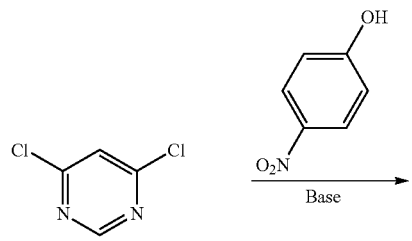

Starting materials for scheme 13 containing pyrimidine and where L is not O can be prepared by analogous to those shown above in scheme 8.

Certain compounds within the definition of intermediate M* in particular intermediate N wherein XNHR³ is 2-aminopyrimidinyl and L is O may be prepared as shown in scheme 16:

Scheme 16

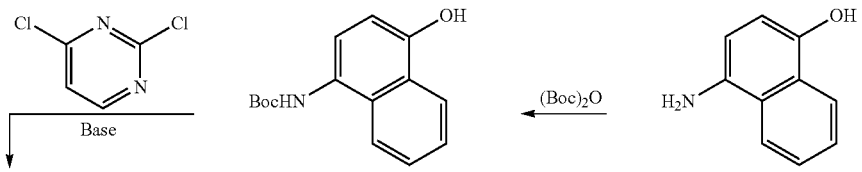

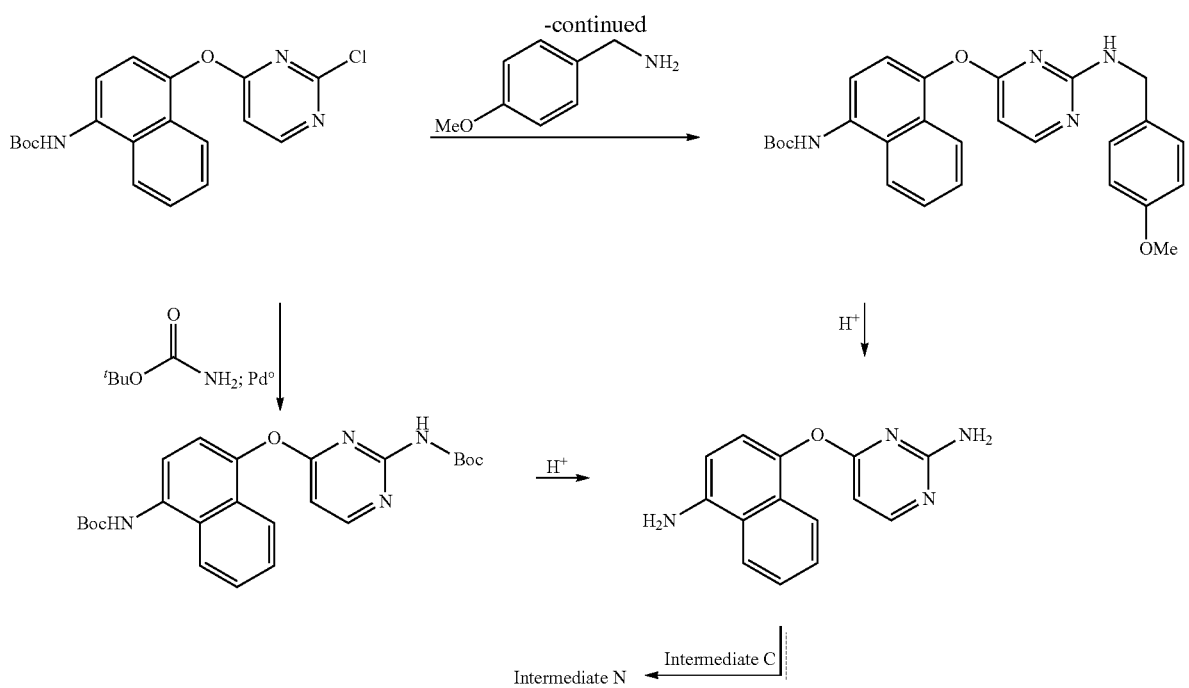

Intermediate K where Q is NRR' may be prepared as summarised in scheme 17 below:

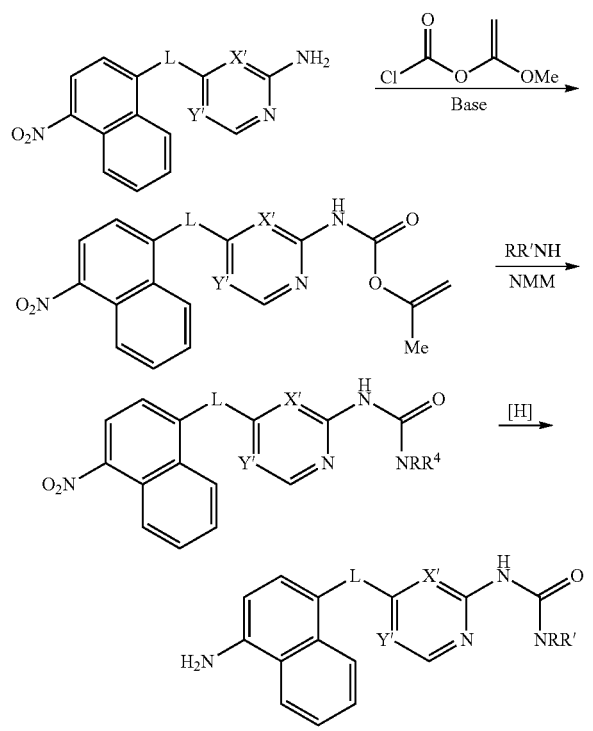

wherein each of X', Y', L, R and R' are defined above.

Compounds of formulae (IIIa), (IIIb), (IV), (IVa), (IVb), (VI), (VIIIa), (VIIIb), (IX), (X), (XII), (XIIa), (XIIb), (XIII), (XIV), (XV), (XVI), (XVI) and (XIX) and certain other compounds illustrated in the schemes are either commercially available, or are known, or are novel and were either obtained using the cited procedure or can be readily prepared by conventional methods. See for example Regan, J. et al.; *J. Med. Chem.*, 2003, 46, 4676-4686, WO00/043384, WO2007/087448 and WO2007/089512.

Protecting groups may be required to protect chemically sensitive groups during one or more of the reactions described above, to ensure that the process is efficient. Thus if desired or necessary, intermediate compounds may be protected by the use of conventional protecting groups. Protecting groups and means for their removal are described in "Protective Groups in Organic Synthesis", by Theodora W. Greene and Peter G. M. Wuts, published by John Wiley & Sons Inc; 4th Rev Ed., 2006, ISBN-10: 0471697540.

Novel intermediates are claimed as an aspect of the invention.

In one aspect the compounds are useful in treatment, for example COPD and/or asthma.

The compounds developed to date have typically been intended for oral administration. This strategy involves optimizing compounds which achieve their duration of action by an appropriate pharmacokinetic profile. This ensures that there is a sufficient drug concentration established and maintained after and between doses to provide clinical benefit. The inevitable consequence of this approach is that all body tissues, especially liver and gut, are likely to be exposed to therapeutically active concentrations of the drug, whether or not they are adversely affected by the disease being treated.

An alternative strategy is to design treatment approaches in which the drug is dosed directly to the inflamed organ (topical therapy). While this approach is not suitable for treating all chronic inflammatory diseases, it has been extensively exploited in lung diseases (asthma, COPD), skin diseases (atopic dermatitis and psoriasis), nasal diseases (allergic rhinitis) and gastrointestinal diseases (ulcerative colitis).

In topical therapy, efficacy can be achieved either by (i) ensuring that the drug has a sustained duration of action and is retained in the relevant organ to minimize the risks of systemic toxicity or (ii) producing a formulation which generates a "reservoir" of the active drug which is available to sustain the drug's desired effects. Approach (i) is exemplified by the anticholinergic drug tiotropium (Spiriva), which is administered topically to the lung as a treatment for COPD, and which has an exceptionally high affinity for its target receptor resulting in a very slow off rate and a consequent sustained duration of action.

There is provided according to one aspect of the present disclosure use of a compound of formulation as a p38 MAP kinase inhibitor, for example administered topically to the lung.

In one aspect of the disclosure the compounds herein are particularly suitable for topical delivery, such as topical delivery to the lungs, in particular for the treatment of COPD.

Thus is one aspect there is provided use of compounds of formula (I) for the treatment of COPD and/or asthma, in particular COPD or severe asthma, by inhalation i.e. topical administration to the lung. Advantageously, administration to the lung allows the beneficial effects of the compounds to be realised whilst minimising the side-effects, for patients.

In one aspect the compounds have a longer duration of actions than BIRB 796.

In one embodiment the compounds are suitable for sensitizing patients to treatment with a corticosteroid.

The compounds herein may also be useful for the treatment of rheumatoid arthritis.

Further, the present invention provides a pharmaceutical composition comprising a compound according to the disclosure optionally in combination with one or more pharmaceutically acceptable diluents or carriers.

Diluents and carriers may include those suitable for parenteral, oral, topical, mucosal and rectal administration.

As mentioned above, such compositions may be prepared e.g. for parenteral, subcutaneous, intramuscular, intravenous, intra-articular or peri-articular administration, particularly in the form of liquid solutions or suspensions; for oral administration, particularly in the form of tablets or capsules; for topical e.g. pulmonary or intranasal administration, particularly in the form of powders, nasal drops or aerosols and transdermal administration; for mucosal administration e.g. to buccal, sublingual or vaginal mucosa, and for rectal administration e.g. in the form of a suppository.

The compositions may conveniently be administered in unit dosage form and may be prepared by any of the methods well-known in the pharmaceutical art, for example as described in Remington's Pharmaceutical Sciences, 17th ed., Mack Publishing Company, Easton, Pa., (1985). Formulations for parenteral administration may contain as excipients sterile water or saline, alkylene glycols such as propylene glycol, polyalkylene glycols such as polyethylene glycol, oils of vegetable origin, hydrogenated naphthalenes and the like. Formulations for nasal administration may be solid and may contain excipients, for example, lactose or dextran, or may be aqueous or oily solutions for use in the form of nasal drops or metered spray. For buccal administration typical excipients include sugars, calcium stearate, magnesium stearate, pregelatinated starch, and the like.

Compositions suitable for oral administration may comprise one or more physiologically compatible carriers and/or excipients and may be in solid or liquid form. Tablets and capsules may be prepared with binding agents, for example, syrup, acacia, gelatin, sorbitol, tragacanth, or poly-vinylpyrrolidone; fillers, such as lactose, sucrose, corn starch, calcium phosphate, sorbitol, or glycine; lubricants, such as magnesium stearate, talc, polyethylene glycol, or silica; and surfactants, such as sodium lauryl sulfate. Liquid compositions may contain conventional additives such as suspending agents, for example sorbitol syrup, methyl cellulose, sugar syrup, gelatin, carboxymethyl-cellulose, or edible fats; emulsifying agents such as lecithin, or acacia; vegetable oils such as almond oil, coconut oil, cod liver oil, or peanut oil; preservatives such as butylated hydroxyanisole (BHA) and butylated hydroxytoluene (BHT). Liquid compositions may be encapsulated in, for example, gelatin to provide a unit dosage form.

Solid oral dosage forms include tablets, two-piece hard shell capsules and soft elastic gelatin (SEG) capsules.

A dry shell formulation typically comprises of about 40% to 60% concentration of gelatin, about a 20% to 30% concentration of plasticizer (such as glycerin, sorbitol or propylene glycol) and about a 30% to 40% concentration of water. Other materials such as preservatives, dyes, opacifiers and flavours also may be present. The liquid fill material comprises a solid drug that has been dissolved, solubilized or dispersed (with suspending agents such as beeswax, hydrogenated castor oil or polyethylene glycol 4000) or a liquid drug in vehicles or combinations of vehicles such as mineral oil, vegetable oils, triglycerides, glycols, polyols and surface-active agents.

Suitably the compound of formula (I) is administered topically to the lung. Hence we provide according to the invention a pharmaceutical composition comprising a compound of the disclosure optionally in combination with one or more topically acceptable diluents or carriers. Topical administration to the lung may be achieved by use of an aerosol formulation. Aerosol formulations typically comprise the active ingredient suspended or dissolved in a suitable aerosol propellant, such as a chlorofluorocarbon (CFC) or a hydrofluorocarbon (HFC). Suitable CFC propellants include trichloromonofluoromethane (propellant 11), dichlorotetrafluoromethane (propellant 114), and dichlorodifluoromethane (propellant 12). Suitable HFC propellants include tetrafluoroethane (HFC-134a) and heptafluoropropane (HFC-227). The propellant typically comprises 40% to 99.5% e.g. 40% to 90% by weight of the total inhalation composition. The formulation may comprise excipients including co-solvents (e.g. ethanol) and surfactants (e.g. lecithin, sorbitan trioleate and the like). Aerosol formulations are packaged in canisters and a suitable dose is delivered by means of a metering valve (e.g. as supplied by Bespak, Valois or 3M).

Topical administration to the lung may also be achieved by use of a non-pressurised formulation such as an aqueous solution or suspension. This may be administered by means of a nebuliser. Topical administration to the lung may also be achieved by use of a dry-powder formulation. A dry powder formulation will contain the compound of the disclosure in finely divided form, typically with a mass mean diameter (MMAD) of 1-10 microns. The formulation will typically contain a topically acceptable diluent such as lactose, usually of large particle size e.g. a mass mean diameter (MMAD) of 100 μm or more. Example dry powder delivery systems include SPINHALER, DISKHALER, TURBOHALER, DISKUS and CLICKHALER.

Compounds according to the disclosure are intended to have therapeutic activity. In a further aspect, the present invention provides a compound of the disclosure for use as a medicament.

Compounds according to the disclosure may also be useful in the treatment of respiratory disorders including COPD (including chronic bronchitis and emphysema), asthma, paediatric asthma, cystic fibrosis, sarcoidosis, idiopathic pulmonary fibrosis, allergic rhinitis, rhinitis, sinusitis, especially asthma, chronic bronchitis and COPD.

Compounds of the disclosure may also re-sensitise the patient's condition to treatment with a corticosteroid, when the patient's condition has become refractory to the same.

Compounds according to the disclosure are also expected to be useful in the treatment of certain conditions which may be treated by topical or local therapy including allergic conjunctivitis, conjunctivitis, allergic dermatitis, contact dermatitis, psoriasis, ulcerative colitis, inflamed joints secondary to rheumatoid arthritis or osteoarthritis.

Compounds of the disclosure are also expected to be useful in the treatment of certain other conditions including rheumatoid arthritis, pancreatitis, cachexia, inhibition of the growth and metastasis of tumours including non-small cell lung carcinoma, breast carcinoma, gastric carcinoma, colorectal carcinomas and malignant melanoma.

Compounds of the disclosure are believed to be useful as anti-viral agents, for example in the treatment of conditions including influenza. In particular the compounds of the present disclosure may be suitable for the use in the treatment or prevention of said viral infection and in particular may be capable of reducing viral load and/or ameliorating symptoms after infection.

Thus, in a further aspect, the present invention provides a compound as described herein for use in the treatment of the above mentioned conditions.

In a further aspect, the present invention provides use of a compound as described herein for the manufacture of a medicament for the treatment of the above mentioned conditions.

In a further aspect, the present invention provides a method of treatment of the above mentioned conditions which comprises administering to a subject an effective amount of a compound of the disclosure or a pharmaceutical composition thereof.

A compound of the disclosure may also be administered in combination with one or more other active ingredients e.g. active ingredients suitable for treating the above mentioned conditions. For example possible combinations for treatment of respiratory disorders include combinations with steroids (e.g. budesonide, beclomethasone dipropionate, fluticasone propionate, mometasone furoate, fluticasone furoate), beta agonists (e.g. terbutaline, salbutamol, salmeterol, formoterol) and/or xanthines (e.g. theophylline).

Abbreviations
AcOH Glacial acetic acid
Aq Aqueous
Ac Acetyl
ATP adenosine-5'-triphosphate
BALF bronchoalveolae lavage fluid
9-BBN 9-borabicyclo[3.3.1]nonane
Boc Tert-butoxycarbonyl
Br Broad
BSA Bovine serum albumin
CatCart® catalytic cartridge
CDI 1,1-carbonyl-diimidazole
COPD chronic obstructive pulmonary disease
D Doublet
DCM Dichloromethane
DIAD Diisopropylazadicarboxylate
DIBAL-H diisobutylaluminium hydride
DIPEA N,N-diisopropylethylamine
DMF N,N-dimethylformamide
DMSO dimethyl sulfoxide
EDAC.HCl 1-ethyl-3-(3-dimethylaminopropyl)carbodiimide
(ES$^+$) electrospray ionization, positive mode
Et Ethyl
EtOAc ethyl acetate
FCS foetal calf serum
HOBt 1-hydroxybenzotriazole
Hr hour(s)
HRP horseradish peroxidase
JNK c-Jun N-terminal kinase
KHMDS potassium hexamethyldisilazane
(M+H)$^+$ protonated molecule
MAPK mitogen protein activated protein kinase
Me Methyl
MeOH Methanol
MHz Megahertz
Min Minute(s)
MTT 3-(4,5-Dimethylthiazol-2-yl)-2,5-diphenyltetrazolium bromide
m/z: mass-to-charge ratio
NMP 1-methylpyrrolidin-2-one (N-methyl-2-pyrrolidone)
NMR nuclear magnetic resonance (spectroscopy)
PBS phosphate buffered saline
Pd$_2$(dba)$_3$ Tris(dibenzylideneacetone)dipalladium(0)
PPh$_3$ Triphenylphosphine
PyBOP® (benzotriazol-1-yloxy)tripyrrolidinophosphonium hexafluorophosphate
Q Quartet
RT Room temperature
RP HPLC reverse phase high performance liquid chromatography
S Singlet
SCX Solid supported cation exchange (resin)
SDS sodium dodecyl sulfate
T Triplet
TFA trifluoroacetic acid
THF Tetrahydrofuran
TMB 3,3',5,5'-tetramethylbenzidine
TNFα tumor necrosis factor alpha
XantPhos 4,5-bis(diphenylphosphino)-9,9-dimethylxanthene

EXAMPLES

Labels given to intermediates in the examples are independent of labels given to intermediates in other parts of the description.

General Procedures

All starting materials and solvents were either obtained from commercial sources or prepared according to the literature citation.

Hydrogenations were preformed on a Thales H-cube flow reactor under the conditions stated. Organic solutions were routinely dried over magnesium sulfate.

SCX was purchased from Supelco and treated with 1M hydrochloric acid prior to use. Unless stated otherwise the reaction mixture to be purified was first diluted with MeOH and made acidic with a few drops of AcOH. This solution was loaded directly onto the SCX and washed with MeOH. The desired material was then eluted by washing with 1% NH$_3$ in MeOH.

Column chromatography was performed on pre-packed silica (230-400 mesh, 40-63 µM) cartridges using the amount indicated.

Preparative Reverse Phase High Performance Liquid Chromatography:

Agilent Scalar column C18, 5 µm (21.2×50 mm), flow rate 28 mL·min$^{-1}$ eluting with a H$_2$O-MeCN gradient containing 0.1% v/v formic acid over 10 mins using UV detection at 215 and 254 nm. Gradient information: 0.0-0.5 min: 95% H$_2$O-5% MeCN; 0.5-7.0 min: Ramped from 95% H$_2$O-5% MeCN to 5% H$_2$O-95% MeCN; 7.0-7.9 min: Held at 5% H$_2$O-95% MeCN; 7.9-8.0 min: Returned to 95% H$_2$O-5% MeCN; 8.0-10.0 min: Held at 95% H$_2$O-5% MeCN.

Analytical Methods
Reverse Phase High Performance Liquid Chromatography:
Agilent Scalar column C18, 5 μm (4.6×50 mm) or Waters XBridge C18, 5 μm (4.6×50 mm) flow rate 2.5 mL·min$^{-1}$ eluting with a H$_2$O-MeCN gradient containing 0.1% v/v formic acid over 7 min employing UV detection at 215 and 254 nm. Gradient information: 0.0-0.1 min: 95% H$_2$O-5% MeCN; 0.1-5.0 min; Ramped from 95% H$_2$O-5% MeCN to 5% H$_2$O-95% MeCN; 5.0-5.5 min: Held at 5% H$_2$O-95% MeCN; 5.5-5.6 min: Held at 5% H$_2$O-95% MeCN, flow rate increased to 3.5 mL·min$^{-1}$; 5.6-6.6 min: Held at 5% H$_2$O-95% MeCN, flow rate 3.5 mL·min$^{-1}$; 6.6-6.75 min: Returned to 95% H$_2$O-5% MeCN, flow rate 3.5 mL·min$^{-1}$; 6.75-6.9 min: Held at 95% H$_2$O-5% MeCN, flow rate 3.5 mL·min$^{-1}$; 6.9-7.0 min: Held at 95% H$_2$O-5% MeCN, flow rate reduced to 2.5 mL·min$^{-1}$.

$^1$H NMR Spectroscopy:
Bruker Avance III 400 MHz using residual undeuterated solvent as reference Intermediate A 1-(4-((2-Aminopyridin-4-yl)methoxy)naphthalen-1-yl)-3-(3-tert-butyl-1-p-tolyl-1H-pyrazol-5-yl)urea 2-Amino-4-((4-nitronaphthalen-1-yloxy)methyl) pyridine (3)

To a solution of 4-nitronaphthol (2) (5.17 g, 27.3 mmol), PPh$_3$ (10.75 g, 41.0 mmol) and 2-aminopyridine-4-methanol (1) (5.09 g, 41.0 mmol) in THF (50 mL) was added dropwise DIAD (8.07 mL, 41.0 mmol) at −15° C. The mixture was stirred overnight at RT and the volatiles removed in vacuo. The crude product was triturated from EtOAc (150 mL), filtered off and washed with EtOAc (100 mL). A second trituration from MeOH (100 mL) gave the title compound (3) (4.54 g, 56%) as a yellow solid: m/z 296 (M+H)$^+$ (ES$^+$).

2-Amino-4-((4-aminonaphthalen-1-yloxy)methyl) pyridine (4)

2-Amino-4-((4-nitronaphthalen-1-yloxy)methyl)pyridine (3) (4.50 g, 15.24 mmol) in MeOH (200 mL) and AcOH (200 mL) was passed through a Thales H-cube (2.0 mL·min$^{-1}$, 40° C., 55 mm 10% Pt/C Cat-Cart, full hydrogen mode) and the volatiles were removed in vacuo. The crude product was subjected to SCX capture and release eluting with 1% NH$_3$ in MeOH solution and the solvent was removed in vacuo to give the title compound (4) (3.82 g, 94%) as a purple solid: m/z 266 (M+H)$^+$ (ES$^+$).

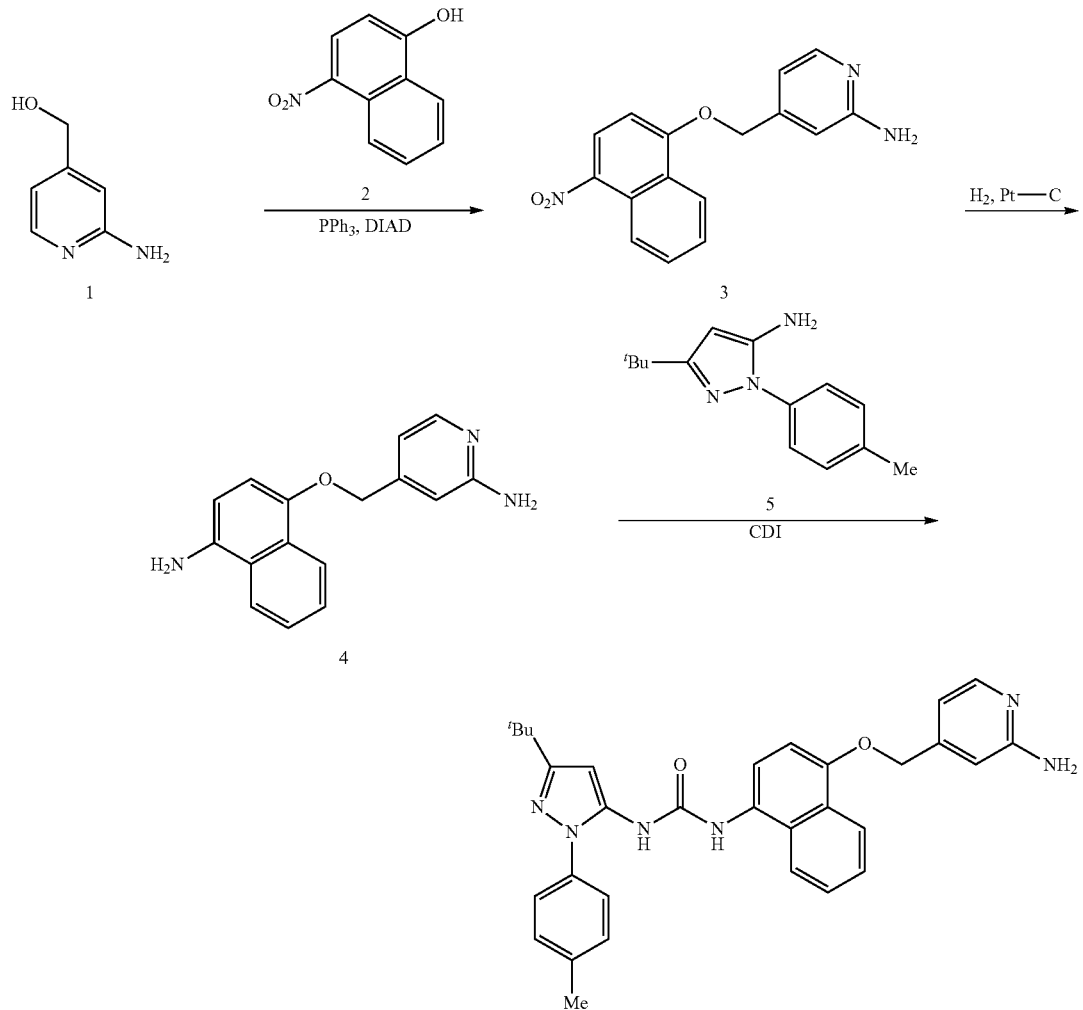

Intermediate A

Intermediate A

1-(4-((2-Aminopyridin-4-yl)methoxy)naphthalen-1-yl)-3-(3-tert-butyl-1-p-tolyl-1H-pyrazol-5-yl)urea To a solution of CDI (4.18 g, 25.8 mmol) in DCM (15 mL) was added dropwise under nitrogen a solution of 3-tert-butyl-1-p-tolyl-1H-pyrazol-5-amine (5) (WO 2000043384) (5.91 g, 25.8 mmol) in DCM (15 mL) over 40 min. The resulting solution was stirred at RT for 1 hr then added dropwise under nitrogen to a solution of 2-amino-4-((4-aminonaphthalen-1-yloxy)methyl)pyridine (4) (3.80 g, 12.9 mmol). The mixture was stirred overnight and the volatiles were removed in vacuo. The crude material was purified by column chromatography (120 g); eluting with 0 to 6% MeOH in DCM to give the title compound (Intermediate A) as an off white solid (4.27 g, 63%): m/z 521 (M+H)$^+$ (ES$^+$).

Example 1

N-(4-((4-(3-(3-tert-Butyl-1-p-tolyl-1H-pyrazol-5-yl)ureido)naphthalen-1-yloxy)methyl)pyridin-2-yl)-2-methoxyacetamide

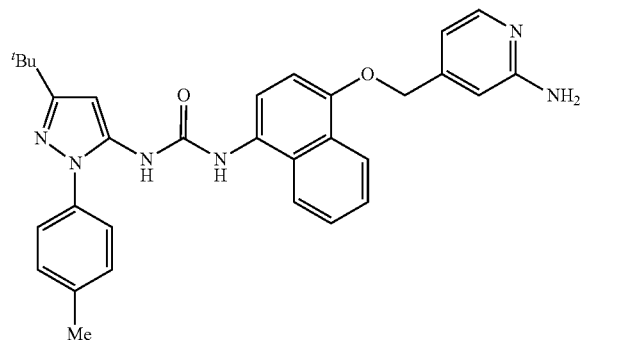

Intermediate A

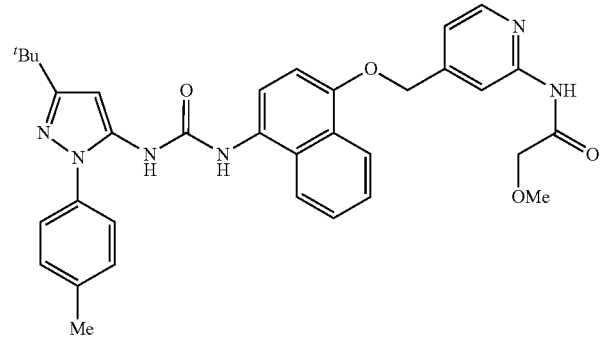

Example 1

To a mixture of Intermediate A (526 mg, 0.96 mmol) and DIPEA (184 μL, 1.06 mmol) in DCM/DMF (10:1, 11 mL) was added methoxyacetyl chloride (92 μL, 1.01 mmol). After stirring for 1 hr at RT, further DIPEA (184 μL, 1.06 mmol) and methoxyacetyl chloride (92 μL, 1.01 mmol) were added sequentially and stirring was continued for 1 hr. After the addition of a solution of 1% NH$_3$ in MeOH (40 mL), the mixture was stirred for 15 min and evaporated in vacuo. The crude product was purified by column chromatography (40 g); eluting with 0 to 6% MeOH in DCM to furnish the title compound (Example 1) as a white solid (286 mg, 49%): m/z 593 (M+H)$^+$ (ES$^+$). $^1$H NMR (400 MHz, DMSO-d$_6$) δ: 1.27 (9 H, s), 2.39 (3 H, s), 3.32 (3 H, s), 4.08 (2H, s), 5.39 (2H, s), 6.36 (1H, s), 7.03 (1H, d), 7.28 (1H, dd), 7.36 (2H, m), 7.44 (2H, m), 7.56-7.64 (3H, m), 7.93 (1H, m), 8.30-8.35 (3H, m), 8.58 (1H, s), 8.79 (1H, s), 10.02 (1H, s).

Example 2

Methyl 4-((4-(3-(3-tert-butyl-1-p-tolyl-1H-pyrazol-5-yl)ureido)naphthalen-1-yloxy)methyl)pyridin-2-ylurea

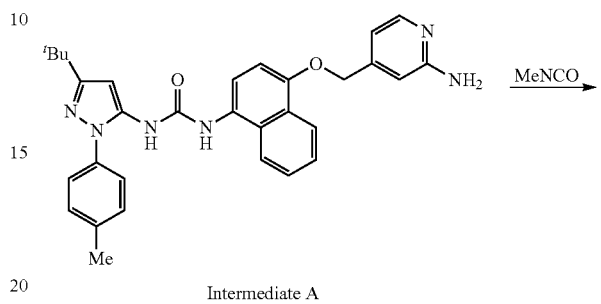

Intermediate A

-continued

Example 2

To a solution of Intermediate A (70 mg, 0.13 mmol) in anhydrous pyridine (1.5 mL) was added methyl isocyanate (14 μL, 0.24 mmol) and the mixture allowed to stir at RT for 72 hr. Pyridine was removed in vacuo and the residue triturated with DCM (3.0 mL). Filtration afforded the title compound (Example 2) as an off-white powder, (36 mg, 45%): m/z 578 (M+H)$^+$ (ES$^+$). $^1$H NMR (400 MHz, DMSO-d$_6$) δ: 1.27 (9H, s), 2.39 (3H, s), 2.74 (3 H, d), 5.30 (2H, s), 6.36 (1H, s), 6.99 (1H, d), 7.05 (d, 1H), 7.35, (2H, d), 7.44 (2H, d), 7.54-7.64 (4H, m), 7.93 (1H, d), 8.19 (1H, d), 8.23 (1H, brs), 8.35 (1H, d), 8.58 (1H, s), 8.79 (1H, s), 9.36 (1H, s).

Example 3

N-(4-((4-(3-(3-tert-Butyl-1-p-tolyl-1H-pyrazol-5-yl)ureido)naphthalen-1-yloxy)methyl)pyridin-2-yl)tetrahydro-2H-pyran-4-carboxamide

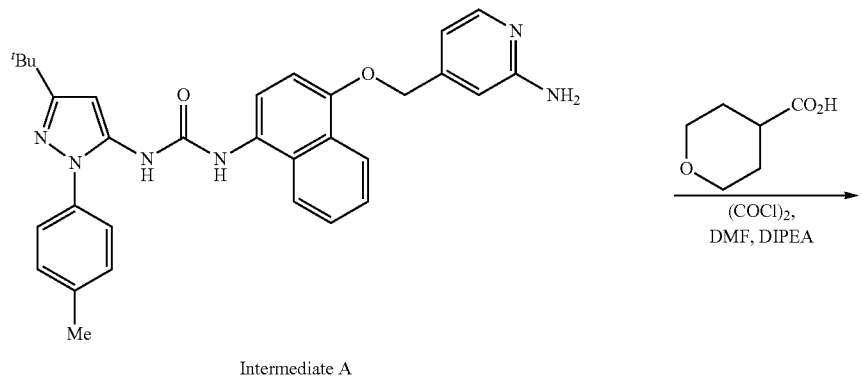

Intermediate A

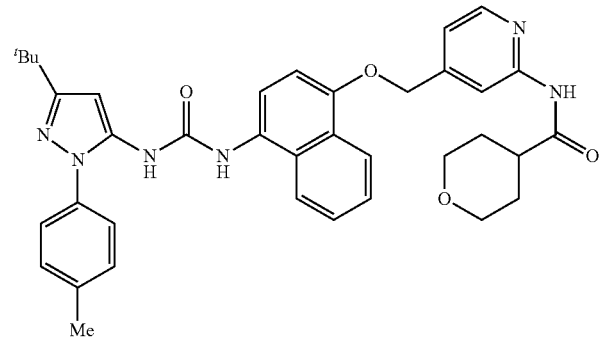

Example 3

Neat DMF (2 drops) was added to a stirred solution of tetrahydropyran-2H-4-carboxylic acid and oxalyl chloride (21 μL, 0.25 mmol) in DCM (1.0 mL) and the resulting solution was stirred at RT for 1 hr. The solution was evaporated in vacuo to give a colourless oil, which was redissolved in DCM (1.0 mL) and added dropwise to a stirred mixture of Intermediate A (50 mg, 0.10 mmol) and DIPEA (84 μL, 0.50 mmol) in DCM (1.0 mL). Stirring was continued for 18 hr. The reaction mixture was stirred in 1% NH$_3$ in MeOH (20 mL) for 30 mins, evaporated in vacuo, pre-adsorbed on silica, and purified by column chromatography (12 g, 0-5% MeOH in DCM, gradient elution) to give the title compound (Example 3) as a light tan solid (18 mg, 28%): m/z 633 (M+H)$^+$ (ES$^+$). $^1$H NMR (400 MHz, DMSO-d$_6$) δ: 1.26 (9H, s), 1.57-1.72 (4H, m), 2.38 (3H, s), 2.75 (1H, m), 3.28-3.33 (2H, m), 3.88 (2H, m), 5.35 (2H, s), 6.34 (1H, s), 6.99 (1H, d), 7.24 (1H, dd), 7.35 (2H, m), 7.43 (2H, m), 7.55-7.64 (3H, m), 7.92 (1H, m), 8.27-8.33 (3H, m), 8.58 (1H, s), 8.78 (1H, s), 10.50 (1H, s).

Example 4

(S)-N-(4-((4-(3-(3-tert-Butyl-1-p-tolyl-1H-pyrazol-5-yl)ureido)naphthalen-1-yloxy)methyl)pyridin-2-yl)-2-methoxypropanamide

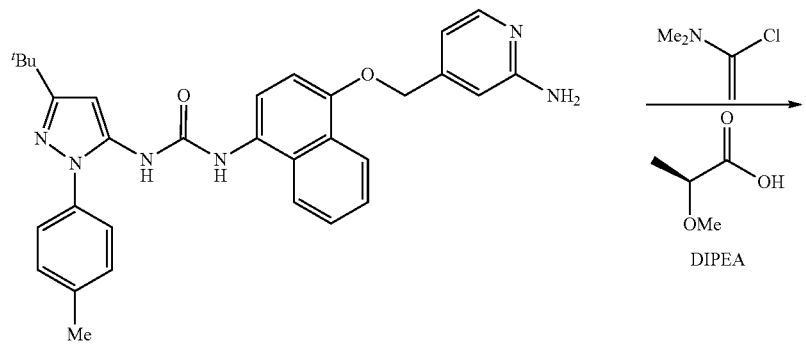

Intermediate A

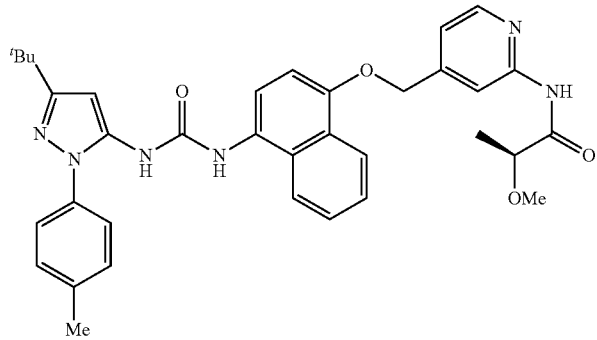

Example 4

1-Chloro-N,N-dimethylethenamine (50 μL, 0.48 mmol) was added to a stirring solution of (S)-2-methoxypropionic acid (50 mg, 0.48 mmol) in DCM (1.0 mL) and the resulting yellow solution was stirred at RT for 1 hr. The solution was added dropwise to a stirring mixture of Intermediate A (50 mg, 0.10 mmol) and DIPEA (167 μL, 0.96 mmol) in DCM (1.0 mL). Stirring was continued overnight. The reaction mixture was stirred in 1% $NH_3$ in MeOH (20 mL), evaporated in vacuo, pre-adsorbed on silica and purified by column chromatography (12 g, 10-50% EtOAc in isohexane, gradient elution) to give the title compound (Example 4) as a colourless solid (18 mg, 30%): m/z 607 (M+H)$^+$ (ES$^+$). $^1$H NMR (400 MHz, DMSO-d$_6$) δ: 1.27 (9H, d), 1.31 (3H, s), 2.38 (3H, s), 3.30 (3H, s), 4.02 (1H, q), 5.39 (2H, s), 6.37 (1H, s), 7.00 (1H, d), 7.29 (1H, dd), 7.35 (2H, m), 7.45 (2H, m), 7.56-7.64 (3H, m), 7.93 (1H, m), 8.30-8.37 (3H, m), 8.58 (1H, s), 8.79 (1H, s), 10.06 (1H, s).

Example 5

(R)-N-(4-((4-(3-(3-tert-Butyl-1-p-tolyl-1H-pyrazol-5-yl)ureido)naphthalen-1-yloxy)methyl)pyridin-2-yl)-2-methoxypropanamide

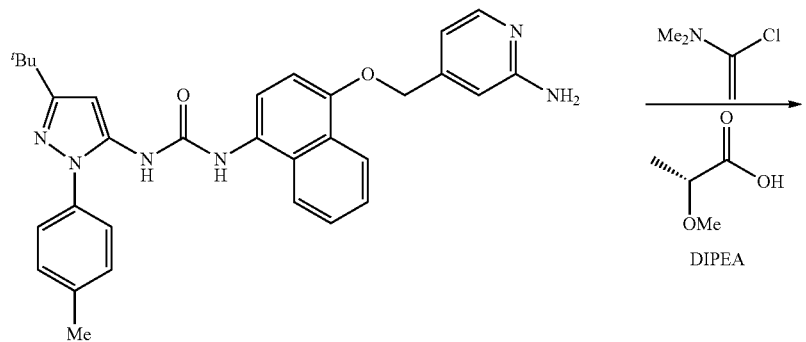

Intermediate A

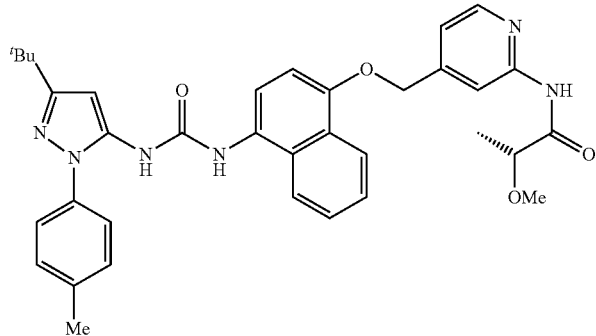

Example 5

1-Chloro-N,N-dimethylethenamine (38 μL, 0.36 mmol) was added to a stirred solution of (R)-2-methoxypropionic acid (37 mg, 0.36 mmol) in DCM (1.0 mL) and the resulting solution was stirred at RT for 1 hr. The solution was added dropwise to a stirred mixture of Intermediate A (75 mg, 0.14 mmol) and DIPEA (75 μL, 0.43 mmol) in DCM (2.0 mL) at 0° C. Stirring was continued for a further 48 hr. The mixture was poured in to 1% $NH_3$ in MeOH (20 mL) and stirred for 1 hr, and evaporated in vacuo to give a yellow residue. Column chromatography (12 g, 20-50% EtOAc in isohexane) gave the title compound (Example 5) as a light pink solid (39 mg, 43%): m/z 607 (M+H)$^+$ (ES$^+$). $^1$H NMR (400 MHz, DMSO-$d_6$) δ: 1.27 (9H, d), 1.30 (3H, s), 2.39 (3H, s), 3.31 (3H, s), 4.02 (1H, q), 5.39 (2H, s), 6.35 (1H, s), 7.02 (1H, d), 7.29 (1H, dd), 7.35 (2H, m), 7.45 (2H, m), 7.56-7.64 (3H, m), 7.93 (1H, m), 8.30-8.37 (3H, m), 8.58 (1H, s), 8.79 (1H, s), 10.09 (1H, s).

Example 6

N-(4-((4-(3-(3-tert-Butyl-1-p-tolyl-1H-pyrazol-5-yl)ureido)naphthalen-1-yloxy)methyl)pyridin-2-yl)-2-(methylsulfonyl)acetamide

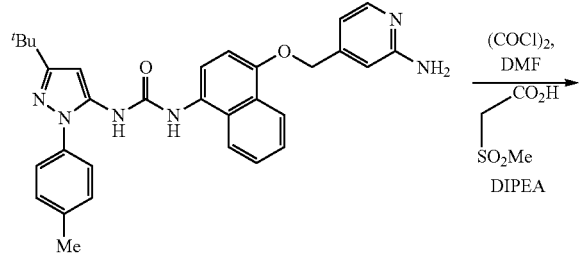

Intermediate A

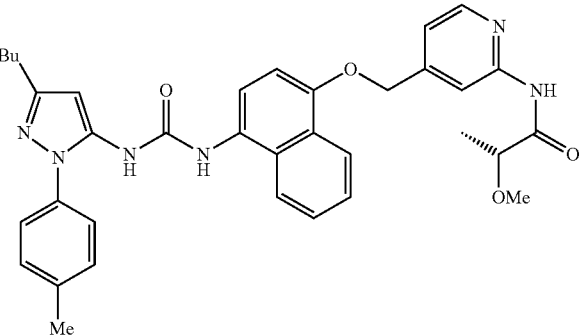

Example 6

To a stirred suspension of methanesulfonylacetic acid (40 mg, 0.29 mmol) and oxalyl chloride (29 μL, 0.34 mmol) in DCM (1.0 mL) was added DMF (1 drop) and the reaction mixture was stirred at RT for 1 hr. The solution was added dropwise to a stirred mixture of Intermediate A (50 mg, 0.10 mmol) and DIPEA (167 μL, 1.0 mmol) in DCM/DMF (10:1 v/v, 1.1 mL) and stirring was continued for 18 hr. The reaction mixture was stirred with 1% $NH_3$ in MeOH (2.0 mL) and evaporated in vacuo. The residue was subjected to capture and release on SCX to afford the title compound (Example 6) as a pale yellow solid (11 mg, 18%): m/z 641 (M+H)$^+$ (ES$^+$). $^1$H NMR (400 MHz, DMSO-$d_6$) δ: 1.27 (9H, s), 2.39 (3H, s), 3.17 (3H, s), 4.44 (2H, s), 5.40 (2H, s), 6.35 (1H, s), 7.02 (1H, d), 7.33 (1H, dd), 7.36 (2H, m), 7.44 (2H, m), 7.56-7.64 (3H, overlapping m), 7.93 (1H, m), 8.30-8.33 (2H, overlapping m), 8.39 (1H, dd), 8.59 (1H, br s), 8.79 (1H, br s), 10.98 (1H, br s).

Example 7

N-(4-((4-(3-(3-tert-Butyl-1-p-tolyl-1H-pyrazol-5-yl)ureido)naphthalen-1-yloxy)methyl)pyridin-2-yl)-2-hydroxyacetamide

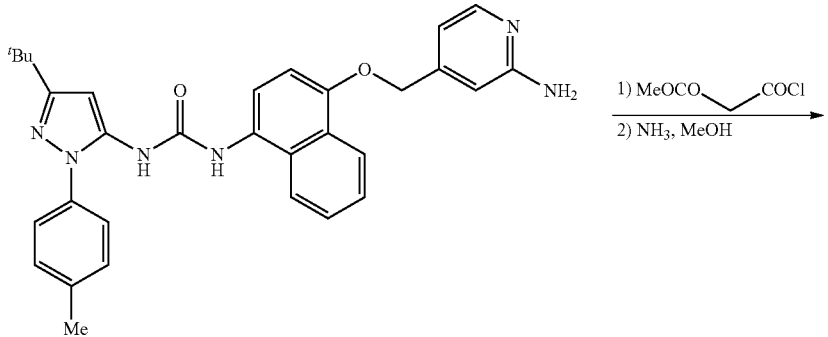

Intermediate A

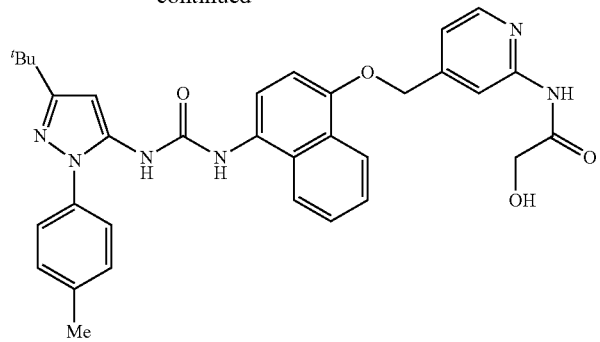

Example 7

To a solution of Intermediate A (75 mg, 0.14 mmol) and DIPEA (125 μL, 0.72 mmol) in DCM/DMF (10:1 v/v, 1.10 mL) was added a solution of acetoxyacetyl chloride (39 μL, 0.36 mmol) in DCM (0.25 mL). The reaction mixture was stirred at RT for 2 hr and then 1% NH$_3$ in MeOH (3.0 mL) was added and stirring continued for 18 hr. The reaction mixture was evaporated in vacuo and the residue was purified by flash column chromatography (SiO$_2$, 12 g, 30-100% EtOAc in isohexane, gradient elution) to afford the title compound (Example 7) as a pale orange solid (24 mg, 28%): m/z 579 (M+H)$^+$ (ES$^+$). $^1$H NMR (400 MHz, DMSO-d$_6$) δ: 1.27 (9H, s), 2.39 (3H, s), 4.06 (2H, d), 5.39 (2H, s), 5.77 (1H, t), 6.35 (1H, s), 7.02 (1H, d), 7.29 (1H, dd), 7.36 (2H, m), 7.44 (2H, m), 7.56-7.64 (3H, overlapping m), 7.93 (1H, m), 8.32 (1H, m) 8.34 (1H, d), 8.36 (1H, br s), 8.60 (1H, br s), 8.81 (1H, br s), 9.75 (1H, br s).

Example 8

N-(4-((4-(3-(3-tert-Butyl-1-p-tolyl-1H-pyrazol-5-yl)ureido)naphthalen-1-yloxy)methyl)pyridin-2-yl)-2-methyl-2-(methylamino)propanamide

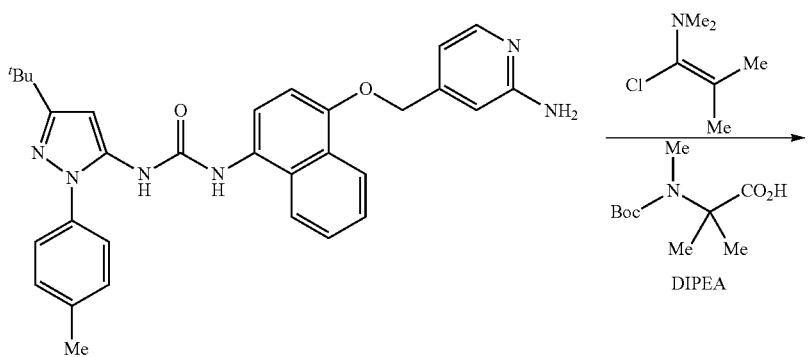

Intermediate A

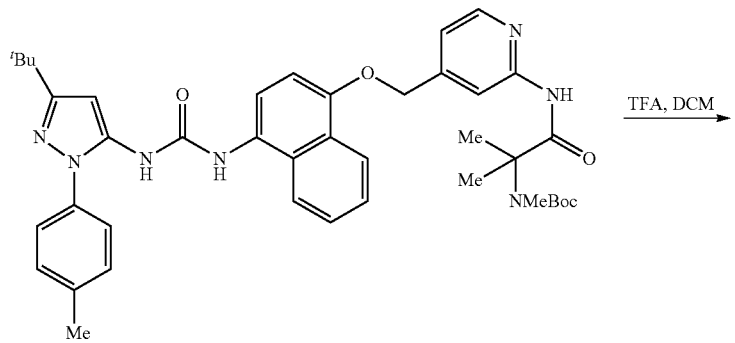

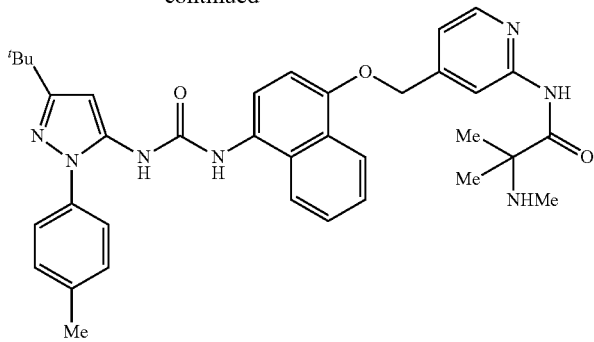

Example 8

To a stirred suspension of 2-(tert-butoxycarbonyl(methyl) amino)-2-methylpropanoic acid (125 mg, 0.58 mmol) in DCM (2.0 mL) was added 1-chloro-N,N,2-trimethylprop-1-en-1-amine (95 µL, 0.72 mmol) and the mixture was stirred at RT for 2 hr. The reaction mixture was then added to a solution of Intermediate A (75 mg, 0.14 mmol) and DIPEA (101 µL, 0.58 mmol) in DCM (1.0 mL) and stirred for 18 hr. A solution of ammonia (7M in MeOH, 1 mL) was added and the mixture was evaporated in vacuo. The residue was purified twice by column chromatography ($SiO_2$, 12 g, 0-100% EtOAc in isohexane, gradient elution) to afford tert-butyl 1-(4-((4-(3-(3-tert-butyl-1-p-tolyl-1H-pyrazol-5-yl)ureido)naphthalen-1-yloxy)methyl)pyridin-2-ylamino)-2-methyl-1-oxopropan-2-yl(methyl)carbamate (6) as an off-white solid (30 mg, 28%): m/z 620 ((M-Boc)+H)$^+$ (ES$^+$).

A solution of the carbamate (6) (25 mg, 0.04 mmol) in DCM/TFA (1:1 v/v, 2.0 mL) was stirred at RT for 30 min. The reaction mixture was evaporated in vacuo and the resulting residue was subjected to SCX capture and release to afford the title compound (Example 8) as a pale brown solid (20 mg, 89%): m/z 620 (M+H)$^+$ (ES$^+$). $^1$H NMR (400 MHz, DMSO-$d_6$) δ: 1.25 (6H, s), 1.27 (9H, s), 2.20 (3H, s), 2.39 (3H, s), 5.38 (2H, s), 6.35 (1H, s), 7.00 (1H, d), 7.27 (1H, dd), 7.36 (2H, m), 7.44 (2H, m), 7.58-7.62 (3H, overlapping m), 7.93 (1H, m), 8.29-8.34 (3H, overlapping m), 8.59 (1H, br s), 8.79 (1H, br s).

Example 9

(S)-N-(4-((4-(3-(3-tert-Butyl-1-p-tolyl-1H-pyrazol-5-yl)ureido)naphthalen-1-yloxy)methyl)pyridin-2-yl)-2-(methylamino)propanamide

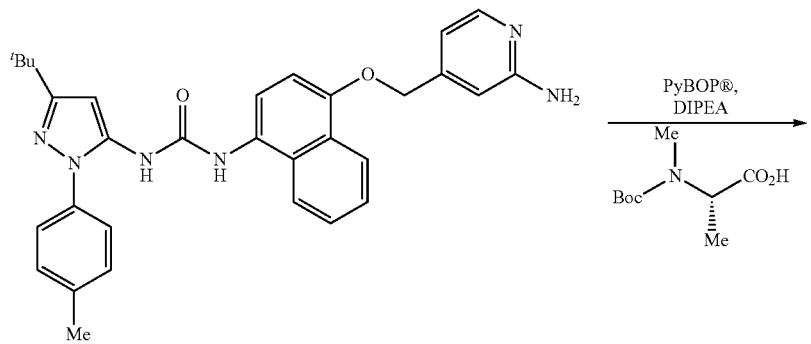

Intermediate A

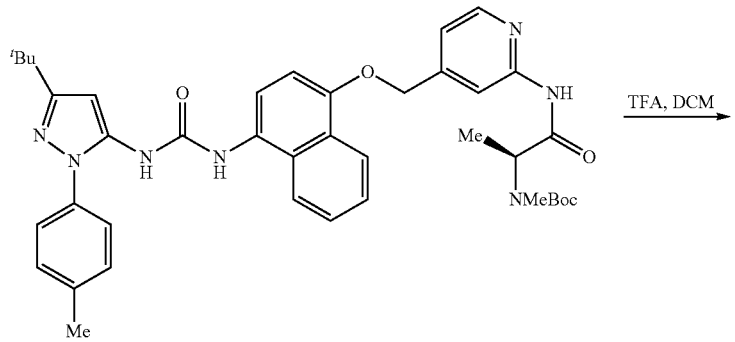

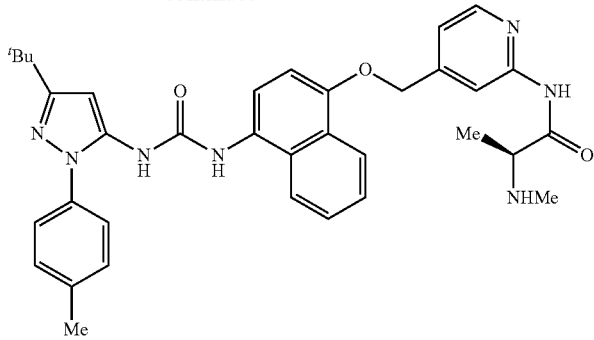

Example 9

To a stirred suspension of N-Boc-methyl-L-alanine (117 mg, 0.58 mmol), PyBOP® (300 mg, 0.58 mmol) and DIPEA (101 μL, 0.58 mmol) in DMF (2.0 mL) was added Intermediate A (75 mg, 0.14 mmol) in one portion. The reaction mixture was heated to 55° C. and stirred for 18 hr and was cooled to RT and partitioned between water (10 mL) and EtOAc (10 mL). The organic layer was separated and evaporated in vacuo and the residue was purified by flash column chromatography (SiO$_2$, 12 g, 0-100% EtOAc in isohexane, gradient elution). The resulting impure product was purified by SCX capture and release to afford (S)-tert-butyl 1-(4-((4-(3-(3-tert-butyl-1-p-tolyl-1H-pyrazol-5-yl)ureido)naphthalen-1-yloxy)methyl)pyridin-2-ylamino)-1-oxopropan-2-yl(methyl)carbamate (7) as a brown solid (25 mg, 23%): m/z 706 (M+H)$^+$ (ES$^+$).

A solution of the carbamate (7) (25 mg, 0.04 mmol) in DCM/TFA (1:1 v/v, 2.0 mL) was stirred at RT for 30 min. The reaction mixture was evaporated in vacuo and the resulting residue was subjected to SCX capture and release and then purified by flash column chromatography (SiO$_2$, 4 g, 0-100% EtOAc in MeOH, gradient elution) to afford the title compound (Example 9) as an off-white solid (13 mg, 57%): m/z 606 (M+H)$^+$ (ES$^+$). $^1$H NMR (400 MHz, DMSO-d$_6$) δ: 1.20 (3H, d), 1.27 (9H, s), 2.26 (3H, s), 2.39 (3H, s), 3.20 (1H, q), 5.38 (2H, s), 6.35 (1H, s), 7.01 (1H, d), 7.28 (1H, dd), 7.36 (2H, m), 7.44 (2H, m), 7.55-7.63 (3H, overlapping m), 7.93 (1H, m), 8.31 (1H, m), 8.34 (1H, dd), 8.36 (1H, br s), 8.60 (1H, s), 8.80 (1H, s).

Example 10

(R)-N-(4-((4-(3-(3-tert-Butyl-1-p-tolyl-1H-pyrazol-5-yl)ureido)naphthalen-1-yloxy)methyl)pyridin-2-yl)morpholine-3-carboxamide

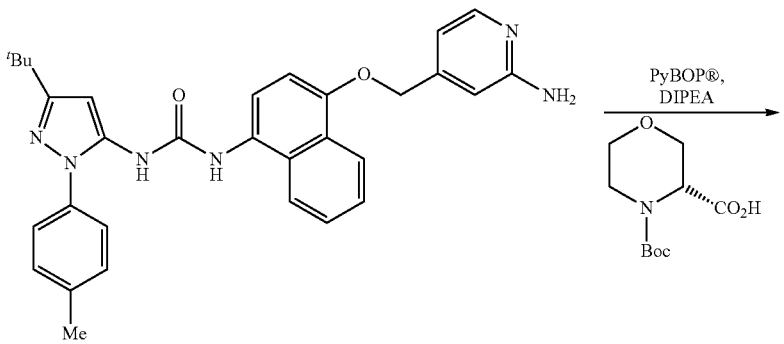

Intermediate A

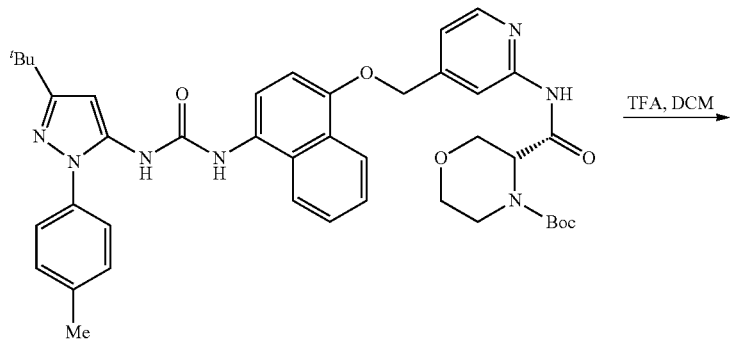

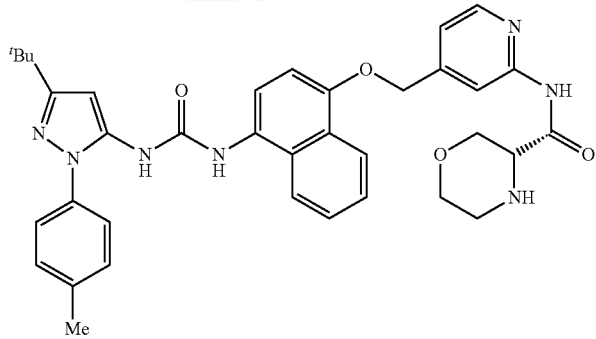

Example 10

To a stirred suspension of (R)-morpholine-3,4-dicarboxylic acid-4-tert-butyl ester (133 mg, 0.58 mmol), PyBOP® (300 mg, 0.58 mmol) and DIPEA (101 µL, 0.58 mmol) in DMF (2.0 mL) was added Intermediate A (75 mg, 0.14 mmol) in one portion. The reaction mixture was heated to 55° C. and stirred for 18 hr. The reaction mixture was cooled to RT and partitioned between water (10 mL) and EtOAc (10 mL). The organic extract was evaporated in vacuo and the residue was purified by flash column chromatography (SiO$_2$, 12 g, 0-100% EtOAc in isohexane, gradient elution) to afford an impure product which was purified further by SCX capture and release to give (R)-tert-butyl 3-(4-((4-(3-(3-tert-butyl-1-p-tolyl-1H-pyrazol-5-yl)ureido)naphthalen-1-yloxy)methyl)pyridin-2-ylcarbamoyl)morpholine-4-carboxylate (8) as a brown solid (28 mg, 25%): m/z 734 (M+H)$^+$ (ES$^+$).

A solution of the carbamate (8) (28 mg, 0.04 mmol) in DCM/TFA (1:1 v/v, 2.0 mL) was stirred at RT for 30 min. The reaction mixture was evaporated in vacuo and the resulting residue was subjected to capture and release on SCX and then triturated from diethyl ether (10 mL) to afford the title compound (Example 10) as an off-white solid (13 mg, 53%): m/z 634 (M+H)$^+$ (ES$^+$). $^1$H NMR (400 MHz, DMSO-d$_6$) δ: 1.26 (9H, s), 2.39 (3H, s), 2.73-2.92 (3H, overlapping m), 3.56-3.64 (4H, overlapping m), 3.82 (1H, m), 5.38 (2H, s), 6.35 (1H, s), 7.00 (1H, d), 7.29 (1H, dd), 7.36 (2H, m), 7.44 (2H, m), 7.58-7.62 (3H, overlapping m), 7.92 (1H, m), 8.28-8.35 (3H, overlapping m), 8.58 (1H, br s), 8.79 (1H, br s), 10.09 (1H, br s) [partial assignment].

Example 11

(S)-N-(4-((4-(3-(3-tert-Butyl-1-p-tolyl-1H-pyrazol-5-yl)ureido)naphthalen-1-yloxy)methyl)pyridin-2-yl)morpholine-3-carboxamide

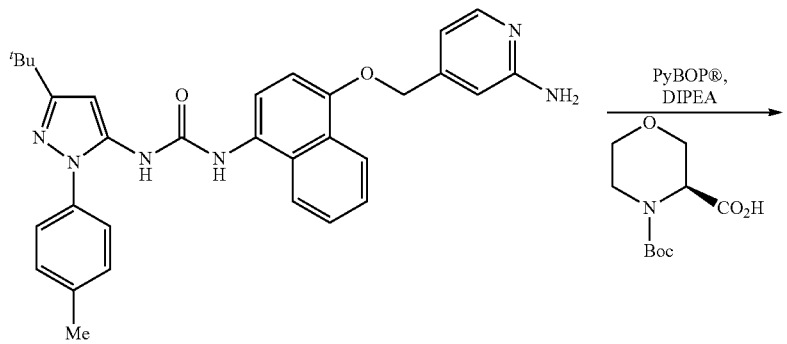

Intermediate A

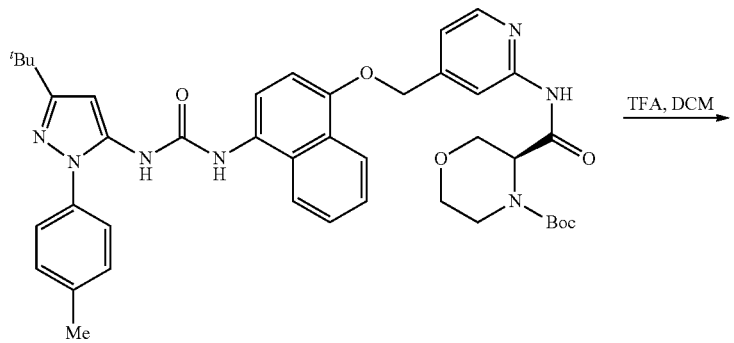

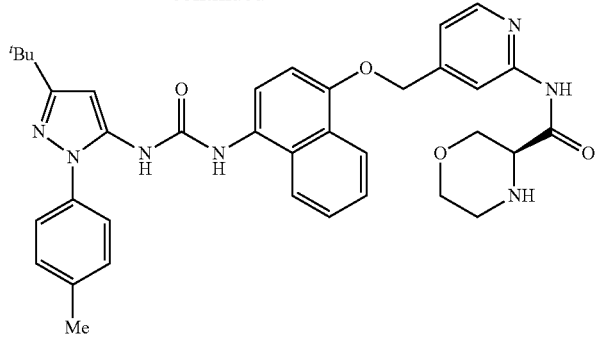

Example 11

To a stirred suspension of (S)-morpholine-3,4-dicarboxylic acid-4-tert-butyl ester (133 mg, 0.58 mmol), PyBOP® (300 mg, 0.58 mmol) and DIPEA (101 μL, 0.58 mmol) in DMF (2.0 mL) was added Intermediate A (75 mg, 0.14 mmol) in one portion. The reaction mixture was heated to 55° C. in a pre-heated oil bath and stirred for 18 hr. The reaction mixture was cooled to RT and partitioned between water (10 mL) and EtOAc (10 mL). The organic layer was separated, evaporated in vacuo and the residue was purified by column chromatography (12 g, 0-100% EtOAc in isohexane, gradient elution). Product fractions were concentrated in vacuo and the residue was triturated from DCM (5.0 mL) and isohexane (5.0 mL) to afford (S)-tert-butyl 3-(4-((4-(3-(3-tert-butyl-1-p-tolyl-1H-pyrazol-5-yl)ureido)naphthalen-1-yloxy)methyl)pyridin-2-ylcarbamoyl)morpholine-4-carboxylate (9) as a white solid (50 mg, 43%): m/z 734 (M+H)$^+$ (ES$^+$).

A solution of the carbamate (9) (30 mg, 0.04 mmol) in DCM/TFA (1:1 v/v, 2.0 mL) was stirred at RT for 1 hr and was then evaporated in vacuo. the resulting residue was subjected to capture and release on SCX and then triturated from DCM (5.0 mL) and isohexane (5.0 mL) to afford the title compound (Example 11) as a brown solid (15 mg, 63%): m/z 634 (M+H)$^+$ (ES$^+$). $^1$H NMR (400 MHz, DMSO-d$_6$) δ: 1.26 (9H, s), 2.39 (3H, s), 2.73-2.92 (3H, overlapping m), 3.56-3.64 (4H, overlapping m), 3.82 (1H, m), 5.38 (2H, s), 6.34 (1H, s), 7.00 (1H, d), 7.29 (1H, dd), 7.35 (2H, m), 7.42 (2H, m), 7.55-7.62 (3H, overlapping m), 7.91 (1H, m), 8.30 (1H, dd), 8.32 (1H, br s), 8.35 (1H, dd), 8.56 (1H, br s), 8.77 (1H, br s) 10.16 (1H, br s).

Example 12

N-(4-((4-(3-(3-tert-Butyl-1-p-tolyl-1H-pyrazol-5-yl)ureido)naphthalen-1-yloxy)methyl)pyridin-2-yl)-4-methylpiperazine-1-carboxamide

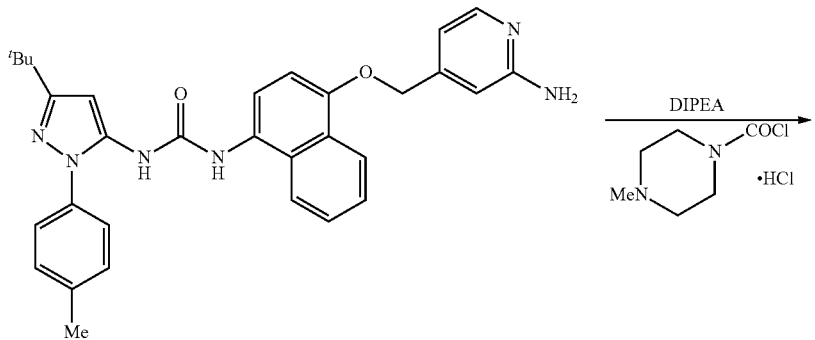

Intermediate A

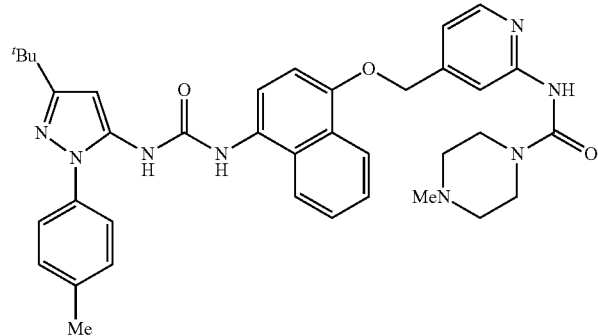

Example 12

To a solution of Intermediate A (50 mg, 0.10 mmol) in pyridine (1.0 mL) was added a suspension of 4-methylpiperazine-1-carbonyl chloride hydrochloride (38 mg, 0.19 mmol) in pyridine (1.50 mL). DIPEA (50 μL, 0.29 mmol) was added and the mixture was stirred at RT for 3 days. The reaction mixture was evaporated in vacuo and the residue was partitioned between DCM (10 mL) and water (10 mL). The organic layer was separated and evaporated in vacuo and the residue was purified by flash column chromatography (SiO$_2$, 4 g, 0-10% DCM in MeOH, gradient elution) to afford the title compound (Example 12) as a brown solid (17 mg, 27%): m/z 647 (M+H)$^+$ (ES$^+$). $^1$H NMR (400 MHz, DMSO-d$_6$) δ: 1.27 (9H, s), 2.18 (3H, s), 2.29 (4H, t), 2.39 (3H, s), 3.46 (4H, t), 5.32 (2H, s), 6.35 (1H, s), 6.99 (1H, d), 7.13 (1H, dd), 7.36 (2H, m), 7.44 (2H, m), 7.55-7.63 (3H, overlapping m), 7.92 (1H, m), 7.99 (1H, s), 8.25 (1H, d), 8.29 (1H, m), 8.60 (1H, br s), 8.80 (1H, br s), 9.22 (1H, br s).

Example 13

N-(4-((4-(3-(3-tert-Butyl-1-p-tolyl-1H-pyrazol-5-yl)ureido)naphthalen-1-yloxy)methyl)pyridin-2-yl)morpholine-4-carboxamide

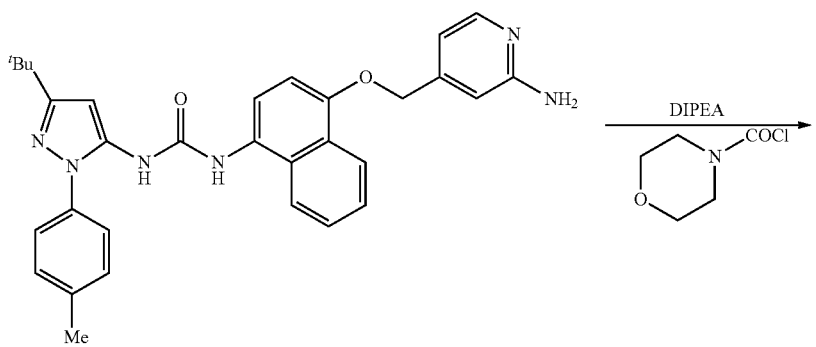

Intermediate A

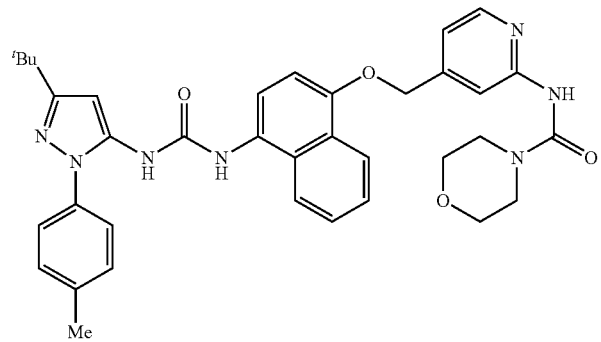

Example 13

To a solution of Intermediate A (70 mg, 0.13 mmol) in pyridine (1.50 mL) was added morpholine-4-carbonyl chloride (28 μL, 0.24 mmol) and the solution was stirred at RT for 18 hr. A further portion of morpholine-4-carbonyl chloride (28 μL, 0.24 mmol) was added to the reaction mixture and stirring continued for 24 hr. The mixture was stirred with 1% NH$_3$ in MeOH (3.0 mL) and then evaporated in vacuo. The residue was purified by flash column chromatography (SiO$_2$, 12 g, 0-5% MeOH in DCM, gradient elution) and recrystallized from isopropanol (5.0 mL) to afford the title compound (Example 13) as a white solid (17 mg, 20%): m/z 634 (M+H)$^+$ (ES$^+$). $^1$H NMR (400 MHz, DMSO-d$_6$) δ: 1.27 (9H, s), 2.39 (3H, s), 3.45 (4H, t), 3.59 (4H, t), 5.33 (2H, s), 6.35 (1H, s), 6.99 (1H, d), 7.14 (1H, dd), 7.36 (2H, m), 7.44 (2H, m), 7.55-7.63 (3H, overlapping m), 7.92 (1H, m), 8.01 (1H, br s), 8.26 (1H, d), 8.29 (1H, m), 8.58 (1H, br s), 8.79 (1H, br s), 9.27 (1H, br s).

Example 14

N-(4-((4-(3-(3-tert-Butyl-1-p-tolyl-1H-pyrazol-5-yl)ureido)naphthalen-1-yloxy)methyl)pyridin-2-yl)-3-methoxypropanamide

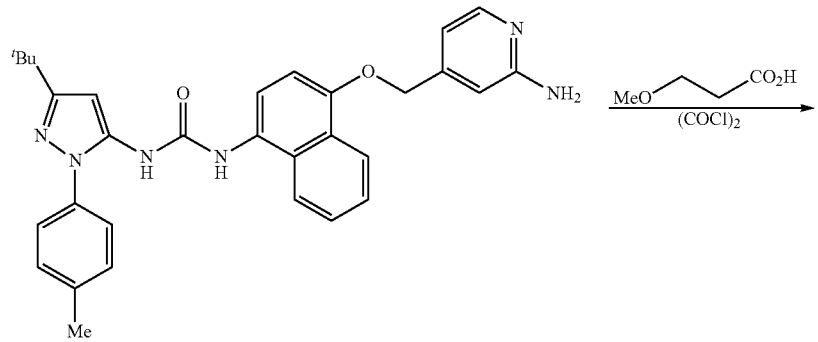

Intermediate A

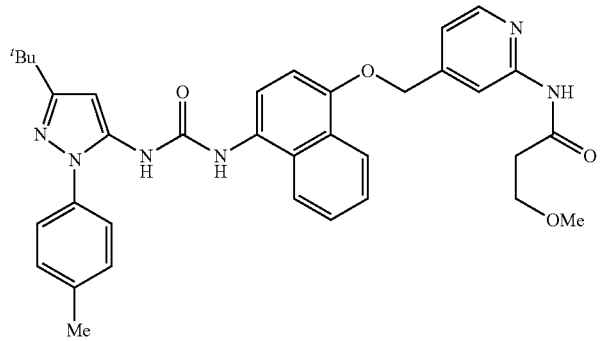

Example 14

Oxalyl chloride (11.0 μL, 0.115 mmol) and then DMF (1 drop) were added to a suspension of 3-methoxypropionic acid (9.0 μL, 0.096 mmol) in DCM (1 mL) and the mixture was stirred at 0° C. for 10 min and then allowed to warm to RT. After 2 hr the solvent was removed in vacuo and the residue was taken up in to DCM (1 mL) and added to a solution of Intermediate A (50 mg, 0.096 mmol) and DIPEA (33.5 μL, 0.192 mmol) in DCM (1 mL). After 16 hr the mixture was quenched by the addition of saturated aqueous NaHCO$_3$ solution. The organic layer was separated and a solution of NH$_3$ in MeOH (7M) was added and the mixture was stirred for 10 min and then evaporated in vacuo. The residue was purified by flash chromatography (SiO$_2$, 4 g, 0 to 100% EtOAc in isohexane, gradient elution) to afford the title compound (Example 14) as a pale yellow solid (15 mg, 26%). m/z 607 (M+H)$^+$ (ES$^+$). $^1$H NMR (400 MHz, DMSO-d$_6$) δ: 1.27 (9H, s), 2.39 (3H, s), 2.65 (2H, t), 3.23 (3H, s), 3.61 (2H, t), 5.37 (2H, s), 6.35 (1H, s), 7.00 (1H, d), 7.25 (1H, d), 7.36 (2H, m), 7.44 (2H, m), 7.56-7.63 (3H, overlapping m), 7.83-7.85 (1H, d), 7.93 (1H, d), 8.29-8.34 (3H, overlapping m), 8.62 (1H, br s), 8.82 (1H, br s), 10.54 (1H, br s).

Example 15

2-(3-(4-((4-(3-(3-tert-Butyl-1-p-tolyl-1H-pyrazol-5-yl)ureido)naphthalen-1-yloxy)methyl)pyridin-2-yl)ureido)-N-(2-methoxyethyl)acetamide

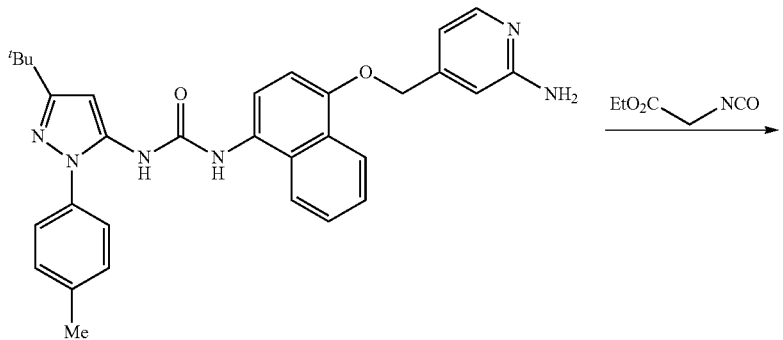

Intermediate A

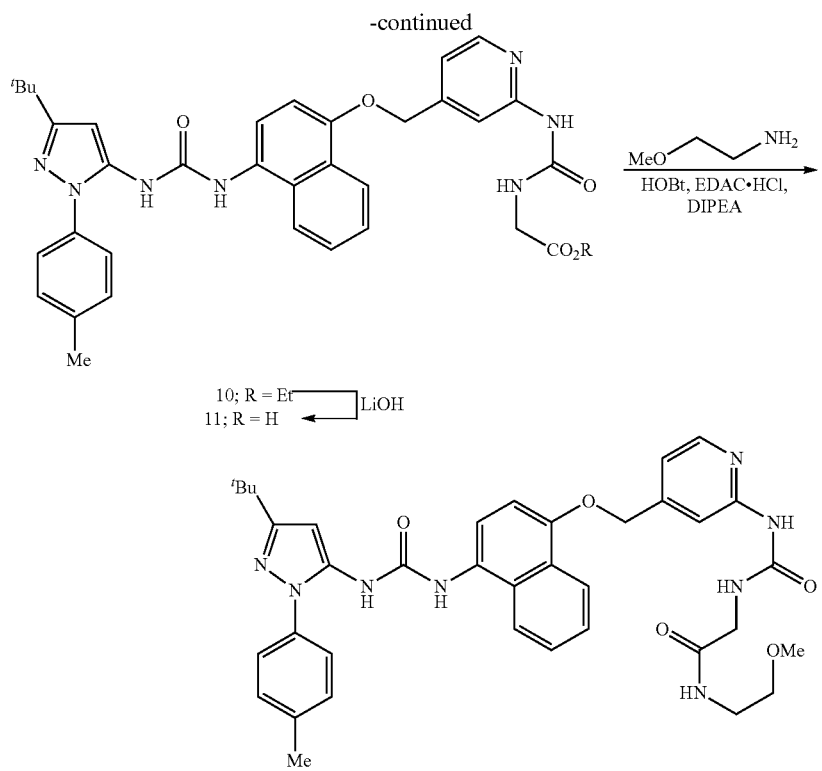

10; R = Et  
11; R = H  ← LiOH

Example 15

To a solution of Intermediate A (200 mg, 0.384 mmol) in pyridine (3 mL) was added ethyl isocyanatoacetate (129 μL, 1.152 mmol) and the reaction was stirred at RT for 16 hr. The mixture was evaporated in vacuo and was then co-evaporated with toluene and the residue was triturated with methanol to afford ethyl 2-(3-(4-((4-(3-(3-tert-butyl-1-p-tolyl-1H-pyrazol-5-yl)ureido)naphthalen-1-yloxy)methyl)pyridin-2-yl)ureido)acetate (10) as a solid (191 mg, 76%): m/z 650 $(M+H)^+$, $(ES^+)$.

To a suspension of the ester (10) (200 mg, 0.308 mmol) in a mixture of $THF/H_2O$ (4:1 v/v, 5 mL) was added lithium hydroxide (10.0 mg, 0.418 mmol) and the mixture was stirred at RT for 1 hr. The reaction mixture was acidified to pH3, by the addition of 1M hydrochloric acid and evaporated in vacuo to half of its original volume. The resulting preciptate was collected by filtration and was washed with water and dried in vacuo to provide 2-(3-(4-((4-(3-(3-)-butyl-1-p-tolyl-1H-pyrazol-5-yl)ureido)naphthalen-1-yloxy)methyl)pyridin-2-yl)ureido)acetic acid (11) (185 mg, 97%): m/z 622 $(M+H)^+$, $(ES^+)$.

To a suspension of the acid (11) (60 mg, 0.097 mmol) in DCM (1.5 mL) was added 2-methoxyethylamine (25.0 μL, 0.290 mmol), HOBt (19.56 mg, 0.145 mmol), DIPEA (50.5 μL, 0.290 mmol), and EDC. HCl (27.8 mg, 0.145 mmol) and the mixture was stirred at RT for 1 hr. The reaction mixture became very viscous and was diluted with DMF (1 mL) and stirred for 16 hr. The reaction mixture was diluted with DCM and was washed with water. The organic phase was dried $(MgSO_4)$ and the solvent was evaporated in vacuo. The residue was triturated with MeOH to afford the title compound (Example 15) as an off white solid (22 mg, 34%): m/z 679 $(M+H)^+$, $(ES^+)$. $^1H$ NMR (400 MHz, DMSO-$d_6$) δ: 1.27 (9H, s), 2.39 (3H, s), 3.24 (3H, s), 3.25 (2H, m), 3.34 (2H, m), 3.82 (2H, d), 5.31 (2H, s), 6.35 (1H, s), 7.00 (1H, d), 7.07 (1H, d), 7.36 (2H, m), 7.44 (2H, m), 7.58-7.65 (4H, overlapping m), 7.93 (1H, m), 8.03 (1H, t), 8.21 (1H, d), 8.34 (1H, m), 8.51 (1H, very br s), 8.58 (1H, br s), 8.79 (1H, br s), 9.46 (1H, br s)

Example 16

N-(4-((4-(3-(3-tert-Butyl-1-p-tolyl-1H-pyrazol-5-yl)ureido)naphthalen-1-yloxy)methyl)pyridin-2-yl)-4-(dimethylamino)butanamide

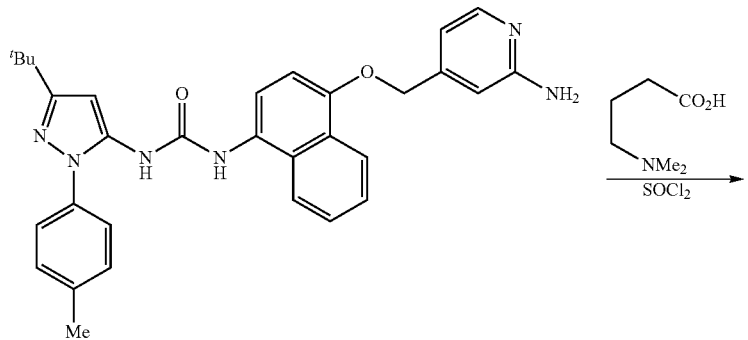

Intermediate A

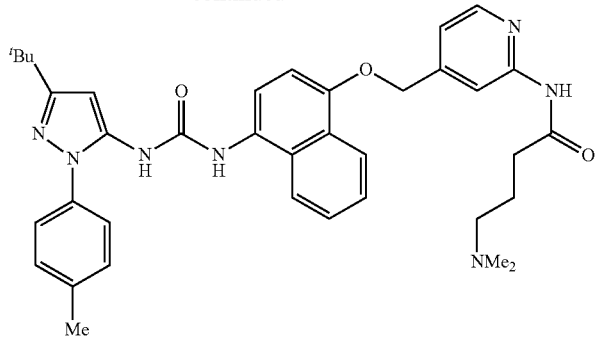

Example 16

To a stirred suspension of 4-(dimethylamino)butyric acid. HCl (97 mg, 0.576 mmol) in DCM (2 mL) at 0° C. was added thionyl chloride (42.0 μL, 0.576 mmol) and DMF (one drop) and the mixture was allowed to warm to RT. After 16 hr the reaction mixture was evaporated in vacuo and the residue was dissolved in DCM/THF (1:1 v/v, 2 mL) and added to a solution of Intermediate A (60 mg, 0.115 mmol) in THF (1 mL) containing DIPEA (101 μL, 0.576 mmol). The mixture was stirred at 55° C. and after 4 hr the mixture was cooled to RT, diluted with water (10 mL) and was extracted with EtOAc (10 mL). The organic layer was separated and was treated with a solution of ammonia (7M in MeOH, 2 mL) for 5 min and the mixture evaporated in vacuo. The residue was purified by flash column chromatography (SiO$_2$, 12 g, (10% NH$_3$ in MeOH)-EtOAc gradient elution) to afford the title compound (Example 16) as a pale brown solid (25 mg, 34%): m/z 634 (M+H)$^+$ (ES$^+$); $^1$H NMR (400 MHz, DMSO-d$_6$) δ: 1.27 (9 H, s), 1.74 (2H, m), 2.21 (6H, s), 2.35 (2H, m), 2.39 (3 H, s), 2.40 (2H, m), 5.36 (2H, s), 6.35 (1H, s), 7.01 (1H, d), 7.24 (1H, d), 7.36 (2H, m), 7.44 (2H, m), 7.54-7.63 (3H, overlapping m), 7.93 (1H, m), 8.30-8.37 (3H, overlapping m), 8.59 (1H, s), 8.79 (1H, s), 10.54 (1H, br s).

Example 17

N-(4-((4-(3-(3-tert-Butyl-1-p-tolyl-1H-pyrazol-5-yl)ureido)naphthalen-1-yloxy)methyl)pyridin-2-yl)-3-(methylsulfonyl)propanamide

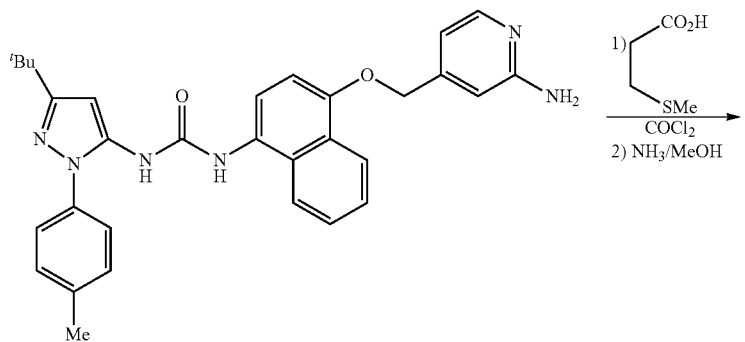

Intermediate A

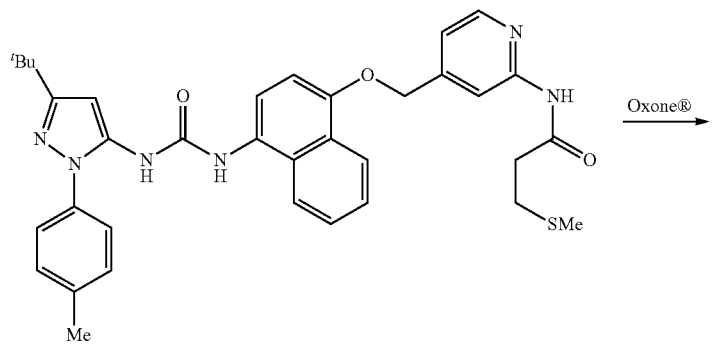

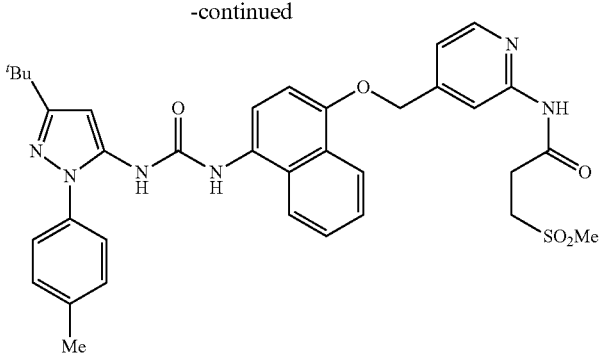

Example 17

To a suspension of 3-methanethiopropionic acid (117 mg, 0.97 mmol) in DCM (1 mL) was added oxalyl chloride (85.0 µL, 0.97 mmol), followed by DMF (2 drops) and the mixture was stirred at RT for 1 hr. The solvent was removed by evaporation in vacuo and the residue was redissolved in DCM (2.5 mL) and then added dropwise to a solution of Intermediate A (145 mg, 0.28 mmol) and DIPEA (218 µL, 1.25 mmol) in DCM (2 mL). After 2 hr a solution of ammonia (7M in MeOH, 3 mL) was added and stirring was continued for 1 hr. The volatiles were evaporated in vacuo and the residue was purified by flash column chromatography (SiO$_2$, 12 g, 0-5% MeOH in DCM, gradient elution) to afford N-(4-((4-(3-(3-tert-butyl-1-p-tolyl-1H-pyrazol-5-yl)ureido)naphthalen-1-yloxy)methyl)pyridin-2-yl)-3-(methylthio)propanamide (12) (0.11 g, 61%): m/z 623 (M+H)$^+$ (ES$^+$).

To a stirred solution of the sulfide (12) (47 mg, 0.075 mmol) in DMF (0.5 mL) was added a solution of Oxone (93 mg, 0.151 mmol) in water (1 mL). After 10 min a precipitate had formed and MeOH (2 mL) was added and stirring continued for 1 hr. The mixture was diluted with a further aliquot of MeOH (2 mL) and glacial AcOH (0.5 mL) was added. The suspension was subjected to SCX capture and release and then purified by flash column chromatography (SiO$_2$, 12 g, 2-8% MeOH in DCM, gradient elution) to afford the title compound (Example 17) (20 mg, 38%): m/z 655 (M+H)$^+$ (ES$^+$). $^1$H NMR (400 MHz, DMSO-d$_6$) δ: 1.27 (9H, s), 2.39 (3H, s), 2.90 (2H, t), 3.01 (3H, s), 3.43 (2H, t), 5.38 (2H, s), 6.35 (1H, s), 7.00 (1H, d), 7.27 (1H, dd), 7.36 (2H, m), 7.44 (2H, m), 7.56-7.65 (3H, overlapping m), 7.93 (1H, m), 8.29-8.33 (2H, overlapping m), 8.34 (1H, d), 8.58 (1H, br s), 8.79 (1H, br s), 10.72 (1H, br s).

Example 18

N-(4-((4-(3-(3-tert-Butyl-1-p-tolyl-1H-pyrazol-5-yl)ureido)naphthalen-1-yloxy)methyl)pyridin-2-yl)-3-(methylsulfonyl)-2-oxoimidazolidine-1-carboxamide

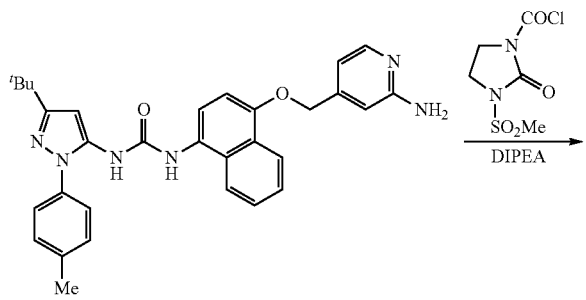

Intermediate A

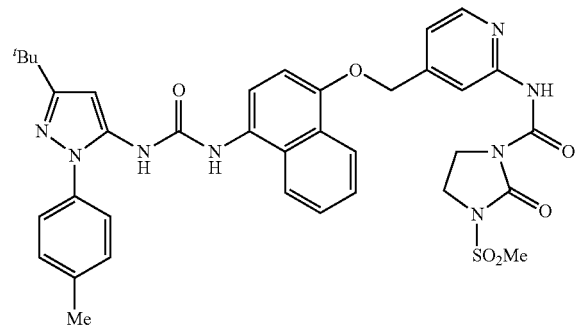

Example 18

To a solution of Intermediate A (100 mg, 0.192 mmol) in pyridine (1.5 mL) was added 3-chlorocarbonyl-1-methanesulfonyl-2-imidazolidinone (131 mg, 0.576 mmol) in pyridine (1.5 mL) and the reaction mixture was stirred at RT. After 3 days the reaction mixture was evaporated in vacuo and the residue was stirred with NH$_3$ (1% v/v in MeOH). The solvent was evaporated in vacuo and the residue was purified by flash column chromatography (SiO$_2$, 4 g, 100% DCM then 2% MeOH in DCM, isocratic elutions) to afford an impure product which was recrystallized from methanol to give the title compound (Example 18) as a white crystalline solid (12 mg, 9%): m/z 711 (M+H)$^+$ (ES$^+$). $^1$H NMR (400 MHz, DMSO-d$_6$) δ: 1.27 (9H, s), 2.39 (3H, s), 3.39 (3H, s), 3.87 (4H, s), 5.40 (2H, s), 6.35 (1H, s), 7.01 (1H, d), 7.31 (1H, dd), 7.36 (2H, m), 7.44 (2H, m), 7.55-7.63 (3H, m), 7.93 (1H, m), 8.21 (1H, br s), 8.31 (1H, m), 8.35 (1H, d), 8.58 (1H, br s), 8.79 (1H, br s), 10.40 (1H, br s).

Intermediate B

N-(4-((4-(3-(3-tert-Butyl-1-p-tolyl-1H-pyrazol-5-yl)ureido)naphthalen-1-yloxy)methyl)pyridin-2-yl)-2-chloroacetamide

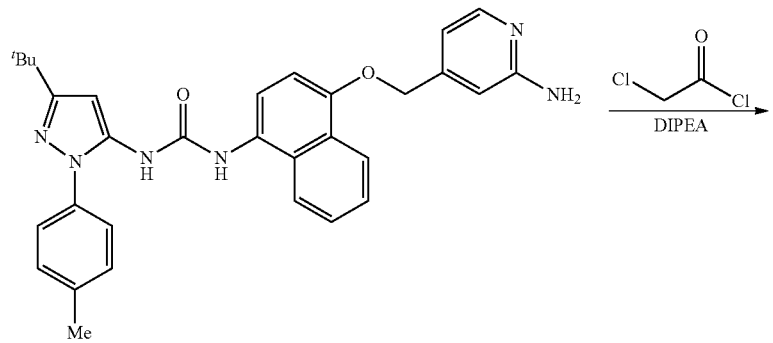

Intermediate A

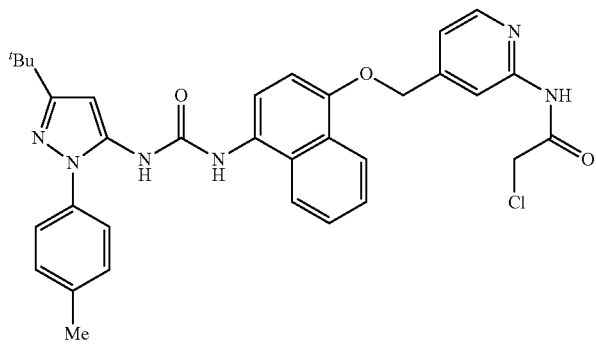

Intermediate B

To a solution of DIPEA (1.37 mL, 7.68 mmol) and Intermediate A (2.00 g, 3.84 mmol) in DCM (40 mL) and DMF (8.0 mL) was added chloroacetyl chloride (0.61 mL, 7.68 mmol). The reaction mixture was stirred at RT for 1 hr and a further portion of chloroacetyl chloride (100 µl, 1.25 mmol) was added. After 1 hr at RT, the reaction mixture was partitioned between DCM (40 mL) and saturated aq NaHCO$_3$ solution (40 mL). The organic phase was concentrated in vacuo and purified by column chromatography (80 g, 0-10% MeOH in DCM, gradient elution). Product fractions were concentrated in vacuo and the residue triturated with diethyl ether (20 mL) and isohexane (20 mL). The solid was collected by filtration to afford the title compound (Intermediate B) as a pale purple solid (1.07 g, 42%): m/z 597, 599 (M+H)$^+$ (ES$^+$).

Example 19

N-(4-((4-(3-(3-tert-Butyl-1-p-tolyl-1H-pyrazol-5-yl)ureido)naphthalen-1-yloxy)methyl)pyridin-2-yl)-2-(methylthio)acetamide

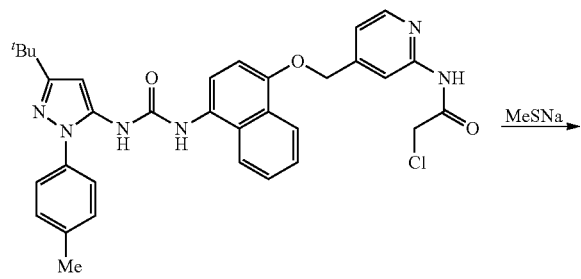

Intermediate B

Example 19

Intermediate B (100 mg, 0.17 mmol) was added portionwise to a stirred solution of sodium thiomethoxide (35 mg, 0.50 mmol) in MeOH (5.0 mL) and the resulting mixture was stirred at RT for 1 hr. The mixture was evaporated in vacuo and partitioned between brine (20 mL) and DCM (30 mL). The organic layer was concentrated in vacuo, the residue pre-adsorbed on silica and purified by column chromatography (SIO$_2$, 12 g, 10-100% EtOAc in isohexane, gradient elution). Product fractions were evaporated in vacuo to give the title compound (Example 19) as a light yellow solid (28 mg, 26%): m/z 610 (M+H)$^+$ (ES$^+$). $^1$H NMR (400 MHz, DMSO-d$_6$) δ: 1.27 (9H, s), 2.16 (3H, s), 2.39 (3H, s), 3.53 (2H, s), 5.37 (2H, s), 6.35 (1H, s), 7.01 (1H, d), 7.26 (1H, dd), 7.35 (2H, m), 7.44 (2H, m), 7.55-7.64 (3H, m), 7.92 (1H, m), 8.30-8.35 (3H, m), 8.58 (1H, s), 8.78 (1H, s), 10.60 (1H, s).

Example 20

N-(4-((4-(3-(3-tert-Butyl-1-p-tolyl-1H-pyrazol-5-yl)ureido)naphthalen-1-yloxy)methyl)pyridin-2-yl)-2-(methylsulfinyl)acetamide

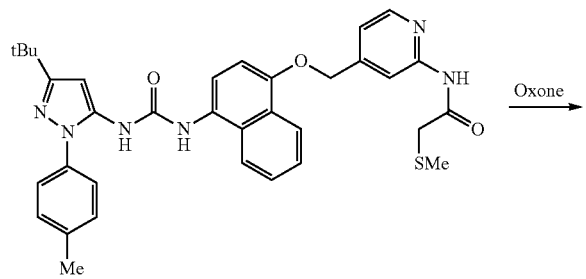

Example 19

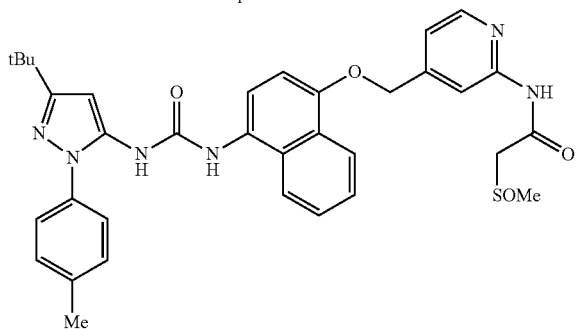

Example 20

To a solution of N-(4-((4-(3-(3-tert-butyl-1-p-tolyl-1H-pyrazol-5-yl)ureido)naphthalen-1-yloxy)methyl)pyridin-2-yl)-2-(methylthio)acetamide (Example 19) (20 mg, 0.03 mmol) in a mixture of DMF/H$_2$O (1:1 v/v, 1.0 mL) was added Oxone (10 mg, 0.03 mmol) and the reaction was stirred at RT for 3 days. A second portion of Oxone® (10 mg, 0.03 mmol) was added, the mixture was stirred for a further 24 hr and was then partitioned between brine (20 mL) and DCM (20 mL). The organic extract was washed with brine (20 mL), dried (MgSO$_4$) and evaporated in vacuo and the residue was purified by flash column chromatography (SiO$_2$, 4 g, 30-100% EtOAc in isohexane, gradient elution) and subjected to SCX capture and release to afford the title compound (Example 20) as a tan coloured solid (11 mg, 52%): m/z 625 (M+H)$^+$(ES$^+$). $^1$H NMR (400 MHz, DMSO-d$_6$) δ: 1.27 (9H, s), 2.39 (3H, s), 2.69 (3H, s), 3.88 (2H, d), 4.04 (2H, d) 5.39 (2H, s), 6.35 (1H, s), 7.02 (1H, d), 7.31 (1H, dd), 7.36 (2H, m), 7.44 (2H, m), 7.58-7.64 (3H, overlapping m), 7.93 (1H, m), 8.30-8.33 (2H, overlapping m), 8.37 (1H, d), 8.59 (1H, br s), 8.79 (1H, br s), 10.85 (1H, br s).

Example 21

N-(4-((4-(3-(3-tert-Butyl-1-p-tolyl-1H-pyrazol-5-yl)ureido)naphthalen-1-yloxy)methyl)pyridin-2-yl)-2-morpholinoacetamide

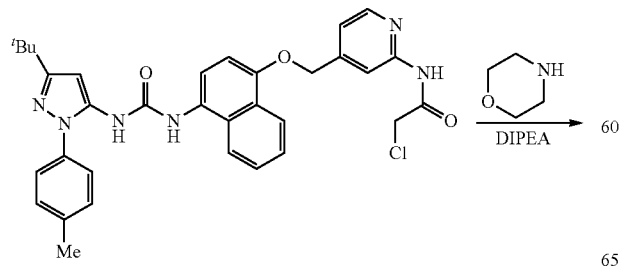

Intermediate B

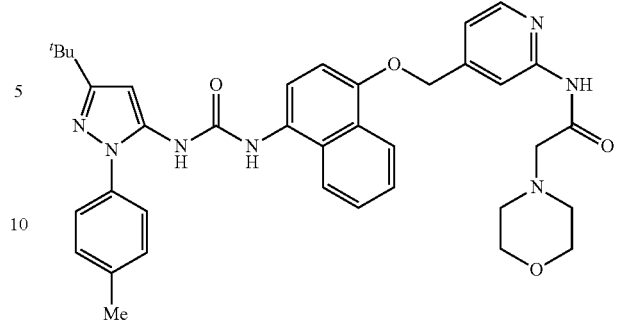

Example 21

To a stirred solution of Intermediate B (50 mg, 0.08 mmol) in a mixture of DCM (1.0 mL), DMF (0.1 mL) and DIPEA (21.9 μL, 0.13 mmol) was added morpholine (11.0 μL, 0.13 mmol). The reaction mixture was stirred at RT for 3 hr and then at 40° C. for 12 hr. A further portion of morpholine (11.0 μL, 0.13 mmol) was added and the reaction mixture stirred at 40° C. for 5 hr. The crude reaction mixture was purified by column chromatography (12 g, 0-10% MeOH in DCM, gradient elution). Product fractions were concentrated in vacuo and the residue was triturated with MeOH (5.0 mL). The solid was collected by filtration to afford the title compound (Example 21) as a light yellow solid (11 mg, 20%): m/z 648 (M+H)$^+$ (ES$^+$). $^1$H NMR (400 MHz, DMSO-d$_6$) δ: 1.27 (9 H, s), 2.39 (3 H, s), 2.54 (4 H, m), 3.20 (2 H, s), 3.63 (4 H, m), 5.39 (2H, s), 6.35 (1H, s), 7.01 (1H, d), 7.28 (1H, d), 7.35 (2H, d), 7.43 (2H, d), 7.63-7.56 (3H, m), 7.92 (1H, d), 8.37-8.29 (3H, m), 8.58 (1H, s), 8.79 (1H, s), 10.01 (1H, s).

Example 22

N-(4-((4-(3-(3-tert-Butyl-1-p-tolyl-1H-pyrazol-5-yl)ureido)naphthalen-1-yloxy)methyl)pyridin-2-yl)-2-(pyrrolidin-1-yl)acetamide

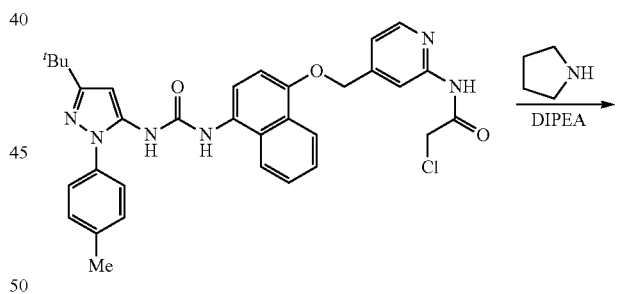

Intermediate B

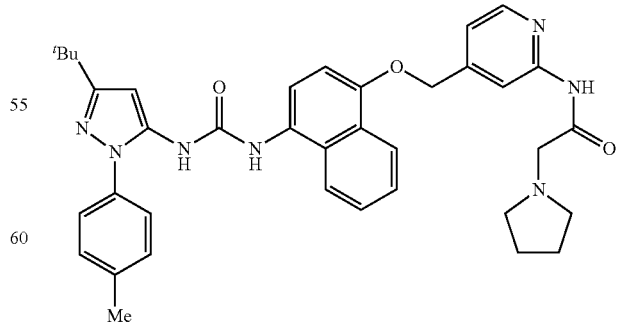

Example 22

To a solution of Intermediate B (50 mg, 0.08 mmol) in DCM (1.0 mL), DMF (0.1 mL) and DIPEA (22 μL, 0.13 mmol) was added pyrrolidine (7.0 μL, 0.08 mmol). The reaction mixture was stirred at RT for 3 hr and then at 40° C. for 12 hr. A further portion of pyrrolidine (7.0 μL, 0.08 mmol) was added and the reaction mixture stirred at 40° C. for 5 hr. The crude reaction mixture was purified by column chromatography (12 g, 0-10% MeOH in DCM, gradient elution) to afford the title compound (Example 22) as a light orange solid (17 mg, 32%): m/z 632 (M+H)$^+$ (ES$^+$). $^1$H NMR (400 MHz, DMSO-d$_6$) δ: 1.27 (9 H, s), 1.76 (4 H, m), 2.39 (3 H, s), 2.62 (4 H, m), 5.39 (2H, s), 6.35 (1H, s), 7.01 (1H, d), 7.28 (1H, d), 7.34 (2H, d), 7.44 (2H, d), 7.65-7.55 (3H, m), 7.92 (1H, d), 8.36-8.29 (3H, m), 8.58 (1H, s), 8.79 (1H, s), 9.93 (1H, s).

Example 23

N-(4-((4-(3-(3-tert-Butyl-1-p-tolyl-1H-pyrazol-5-yl)ureido)naphthalen-1-yloxy)methyl)pyridin-2-yl)-2-(4-methylpiperazin-1-yl)acetamide

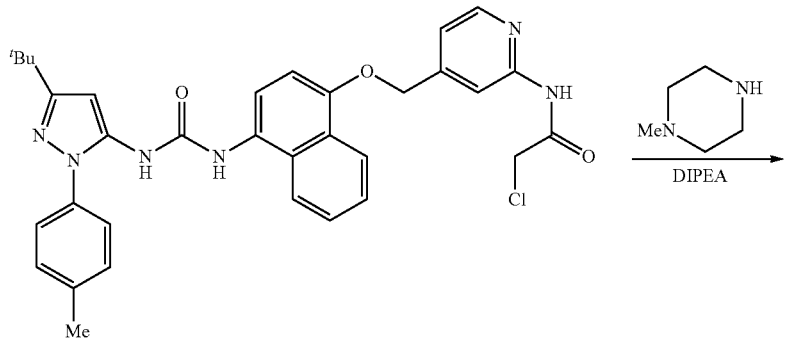

Intermediate B

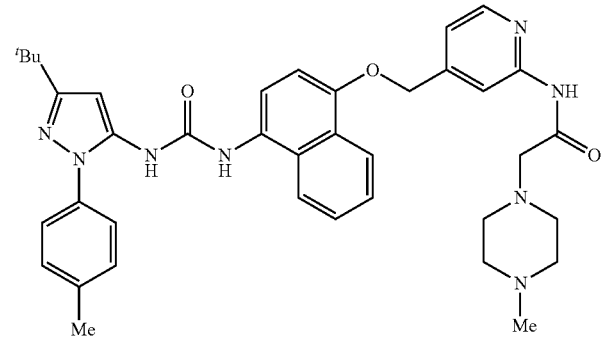

Example 23

To a solution of Intermediate B (50 mg, 0.08 mmol) in a mixture of DCM (1.0 mL), DMF (0.1 mL) and DIPEA (22 μL, 0.13 mmol) was added N-methyl piperazine (9.3 μL, 0.08 mmol). The reaction mixture was stirred at RT for 3 hr and then at 40° C. for 12 hr. A further portion of N-methyl piperazine (9.0 μL, 0.08 mmol) was added and the reaction mixture stirred at 40° C. for 5 hr. The crude reaction mixture was purified by column chromatography (12 g, 0-10% MeOH in DCM, gradient elution). Product fractions were concentrated in vacuo and the residue triturated with a mixture of diethyl ether, DCM and isohexane (2:1:2, 5.0 mL) to give the title compound (Example 23) as a light orange solid (26 mg, 47%): m/z 661 (M+H)$^+$ (ES$^+$). $^1$H NMR (400 MHz, DMSO-d$_6$) δ: 1.27 (9 H, s), 2.39 (3 H, s), 2.69-2.60 (3 H, br m), 2.88-2.73 (3 H, br m), 3.17-2.95 (4 H, br m), 5.39 (2H, s), 6.34 (1H, s), 7.00 (1H, d), 7.29 (1H, d), 7.35 (2H, d), 7.45 (2H, d), 7.66-7.56 (3H, m), 7.98 (1H, d), 8.37-8.28 (3H, m), 8.73 (1H, s), 8.91 (1H, s), 10.12 (1H, s).

Example 24

N-(4-((4-(3-(3-tert-Butyl-1-p-tolyl-1H-pyrazol-5-yl) ureido)naphthalen-1-yloxy)methyl)pyridin-2-yl)-2-(4-(2-methoxyethyl)piperazin-1-yl)acetamide

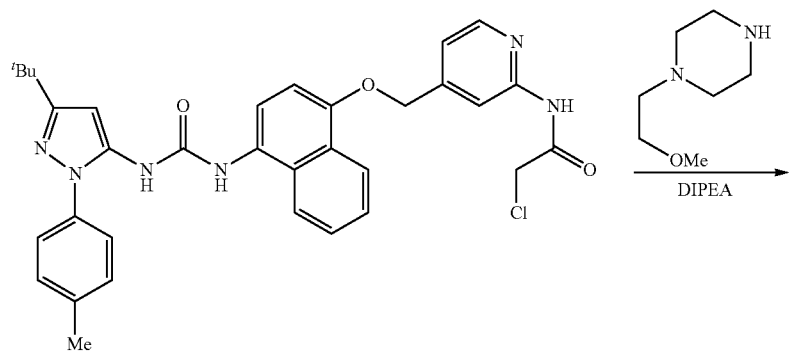

Intermediate B

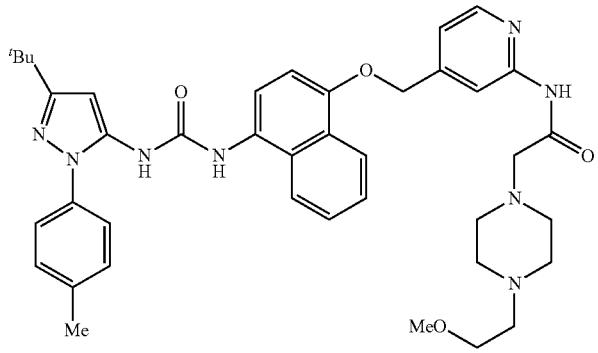

Example 24

To a solution of Intermediate B (50 mg, 0.08 mmol) in a mixture of DCM (1.0 mL), DMF (0.1 mL) and DIPEA (22 µL, 0.13 mmol) was added N-methoxyethyl piperazine (12.5 µL, 0.08 mmol). The reaction mixture was stirred at RT for 3 hr and then at 40° C. for 12 hr. A further portion of N-methoxyethyl piperazine (12.5 µL, 0.08 mmol) was added and the reaction mixture stirred at 40° C. for 5 hr. The crude reaction mixture was purified by column chromatography (SiO$_2$, 12 g, 0-10% MeOH in DCM, gradient elution) to afford the title compound (Example 24) as a light orange solid (45 mg, 73%): m/z 705 (M+H)$^+$ (ES$^+$). $^1$H NMR (400 MHz, DMSO) δ: 1.27 (9 H, s), 2.39 (3 H, s), 2.46-2.48 (3 H, m, obscured by DMSO), 2.57-2.50 (4 H, m), 3.17 (2 H, s), 3.23 (3 H, s), 3.42 (2 H, t), 5.39 (2H, s), 6.35 (1H, s), 7.01 (1H, d), 7.29 (1H, d), 7.35 (2H, d), 7.43 (2H, d), 7.65-7.55 (3H, m), 7.93 (1H, d), 8.36-8.30 (3H, m), 8.58 (1H, s), 8.79 (1H, s), 9.92 (1H, s).

Example 25

N-(4-((4-(3-(3-tert-Butyl-1-p-tolyl-1H-pyrazol-5-yl) ureido)naphthalen-1-yloxy)methyl)pyridin-2-yl)-2-(2-methoxyethylamino)acetamide

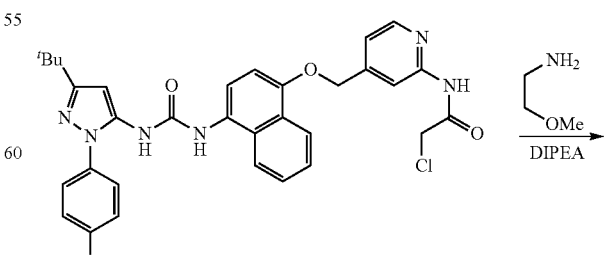

Intermediate B

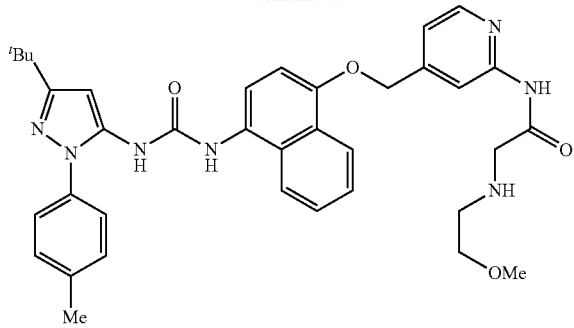

Example 25

To a solution of Intermediate B (50 mg, 0.08 mmol) in a mixture of DCM (1.0 mL), DMF (0.1 mL) and DIPEA (17 µL, 0.10 mmol) was added 2-methoxyethylamine (7.0 µL, 0.08 mmol). The reaction mixture was heated to 40° C. and stirred for 12 hr. The crude reaction mixture was purified by column chromatography (SiO$_2$, 12 g, 0-10% MeOH in DCM, gradient elution). Product fractions were concentrated in vacuo and the residue triturated with a mixture of diethyl ether, DCM and iso-hexane (2:1:2, 5.0 mL) to afford the title compound (Example 25) as an off-white solid (6 mg, 11%): m/z 637 (M+H)$^+$ (ES$^+$). $^1$H NMR (400 MHz, DMSO-d$_6$) δ: 1.27 (9 H, s), 2.39 (3 H, s), 2.71 (2 H, t), 3.24 (3 H, s), 3.33 (2H, m (obscured by DHO)), 3.40 (2 H, t), 5.38 (2H, s), 6.35 (1H, s), 7.01 (1H, d), 7.27 (1H, d), 7.36 (2H, d), 7.43 (2H, d), 7.64-7.57 (3H, m), 7.92 (1H, m), 8.36-8.30 (3H, m), 8.59 (1H, s), 8.79 (1H, s).

Example 26

N-(4-((4-(3-(3-tert-Butyl-1-p-tolyl-1H-pyrazol-5-yl)ureido)naphthalen-1-yloxy)methyl)pyridin-2-yl)-2-(dimethylamino)acetamide

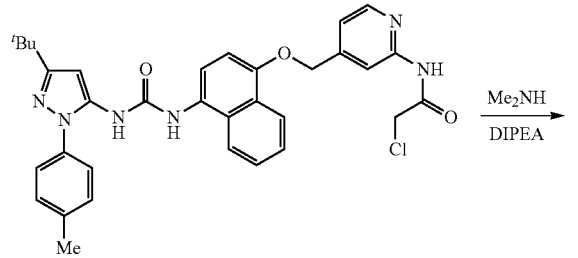

Intermediate B

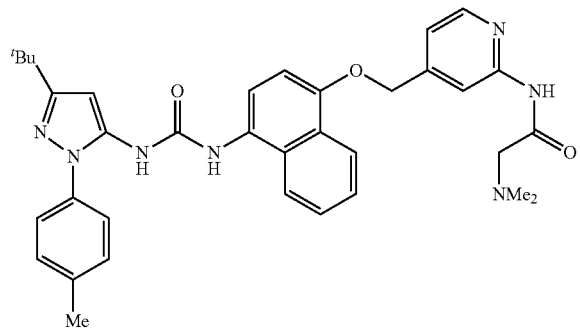

Example 26

To a solution of Intermediate B (50 mg, 0.08 mmol) in DCM (1.0 mL), DMF (0.1 mL) and DIPEA (17 µL, 0.1 mmol) was added dimethylamine (2.0M solution in THF) (41 µL, 0.08 mmol). The reaction mixture was heated to 40° C. and stirred for 12 hr. The crude reaction mixture was purified by column chromatography (12 g silica, 0-10% MeOH in DCM, gradient elution). Product fractions were concentrated in vacuo and the residue triturated with a mixture of diethyl ether, DCM and isohexane (2:1:2, 5.0 mL) to afford the title compound (Example 26) as an orange solid (18 mg, 35%): m/z 607 (M+H)$^+$ (ES$^+$). $^1$H NMR (400 MHz, DMSO-d$_6$) δ: 1.27 (9 H, s), 2.31 (6 H, s), 2.39 (3 H, s), 3.14 (2 H, s), 5.39 (2H, s), 6.35 (1H, s), 7.01 (1H, d), 7.29 (1H, d), 7.35 (2H, d), 7.44 (2H, d), 7.65-7.55 (3H, m), 7.94 (1H, m), 8.38-8.28 (3H, m), 8.59 (1H, s), 8.79 (1H, s), 9.93 (1H, s).

Example 27

N-(4-((4-(3-(3-tert-Butyl-1-p-tolyl-1H-pyrazol-5-yl)ureido)naphthalen-1-yloxy)methyl)pyridin-2-yl)-2-(methylamino)acetamide

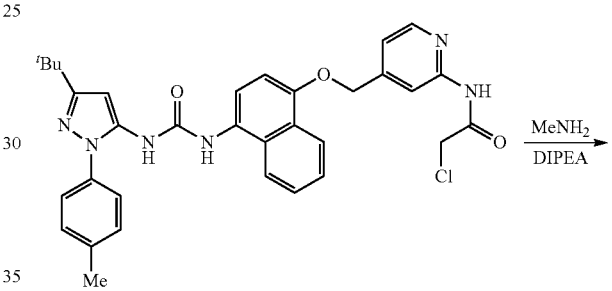

Intermediate B

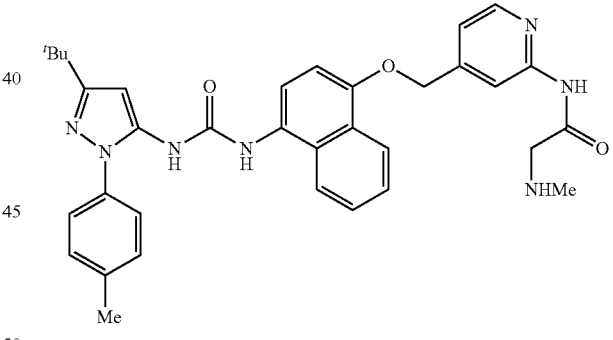

Example 27

To a solution of Intermediate B (50 mg, 0.08 mmol) in a mixture of DCM (1.0 mL), DMF (0.2 mL) and DIPEA (17 µL, 0.10 mmol) was added methylamine (2.0M solution in THF) (41 µL, 0.08 mmol). The reaction mixture was heated to 40° C. and stirred for 12 hr. The crude reaction mixture was purified by column chromatography (12 g, 0-10% MeOH in DCM, gradient elution). Product fractions were contaminated with an impurity and the crude material was re-purified by column chromatography (SiO$_2$, 12 g, 0-10% MeOH in DCM, gradient elution) to give the title compound (Example 27) as a light brown solid (6 mg, 12%): m/z 593 (M+H)$^+$ (ES$^+$). $^1$H NMR (400 MHz, DMSO-d$_6$) δ: 1.27 (9 H, s), 2.32 (3 H, s), 2.39 (3 H, s), 3.28 (2 H, s), 5.39 (2H, s), 6.35 (1H, s), 7.01 (1H, d), 7.27 (1H, d), 7.35 (2H, d), 7.44 (2H, d), 7.63-7.55 (3H, m), 7.93 (1H, m), 8.37-8.30 (3H, m), 8.59 (1H, s), 8.80 (1H, s).

Example 28

N-(4-((4-(3-(3-tert-Butyl-1-p-tolyl-1H-pyrazol-5-yl)ureido)naphthalen-1-yloxy)methyl)pyridin-2-yl)-2-((4-methoxybenzyl)(methyl)amino)acetamide

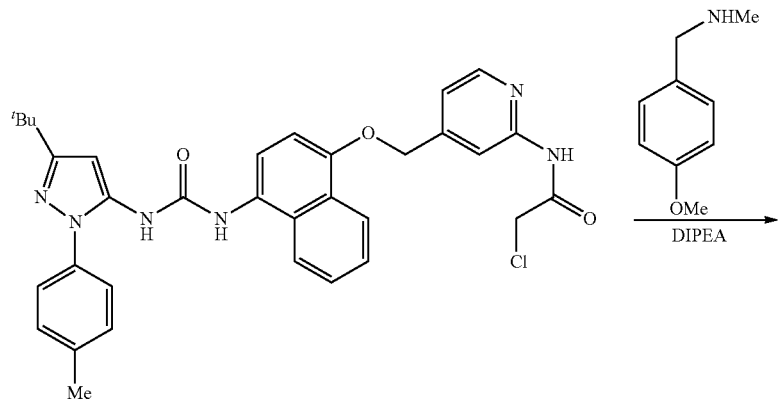

Intermediate B

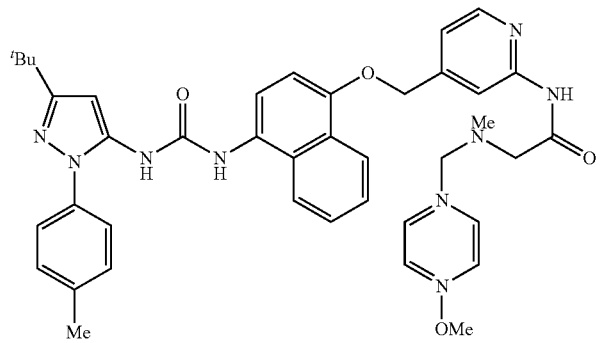

Example 28

To a solution of Intermediate B (50 mg, 0.08 mmol) in a mixture of DCM (1.0 mL), DMF (0.2 mL) and DIPEA (17.5 μL, 0.10 mmol) was added N-(4-methoxybenzyl)-N-methylamine (15.5 μL, 0.09 mmol) and the reaction mixture was stirred at 55° C. for 12 hr. The crude reaction mixture was purified by column chromatography (SiO$_2$, 12 g, 0-10% MeOH in DCM, gradient elution). Product fractions were concentrated in vacuo and the residue triturated with a mixture of diethyl ether, DCM and isohexane (2:1:2, 5.0 mL) to afford the title compound (Example 28) as a white solid (7 mg, 11%): m/z 713 (M+H)$^+$ (ES$^+$). $^1$H NMR (400 MHz, DMSO-d$_6$) δ: 1.27 (9 H, s), 2.25 (3 H, s), 2.39 (3 H, s), 3.22 (2 H, s), 3.59 (2 H, s), 3.72 (3 H, s), 5.38 (2H, s), 6.35 (1H, s), 6.90 (2H, m), 7.01 (1H, m), 7.27 (3H, m), 7.35 (2H, m), 7.43 (2H, m), 7.64-7.55 (3H, m), 7.94 (1H, m), 8.37-8.28 (3H, m), 8.58 (1H, s), 8.79 (1H, s), 9.97 (1H, s).

Example 29

N-(4-((4-(3-(3-tert-Butyl-1-p-tolyl-1H-pyrazol-5-yl)ureido)naphthalen-1-yloxy)methyl) pyridin-2-yl)-2-(2-methoxyethylthio)acetamide

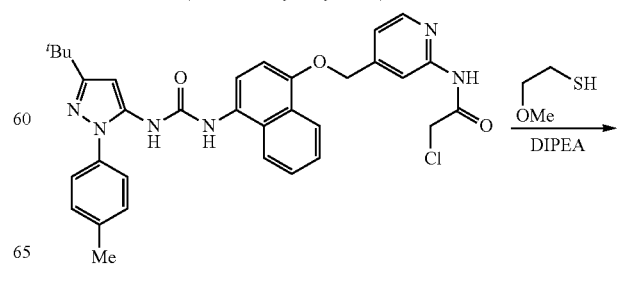

Intermediate B

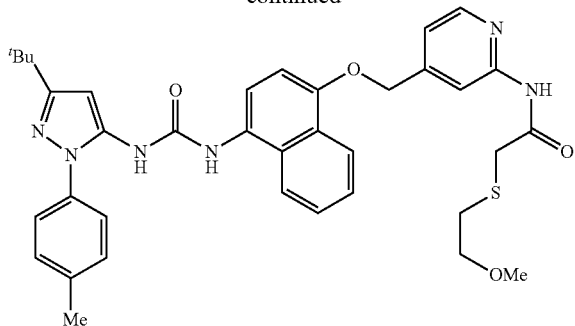

Example 29

To a solution of Intermediate B (50 mg, 0.08 mmol) in a mixture of DCM (1.0 mL), DMF (0.1 mL) and DIPEA (17 µL, 0.10 mmol) was added 2-methoxyethane-1-thiol (8.0 µL, 0.10 mmol). The reaction mixture was heated to 40° C. and stirred for 18 hr, after which further portions of 2-methoxyethane-1-thiol (8.0 µL, 0.10 mmol) and DIPEA (17 µL, 0.10 mmol) were added and stirring continued at 40° C. for 2 days. The reaction mixture was evaporated in vacuo and the residue was purified by flash column chromatography (SiO$_2$, 12 g, 0-10% MeOH in DCM, gradient elution) to afford an impure product which was triturated with diethyl ether (3.0 mL) and further purified by SCX capture and release to give the title compound (Example 29) (25 mg, 44%): m/z 653 (M+H)$^+$ (ES$^+$). $^1$H NMR (400 MHz, DMSO-d$_6$) δ: 1.27 (9H, s), 2.39 (3H, s), 2.80 (2H, t), 3.22 (3H, s), 3.41 (2H, s), 3.51 (2H, t), 5.38 (2H, s), 6.35 (1H, s), 7.01 (1H, d), 7.27 (1H, dd), 7.36 (2H, m), 7.44 (2H, m), 7.56-7.64 (3H, overlapping m), 7.93 (1H, m), 8.29-8.33 (2H, overlapping m), 8.35 (1H, m), 8.58 (1H, br s), 8.79 (1H, br s), 10.61 (1H, br s).

Example 30

N-(4-((4-(3-(3-tert-Butyl-1-p-tolyl-1H-pyrazol-5-yl)ureido)naphthalen-1-yloxy)methyl)pyridin-2-yl)-2-(2-(2-methoxyethoxy)ethylthio)acetamide

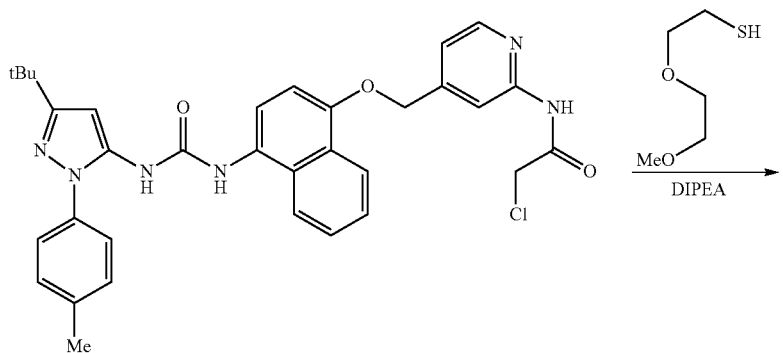

Intermediate B

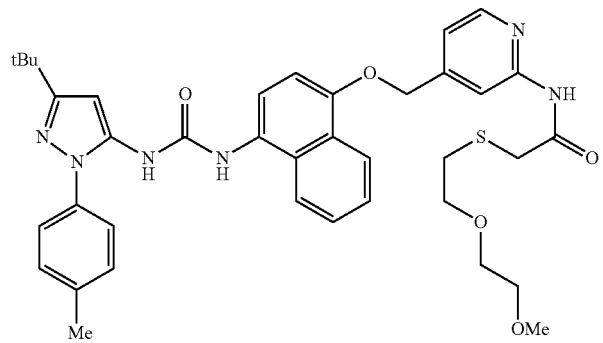

Example 30

To a solution of Intermediate B (50 mg, 0.08 mmol) in a mixture of DCM (1.0 mL), DMF (0.1 mL) and DIPEA (17 μL, 0.10 mmol) was added 2-(2-methoxyethoxy)ethanethiol (14 μL, 0.10 mmol). The reaction mixture was heated to 40° C. and stirred for 18 hr, after which further portions of 2-(2-methoxyethoxy)ethanethiol (14 μL, 0.10 mmol) and DIPEA (17 μL, 0.10 mmol) were added and stirring continued at 40° C. for 2 days. The reaction mixture was evaporated in vacuo and the residue was purified by flash column chromatography (SiO$_2$, 12 g, 0-10% MeOH in DCM, gradient elution) to afford an impure product which was triturated with diethyl ether (3.0 mL) and further purified by SCX capture and release to give the title compound (Example 30) (19 mg, 32%): m/z 697 (M+H)$^+$ (ES$^+$). $^1$H NMR (400 MHz, DMSO-d$_6$) δ: 1.27 (9H, s), 2.39 (3H, s), 2.79 (2H, t), 3.21 (3H, s), 3.39-3.42 (4H, overlapping m), 3.49 (1H, d), 3.50 (1H, dd), 3.59 (2H, t), 5.38 (2H, s), 6.35 (1H, s), 7.01 (1H, d), 7.27 (1H, dd), 7.36 (2H, m), 7.44 (2H, m), 7.56-7.64 (3H, overlapping m), 7.93 (1H, m), 8.29-8.32 (2H, overlapping m), 8.35 (1H, dd), 8.58 (1H, br s), 8.79 (1H, br s), 10.61 (1H, br s).

Example 31

N-(4-((4-(3-(3-tert-Butyl-1-p-tolyl-1H-pyrazol-5-yl)ureido)naphthalen-1-yloxy)methyl)pyridin-2-yl)-2-(2-morpholinoethylthio)acetamide

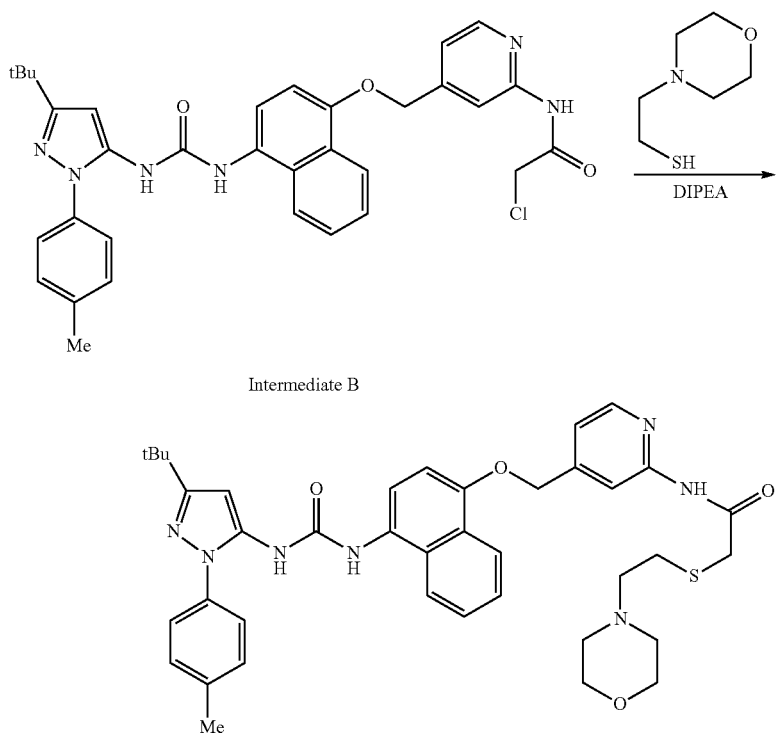

Intermediate B

Example 31

To a solution of Intermediate B (50 mg, 0.08 mmol) in a mixture of DCM (1.0 mL), DMF (0.1 mL) and DIPEA (17 μL, 0.10 mmol) was added 2-morpholin-4-yl-ethane-1-thiol (12 μL, 0.10 mmol). The reaction mixture was heated to 40° C. and stirred for 18 hr after which further portions of 2-morpholin-4-yl-ethane-1-thiol (12 μL, 0.10 mmol) and DIPEA (17 μL, 0.10 mmol) were added and stirring continued at 40° C. for 2 days. The reaction mixture was evaporated in vacuo and purified by flash column chromatography (SiO$_2$, 12 g, 0-10% MeOH in DCM, gradient elution) to afford impure product which was triturated with a mixture of diethyl ether (3.0 mL), DCM (3.0 mL) and isohexane (5.0 mL) and further purified by SCX capture and release to provide the title compound (Example 31) (14 mg, 21%): m/z 708 (M+H)$^+$ (ES$^+$). $^1$H NMR (400 MHz, DMSO-d$_6$) δ: 1.27 (9H, s), 2.39 (3H, s), 2.43 (4H, very br s), 2.59 (2H, very br s), 2.78 (2H, br t), 3.42 (2H, s), 3.55 (4H, br s), 5.38 (2H, s), 6.35 (1H, s), 7.01 (1H, d), 7.27 (1H, dd), 7.36 (2H, m), 7.44 (2H, m), 7.55-7.64 (3H, overlapping m), 7.95 (1H, m), 8.29-8.32 (2H, overlapping m), 8.35 (1H, dd), 8.63 (1H, s), 8.83 (1H, s), 10.63 (1H, s).

Example 32

N-(4-((4-(3-(3-tert-Butyl-1-p-tolyl-1H-pyrazol-5-yl)ureido)naphthalen-1-yloxy)methyl)pyridin-2-yl)-2-(2-morpholinoethylsulfonyl)acetamide

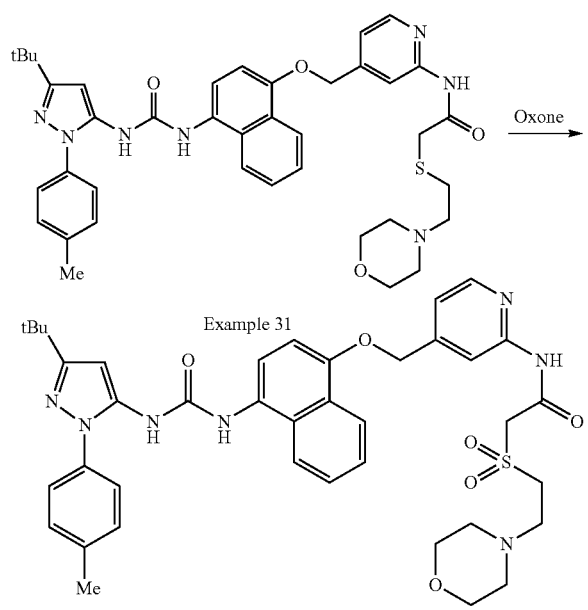

A solution of Oxone (39 mg, 0.13 mmol) in water (0.4 mL) was added to a solution of N-(4-((4-(3-(3-tert-butyl-1-p-tolyl-1H-pyrazol-5-yl)ureido)naphthalen-1-yloxy)methyl)pyridin-2-yl)-2-(2-morpholinoethylthio)acetamide (Example 31) (30 mg, 0.04 mmol) in DMF (2.0 mL) and the mixture was stirred at RT for 18 hr. The reaction mixture was diluted with glacial AcOH (1.0 mL) and brine (4.0 mL) and extracted with DCM (4.0 mL). The organic phase was evaporated in vacuo and the residue was subjected to SCX capture and release and was then purified by flash column chromatography (SiO$_2$, 12 g, 0-10% (1% NH$_3$ in MeOH) in DCM, gradient elution). The impure product so obtained was triturated with DCM (0.5 mL) and isohexane (3.0 mL) to afford the title compound (Example 32) as a white solid (7 mg, 21%): m/z 740 (M+H)$^+$ (ES$^+$). $^1$H NMR (400 MHz, DMSO-d$_6$) δ: 1.27 (9H, s), 2.39 (3H, s), 2.43 (4H, br m), 2.77 (2H, t), 3.51 (2H, t), 3.56 (4H, br t), 4.53 (2H, s), 5.40 (2H, s), 6.35 (1H, s), 7.01 (1H, d), 7.32 (1H, m), 7.35 (2H, m), 7.44 (2H, m), 7.54-7.63 (3H, overlapping m), 7.93 (1H, m), 8.30-8.32 (2H, overlapping m), 8.38 (1H, d), 8.64 (1H, br s), 8.84 (1H, br s), 10.98 (1H, br s).

Example 33

2-(Bis(2-methoxyethyl)amino)-N-(4-((4-(3-(3-tert-butyl-1-p-tolyl-1H-pyrazol-5-yl)ureido)naphthalen-1-yloxy)methyl)pyridin-2-yl)acetamide

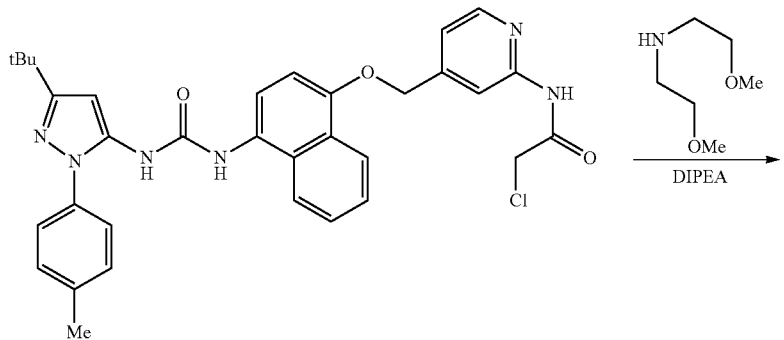

Intermediate B

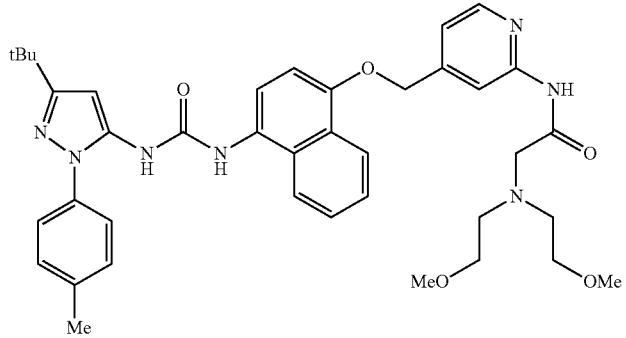

Example 33

To a solution of Intermediate B (50 mg, 0.08 mmol) in a mixture of DCM (1.0 mL), DMF (0.1 mL) and DIPEA (17 μL, 0.10 mmol) was added bis(2-methoxyethyl)amine (15 μL, 0.10 mmol). The reaction mixture was stirred at 40° C., for 18 hr and then further portions of bis(2-methoxyethyl)amine (15 μL, 0.10 mmol) and DIPEA (17 μL, 0.10 mmol) were added and stirring continued at 40° C. for 4 days. The reaction mixture was evaporated in vacuo and the residue was purified three times by flash column chromatography (SiO$_2$, 2×12 g, 0-20% MeOH in DCM and SiO$_2$, 4 g, 0-10% [1% NH$_3$ in MeOH] in DCM, gradient elution) to afford the title compound (Example 33) (13 mg, 22%): m/z 694 (M+H)$^+$ (ES$^+$).

$^1$H NMR (400 MHz, DMSO-d$_6$) δ: 1.27 (9H, s), 2.39 (3H, s), 2.79-2.81 (4H, t), 3.21 (6H, s), 3.34 (2H, s), 3.42 (4H, t), 5.38 (2H, s), 6.35 (1H, s), 7.01 (1H, d), 7.27 (1H, dd), 7.36 (2H, m), 7.44 (2H, m), 7.56-7.63 (3H, overlapping m), 7.93 (1H, m), 8.30-8.35 (2H, overlapping m), 8.38 (1H, br s), 8.58 (1H, br s), 8.79 (1H, br s), 10.14 (1H, br s).

Intermediate C 1-(4-((3-Aminopyridin-4-yl)methoxy)naphthalen-1-yl)-3-(3-tert-butyl-1-p-tolyl-1H-pyrazol-5-yl)urea

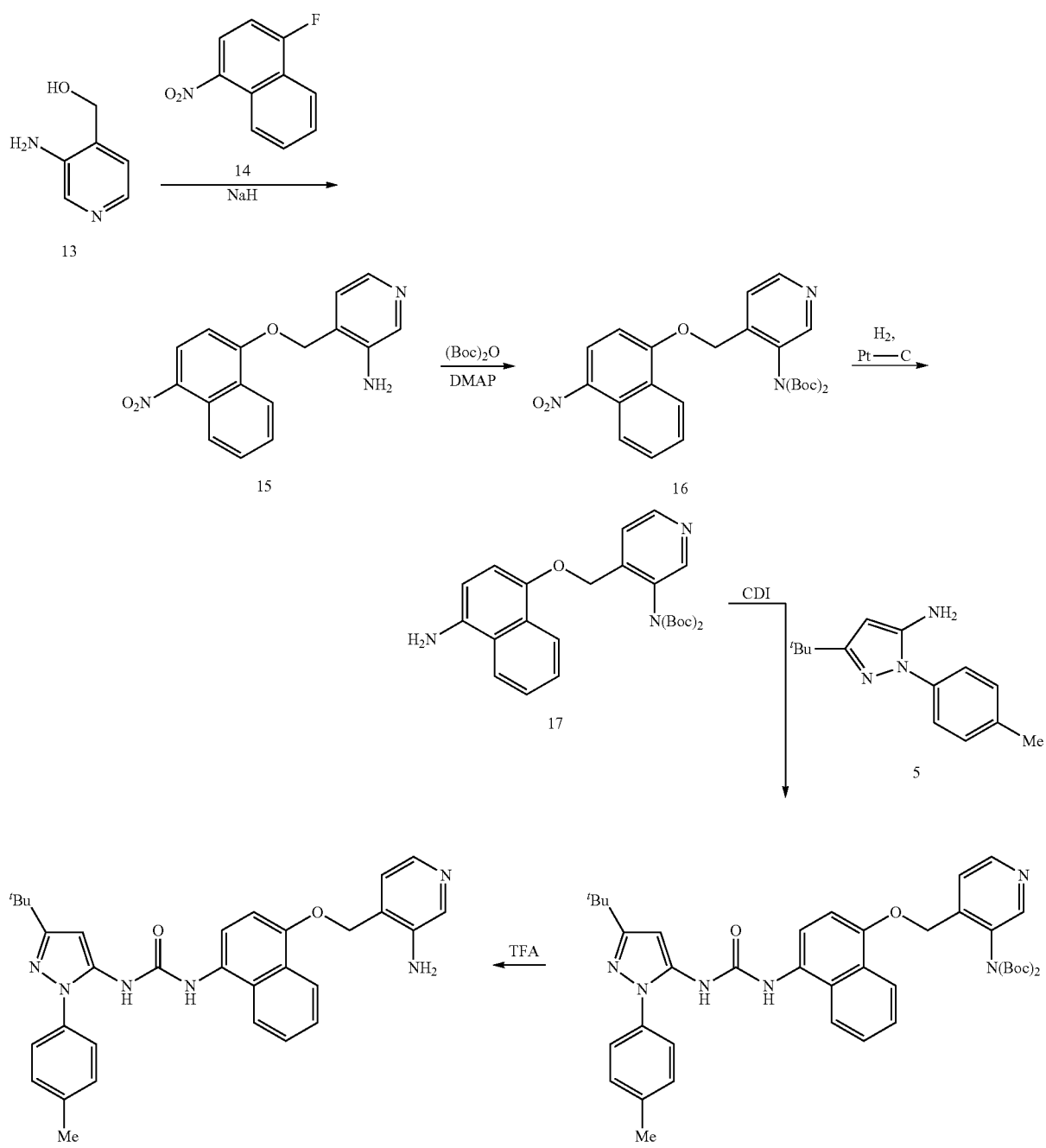

4-((4-Nitronaphthalen-1-yloxy)methyl)pyridin-3-amine (15)

To a solution of (3-amino-pyridin-4-yl)-methanol (13) (4.00 g, 32.2 mmol) in anhydrous THF (160 mL) at 0° C. was added sodium hydride (1.55 g, 38.7 mmol, 60 wt %). After stirring for 20 min, 1-fluoro-4-nitronaphthalene (14) (6.16 g, 32.2 mmol) was added, the ice bath was removed and the reaction mixture left to warm to RT and stirred for 12 hr. The reaction mixture was partitioned between EtOAc (200 mL) and saturated aq NaHCO$_3$ solution (150 mL). The remaining yellow solid was collected by filtration and washed sequentially with water (50 mL), MeOH (50 mL) and diethyl ether (100 mL) and was identified as the desired product by LC-MS and $^1$H NMR. The filtrate was returned to a separating funnel; the organic phase was collected and washed with brine (100 mL), dried and concentrated in vacuo to afford an orange residue. Trituration of the orange residue with MeOH (200 mL) afforded an orange solid which was washed with diethyl ether (200 mL). LC-MS and $^1$H NMR analysis of the orange solid was identical to that observed for the insoluble solid obtained earlier. The two products were combined to afford the title compound (15) (7.80 g, 77%): m/z 296 (M+H)$^+$ (ES$^+$).

Di-tert-butyl 4-((4-nitronaphthalen-1-yloxy)methyl)pyridin-3-yliminodicarbonate (16)

To a suspension of 4-((4-nitronaphthalen-1-yloxy)methyl)pyridin-3-amine (15) (3.00 g, 10.2 mmol) and DMAP (0.25 g, 2.03 mmol) in THF (30 mL) was added a solution of di-tert-butyldicarbonate (2.33 g, 10.7 mmol) in THF (15 mL). After 2-3 min a solution was obtained. The reaction mixture was stirred at RT for 12 hr whereupon further di-tert-butyldicarbonate (2.33 g, 10.7 mmol) was added and the reaction mixture was stirred at RT for 12 hr. The reaction was partitioned between EtOAc (100 mL) and saturated aq NaHCO$_3$ solution (50 mL). The organic layer was collected, dried and concentrated in vacuo to afford an orange oil. The oil was purified by column chromatography (0-50% EtOAc in isohexane, gradient elution) to afford the title compound (16) as an orange oil which crystallised on standing (2.33 g, 43%): m/z 496 (M+H)$^+$ (ES$^+$).

Di-tert-butyl 4-((4-aminonaphthalen-1-yloxy)methyl)pyridin-3-yliminodicarbonate (17)

A solution of di-tert-butyl 4-((4-nitronaphthalen-1-yloxy)methyl)pyridin-3-yliminodicarbonate (16) (2.30 g, 4.64 mmol) in MeOH (100 mL) and AcOH (20 mL) was passed through a Thales H-cube (1.0 mL·min$^{-1}$, 25° C., 55 mm 10% Pt/C Cat-Cart, full hydrogen mode) and the volatiles were removed in vacuo to afford the title compound (17) as a brown oil (2.12 g, 82%): m/z 466 (M+H)$^+$ (ES$^+$).

Di-tert-butyl 4-((4-(3-(3-tert-butyl-1-p-tolyl-1H-pyrazol-5-yl)ureido)naphthalen-1-yloxy)methyl)pyridin-3-yliminodicarbonate (18)

A solution of 3-tert-butyl-1-p-tolyl-1H-pyrazol-5-amine (5) (1.55 g, 6.77 mmol) in DCM (4.0 mL) was added dropwise over 25 min to a suspension of CDI (1.10 g, 6.77 mmol) in DCM (4.0 mL) at RT. The reaction mixture was stirred for 80 min at RT and a solution of di-tert-butyl 4-((4-aminonaphthalen-1-yloxy)methyl)pyridin-3-yliminodicarbonate (17) (2.10 g, 4.51 mmol) in DCM (10 mL) was added to the reaction mixture in one portion and stirred for 12 hr. The reaction mixture was partitioned between saturated aq NaHCO$_3$ solution (20 mL) and DCM (20 mL). The organic layer was collected, dried and concentrated in vacuo to afford a purple residue. The crude material was purified by column chromatography (80 g, 0-100% EtOAc in isohexane, gradient elution), to afford the title compound (18) as a purple solid (1.77 g, 53%): m/z 721 (M+H)$^+$ (ES$^+$).

Intermediate C

1-(4-((3-aminopyridin-4-yl)methoxy)naphthalen-1-yl)-3-(3-tert-butyl-1-p-tolyl-1H-pyrazol-5-yl)urea TFA (2.0 mL) was added to a solution of the iminodicarbonate (18) (1.70 g, 2.36 mmol) in DCM (10 mL). After for 1 hr stirring at RT further TFA (2.0 mL) was added and the reaction mixture stirred for 12 hr at RT. The solvents were removed in vacuo and the product purified by SCX capture and release, followed by trituration with DCM (20 mL) to afford the title compound (Intermediate C) as a pale buff solid (0.96 g, 77%): m/z 521 (M+H)$^+$ (ES$^+$). $^1$H NMR (400 MHz, DMSO-d$_6$) δ: 1.27 (9 H, s), 2.39 (3 H, s), 5.16 (2 H, s), 5.38 (2 H, s), 6.35 (1H, s), 7.05 (1H, d), 7.32 (1H, d), 7.35 (2H, d), 7.43 (2H, m), 7.64-7.51 (2H, m), 7.63 (1H, d), 7.82 (1H, d), 7.91 (1H, m), 8.03 (1H, s), 8.29 (1H, m), 8.57 (1H, s), 8.78 (1H, s).

Example 34

1-(4-((3-Methylureidopyridin-4-yl)methoxy)naphthalen-1-yl)-3-(3-tert-butyl-1-p-tolyl-1H-pyrazol-5-yl)urea

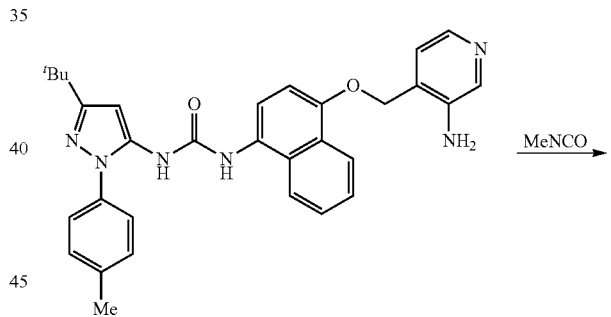

Intermediate C

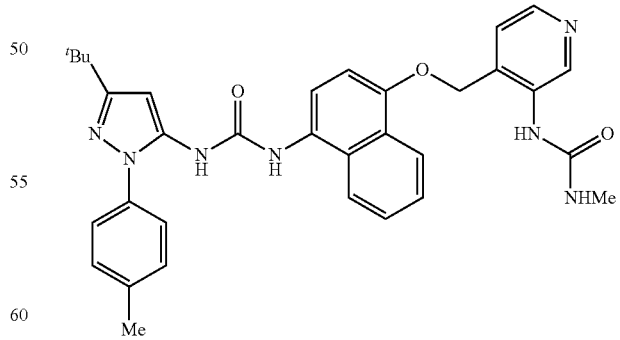

Example 34

Methyl isocyanate (8.5 µL, 0.14 mmol) was added to a solution of Intermediate C (50 mg, 0.10 mmol) in pyridine (1.0 mL). The reaction mixture was stirred for 2 hr at RT and a further portion of methyl isocyanate (8.5 μL, 0.14 mmol) was added and stirring continued for 72 hr at RT. The solvent was removed in vacuo and the crude product was purified by column chromatography (SiO$_2$, 4 g, 10-25% MeOH in DCM, gradient elution). The crude product fractions were combined and triturated with DCM (20 mL). The solid was filtered off to afford the title compound (Example 34) (8 mg, 14%): m/z 578 (M+H)$^+$ (ES$^+$). $^1$H NMR (400 MHz, DMSO-d$_6$) δ: 1.27 (9 H, s), 2.39 (3 H, s), 2.68 (3 H, d), 5.27 (2H, s), 6.35 (1H, s), 6.53 (1H, m), 6.98 (1H, d), 7.35 (2H, d), 7.45 (2H, d), 7.65-7.52 (4H, m), 7.92 (1H, d), 8.16 (1H, s), 8.28 (2H, m), 8.61 (1H, s), 8.82 (1H, s), 8.88 (1H, s).

Example 35

N-(4-((4-(3-(3-tert-Butyl-1-p-tolyl-1H-pyrazol-5-yl)ureido)naphthalen-1-yloxy)methyl)pyridin-3-yl)-2-methoxyacetamide

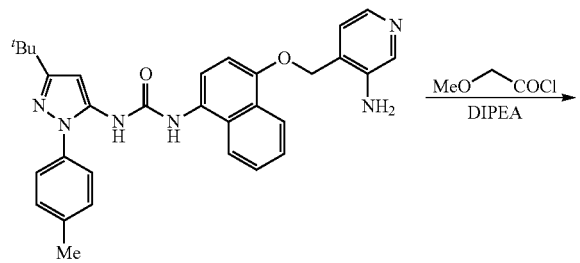

Intermediate C

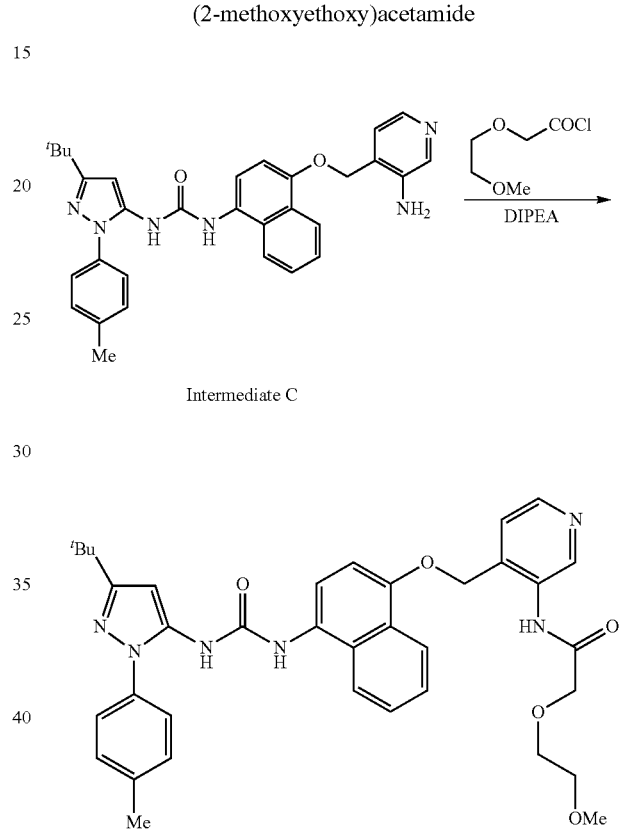

Example 35

To a solution of Intermediate C (50 mg, 0.10 mmol) and DIPEA (33.5 μL, 0.19 mmol) in anhydrous DCM (1.0 mL) and anhydrous DMF (0.1 mL) was added methoxyacetyl chloride (10 μL, 0.11 mmol) and the reaction mixture stirred for 12 hr at RT Additional methoxyacetyl chloride (10 μL, 0.11 mmol) was added and the reaction mixture was stirred at RT for 5 hr. A further portion of methoxyacetyl chloride (8 μl, 0.09 mmol) was added and after 2 hr a solution of ammonia (1% in MeOH, 10 mL) was added and the reaction mixture was stirred for 20 min at RT. The solvents were removed in vacuo to afford a purple oily solid. This was dissolved in MeOH (2.0 mL) and 3 drops of AcOH were added. The solution was subjected to SCX capture and release, eluting the product with 1% NH$_3$ in MeOH. The solvent was removed in vacuo and the residue was triturated with diethyl ether (10 mL) to afford the title compound (Example 35) as a light purple solid (24 mg, 41%) m/z 593 (M+H)$^+$ (ES$^+$). $^1$H NMR (400 MHz, DMSO-d$_6$) δ: 1.27 (9 H, s), 2.39 (3 H, s), 3.31 (3H, s (obscured by DHO peak)), 4.06 (2H, s), 5.34 (2H, s), 6.35 (1H, s), 6.96 (1H, d), 7.35 (2H, d), 7.43 (2H, d), 7.64-7.54 (4H, m), 7.93 (1H, d), 8.29 (1H, dd), 8.45 (1H, d), 8.58 (1H, s), 8.70 (1H, s), 8.79 (1H, s), 9.76 (1H, s).

Example 36

N-(4-((4-(3-(3-tert-Butyl-1-p-tolyl-1H-pyrazol-5-yl)ureido)naphthalen-1-yloxy)methyl)pyridin-3-yl)-2-(2-methoxyethoxy)acetamide Example 36

To a solution of Intermediate C (50 mg, 0.10 mmol) and DIPEA (33.5 μL, 0.19 mmol) in a mixture of anhydrous DCM (1.0 mL) and anhydrous DMF (0.2 mL) was added 2-(2-methoxyethoxy)acetyl chloride (15 μL 0.11 mmol) and the reaction mixture was stirred for 12 hr at RT. A second aliquot of 2-(2-methoxyethoxy)acetyl chloride (15 μL, 0.11 mmol) was added and the reaction mixture stirred at RT for 6 hr. Methanol (2.0 mL) and AcOH (5 drops) were added and the reaction mixture was subjected to SCX capture and release, eluting with 1% NH$_3$ in MeOH. The solvent was removed in vacuo and the crude material purified by column chromatography (SiO$_2$, 4 g, 0-10% MeOH in EtOAc, gradient elution) to afford the title compound (Example 36) as a white solid (27 mg, 43%): m/z 637 (M+H)$^+$ (ES$^+$). $^1$H NMR (400 MHz, DMSO-d$_6$) δ: 1.27 (9 H, s), 2.39 (3 H, s), 3.18 (3 H, s), 3.36 (2 H, m), 3.61 (2 H, m), 4.14 (2H, s), 5.33 (2H, s), 6.35 (1H, s), 6.97 (1H, d), 7.35 (2H, d), 7.43 (2H, d), 7.67-7.55 (4H, m), 7.92 (1H, d), 8.27 (1H, d), 8.46 (1H, d), 8.58 (1H, s), 8.74 (1H, s), 8.80 (1H, s), 9.65 (1H, s).

Intermediate D 1-(4-(2-(2-Aminopyridin-4-yl)ethoxy)naphthalen-1-yl)-3-(3-tert-butyl-1-p-tolyl-1H-pyrazol-5-yl)urea

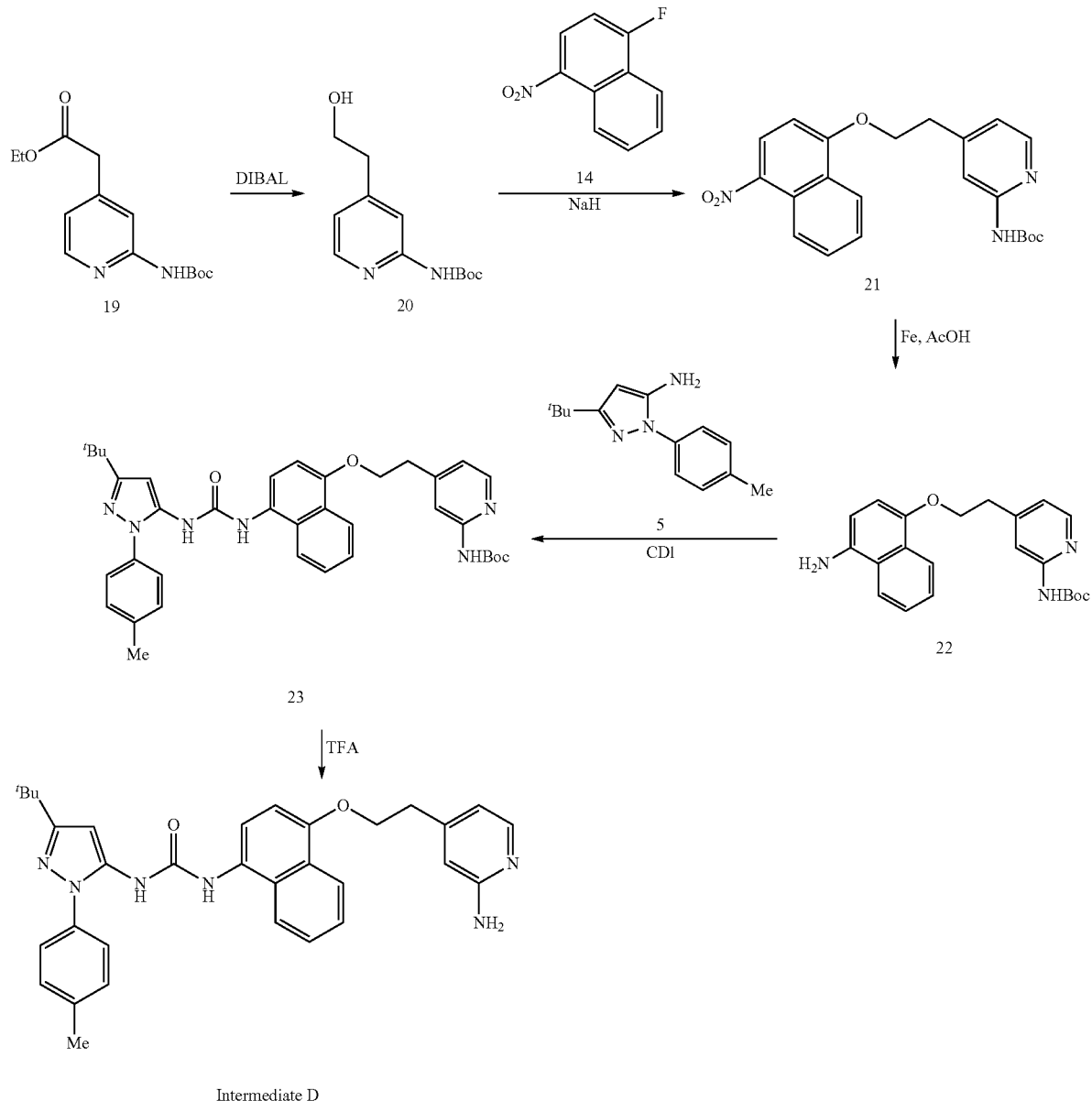

Intermediate D tert-Butyl 4-(2-hydroxyethyl)pyridin-2-ylcarbamate (20)

To a solution of ethyl 2-(2-(tert-butoxycarbonylamino)pyridin-4-yl)acetate (19) (WO 2007089512) (10.0 g, 35.7 mmol) under nitrogen in THF (100 mL), at −78° C., was added DIBAL (1M solution in THF, 71.3 mL, 71.3 mmol) over 1 hr. The reaction mixture was stirred at −78 to −60° C. for 40 min and then warmed to −15° C. over 1 hr. The solution was re-cooled to −78° C. and treated with further DIBAL (1M solution in THF, 35 mL, 35.7 mmol). The mixture was allowed to warm to −40° C. and stirred for 1 hr. Water (10 mL) was added cautiously to quench the reaction followed by MgSO$_4$ (20 g) and the solids removed by filtration. The filtrate was evaporated to dryness in vacuo and the residue subjected to column chromatography (SiO$_2$, 330 g, 65% EtOAc in hexanes) to give the title compound (20) (6.00 g, 64%) as a yellow solid: m/z 239 (M+H)$^+$ (ES$^+$).

tert-Butyl 4-(2-(4-nitronaphthalen-1-yloxy)ethyl)pyridin-2-ylcarbamate (21)

To a solution of tert-butyl 4-(2-hydroxyethyl)pyridin-2-ylcarbamate (20) (6.00 g, 25.2 mmol) in THF (70 mL) was added sodium hydride (2.52 g, 63.0 mmol, 60 wt %) at 0° C. The bright yellow suspension was stirred for 20 min at 0° C. and the 1-fluoro-4-nitronaphthalene (14) (4.81 g, 25.2 mmol) added in a single portion. After stirring at RT for 2 hr, water (100 mL) was added followed by EtOAc (100 mL). The solid formed between the layers was collected by filtration and the organic phase was washed with saturated aq NaHCO$_3$ solution (100 mL), brine (100 mL) and dried. The volatiles were removed to give an orange solid. The solids were combined and triturated from MeOH (50 mL) to give the title compound (21) as a yellow solid (11.0 g, 98%): m/z 410 (M+H)+ (ES+).

tert-Butyl 4-(2-(4-aminonaphthalen-1-yloxy)ethyl) pyridin-2-ylcarbamate (22)

A mixture of tert-butyl 4-(2-(4-nitronaphthalen-1-yloxy) ethyl)pyridin-2-ylcarbamate (21) (5.20 g, 12.7 mmol) and iron mesh (4.30 g, 76 mmol) was suspended in AcOH and EtOH (1:2, 120 mL) and was heated to 60° C. and stirred rapidly until the reaction was judged to be complete by LC-MS. The mixture was cooled to RT, poured carefully onto saturated aq NaHCO$_3$ solution (1000 mL) and extracted with EtOAc (500 mL×2). The combined organic layers were washed with saturated aq NaHCO$_3$ solution (1000 mL), water (1000 mL), brine (1000 mL) and dried. The solution was filtered and evaporated in vacuo to give the title compound (22) as a yellow oil (5.00 g, 95%): m/z 380 (M+H)+ (ES+).

tert-Butyl-4-(2-(4-(3-(3-tert-butyl-1-p-tolyl-1H-pyrazol-5-yl)ureido)naphthalen-1-yloxy)ethyl)pyridin-2-ylcarbamate (23)

To a stirred suspension of CDI (3.00 g, 18.18 mmol) in DCM (15 mL) was added a solution of the pyrazole amine (5) (4.17 g, 18.18 mmol) in DCM (40 mL) over 1.5 hrs. After 2 hr at RT a solution of the naphthyl amine (22) (3.00 g, 7.91 mmol) in DCM (15 mL) was added. After stirring overnight, the solution was diluted with MeOH (10 mL) and absorbed onto silica gel (30 g) and subjected to column chromatography (SiO$_2$, 330 g, 30% to 100% EtOAc in isohexane and then 0% to 6% MeOH in EtOAc) to give the title compound (23) as a beige solid (4.20 g, 80%): m/z 635 (M+H)+ (ES+).

Intermediate D 1-(4-(2-(2-Aminopyridin-4-yl)ethoxy)naphthalen-1-yl)-3-(3-tert-butyl-1-p-tolyl-1H-pyrazol-5-yl)urea To a suspension of the carbamate (23) (1.35 g, 2.20 mmol) in DCM (10 mL) was added TFA (10 mL). After stirring at RT for 2 hr, the volatiles were evaporated and the residue was taken up in EtOAc (50 mL) and extracted with saturated aq NaHCO$_3$ solution (50 mL). The organic layer was separated and was washed with brine (50 mL), and then dried and evaporated to give the title compound (Intermediate D) as a pale pink solid (1.20 g, 100%): m/z 535 (M+H)+ (ES+).

Example 37

N-(4-(2-(4-(3-(3-tert-Butyl-1-p-tolyl-1H-pyrazol-5-yl)ureido)naphthalen-1-yloxy)ethyl)pyridin-2-yl)-2-methoxyacetamide

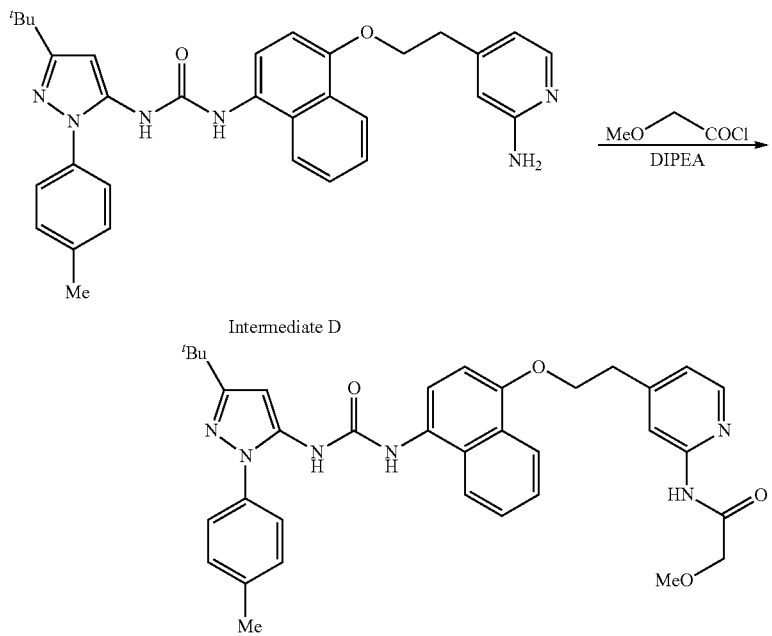

Example 37

To a suspension of Intermediate D (35 mg, 0.065 mmol) in DCM (0.5 mL) was added DIPEA (23 µL, 0.131 mmol) and methoxyacetyl chloride (7 µL, 0.072 mmol) and the mixture stirred at RT, until judged to be complete by LC-MS. The reaction mixture was diluted with saturated aq NaHCO$_3$ solution (1.5 mL) and the layers were separated through a phase separator cartridge. The organics were collected, evaporated under reduced pressure and the residue subjected to SCX capture and release. The resulting residue was purified further by preparative RP HPLC to give the title compound (Example 37) as a white solid (5 mg, 13%): m/z 607 (M+H)+ (ES+). $^1$H NMR (400 MHz, DMSO-d$_6$) δ: 1.26 (9 H, s), 2.37 (3 H, s), 3.20 (2 H, t), 3.37 (3 H, s), 4.06 (2 H, s), 4.38 (2 H, t), 6.33 (1 H, s), 6.95 (1 H, d), 7.19 (1 H, dd), 7.33 (2 H, m), 7.42-7.47 (3 H, m), 7.54 (1 H, m), 7.59 (1 H, d), 7.87 (1 H, d), 8.12 (1 H, d), 8.18 (1 H, br s), 8.23 (1 H, d), 8.67 (1 H, s), 8.84 (1 H, s), 9.89 (1 H, s).

Example 38

N-(4-(2-(4-(3-(3-tert-Butyl-1-p-tolyl-1H-pyrazol-5-yl)ureido)naphthalen-1-yloxy)ethyl)pyridin-2-yl)-2-(2-methoxyethoxy)acetamide

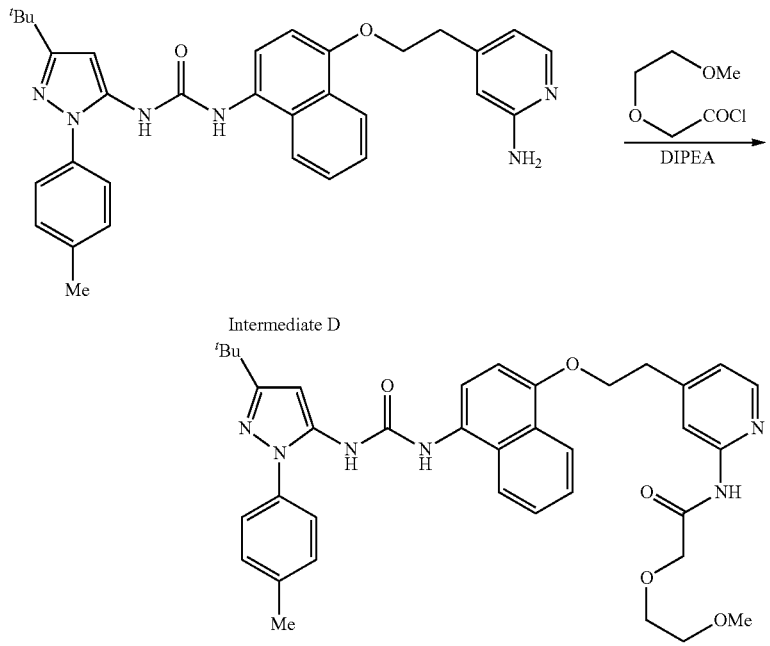

Intermediate D

Example 38

To a suspension of Intermediate D (35 mg, 0.065 mmol) in DCM (0.5 mL) was added DIPEA (23 μL, 0.131 mmol) and 2-(2-methoxy)ethoxyacetyl chloride (11 mg, 0.072 mmol) and the mixture stirred at RT until judged to be complete by LC-MS. The reaction mixture was diluted with saturated aq NaHCO$_3$ solution (1.5 mL) and the layers were separated through a phase separator cartridge. The organics were collected, evaporated under reduced pressure and the residue subjected to SCX capture and release. The resulting residue was purified further by preparative RP HPLC to give the title compound (Example 38) as an off white solid (13 mg, 31%): m/z 651 (M+H)$^+$ (ES$^+$). $^1$H NMR (400 MHz, DMSO-d$_6$) δ: 1.26 (9 H, s), 2.38 (3 H, s), 3.21 (2 H, t), 3.28 (3 H, s), 3.49-3.51 (2 H, m), 3.66-3.68 (2 H, m), 4.13 (2 H, s), 4.38 (2 H, t), 6.34 (1 H, s), 6.95 (1 H, d), 7.19 (1 H, dd), 7.34 (2 H, m), 7.41-7.48 (3 H, m), 7.51-7.56 (1 H, m), 7.59 (1H, d), 7.87 (1 H, d), 8.11-8.14 (1 H, dd), 8.20 (1 H, br s), 8.23-8.25 (1 H, dd), 8.55 (1 H, s), 8.75 (1 H, s), 9.83 (1 H, s).

Example 39

4-(2-(4-(3-(3-tert-Butyl-1-p-tolyl-1H-pyrazol-5-yl)ureido)naphthalen-1-yloxy)ethyl)-1-methyl-3-(pyridin-2-yl)urea

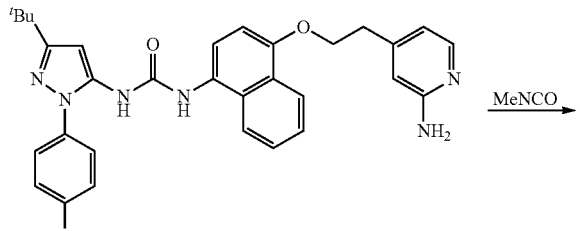

Intermediate D

-continued

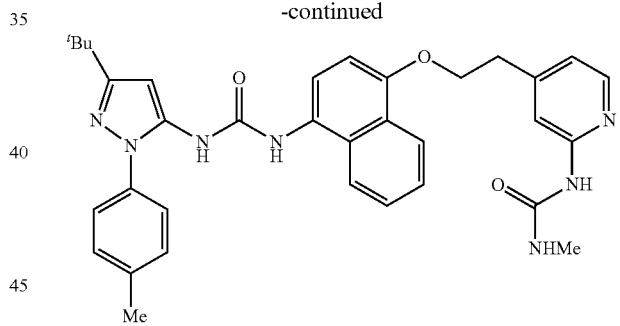

Example 39

To a solution of Intermediate D (50 mg, 0.094 mmol) in pyridine (1.0 mL) was added methyl isocyanate (5.3 mg, 0.094 mmol) and the mixture was stirred at RT for 72 hr. The solvent was evaporated under reduced pressure and the resulting residue was triturated from MeOH (5.0 mL) to give the title compound (Example 39) as an off white solid (7 mg, 13%): m/z 592 (M+H)$^+$ (ES$^+$). $^1$H NMR (400 MHz, DMSO-d$_6$) δ: 1.26 (9 H, s), 2.38 (3 H, s), 3.13 (2 H, t), 3.31 (3 H, s, obscured by H$_2$O), 4.32 (2 H, t), 6.34 (1 H, s), 6.93 (1 H, d), 7.34 (2 H, m), 7.40-7.48 (6 H, m), 7.53-7.57 (1 H, m), 7.61 (1

H, d), 7.81-7.83 (2 H, d), 7.86-7.89 (1 H, d), 8.02-8.04 (1 H, dd), 8.55 (1 H, s), 8.75 (1 H, s).

Example 40

4-(2-(4-(3-(3-tert-Butyl-1-p-tolyl-1H-pyrazol-5-yl)ureido)naphthalen-1-yloxy)ethyl)-3-(pyridin-2-yl)urea

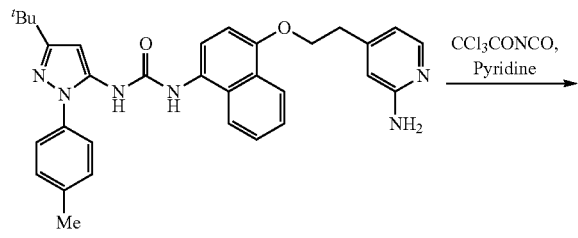

Intermediate D

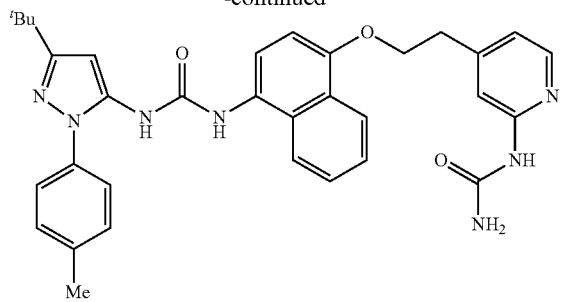

Example 40

To a solution of Intermediate D (50 mg, 0.094 mmol) in pyridine (1.0 mL) was added trichloroacetylisocyanate (12 µL, 0.103 mmol) and the mixture was stirred at RT until judged to be complete by LC-MS. The solvent was evaporated in vacuo and the resulting residue was subjected to SCX capture and release and then triturated from DCM (10 mL) to give the title compound (Example 40) as an off white solid (25 mg, 44%): m/z 578 (M+H)$^+$ (ES$^+$). $^1$H NMR (400 MHz, DMSO-$d_6$) δ: 1.26 (9 H, s), 2.38 (3 H, s), 3.12 (2 H, t), 4.35 (2 H, t), 6.34 (1 H, s), 6.94-6.99 (2 H, m), 7.19 (1 H, dd), 7.33-7.35 (2 H, m), 7.41-7.50 (5 H, m), 7.52-7.56 (1 H, m), 7.60 (1 H, d), 7.87 (1 H, d), 8.09-8.13 (2 H, m), 8.54 (1 H, s), 8.75 (1 H, s), 9.08 (1 H, s).

Intermediate E 1-(4-(2-(3-Aminopyridin-4-yl)ethoxy)naphthalen-1-yl)-3-(3-tert-butyl-1-p-tolyl-1H-pyrazol-5-yl)urea

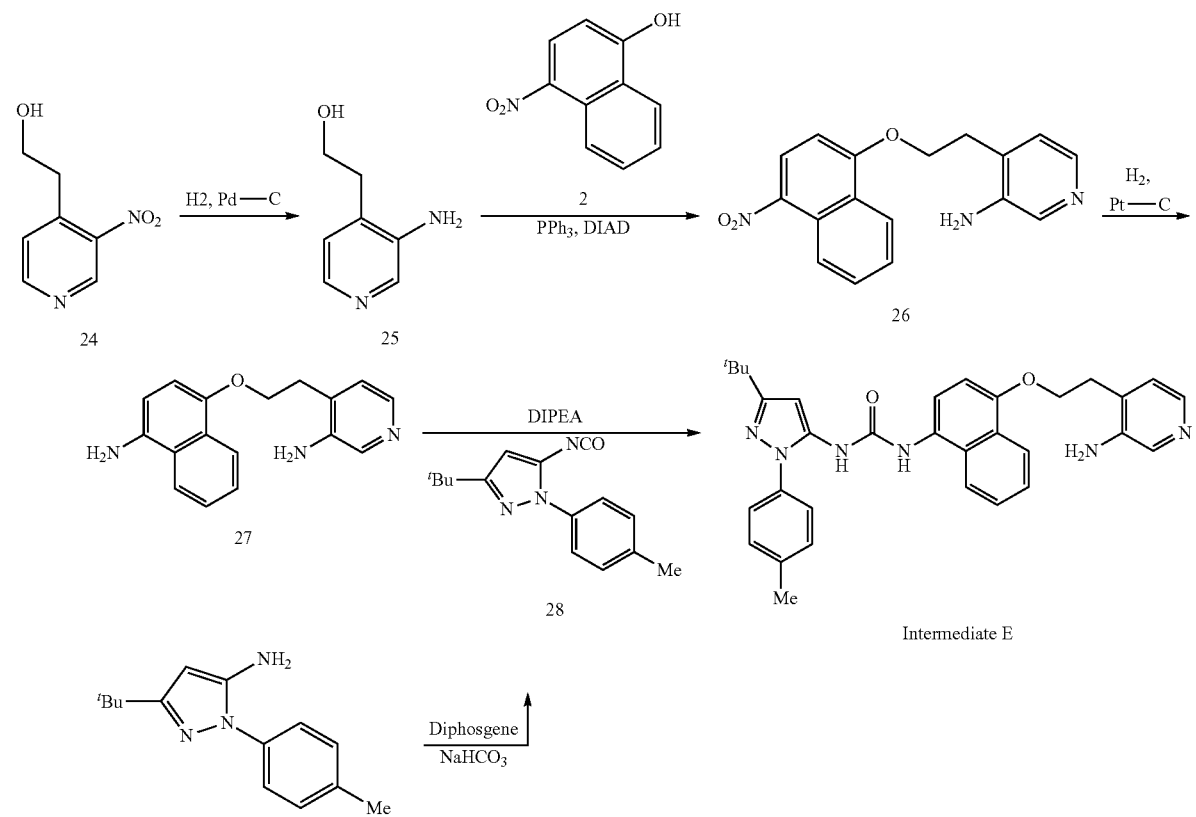

2-(3-Aminopyridin-4-yl)ethanol (25)

A solution of 2-(3-nitropyridin-4-yl)ethanol (24) (WO 2006136562) (2.00 g, 11.89 mmol) in MeOH (150 mL) was passed through a Thales H-cube (2.0 mL·min⁻¹, 30° C., 30 bar, Pd/C Cat-Cart, 55 mm, controlled mode). Analysis by LC-MS showed a significant amount of starting material was still present and the solution was passed through the H-cube twice more (2.0 mL·min⁻¹, full hydrogen mode, RT, and 2.0 mL·min⁻¹, full hydrogen mode, 40° C.). Evaporation of the volatiles gave the title compound (25) as a purple oil (1.30 g, 81%): m/z 139 (M+H)⁺ (ES⁺).

4-(2-(4-Nitronaphthalen-1-yloxy)ethyl)pyridin-3-amine (26)

To a solution of 4-nitronaphthol (2) (0.95 g, 5.00 mmol), PPh₃ (1.97 g, 7.50 mmol) and 2-(3-aminopyridin-4-yl)ethanol (25) (1.04 g, 7.50 mmol) in THF (20 mL) was added dropwise DIAD (590 µL, 3.75 mmol) at −15° C. The mixture was stirred for 1 hr at RT and the volatiles removed in vacuo. The residues was absorbed on silica (20 g) and purified by column chromatography (SiO₂, 80 g, 50-100% EtOAc in isohexane, gradient elution and then 5% MeOH in EtOAc, isocratic elution) to give the title compound (26) (1.36 g, 88%): m/z 310 (M+H)⁺ (ES⁺).

4-(2-(4-Aminonaphthalen-1-yloxy)ethyl)pyridin-3-amine (27)

A solution of 4-(2-(4-nitronaphthalen-1-yloxy)ethyl)pyridin-3-amine (26) (700 mg, 2.263 mmol) in a mixture of MeOH (50 mL), EtOAc (25 mL), and DCM (25 mL) was passed through a Thales H-cube (10% Pt/C, 30 mm, 1.0 mL·min⁻¹, 40° C., full hydrogen mode). The solvent was removed in vacuo to give the title compound (27) as a brown solid (612 mg, 92%). m/z 280 (M+H)⁺ (ES⁺).

3-tert-Butyl-5-isocyanato-1-p-tolyl-1H-pyrazole (28)

To a solution of 3-tert-butyl-1-p-tolyl-1H-pyrazol-5-amine (5) (1.00 g, 4.36 mmol) in DCM (90 mL) was added a saturated aq solution of NaHCO₃ (60 mL). The mixture was stirred vigorously, cooled to 0° C. and diphosgene (2.1 mL, 17.4 mmol) was added in a single portion. After stirring for 1 hr at RT, the layers were separated and the organics dried and evaporated to give a brown oil. The oil was triturated with isohexane (5.0 mL) and the solid filtered. The filtrate was concentrated in vacuo to give the title compound (28) as a light brown oil (1.00 g, 3.92 mmol, 90%). m/z 288 (in MeOH) (M+H+MeOH)⁺ (ES⁺).

Intermediate E

1-(4-(2-(3-Aminopyridin-4-yl)ethoxy)naphthalen-1-yl)-3-(3-tert-butyl-1-p-tolyl-1H-pyrazol-5-yl)urea A solution of 3-tert-butyl-5-isocyanato-1-p-tolyl-1H-pyrazole (28) (530 mg, 2.076 mmol) in THF (2.0 mL) was added to a solution of 4-(2-(4-aminonaphthalen-1-yloxy)ethyl)pyridin-3-amine (27) (580 mg, 2.076 mmol) and DIPEA (1085 µL, 6.23 mmol) in THF (10 mL) and MeCN (1.0 mL) and the reaction mixture stirred at RT overnight. The mixture was poured into brine (25 mL) and extracted with EtOAc (2×25 mL), dried, filtered and the solvent removed in vacuo. The product was pre-adsorbed onto hyflo (10 g), and purified by reverse phase column chromatography (40 g, C₁₈ [from Silicycle], acetonitrile/water, 0 to 100%) and the product fractions concentrated in vacuo to give the title compound (Intermediate E) as an off white solid (410 mg, 36%). m/z 535 (M+H)⁺ (ES⁺).

Example 41

N-(4-(2-(4-(3-(3-tert-Butyl-1-p-tolyl-1H-pyrazol-5-yl)ureido)naphthalen-1-yloxy)ethyl)pyridin-3-yl)-2-methoxyacetamide

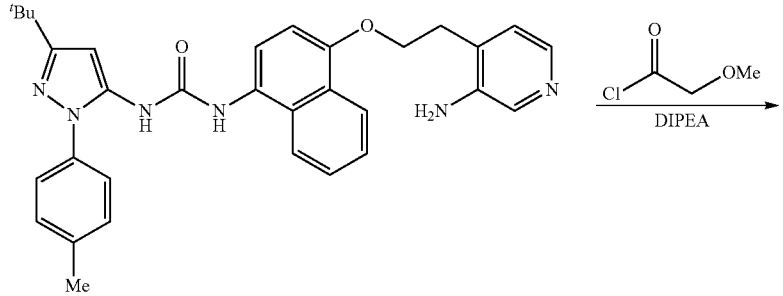

Intermediate E

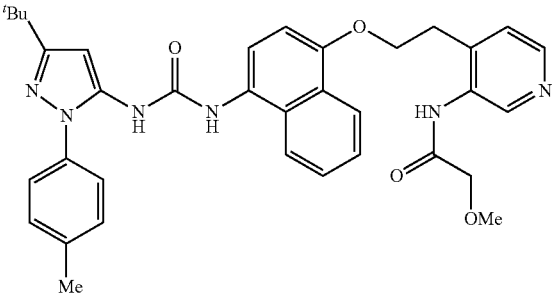

Example 41

To a solution of Intermediate E (50 mg, 0.094 mmol) and DMAP (5.71 mg, 0.047 mmol) in DCM (3.0 mL) was added methoxyacetyl chloride (25.7 μL, 0.281 mmol) at 0° C. and the reaction mixture stirred at RT for 1.5 hr. The solvent was removed in vacuo and the residue subjected to SCX capture and release. The impure product was purified by flash column chromatography (SiO$_2$, 4.0 g, 0-10% MeOH in DCM, gradient elution) to give the title compound (Example 41) as a pale pink solid (45 mg, 77%): m/z 607 (M+H)$^+$ (ES$^+$). $^1$H NMR (400 MHz, DMSO-d$_6$) δ: 1.27 (9H, s), 2.39 (3H, s), 3.18 (2H, t), 3.40 (3H, s), 4.08 (2H, s), 4.39 (2H, t), 6.35 (1H, s), 6.96 (1H, d), 7.35 (2H, m), 7.43 (2H, m), 7.50 (2H, m), 7.58 (1H, m), 7.61 (1H, d), 7.88 (1H, d), 8.09 (1H, dd), 8.37 (1H, d), 8.52 (1H, s), 8.56 (1H, br s), 8.76 (1H, br s), 9.66 (1H, br s.).

Example 42

N-(4-(2-(4-(3-(3-tert-Butyl-1-p-tolyl-1H-pyrazol-5-yl)ureido)naphthalen-1-yloxy)ethyl)pyridin-3-yl)-2-(2-methoxyethoxy)acetamide

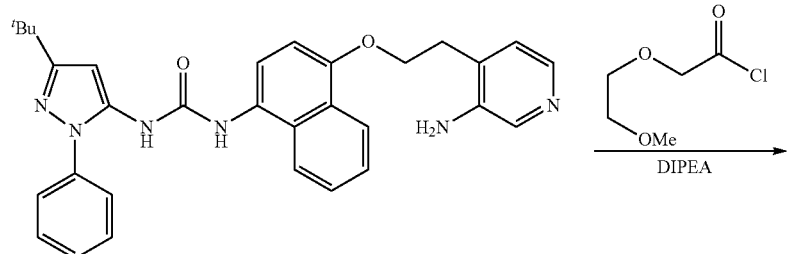

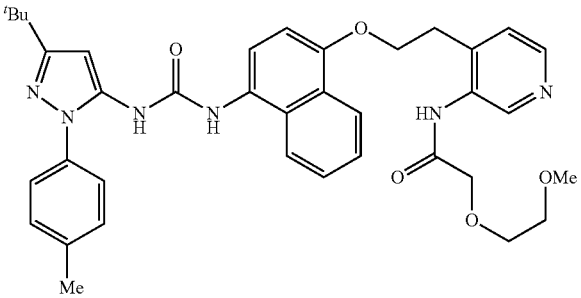

Example 42

To a solution of Intermediate E (50 mg, 0.094 mmol) and DMAP (5.71 mg, 0.047 mmol) in DCM (3.0 mL) was added 2-(2-methoxyethoxy)acetyl chloride (30 μL, 0.281 mmol) at 0° C. and the reaction mixture stirred at RT for 1.5 hr. The solvent was removed in vacuo and the residue subjected to SCX capture and release. The residue was purified by column chromatography (SiO$_2$, 4.0 g, 0-8% MeOH in DCM, gradient elution) and the product fractions concentrated in vacuo to give the title compound (Example 42) as a light purple solid (35 mg, 56%): m/z 651 (M+H)$^+$ (ES$^+$). $^1$H NMR (400 MHz, DMSO-d$_6$) δ: 1.25 (9H, s), 2.40 (3H, s), 3.26 (5H, m), 3.50 (2H, m), 3.70 (2H, m), 4.15 (2H, s), 4.40 (2H, t), 6.35 (1H, s), 6.98 (1H, d), 7.35 (2H, m), 7.42 (2H, m), 7.50 (3H, m), 7.62 (1H, d), 7.87 (1H, d), 8.07 (1H, dd), 8.36 (1H, d), 8.56 (1H, br s), 8.60 (1H, s), 8.76 (1H, br s), 9.55 (1H, br s.).

Intermediate F 1-(4-(2-(2-Aminopyridin-4-yloxy)ethyl)naphthalen-1-yl)-3-(3-tert-butyl-1-p-tolyl-1H-pyrazol-5-yl)urea

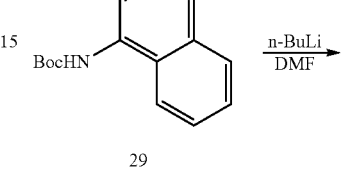

29

-continued

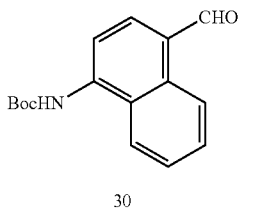

30

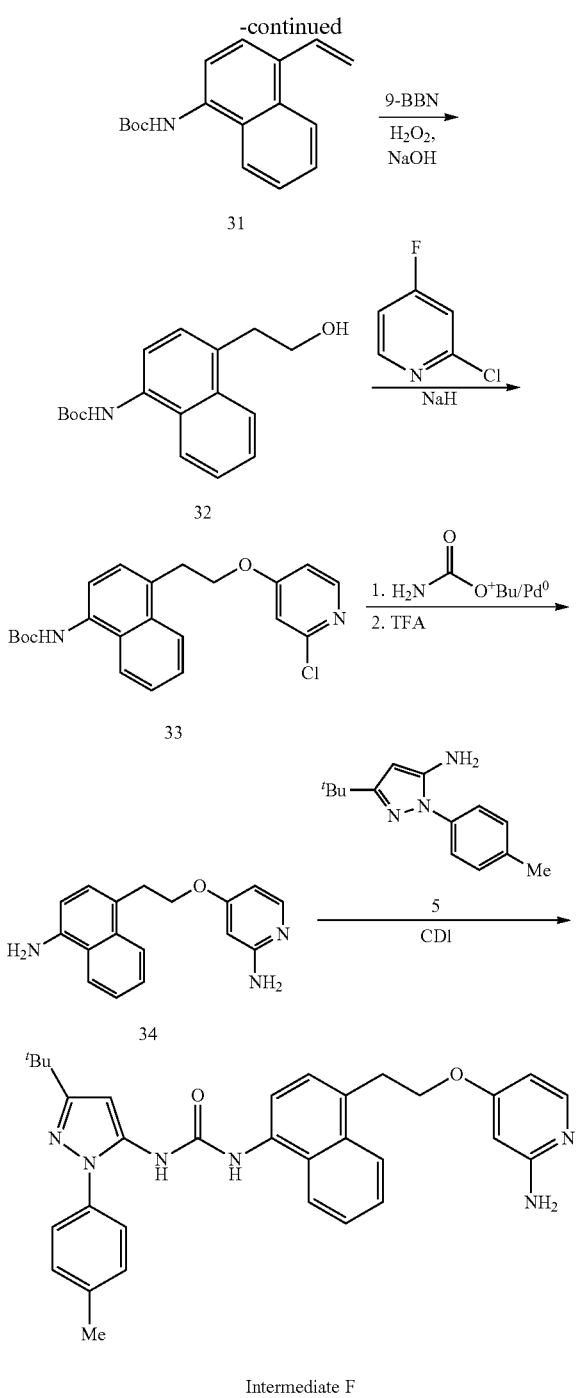

tert-Butyl 4-formylnaphthalen-1-ylcarbamate (30)

To a solution of tert-butyl 4-bromonaphthalen-1-ylcarbamate (29) (3.00 g, 9.31 mmol) in THF (100 mL) at −78° C. under nitrogen was added n-BuLi (1.6M in hexane, 20.4 mL, 32.6 mmol) and the reaction mixture was stirred at −78° C. for 1 hr. Neat DMF (4.50 mL, 58.1 mmol) was added and the reaction mixture was stirred at −78° C. for 1 hr, then warmed to RT and stirred for a further 1 hr. Water (5 mL) was added and the mixture was partitioned between ethyl acetate (100 mL) and water (100 mL). The organic phase was washed with brine, dried (MgSO$_4$) and evaporated in vacuo. The residue was triturated with isohexane to afford the title compound (30) as a beige solid (2.20 g, 87%): m/z 272 (M+H)$^+$ (ES)$^+$.

tert-Butyl 4-vinylnaphthalen-1-ylcarbamate (31)

To a suspension of methyltriphenylphosphonium bromide (3.82 g, 10.69 mmol) in THF (20 mL) at 0° C. under nitrogen was added potassium tert-butoxide (1.20 g, 10.69 mmol) and the reaction mixture was stirred at 0° C. for 15 min, then warmed to RT and stirred for a further 45 min. The suspension was cooled to 0° C. and a solution of tert-butyl 4-formylnaphthalen-1-ylcarbamate (30) (1.16 g, 4.28 mmol) in THF (10 mL) was added dropwise. The reaction mixture was warmed to RT and stirred for 2 hr. Saturated aqueous NH$_4$Cl solution (30 mL) was added and the mixture was extracted with ethyl acetate. The ethyl acetate extract was washed with brine, dried (MgSO$_4$) and evaporated in vacuo. The residue was purified by flash column chromatography (SiO$_2$, 0-10% ethyl acetate in isohexane, gradient elution) to afford the title compound (31) as a white solid (0.831 g, 72%): m/z 268 (m-H)$^-$ (ES$^-$)

tert-Butyl 4-(2-hydroxyethyl)naphthalen-1-ylcarbamate (32)

To a solution of tert-butyl 4-vinylnaphthalen-1-ylcarbamate (31) (0.83 g, 3.08 mmol) in THF (10 mL) was added 9-BBN (0.5M in THF, 9.9 mL, 4.95 mmol) dropwise under nitrogen at 0° C. The mixture was warmed to RT and stirred for 16 hr. Water (1 mL), aqueous NaOH solution (3M, 10.0 mL, 30 mmol) and hydrogen peroxide (35% in water, 8.0 mL) were added. The reaction mixture was warmed to 50° C. and stirred for 2 hr and was then extracted with ethyl acetate. The ethyl acetate extract was washed with water and brine, dried (MgSO$_4$) and evaporated in vacuo. The residue was purified by flash column chromatography (SiO$_2$, 10-60% ethyl acetate in isohexane, gradient elution) to afford the title compound (32) (0.763 g, 86%); m/z 288 (M+H)$^+$, (ES$^+$).

tert-Butyl 4-(2-(2-chloropyridin-4-yloxy)ethyl)naphthalen-1-ylcarbamate (33)

To a degassed solution of tert-butyl 4-(2-hydroxyethyl)naphthalen-1-ylcarbamate (32) (0.64 g, 2.23 mmol) in DMF (10 mL) was added sodium hydride (0.267 g, 60% dispersion in mineral oil, 6.68 mmol) under nitrogen at 0° C. The solution was warmed to RT and was stirred for 30 min and then cooled to 0° C. To this mixture was added a solution of 2-chloro-4-fluoro-pyridine (0.381 g, 2.90 mmol) in DMF (5.0 mL) and the reaction mixture was warmed to RT and stirred for 16 hr. Water was added and the mixture was extracted with ethyl acetate. The ethyl acetate extract was washed with brine (3×), dried (MgSO$_4$) and evaporated in vacuo. The residue was purified by flash column chromatography (SiO$_2$, 0-40% ethyl acetate in isohexane, gradient elution) to afford the title compound (33) (0.67 g, 75%); m/z 399 (M+H)$^+$, (ES$^+$).

4-(2-(4-Aminonaphthalen-1-yl)ethoxy)pyridin-2-amine (34)

To a degassed suspension of tert-butyl 4-(2-(2-chloropyridin-4-yloxy)ethyl)naphthalen-1-ylcarbamate (33) (600 mg, 1.50 mmol), tert-butyl carbamate (176 mg, 1.50 mmol), Cs$_2$CO$_3$ (733 mg, 2.26 mmol) and Xathphos (43 mg, 0.075 mmol) in THF (10 mL) was added Pd$_2$dba$_3$ (34 mg, 0.038 mmol) and the reaction mixture was heated at reflux under nitrogen for 16 hr. Water was added and the reaction mixture was extracted with ethyl acetate. The organic extract was washed with brine, dried and evaporated in vacuo. The residue was purified by flash column chromatography (SiO$_2$, 0-50% hexane in ethyl acetate, gradient elution) to afford a mixture of the desired Boc protected product and starting material, which was dissolved in a mixture of DCM (2 mL) and TFA (2 mL) and stirred at RT for 1 hr. The solvent was evaporated in vacuo and the residue was dissolved in DCM and washed with saturated aqueous NaHCO$_3$ solution and brine, then dried (MgSO$_4$) and evaporated in vacuo. The residue was purified by flash column chromatography (SiO$_2$, 5% MeOH in DCM, isocratic elution) to afford the title compound (34) (45 mg, 11%); m/z 280 (M+H)$^+$, (ES$^+$).

Intermediate F 1-(4-(2-(2-Aminopyridin-4-yloxy)ethyl)naphthalen-1-yl)-3-(3-tert-butyl-1-p-tolyl-1H-pyrazol-5-yl)urea To a suspension of CDI (122 mg, 0.752 mmol) in DCM (2 mL) was added a solution of 3-tert-butyl-1-p-tolyl-1H-pyrazol-5-amine (172 mg, 0.752 mmol) in DCM (2.0 mL) and the reaction mixture was stirred at RT for 16 hr. An aliquot (1.0 mL) of this reaction mixture was added to a stirred suspension of 4-(2-(4-aminonaphthalen-1-yl)ethoxy)pyridin-2-amine (34) (42 mg, 0.150 mmol) in DCM (2.0 mL). THF (0.5 mL) was added and the reaction mixture was stirred for 1 hr. A second aliquot (1.0 mL) of the CDI reaction mixture was added and the mixture was stirred for a further 20 hr at RT. Methanol was added and stirring continued for 30 min. The solvent was evaporated and the residue was purified by flash column chromatography (SiO$_2$, 0-5% MeOH in DCM, gradient elution). The resulting impure product was dissolved in ethyl acetate, washed with water and brine, dried (MgSO$_4$) and evaporated in vacuo to afford the title compound (Intermediate F) (42 mg, 52%); m/z 535 (M+H)$^+$, (ES$^+$).

Example 43

N-(4-(2-(4-(3-(3-tert-butyl-1-p-tolyl-1H-pyrazol-5-yl)ureido)naphthalen-1-yl)ethoxy)pyridin-2-yl)-2-methoxyacetamide

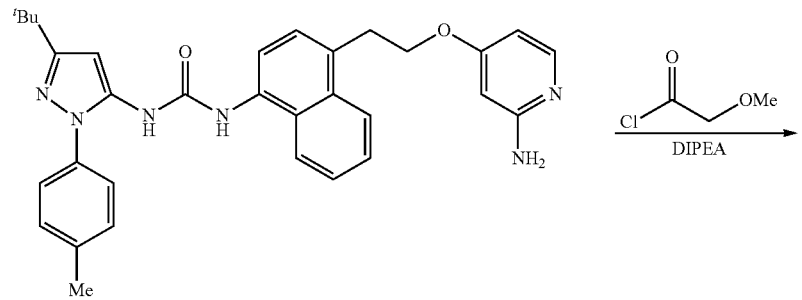

Intermediate F

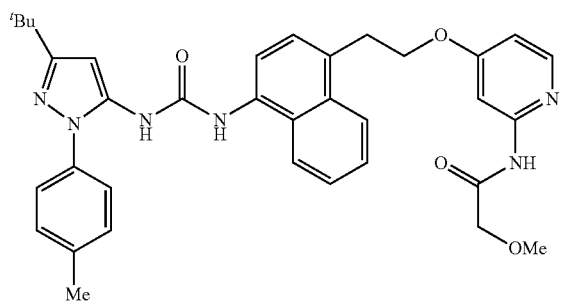

Example 43

To a solution of Intermediate F (40 mg, 0.075 mmol) and DIPEA (0.059 mL, 0.337 mmol) in DCM (1.5 mL) was added methoxyacetyl chloride (32 mg, 0.299 mmol) and the reaction mixture was stirred for 16 hr at RT. A solution of ammonia (1% in methanol) was added and the stirring continued for 30 min. The solvent was evaporated in vacuo and the residue was purified by SCX capture and release. The crude product was purified by flash column chromatography (SiO$_2$, 0-5% MeOH in DCM, gradient elution) to afford the title compound (Example 43) (10 mg, 20%): m/z 607 (M+H)$^+$ (ES$^+$); $^1$H NMR (400 MHz, DMSO-d$_6$) δ: 1.28 (9H, s), 2.39 (3H, s), 3.35 (3H, s), 3.51 (2H, t), 4.03 (2H, s), 4.35 (2H, t), 6.39 (1H, s), 6.72 (1H, dd), 7.35 (2H, d), 7.42-7.47 (3H, overlapping m), 7.55-7.63 (2H, overlapping m), 7.67 (1H, d), 7.82 (1H, d), 8.03 (1H, m), 8.10 (1H, d), 8.19 (1H, d), 8.72 (1H, br s), 9.01 (1H, br s), 9.87 (1H, br s).

Intermediate G 1-(4-(1-(2-aminopyridin-4-yl)ethoxy)naphthalen-1-yl)-3-(3-tert-butyl-1-p-tolyl-1H-pyrazol-5-yl)urea

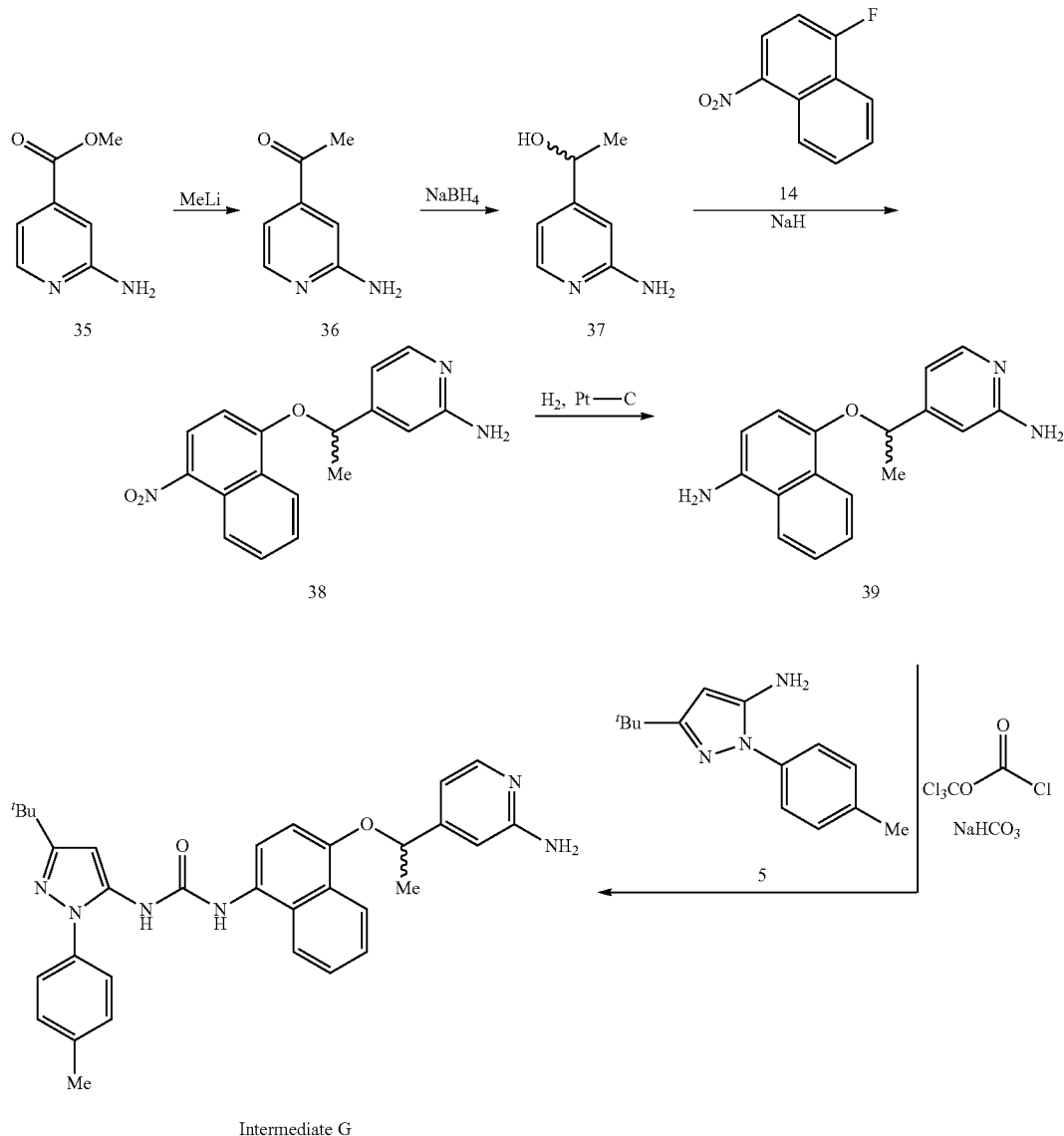

Intermediate G

1-(2-Aminopyridin-4-yl)ethanone (36)

To a stirred solution of methyl-2-aminopyridine-4-carboxylate (35) (1.00 g, 6.57 mmol) in THF (100 mL), at −78° C. under nitrogen, was added methyllithium (1.6 M in diethyl ether, 16.4 mL, 26.3 mmol), over 10 min. After a further 30 min at −78° C., the viscous reaction mixture was warmed to 0° C. After a further 3 hr, the reaction was quenched at 0° C. by the cautious addition of iso-propanol (8.0 mL). The mixture was warmed to RT, brine (200 mL) and EtOAc (150 mL) were added, and the layers were separated. The aqueous layer was extracted with EtOAc (3×100 mL), and the combined organic extracts were dried and the solvents removed in vacuo. The crude residue was purified by column chromatography (SiO$_2$, 80 g, 0-8% MeOH in EtOAc, gradient elution) to give the title compound (36) (176 mg, 20%) as a yellow powder: m/z 137 (M+H)$^+$ (ES$^+$).

1-(2-Aminopyridin-4-yl)ethanol (37)

To a mixture of 1-(2-aminopyridin-4-yl)ethanone (36) (168 mg, 1.234 mmol) in MeOH (10 mL), under nitrogen at 0° C., was added sodium borohydride (46.7 mg, 1.234 mmol). The reaction mixture was stirred at RT for 2 hr, and the volatiles were removed under reduced pressure. The residue was taken up into EtOAc (25 mL), and extracted with saturated aq NaHCO$_3$ solution (30 mL). The aqueous layer was back extracted with EtOAc (2×20 mL), and the combined organic extracts were washed with brine (30 mL), dried and the solvents removed in vacuo to give the title compound (37) (77 mg, 45%) as a yellow oil: m/z 139 (M+H)$^+$ (ES$^+$).

4-(1-(4-Nitronaphthalen-1-yloxy)ethyl)pyridin-2-amine (38)

To a stirred solution of 1-(2-aminopyridin-4-yl)ethanol (37) (73 mg, 0.528 mmol) in DMF (1.5 mL), under nitrogen at 0° C., was added sodium hydride (32 mg, 0.793 mmol, 60 wt %). The resulting mixture was stirred at 0° C. for 40 min, and a solution of 1-fluoro-4-nitronaphthalene (14) (101 mg, 0.528 mmol) in DMF (1.5 mL) was added dropwise. The resulting dark-red mixture was stirred at 0° C. for 5 min and at RT for 40 min and was quenched by the addition of 1.0 mL of NH$_4$Cl solution. Water (20 mL) and EtOAc (20 mL) were added, and the layers were separated. The aqueous layer was extracted with EtOAc (3×15 mL). The combined organic extracts were washed with brine, dried and the solvents removed in vacuo. The crude material was purified by column chromatography (SiO$_2$, 12 g, 0-80% EtOAc in isohexane, gradient elution) to give the title compound (38) (94.6 mg, 57%) as an orange gum: m/z 310 (M+H)$^+$ (ES$^+$).

4-(1-(4-Aminonaphthalen-1-yloxy)ethyl)pyridin-2-amine (39)

A solution of 4-(1-(4-Nitronaphthalen-1-yloxy)ethyl)pyridin-2-amine (38) (91 mg, 0.294 mmol) in MeOH (15 mL) and AcOH (3.0 mL) was passed through a Thales H-cube (1.0 mL·min$^{-1}$, 30° C., 55 mm, 10% Pt/C Cat-Cart, full hydrogen mode). The volatiles were removed under reduced pressure, leaving a purple solid, which was then subjected to SCX capture and release to give the title compound (39) (81 mg, 99%) as a purple oil: m/z 280 (M+H)$^+$ (ES$^+$).

Intermediate G 1-(4-(1-(2-Aminopyridin-4-yl)ethoxy)naphthalen-1-yl)-3-(3-tert-butyl-1-p-tolyl-1H-pyrazol-5-yl)urea To a solution of 3-tert-butyl-1-p-tolyl-1H-pyrazol-5-amine (5) (57 mg, 0.250 mmol) in DCM (6.0 mL) was added saturated aq NaHCO$_3$ solution (4.0 mL) The mixture was stirred vigorously and was cooled to 0° C. and trichloromethylchloroformate (0.091 mL, 0.750 mmol) was added in one portion. The resulting mixture was stirred at 0° C. for 1.5 hr. The biphasic mixture was separated and the organic extract was dried and the solvents removed under reduced pressure to afford an oil, which was dried under high vacuum, at 35° C. for 35 min. The resulting oil was taken up into THF (5.0 mL), and then added to 4-(1-(4-aminonaphthalen-1-yloxy)ethyl)pyridin-2-amine (39) (81 mg, 0.290 mmol). DIPEA (179 µL, 1.029 mmol) was added, and the reaction mixture was stirred at RT for 16 hr. Water (15 mL) and EtOAc (10 mL) were added to the reaction mixture and the layers were separated. The aqueous layer was extracted with EtOAc (15 mL). The combined organic extracts were washed with brine (20 mL), dried and the solvents removed under reduced pressure. The resulting residue was dissolved in MeOH (5.0 mL) and AcOH (2.0 mL) and subjected to SCX capture and release. The crude mixture was purified by column chromatography (SiO$_2$, 12 g, 0-10% MeOH in DCM, gradient elution) to give the target compound (Intermediate G) (63 mg, 38%) as a beige powder: m/z 535 (M+H)$^+$ (ES$^+$).

Example 44

N-(4-(1-(4-(3-(3-tert-Butyl-1-p-tolyl-1H-pyrazol-5-yl)ureido)naphthalen-1-yloxy)ethyl)pyridin-2-yl)-2-methoxyacetamide

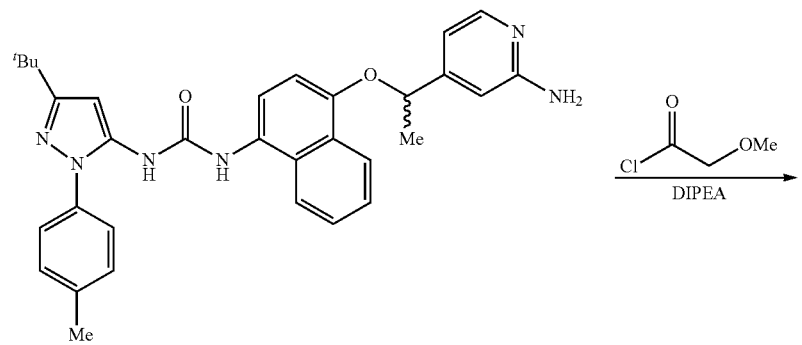

Intermediate G

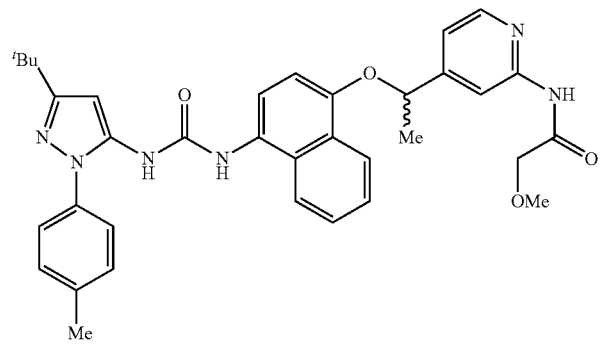

Example 44

Methoxyacetyl chloride (17.5 μL, 0.192 mmol) was added dropwise to a solution of Intermediate G (41 mg, 0.077 mmol) and DIPEA (40.1 μL, 0.230 mmol) in DCM (3 mL) under nitrogen at 0° C. After 15 min the reaction mixture was warmed to RT and was stirred for 1.5 hr. A solution of $NH_3$ (1% in MeOH, 1.5 mL) was added and stirring continued for a further 2 hr. The reaction mixture was evaporated in vacuo and the residue was subjected to SCX capture and release. Fractions containing the desired material were combined, evaporated in vacuo and purified by flash column chromatography ($SiO_2$, 12 g, 3-6% MeOH in DCM, gradient elution; then $SiO_2$, 12 g, 0-40% EtOAc in ether, gradient elution) to give the title compound (Example 44) as a beige solid (24 mg, 51%): m/z 607 $(M+H)^+$ $(ES^+)$; $^1H$ NMR (400 MHz, DMSO $d_6$) δ: 1.26 (9H, s), 1.67 (3H, d), 2.38 (3H, s), 4.03 (2H, s), 5.75 (1H, q), 6.32 (1H, s), 6.81 (1H, d), 7.22 (1H, dd), 7.35 (2H, m), 7.42 (2H, m), 7.48 (1H, s), 7.59 (2H, m), 7.88 (1H, m), 8.24 (1H, br s), 8.27 (1H, d), 8.36 (1H, m), 8.59 (1H, br s), 8.76 (1H, br s), 9.99 (1H, br s).

Intermediate H 1-(4-(1-(2-Aminopyridin-4-yl)-2-methylpropan-2-yloxy)naphthalen-1-yl)-3-(3-tert-butyl-1-p-tolyl-1H-pyrazol-5-yl)urea

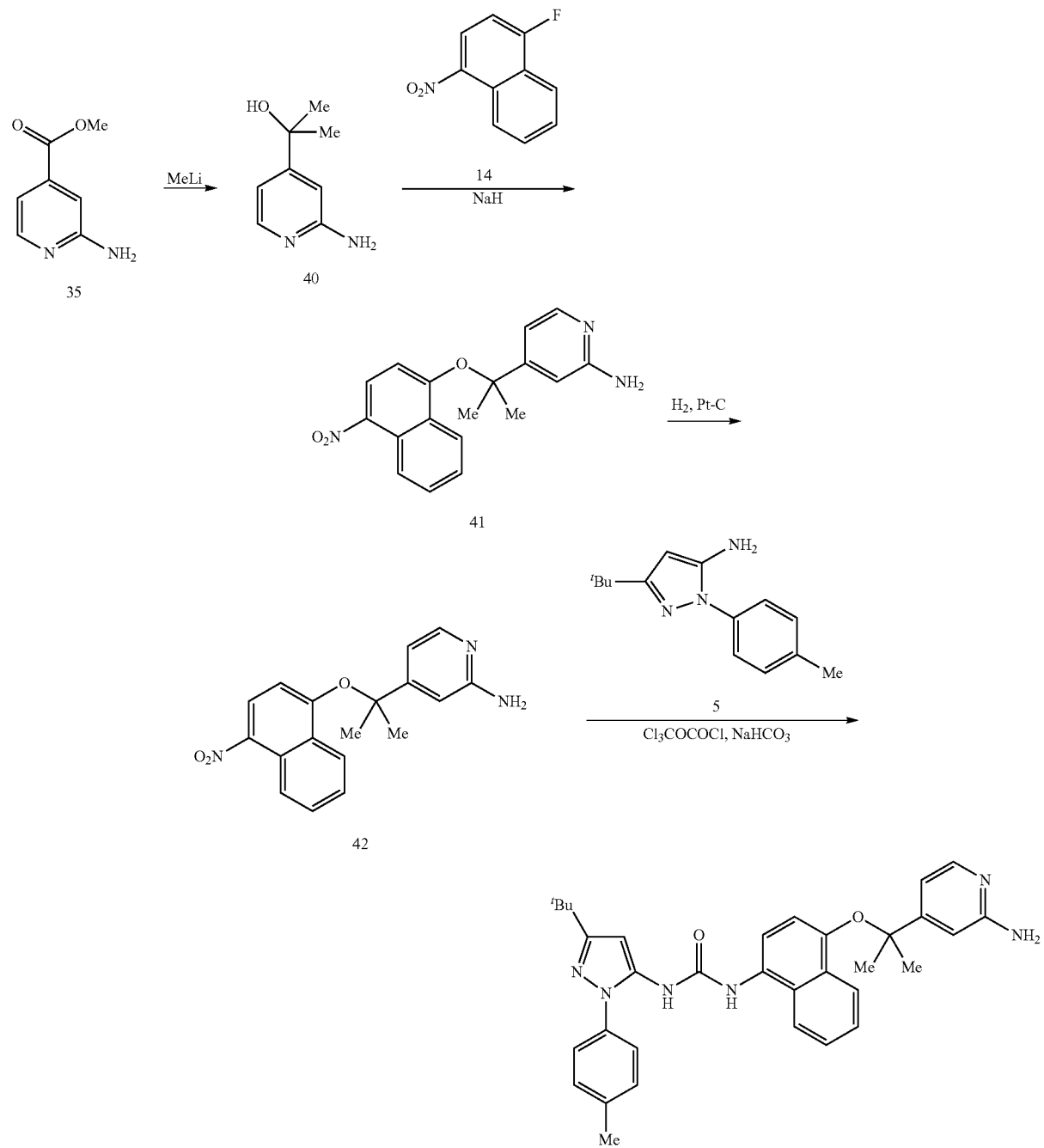

Intermediate H

2-(2-Aminopyridin-4-yl)propan-2-ol (40)

To a stirred solution of methyl-2-aminopyridine-4-carboxylate (35) (2.00 g, 13 mmol) in THF (200 mL), at −78° C. under nitrogen, was added methyllithium (1.6 M in diethyl ether, 33 mL, 53 mmol) over 10 min. After 30 min the viscous reaction mixture was warmed to 0° C. for 3.5 hr and was quenched at 0° C. by the cautious addition of isopropanol (15 mL). The mixture was warmed to RT, and brine (400 mL) and EtOAc (300 mL) were added. The aqueous layer was separated and extracted with EtOAc (3×200 mL) and the combined organic extracts were dried (MgSO$_4$) and evaporated in vacuo. The crude residue was purified by flash column chromatography (SiO$_2$, 120 g, 0-10% MeOH in EtOAc, gradient elution) to afford the title compound (40) (1.27 g, 63%) as a yellow amorphous solid: $^1$H NMR (400 MHz, CD$_3$OD) δ: 1.47 (6H, s), 6.68-6.71 (2H, overlapping m), 7.80-7.81 (1H, dd).

4-(2-(4-Nitronaphthalen-1-yloxy)propan-2-yl)pyridin-2-amine (41)

To a stirred solution of 2-(2-aminopyridin-4-yl)propan-2-ol (40) (1.55 g, 10.0 mmol) in DMF (30 mL), under nitrogen at 0° C., was added sodium hydride (60% wt, 0.61 g, 15.0 mmol) and the resulting mixture was stirred at 0° C. for 5 min. A solution of 1-fluoro-4-nitronaphthalene (14) (1.95 g, 10 mmol) in DMF (30 mL) was added dropwise and the resulting dark-red mixture was stirred at 0° C. for a further 5 min and then at RT for 2 hr. The reaction mixture was quenched by the addition of saturated aq NH$_4$Cl solution (10 mL). Water (150 mL) and EtOAc (150 mL) were added, and the layers were separated. The aqueous layer was extracted with EtOAc (3×100 mL) and the combined organic extracts were washed with brine, dried (MgSO$_4$) and evaporated in vacuo. The crude residue was purified by flash column chromatography (SiO$_2$, 80 g, 0-60% EtOAc in isohexane, gradient elution) to afford the title compound (41) (282 mg, 8%) as a red oil: m/z 324 (M+H)$^+$ (ES$^+$).

4-(2-(4-Aminonaphthalen-1-yloxy)propan-2-yl)pyridin-2-amine (42)

A solution of 4-(2-(4-nitronaphthalen-1-yloxy)propan-2-yl)pyridin-2-amine (41) (282 mg, 0.87 mmol) in MeOH (45 mL) was passed through a Thales H-cube (1.0 mL·min$^{-1}$, 30° C., 55 mm 10% Pt/C Cat-Cart, full hydrogen mode). The reaction mixture was evaporated in vacuo to afford the title compound (42) (253 mg, 89%) as a brown foam: m/z 294 (M+H)$^+$ (ES$^+$).

Intermediate H

1-(4-(2-(2-Aminopyridin-4-yl)propan-2-yloxy)naphthalen-1-yl)-3-(3-tert-butyl-1-p-tolyl-1H-pyrazol-5-yl)urea To a solution of 3-tert-butyl-1-p-tolyl-1H-pyrazol-5-amine (5) (447 mg, 1.75 mmol) in DCM (40 mL) was added saturated aq NaHCO$_3$ solution (27 mL). The mixture was stirred vigorously and was cooled to 0° C. and then trichloromethylchloroformate (0.63 mL, 5.25 mmol) was added in one portion. The resulting mixture was stirred at 0° C. for 1.5 hr. The biphasic mixture was separated and the organic layer was dried (MgSO$_4$) and evaporated in vacuo. The oily residue which was taken up in THF (15 mL) and was added to a solution of 4-(2-(4-aminonaphthalen-1-yloxy)propan-2-yl)pyridin-2-amine (42) (253 mg, 0.86 mmol) in THF (2.0 mL). Neat DIPEA (451 µL, 2.59 mmol) was added and the reaction mixture was stirred at RT for 2 hr. Water (30 mL) and EtOAc (20 mL) were added and the layers were separated. The aqueous layer was extracted with EtOAc (3×15 mL) and the combined organic layers were washed with brine (40 mL), dried (MgSO$_4$), and evaporated in vacuo. The residue was purified by flash column chromatography (SiO$_2$, 40 g, 0-10% MeOH in DCM, gradient elution) to afford the title compound (Interm. H) (249 mg, 51%) as a purple amorphous solid: m/z 549 (M+H)$^+$ (ES$^+$).

Example 45

N-(4-(2-(4-(3-(3-tert-Butyl-1-p-tolyl-1H-pyrazol-5-yl)ureido)naphthalen-1-yloxy)-2-methylpropyl)pyridin-2-yl)-2-methoxyacetamide

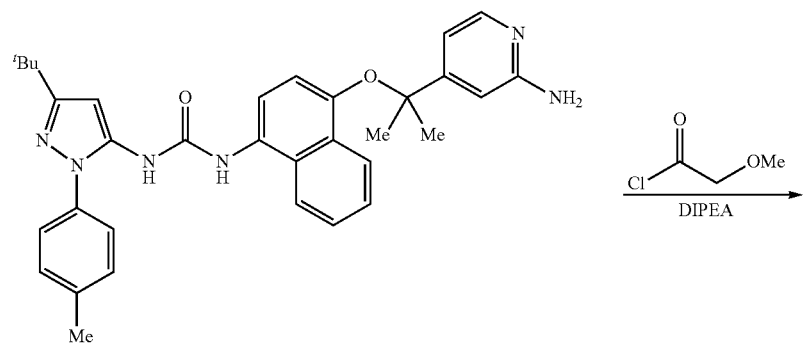

Intermediate H

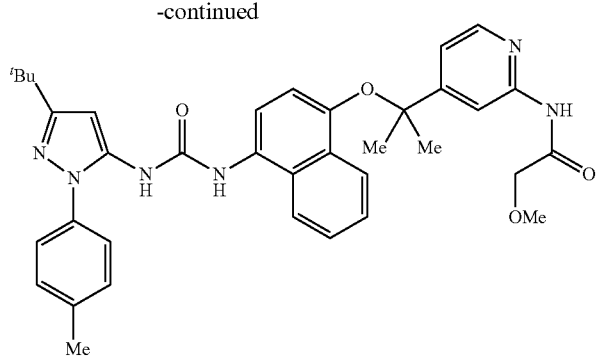

Example 45

Methoxyacetyl chloride (28 µL, 0.30 mmol) was added dropwise under nitrogen to a solution of Intermediate H (66 mg, 0.12 mmol) in DCM (3.0 mL) and DIPEA (63 µL, 0.36 mmol) at 0° C. The reaction mixture was stirred at 0° C. for 15 min and then at RT for 2.5 hr. A solution of $NH_3$ (1% in MeOH, 1.5 mL) was added and the mixture was stirred for 30 min and was then evaporated in vacuo. The residue was subjected to SCX capture and release then purified three times by column chromatography ($SiO_2$, 12 g, 0-7% MeOH in DCM, gradient elution; $C_{18}$, 12 g, 0-100% MeCN in water, gradient elution and $SiO_2$, 12 g, 0-65% EtOAc in $Et_2O$, gradient elution) to afford the title compound (Example 45) as a white solid (18 mg, 24%): m/z 621 $(M+H)^+$ $(ES^+)$. $^1$H NMR (400 MHz, DMSO-$d_6$) δ: 1.28 (9H, s), 1.39 (6H, s), 2.39 (3H, s), 3.22 (3H, s), 3.80 (1H, d), 4.16 (1H, d), 5.27 (1H, s), 6.41 (1H, s), 7.26 (1H, dd), 7.37 (2H, m), 7.46 (2H, m), 7.56 (1H, d), 7.60 (2H, overlapping m), 7.76 (1H, br s), 7.95 (1H, m), 8.01 (1H, d), 8.09 (1H, m), 8.22 (1H, d), 8.94 (1H, br s), 9.28 (1H, br s).

Intermediate J 1-(4-(1-(2-Aminopyridin-4-yl)propan-2-yloxy)naphthalen-1-yl)-3-(3-tert-butyl-1-o-tolyl-1H-pyrazol-5-yl)urea

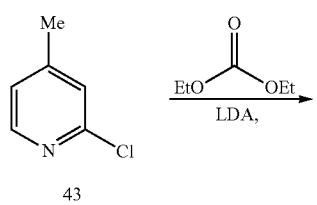

43

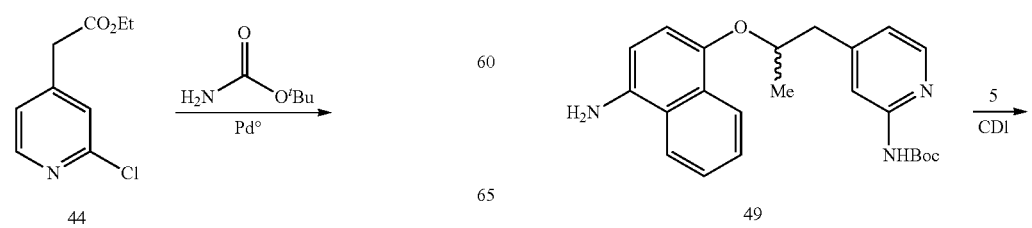

44

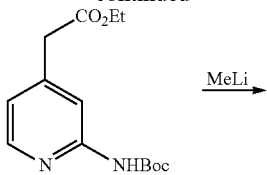

45

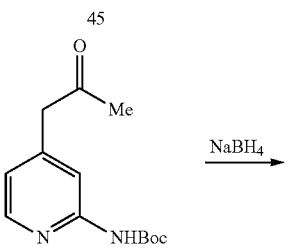

46

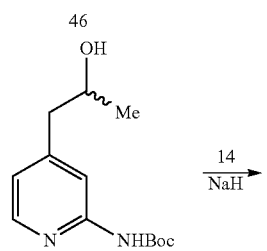

47

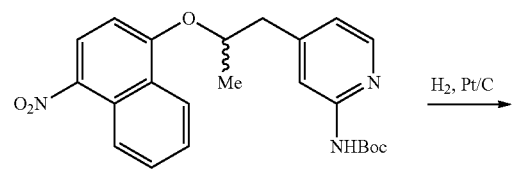

48

49

-continued

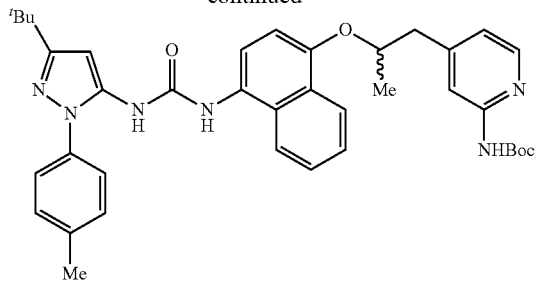

TFA ⌈ 50; R = Boc;
     ⌊→ Intermediate J; R = H;

Ethyl 2-(2-chloropyridin-4-yl)acetate (44)

A solution of LDA (2.0 M in THF, 809 mL, 1.62 mol) was added dropwise over 3 hr to a stirred solution of 2-chloropicoline (43) (59.1 mL, 674 mmol) in THF (500 mL) at −78° C. The reaction mixture was stirred for a further 15 min and then diethylcarbonate (106 mL, 876 mmol) was added in a single portion. After 10 min the reaction mixture was allowed to warm to 0° C., was stirred at this temperature for 20 min and then a saturated aqueous solution of $NH_4Cl$ (800 mL) was added. The mixture was extracted with ether and the organic phase was washed with water, dried ($MgSO_4$), and evaporated in vacuo to give a dark oil, (~200 g) which was purified in three batches by flash column chromatography ($SiO_2$, 330 g, 5-20% EtOAc in isohexane, gradient elution) to give the title compound (44) (72 g, 51%): m/z 200 (M+H)$^+$ (ES$^+$)

Ethyl 2-(2-(tert-butoxycarbonylamino)pyridin-4-yl) acetate (45)

A mixture of ethyl 2-(2-chloropyridin-4-yl)acetate (44) (15.0 g, 75.0 mmol), tert-butylcarbamate (26.4 g, 225 mmol), $Pd_2(dba)_3$ (1.719 g, 1.88 mmol), caesium carbonate (36.7 g, 113 mmol) and Xantphos® (2.17 g, 3.76 mmol) in THF (100 mL) was purged with nitrogen and was then stirred at 65° C. for 8 hr. The mixture was cooled to RT and was diluted with water and extracted with ether. The ether extracts were combined and washed with water and brine and then dried ($MgSO_4$), and evaporated in vacuo. The residue was purified by flash column chromatography ($SiO_2$, 330 g, 5-20% EtOAc in isohexane, gradient elution) then subjected to SCX capture and release to provide the title compound (45) (12.0 g, 51%): m/z 281 (M+H)$^+$ (ES$^+$).

tert-Butyl 4-(2-oxopropyl)pyridin-2-ylcarbamate (46)

A solution of methyllithium (1.6 M in diethyl ether, 17.4 mL, 27.9 mmol) was added dropwise over 12 min to a stirred solution of ethyl 2-(2-(tert-butoxycarbonylamino)pyridin-4-yl)acetate (45) (1.56 g, 5.58 mmol) in THF (140 mL) under nitrogen at −78° C. After 3 hr isopropanol (5.0 mL) was added and the reaction mixture was partitioned between water and EtOAc. The aqueous layer was extracted twice with EtOAc and the combined organic extracts were washed with brine then dried ($MgSO_4$) and evaporated in vacuo. The residue was purified by flash column chromatography ($SiO_2$, 80 g, 0-80% EtOAc in isohexane, gradient elution) to afford the title compound (46) (300 mg, 21%) as a white solid: m/z 251.0 (M+H)$^+$ (ES$^+$).

tert-Butyl 4-(2-hydroxypropyl)pyridin-2-ylcarbamate (47)

To a stirred solution of tert-butyl 4-(2-oxopropyl)pyridin-2-ylcarbamate (46) (300 mg, 1.20 mmol) in methanol (12 mL) at 0° C., under nitrogen, was added sodium borohydride (45.3 mg, 1.20 mmol). After 10 min the reaction mixture was warmed to RT and stirring continued for 75 min. The mixture was evaporated in vacuo and the residue was taken up into EtOAc and washed with aqueous $NaHCO_3$ solution. The aqueous layer was extracted twice with EtOAc and the combined organic extracts were washed with brine, then dried ($MgSO_4$) and evaporated in vacuo. The residue was purified by flash column chromatography ($SiO_2$, 12 g, 10-80% EtOAc in isohexane, gradient elution) to afford the title compound (47) (262 mg, 85%) as a white powder; m/z 253.0 (M+H)$^+$ (ES$^+$).

tert-Butyl 4-(2-(4-nitronaphthalen-1-yloxy)propyl) pyridin-2-ylcarbamate (48)

Sodium hydride (119 mg, 2.97 mmol) was added to a stirred solution of tert-butyl 4-(2-hydroxypropyl)pyridin-2-ylcarbamate (47) (250 mg, 0.991 mmol) in DMF (6 mL) at 0° C., under nitrogen and after 45 min a solution of 1-fluoro-4-nitronaphthalene (14) (189 mg, 0.991 mmol) in DMF (6 mL) was added dropwise, over 2 min. The resulting dark-brown reaction mixture was stirred at 0° C. for 5 min, and was then warmed to RT. After 70 min, a saturated aqueous solution of $NH_4Cl$ (3 mL) was added and the mixture was partitioned between water and EtOAc. The aqueous layer was extracted twice with EtOAc and the combined organic extracts were washed with brine, dried ($MgSO_4$) and evaporated in vacuo. The residue was purified by flash column chromatography ($SiO_2$, 40 g; 0-70% EtOAc in isohexane, gradient elution) to afford the title compound (48) (293 mg, 65%) as an orange foam: m/z 424.0 (M+H)$^+$ (ES$^+$).

tert-Butyl 4-(2-(4-aminonaphthalen-1-yloxy)propyl) pyridin-2-ylcarbamate (49)

A solution of tert-butyl 4-(2-(4-nitronaphthalen-1-yloxy)propyl)pyridin-2-ylcarbamate (48) (271 mg, 0.614 mmol) in MeOH (30 mL) was passed through a Thales H-cube (1.0 mL·min$^{-1}$, 30° C., 55 mm, 10% Pt/C Cat-Cart, full hydrogen mode) and the volatiles were removed in vacuo to afford the title compound (49) (241 mg, 100%) as a purple foam: m/z 394.0 (M+H)$^+$ (ES$^+$).

tert-Butyl 4-(2-(4-(3-(3-tert-butyl-1-p-tolyl-1H-pyrazol-5-yl)ureido)naphthalen-1-yloxy) propyl)pyridin-2-ylcarbamate (50)

A solution of 3-tert-butyl-1-p-tolyl-1H-pyrazol-5-amine (5) (212 mg, 0.923 mmol) in DCM (1 mL) was added to a stirred solution of CDI (150 mg, 0.923 mmol) in DCM (1 mL), under nitrogen at RT over 5 min. After 1.5 hr a solution of tert-butyl 4-(2-(4-aminonaphthalen-1-yloxy)propyl)pyridin-2-ylcarbamate (49) (242 mg, 0.615 mmol) in DCM (2 mL) was added and stirring was continued at RT for 16 hr. A second portion of 3-tert-butyl-1-p-tolyl-1H-pyrazol-5-amine (141 mg, 0.615 mmol) in DCM (1 mL) was processed in a similar manner to the first, by reaction with CDI (100 mg, 0.615 mmol) in DCM (1 mL) and the resulting adduct was then added to the reaction mixture. After a further 2.5 hr the mixture was partitioned between water and DCM. The aqueous layer was extracted with DCM and the combined organic extracts were washed with brine and then dried (MgSO$_4$) and evaporated in vacuo. The residue was purified by flash column chromatography (SiO$_2$, 40 g, 0-100% EtOAc in isohexane, gradient elution) to afford the title compound (50) (163 mg, 40%) as a purple foam: m/z 649 (M+H)$^+$ (ES$^+$).

Intermediate J 1-(4-(1-(2-Aminopyridin-4-yl)propan-2-yloxy)naphthalen-1-yl)-3-(3-tert-butyl-1-p-tolyl-1H-pyrazol-5-yl)urea

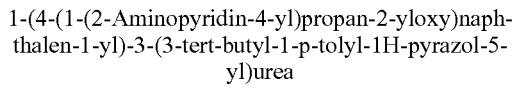

To a stirred solution of the tert-butyl carbamate (50) (158 mg, 0.244 mmol) in DCM (4 mL) at 0° C. under nitrogen was added TFA (2 mL). After 5 min the reaction mixture was warmed to RT and stirred for a further 2 hr. The mixture was evaporated in vacuo and the residue was subjected to SCX capture and release to afford the title compound (Intermediate J) (138 mg, >100%): m/z 549 (M+H)$^+$ (ES$^+$).

Example 46

N-(4-(2-(4-(3-(3-tert-Butyl-1-p-tolyl-1H-pyrazol-5-yl)ureido)naphthalen-1-yloxy)propyl)pyridin-2-yl)-2-methoxyacetamide

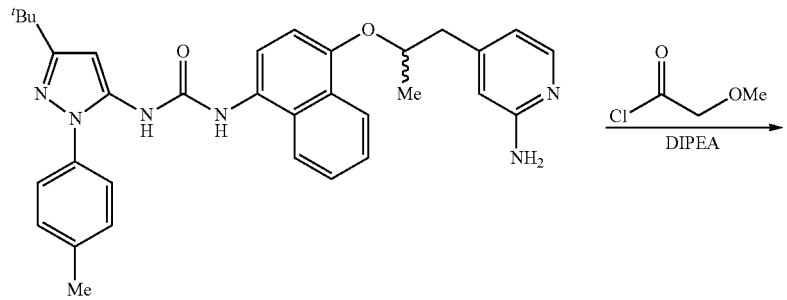

Intermediate J

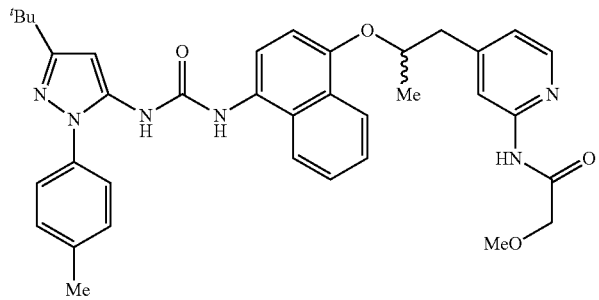

Example 46

Methoxyacetyl chloride (17 μL, 0.18 mmol) was added dropwise to a stirred solution of Intermediate J (40 mg, 0.073 mmol) and DIPEA (38 μL, 0.22 mmol) in DCM (3 mL) at 0° C. under nitrogen. After 20 min the reaction mixture was warmed to RT. After a further 4 hr a solution of NH$_3$ (1% in MeOH, 3 mL) was added and stirring continued for 1 hr. The reaction mixture was evaporated in vacuo and the residue was subjected to SCX capture and release and was then purified by flash column chromatography (SiO$_2$, 12 g, 0-5% MeOH in DCM, gradient elution) to give the title compound (Example 46) (5.6 mg, 12%): m/z 621 (M+H)$^+$ (ES$^+$). $^1$H NMR (400 MHz, CDCl$_3$) δ: 1.31 (9H, s), 1.45 (3H, d), 2.22 (3H, s), 3.06 (1H, dd), 3.20 (1H, dd), 3.47 (3H, s), 3.95 (2H, s), 4.86 (1H, m), 6.42 (1H, s), 6.50 (1H, br s), 6.56 (1H, br s), 6.71 (1H, d), 6.89 (2H, br d), 6.97 (2H, br d), 7.00 (1H, dd) 7.31 (1H, d), 7.49 (2H, m), 7.81 (1H, br m), 8.17 (1H, d), 8.19 (1H, br s), 8.26 (1H, m), 8.83 (1H, br s).

Intermediate K 1-(4-(2-(2-Aminopyridin-4-yl)propoxy)naphthalen-1-yl)-3-(3-tert-butyl-1-p-tolyl-1H-pyrazol-5-yl)urea

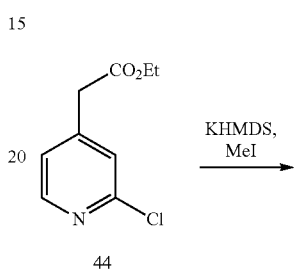

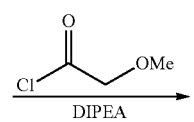

-continued

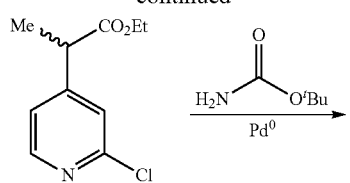

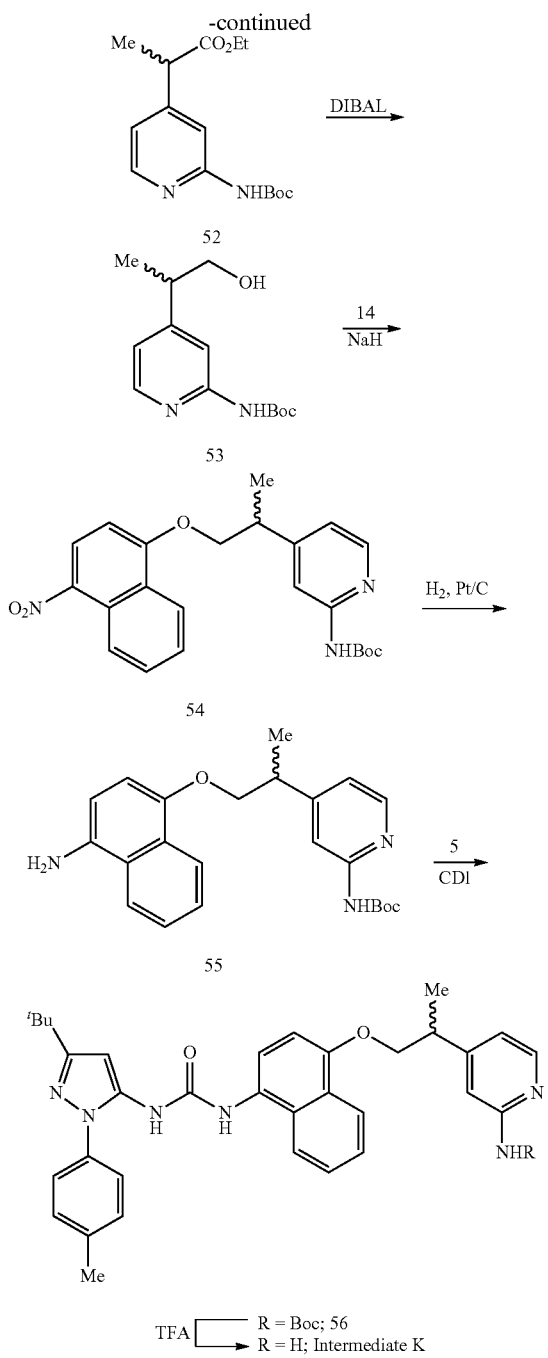

Ethyl 2-(2-chloropyridin-4-yl)propanoate (51)

To a stirred solution of ethyl 2-(2-chloropyridin-4-yl)acetate (44) (2.5 g, 12.52 mmol) in THF (25 mL), under nitrogen at −78° C. was added a solution of KHMDS (0.5M in toluene, 26.3 mL, 13.2 mmol). The mixture was warmed to RT for 10 min, then re-cooled to −78° C. and methyl iodide (0.820 mL, 13.15 mmol) added in a single portion and the mixture allowed to warm to RT. Saturated aqueous NH$_4$Cl solution was added and the mixture was diluted with ether. The organic layer was washed with water and brine and then dried (MgSO$_4$) and evaporated in vacuo. The residue was purified by flash column chromatography (SiO$_2$, 100 g, 5-10% EtOAc in isohexane, gradient elution) to afford the title compound (51) (1.57 g, 56%): m/z 214 (M+H)$^+$ (ES$^+$).

Ethyl 2-(2-(tert-butoxycarbonylamino)pyridin-4-yl)propanoate (52)

A mixture of ethyl 2-(2-chloropyridin-4-yl)propanoate (51) (1.55 g, 7.25 mmol), tert-butylcarbamate (2.55 g, 21.76 mmol), Pd$_2$dba$_3$ (0.166 g, 0.181 mmol), caesium carbonate (3.55 g, 10.88 mmol) and Xantphos (0.210 g, 0.363 mmol) in THF (10 mL) was purged with nitrogen and heated at 65° C. for 48 hr. The mixture was then cooled to RT, diluted with water and extracted with ether. The ether layer was washed with water and brine and then dried (MgSO$_4$) and evaporated in vacuo. The residue was purified by flash column chromatography (SiO$_2$, 100 g, 5-10% EtOAc in isohexane, gradient elution) to afford the title compound (52) (1.35 g, 61%): m/z 295 (M+H)$^+$ (ES$^+$).

tert-Butyl 4-(1-hydroxypropan-2-yl)pyridin-2-ylcarbamate (53)

A solution of DIBAL (1M in DCM, 13.8 mL, 13.8 mmol) was added dropwise over 10 min to a stirred solution of the ester (52) (1.35 g, 4.59 mmol) in THF (25 mL) under nitrogen at −78° C. The reaction mixture was warmed to RT and then re-cooled to −78° C. and a second aliquot of DIBAL (1M in DCM, 4.5 mL, 4.5 mmol) was added. The reaction mixture was allowed to warm to RT, then cooled to 0° C. and water (5 mL) and then MgSO$_4$ were added. The mixture was diluted with DCM and filtered to remove the solids. The filter cake was washed with EtOAc, MeOH and DCM and the combined filtrate and washings were evaporated in vacuo. The residue was purified by flash column chromatography (SiO$_2$, 40 g, 25-50% EtOAc in isohexane, gradient elution) to afford the title compound (53) (0.62 g, 50%): m/z 253 (M+H)$^+$ (ES$^+$).

tert-Butyl 4-(1-(4-nitronaphthalen-1-yloxy)propan-2-yl)pyridin-2-ylcarbamate (54)

To a solution of the alcohol (53) (0.62 g, 2.46 mmol) in DMF (4 mL) was added sodium hydride (60% dispersion in mineral oil, 0.246 g, 6.14 mmol) in a single portion and the mixture sonicated under a flow of nitrogen and then stirred at RT for 30 min. The resulting yellow suspension was cooled to 0° C. and a solution of 1-fluoro-4-nitronaphthalene (14) (0.470 g, 2.457 mmol) in DMF (2 mL) was added over 10 min. The reaction mixture was warmed to RT and glacial acetic (1.0 mL) was added. The mixture was poured onto saturated aqueous NaHCO$_3$ solution and extracted with EtOAc. The organic layer was washed with saturated aqueous Na$_2$CO$_3$, solution, three times with water and twice with brine then dried (MgSO$_4$) and evaporated in vacuo to give a yellow solid. The solid was suspended in MeOH (20 mL) and sonicated and the insoluble residue was collected by filtration and was washed with MeOH (10 mL) and then ether to afford the title compound (54) as an off white solid (0.73 g, 67%): m/z 424 (M+H)$^+$ (ES$^+$).

tert-Butyl 4-(1-(4-aminonaphthalen-1-yloxy)propan-2-yl)pyridin-2-ylcarbamate (55)

A solution of the nitroarene (54) (0.61 g, 1.441 mmol) in a mixture of MeOH (20.0 mL), AcOH (5.0 mL) and EtOAc (10.0 mL) was passed through a Thales H-Cube (1.0 mL·min$^{-1}$, 45° C., 55 mm, 10% Pt/C Cat-Cart, full hydrogen mode). The solvent was evaporated in vacuo and the residue was partitioned between saturated aqueous NaHCO$_3$ solution and EtOAc. The organic layer was washed with water and brine and then dried (MgSO$_4$) and evaporated in vacuo to furnish the title compound (55) (0.61 g, 97%): m/z 394 (M+H)$^+$ (ES$^+$).

tert-Butyl 4-(1-(4-(3-(3-tert-butyl-1-p-tolyl-1H-pyrazol-5-yl)ureido)naphthalen-1-yloxy)propan-2-yl)pyridin-2-ylcarbamate (56)

A solution of 3-tert-butyl-1-p-tolyl-1H-pyrazol-5-amine (5) 612 mg, 2.67 mmol) in DCM (2.0 mL) was added dropwise over 1.5 hr to a suspension of CDI (433 mg, 2.67 mmol) in DCM (2.0 mL) under nitrogen and the solution was stirred at RT for 1 hr. A solution of the naphthyl amine (55) (700 mg, 1.78 mmol) in DCM (4.0 mL) was added in a single portion and the solution was stirred for 16 hr, during which time a precipitate formed. The reaction mixture was taken up in DCM (10 mL) and purified by flash column chromatography (SiO$_2$, 80 g, 0-20% EtOAc in isohexane, gradient elution) to afford the title compound (56) (0.59 g, 50%): m/z 649 (M+H)$^+$ (ES$^+$)

Intermediate K 1-(4-(2-(2-Aminopyridin-4-yl)propoxy)naphthalen-1-yl)-3-(3-tert-butyl-1-p-tolyl-1H-pyrazol-5-yl)urea To a suspension of the tert-butyl carbamate (56) (0.57 g, 0.88 mmol) in DCM (10.0 mL) was added TFA (5.0 mL) and the resulting dark green solution stirred at RT for 1 hr. The mixture was evaporated in vacuo and the residue was dissolved in MeOH (10.0 mL) and subjected to SCX capture and release to afford the title compound (Intermediate K) as a red oil (488 mg, 98%): m/z 549 (M+H)$^+$ (ES$^+$).

Example 47

N-(4-(1-(4-(3-(3-tert-Butyl-1-p-tolyl-1H-pyrazol-5-yl)ureido)naphthalen-1-yloxy)propan-2-yl)pyridin-2-yl)-2-methoxyacetamide To a stirred solution of Intermediate K (58 mg, 0.106 mmol) in DCM (2.0 mL) was added methoxyacetyl chloride (9.7 µL, 0.106 mmol) followed by DIPEA (18.4 µL, 0.106 mmol) and the mixture stirred at RT for 1 hr. A solution of NH$_3$ (1% in MeOH, 3.0 mL) was added and the mixture was stirred for 30 min and was then evaporated in vacuo. The residue was subjected to SCX capture and release and the product was triturated with MeCN (5.0 mL) and was washed with MeCN (5.0 mL) and then ether (5.0 mL) to afford the title compound (Example 47) as a white solid (32 mg, 48%): m/z 621 (M+H)$^+$ (ES$^+$); $^1$H NMR (400 MHz, DMSO-d$_6$) δ: 1.27 (9H, s), 1.42 (3H, d), 2.39 (3H, s), 3.38 (3H, s), 3.40 (1H, m), 4.07 (2H, s), 4.21-4.30 (2H, overlapping m), 6.35 (1H, s), 6.95 (1H, d), 7.22 (1H, dd), 7.35 (2H, d), 7.40-7.47 (3H, overlapping m), 7.54 (1H, m), 7.60 (1H, d), 7.86 (1H, d), 8.07 (1H, d), 8.20 (1H, br s), 8.25 (1H, d), 8.55 (1H, br s), 8.75 (1H, d), 9.94 (1H, br s).

Intermediate L 1-(4-(2-(2-aminopyridin-4-yl)-2-methylpropoxy)naphthalen-1-yl)-3-(3-tert-butyl-1-p-tolyl-1H-pyrazol-5-yl)urea

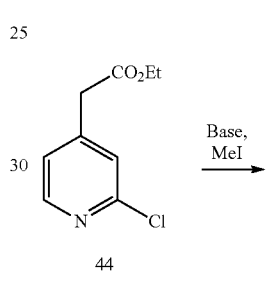

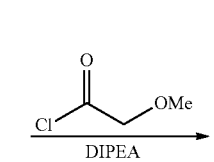

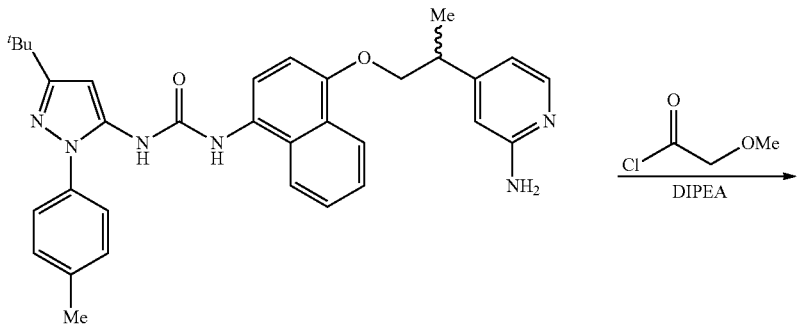

Intermediate K

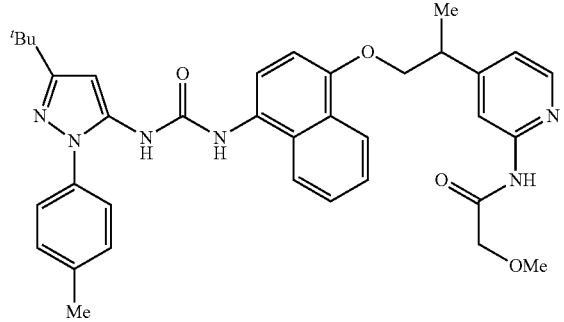

Example 47

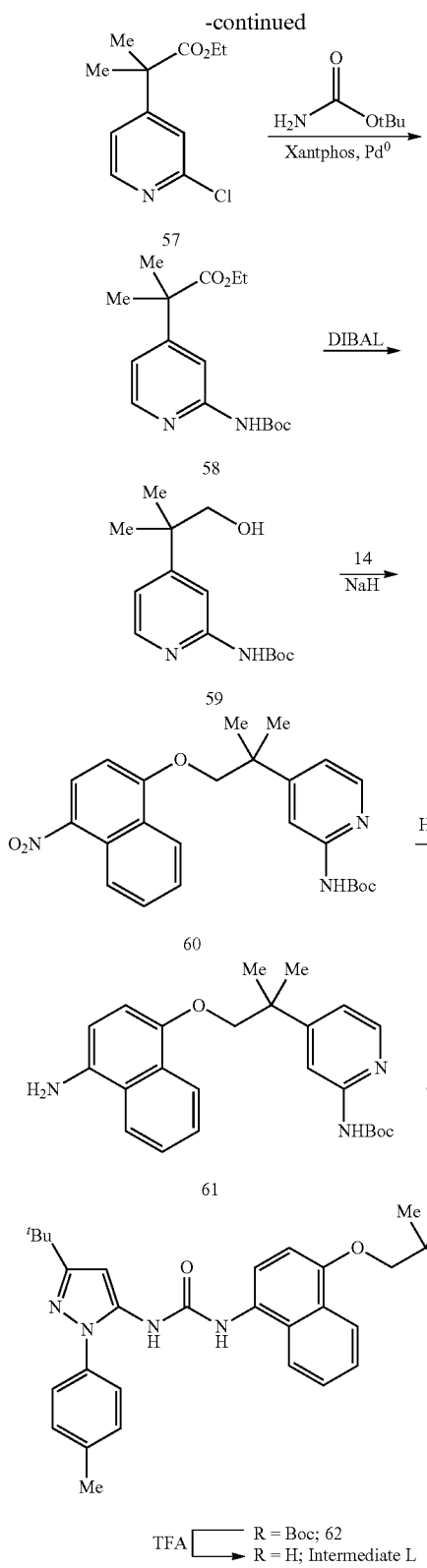

Ethyl 2-(2-chloropyridin-4-yl)-2-methylpropanoate (57)

To a stirred solution of ethyl 2-(2-chloropyridin-4-yl)acetate (44) (3.47 g, 17.4 mmol) in THF (40 mL), under nitrogen at −78° C. was added a solution of KHMDS (36.5 mL, 0.5M in toluene, 18.25 mmol) in a single portion The mixture was warmed to RT for 10 min and then re-cooled to −78° C., and treated with methyl iodide (1.14 mL, 18.3 mmol). The mixture was warmed to RT during which time a precipitated was thrown down. The mixture was cooled to −78° C. and a further aliquot of the KHMDS solution (36.5 mL, 0.5M in toluene, 18.25 mmol) was added. The mixture was warmed to RT for 10 min and the suspension then re-cooled to −78° C., and a second aliquot of methyl iodide (1.1 mL, 18.3 mmol) was added. The mixture was warmed to RT and sodium hydride (0.730 g, 18.25 mmol) was added and the mixture stirred at this temperature for 1 hr and then a third aliquot of methyl iodide (1.1 mL, 18 3 mmol) was added. After 1 hr, a saturated aq solution of $NH_4Cl$ was added and the mixture was extracted with ether. The combined organic layers were washed with water and brine and then dried ($MgSO_4$) and evaporated in vacuo. The residue was purified by flash column chromatography ($SiO_2$, 100 g, 5-10% EtOAc in isohexane, gradient elution) to afford the title compound (57) (2.81 g, 67%): m/z 228 $(M+H)^+$ $(ES^+)$.

Ethyl 2-(2-(tert-butoxycarbonylamino)pyridin-4-yl)acetate (58)

A mixture of ethyl 2-(2-chloropyridin-4-yl)-2-methylpropanoate (57) (2.80 g, 12.3 mmol), tert-butylcarbamate (4.32 g, 36.9 mmol), $Pd_2(dba)_3$ (281 mg, 0.307 mmol), Xantphos (355 mg, 0.615 mmol) and caesium carbonate (6.01 g, 18.5 mmol) in THF (10.0 mL) was purged with nitrogen and then stirred at 65° C. for 72 hr. The mixture was cooled to RT and was diluted with water and extracted with ether. The organic layer was washed with water and brine and then dried ($MgSO_4$), and evaporated in vacuo. The residue was purified by flash column chromatography ($SiO_2$, 120 g, 5-8% EtOAc in isohexane, gradient elution) to give the title compound (58) (1.47 g, 37%): m/z 309 $(M+H)^+$ $(ES^+)$ tert-Butyl 4-(1-hydroxy-2-methylpropan-2-yl)pyridin-2-ylcarbamate (59)

To a stirred solution of the ester (58) (1.43 g, 4.64 mmol) in THF (25 mL) at −78° C. under nitrogen was added a solution of DIBAL (18.5 mL, 1M in DCM, 18.5 mmol) dropwise over 10 min. The reaction mixture was warmed to RT then cooled to 0° C. and water (5.0 mL) was added, followed by $MgSO_4$. The mixture was diluted with DCM and filtered and the filter cake was washed consecutively with EtOAc, MeOH and DCM. The filtrate and washings were combined, and evaporated in vacuo and the residue was purified by flash column chromatography ($SiO_2$, 40 g, 25-50% EtOAc in isohexane, gradient elution) to yield the title compound (59) (1.13 g, 86%): m/z 267 $(M+H)^+$ $(ES^+)$.

tert-Butyl 4-(2-methyl-1-(4-nitronaphthalen-1-yloxy)propan-2-yl)pyridin-2-ylcarbamate (60)

To a stirred solution of the alcohol (59) (1.11 g, 4.17 mmol) in DMF (10.0 mL) at 0° C. under nitrogen was added sodium hydride (350 mg, 8.75 mmol) in a single portion. The mixture was warmed to RT for 30 min and was then sonicated, flushed with nitrogen and re-cooled to 0° C. A solution of 1-fluoro-4-nitronaphthalene (14) (797 mg, 4.17 mmol) in DMF (4.0 mL) was added over 5 min and the reaction mixture allowed to warm to RT and after 30 min glacial acetic acid (1.0 mL) was added. The reaction mixture was poured onto saturated aqueous $NaHCO_3$ solution and extracted twice with EtOAc. The combined organic extracts were washed three times with water and with brine and then dried ($MgSO_4$), and evaporated in vacuo. The residue was triturated from EtOAc and washed with ether (20 mL) to afford the title compound (60) as a yellow solid (1.23 g, 64%): m/z 438 (M+H)$^+$ (ES$^+$).

tert-Butyl 4-(1-(4-aminonaphthalen-1-yloxy)-2-methylpropan-2-yl)pyridin-2-yl carbamate (61)

A solution of the nitroarene (60) (1.15 g, 2.63 mmol) in a mixture of MeOH (40 mL), AcOH (10 mL) and DCM (20 mL) was passed through a Thales H-cube (1.0 mL·min$^{-1}$, 45° C., 55 mm 10% Pt/C Cat-Cart, full hydrogen mode). The solvent was evaporated in vacuo and the residue subjected to SCX capture and release to furnish the title compound (61) (1.15 g, 84%): m/z 408 (M+H)$^+$ (ES$^+$).

tert-Butyl 4-(1-(4-(3-(3-tert-butyl-1-p-tolyl-1H-pyrazol-5-yl)ureido)naphthalen-1-yloxy)-2-methylpropan-2-yl)pyridin-2-ylcarbamate (62)

A solution of 3-tert-butyl-1-p-tolyl-1H-pyrazol-5-amine (5) (760 mg, 3.31 mmol) in DCM (2.0 mL) was added dropwise over 1.5 hr to a suspension of CDI (537 mg, 3.31 mmol) in DCM (2.0 mL) under nitrogen and the solution was stirred at RT for 1 hr. A solution of the naphthyl amine (61) (1.00 g, 2.21 mmol) in DCM (4.0 mL) was added in a single portion and the solution was stirred for 16 hr, during which time a precipitate formed. The reaction mixture was taken up in DCM (10 mL) and purified by flash column chromatography (SiO$_2$, 80 g, 20-80% EtOAc in isohexane, gradient elution) to afford the title compound (62) (780 mg, 52%): m/z 663 (M+H)$^+$ (ES$^+$).

Intermediate L

1-(4-(2-(2-Aminopyridin-4-yl)-2-methylpropoxy)naphthalen-1-yl)-3-(3-tert-butyl-1-p-tolyl-1H-pyrazol-5-yl)urea To a suspension of the tert-butyl carbamate (62) (780 mg, 1.18 mmol) in DCM (10 mL) was added TFA (8.0 mL) and the resulting dark green solution stirred at RT for 2 hr. The mixture was evaporated in vacuo and the residue was taken up in MeOH (10 mL) and subjected to SCX capture and release to afford the title compound (Intermediate L) (690 mg, 100%): m/z 563 (M+H)$^+$ (ES$^+$).

Example 48

N-(4-(1-(4-(3-(3-tert-Butyl-1-p-tolyl-1-pyrazol-5-yl)ureido)naphthalen-1-yloxy)-2-methylpropan-2-yl)pyridin-2-yl)-2-methoxyacetamide

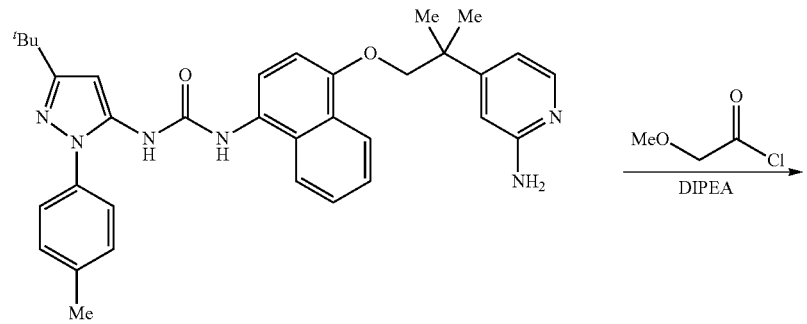

Intermediate L

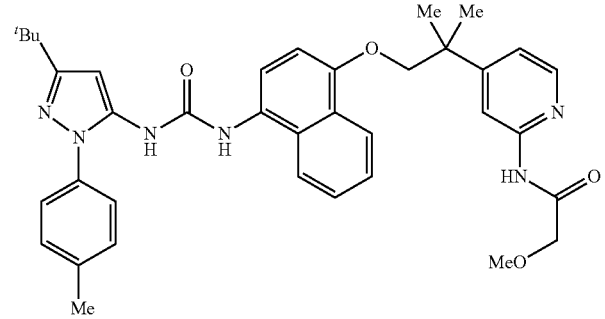

Example 48

To a solution of (Intermediate L) (52 mg, 0.092 mmol) in DCM (2.0 mL) was added methoxyacetyl chloride (8.5 μL, 0.092 mmol) followed by DIPEA (16 μL, 0.092 mmol) and the mixture was stirred at RT for 1 hr. A solution of NH$_3$ (1% in MeOH, 3 mL) was added and the mixture was stirred for 30 min and was then evaporated in vacuo. The residue was purified by flash column chromatography (SiO$_2$, 12 g, 0-100% EtOAc in isohexane, gradient elution) to afford the title compound (Example 48) (32 mg, 53%): m/z 635 (M+H)$^+$ (ES$^+$); $^1$H NMR (400 MHz, DMSO-d$_6$) δ 1.27 (9H, s), 1.50

(6H, s), 2.39 (3H, s), 3.37 (3H, s), 4.06 (2H, s), 4.19 (2H, s), 6.35 (1H, s), 6.95 (1H, d), 7.30 (1H, dd), 7.34 (2H, m), 7.43 (2H, m), 7.45 (1H, m), 7.53 (1H, m), 7.61 (1H, d), 7.87 (1H, d), 8.02 (1H, dd), 8.25 (1H, d), 8.34 (1H, br s) 8.54 (1H, br s), 8.75 (1H, br s), 9.90 (1H, br s).

Evaporation in vacuo furnished the title compound (Intermediate M) as a brown solid (25.0 g, 77%): m/z 338 (M+H)$^+$ (ES$^+$).

Intermediate N 3-tert-Butyl-1-(4-((tert-butyldimethylsilyloxy)methyl)phenyl)-1H-pyrazol-5-amine Intermediate M N-(4-((4-aminonaphthalen-1-yloxy)methyl)pyridin-2-yl)-2-methoxy acetamide

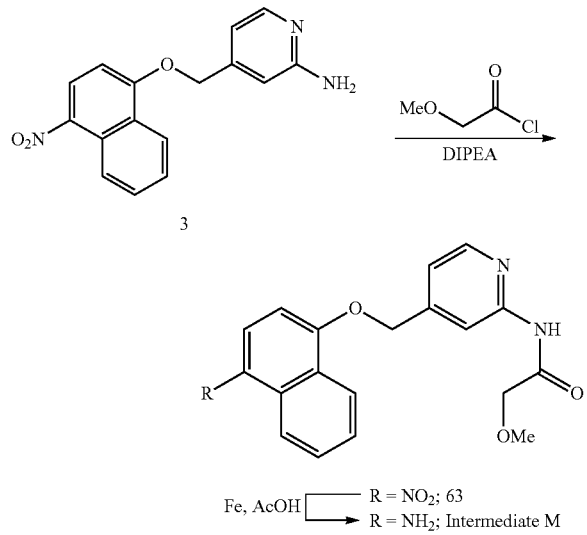

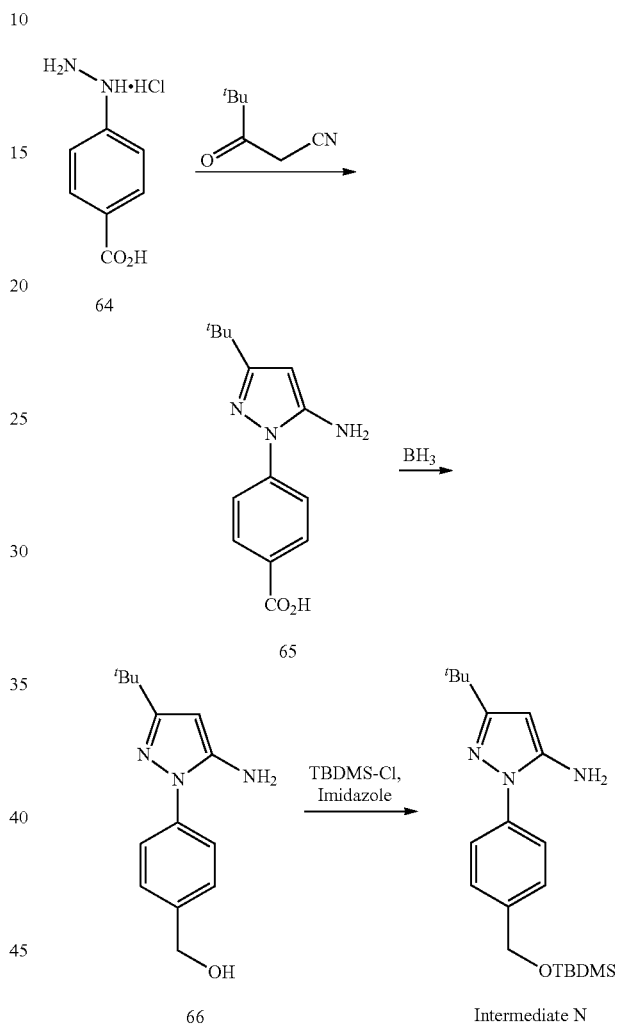

2-Methoxy-N-(4-((4-nitronaphthalen-1-yloxy)methyl)pyridin-2-yl)acetamide (63)

Methoxyacetyl chloride (24.2 mL, 264 mmol) was added dropwise over 10 min to a stirred suspension of the amine (3) (60.0 g, 203 mmol) in a mixture of DCM (300 mL), THF (450 mL) and DIPEA (53.1 mL, 305 mmol) under nitrogen at −5° C. After 10 min the reaction mixture was allowed to warm to RT during which time a dark solution formed. After 30 min a solution of NH$_3$ (7M in MeOH, 30 mL) was added and stirring continued for 1 hr during which time a precipitate formed. The suspension was evaporated in vacuo and the residue was triturated with water (500 mL). The precipitate was collected by filtration, was washed with water (300 mL) and diethyl ether (500 mL) and then dried in vacuo at 60° C. to furnish the title compound (63) as a yellow solid (68 g, 88%): m/z 368 (M+H)$^+$ (ES$^+$).

Intermediate M

N-(4-((4-aminonaphthalen-1-yloxy)methyl)pyridin-2-yl)-2-methoxy acetamide

A suspension of the nitroarene (63) (30.0 g, 82.0 mmol) and iron powder (22.8 g, 408 mmol) in AcOH (300 mL) was heated at 50° C. for 1.5 hr, and was then cooled to RT. Solid sodium carbonate was added portionwise to the reaction mixture until effervescence was no longer observed. The mixture was extracted with ethyl acetate (2×700 mL) and the combined organic extracts were washed with saturated aqueous sodium carbonate and with brine and then dried (MgSO$_4$).

4-(5-Amino-3-tert-butyl-1H-pyrazol-1-yl)benzoic acid (64)

To a suspension of 4-hydrazinobenzoic acid (64) (1.00 g, 5.30 mmol) in EtOH (20 mL) containing conc hydrochloric acid (0.5 mL) was added pivaloylacetonitrile (0.730 g, 5.83 mmol) and the mixture heated to reflux for 5 hr. The reaction mixture was stirred at RT for 64 hr and the solvent evaporated in vacuo. The residue was suspended in THF and an aqueous solution of LiOH (1M, 30 mL, 30 mmol) was added and the mixture was stirred at RT for 2 hr. The THF was removed by evaporation in vacuo and the resulting aqueous solution was diluted with AcOH and subjected to SCX capture and release. Fractions containing the desired compound were combined and evaporated in vacuo. The residue was dissolved in DCM and was dried (MgSO$_4$) and evaporated in vacuo Co-evaporation with acetonitrile in vacuo furnished the title compound

(65) as an orange solid (1.50 g, >100% recovery): m/z 260 (M+H)+ (ES+); 258 (M–H)− (ES−).

(4-(5-Amino-3-tert-butyl-1H-pyrazol-1-yl)phenyl)methanol (66)

To a stirred solution of the benzoic acid (65) (1.50 g, 5.7 mmol) in THF at 0° C. was added a solution of borane (2M in THF, 17.4 mL, 34.8 mmol). The reaction mixture was warmed to RT and was stirred for 16 hr. An additional aliquot of the BH$_3$ solution (2M in THF, 8.0 mL, mmole) was added and stirring continued for a further 3 hr. The reaction mixture was cooled to 0° C. and 1M hydrochloric acid was added to quench the reaction. The solution was neutralized and extracted into EtOAc. The extracts were washed with aqueous Na$_2$CO$_3$ solution and brine and then dried (MgSO$_4$) and evaporated in vacuo to afford the title compound (66) (0.64 g, 45%).

Intermediate N

3-tert-Butyl-1-(4-((tert-butyldimethylsilyloxy)methyl)phenyl)-1H-pyrazol-5-amine To a stirred solution of the benzyl alcohol (66) (640 mg, 2.61 mmol) and imidazole (266 mg, 3.91 mmol) in DMF (5.0 mL) at RT was added TBDMS-Cl (590 mg, 3.91 mmol). After 3 hr the reaction mixture was diluted with water and extracted with Et$_2$O. The organic layer was washed with brine, dried (MgSO$_4$) and then evaporated in vacuo to afford the title compound (Intermediate N) (875 mg, 89%): m/z 360 (M+H)+ (ES+)

Example 49

N-(4-((4-(3-(3-tert-Butyl-1-(4-(hydroxymethyl)phenyl)-1H-pyrazol-5-yl)ureido)naphthalen-1-yloxy)methyl)pyridin-2-yl)-2-methoxyacetamide

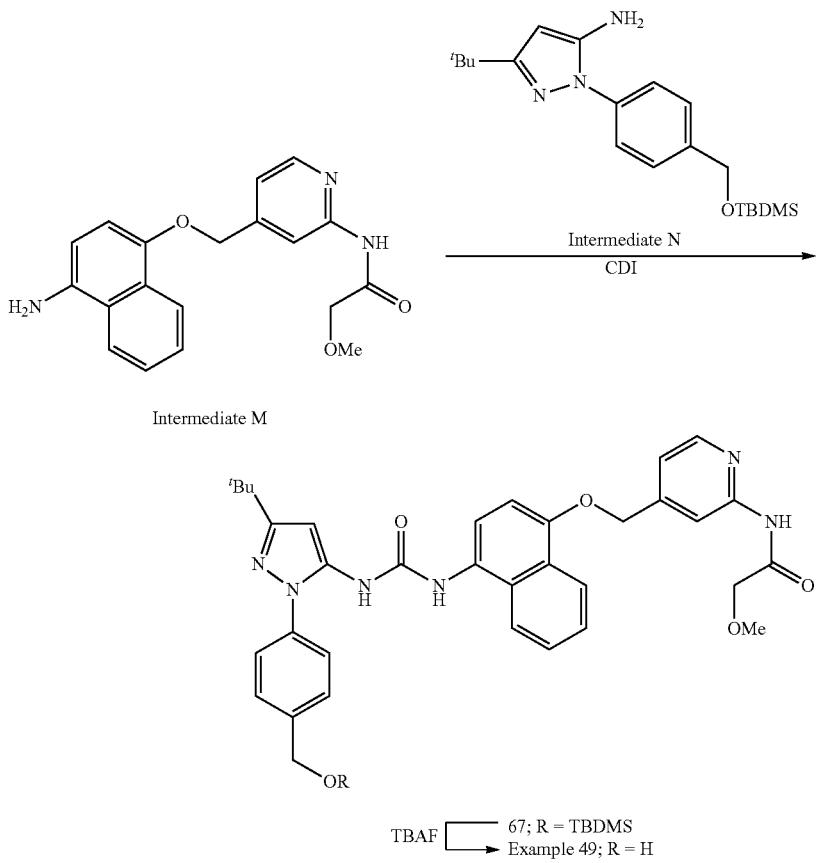

The pyrazole amine Intermediate N (100 mg, 0.278 mmol) was added portionwise to a stirred suspension of CDI (45.1 mg, 0.278 mmol) in DCM (0.5 mL) over 1 hr and the reaction mixture was stirred at RT for 16 hr. A solution of the naphthylamine, Intermediate M, (47 mg, 0.139 mmol) in DCM (0.5 mL) was added dropwise over 2 hr. After a further 2 hr the mixture was evaporated in vacuo and the residue was purified by flash column chromatography (SiO$_2$, 12 g, 30-70% EtOAc in isohexane, gradient elution) to yield N-(4-((4-(3-(3-tert-butyl-1-(4-((tert-butyldimethylsilyloxy)methyl)phenyl)-1H-pyrazol-5-yl)ureido)naphthalen-1-yloxy)methyl)pyridin-2-yl)-2-methoxyacetamide (67) (42 mg, 20%): m/z 723 (M+H)+ (ES+) To a solution of the silyl ether (67) (42 mg, 58 μmol) in THF under nitrogen at −5° C. was added a solution of TBAF (1M in THF, 58 μL, 58 μmol). The mixture was warmed to RT and a second aliquot of TBAF (1M in THF, 58 μL, 58 μmol) was added. After 1 hr the mixture was diluted with EtOAc and washed with saturated aqueous ammonium chloride. The aqueous layer was extracted with EtOAc and the combined organic layers were washed with water and brine and then dried (MgSO$_4$) and evaporated in vacuo. The residue was purified by flash column chromatography (SiO$_2$, 12 g, 2-6% MeOH in DCM, gradient elution) to provide the title compound (Example 49) (23 mg, 63%): m/z 609 (M+H)+ (ES+); $^1$H NMR (400 MHz, DMSO-d$_6$) δ: 1.28 (9 H, s), 3.37

(3H, s) 4.08 (2H, s), 4.59 (2H, d), 5.32 (1H, t), 5.39 (2H, s), 6.36 (1H, s), 7.02 (1H, d), 7.29 (1H, dd), 7.48 (2H, m), 7.52 (2H, m), 7.54-7.63 (3H, overlapping m), 7.93 (1H, m), 8.30-8.37 (3H, overlapping m), 8.63 (1H, s), 8.81 (1H, s), 10.02 (1H, br s).
Intermediate P
1-(4-((2-Aminopyrimidin-4-yl)methoxy)naphthalen-1-yl)-3-(3-tert-butyl-1-p-tolyl-1H-pyrazol-5-yl)urea
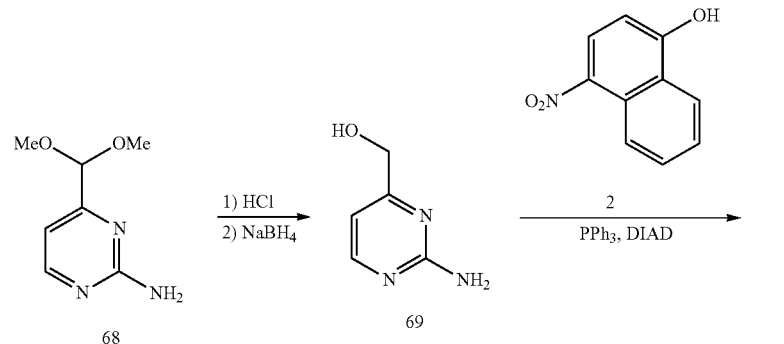
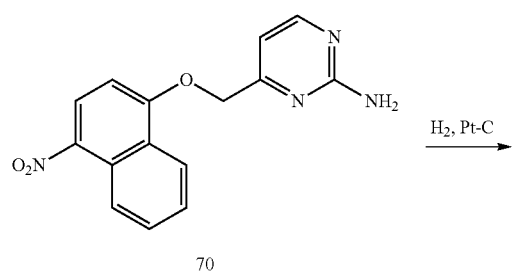
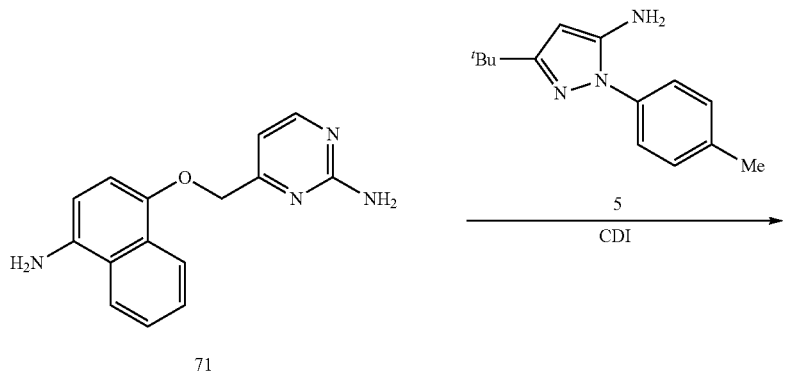
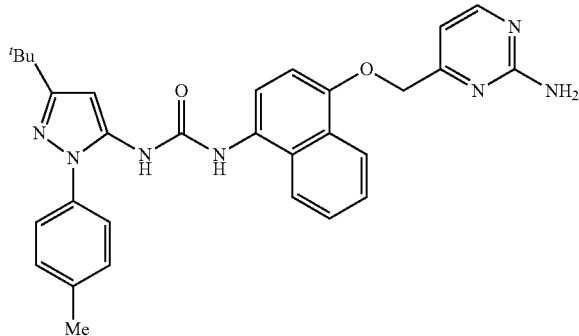
Intermediate P

(2-Aminopyrimidin-4-yl)methanol (31)

Hydrochloric acid (2M, 207 mL, 414 mmol) was added to 4-(dimethoxymethyl)pyrimidin-2-amine (68) (WO 2007096764) (14.0 g, 83 mmol) and the mixture heated at 48° C. for 16 hr. The mixture was cooled to RT and was neutralized with solid $Na_2CO_3$ which produced a precipitate at pH 7. The suspension was diluted with EtOAc (300 mL) and the solid removed by filtration. The organic layer was separated and the aqueous layer was extracted with 1% MeOH in THF (4×300 mL). The organics were combined, dried and then evaporated in vacuo. The residue (ca. 4.0 g) was suspended in a mixture of MeOH (100 mL), THF (100 mL) and water (100 mL) and treated with $NaBH_4$ (1.57 g, 41.4 mmol). After stirring for 1 hr a solution of NaOH (1M, 20 mL) was added and the mixture was allowed to stand at RT for 48 hr. The solvents were evaporated to give a yellow solid which was partitioned between water (50 mL) and EtOAc (100 mL). The solid which formed at the interface was removed by filtration and the aqueous layer was extracted with THF (3×300 mL) then dried and evaporated to give a yellow solid. The material was suspended in THF (100 mL) and MeOH (50 mL) and absorbed onto silica gel (20 g) and subjected to column chromatography (80 g, 15% MeOH in DCM isocratic elution) to give the title compound (369) as an off-white solid (720 mg, 7%): m/z 126 $(M+H)^+$ $(ES^+)$.

4-((4-Nitronaphthalen-1-yloxy)methyl)pyrimidin-2-amine (70)

To a stirred mixture of (2-aminopyrimidin-4-yl)methanol (69) (700 mg, 3.92 mmol), 4-nitronaphthol (2) (741 mg, 3.92 mmol) and $PPh_3$ (1.23 g, 4.70 mmol) in THF (20 mL) under nitrogen at −50° C. was added DIAD (996 µL, 4.70 mmol) dropwise over 5 min. The mixture was allowed to warm to RT and stirred for 1 hr during which time a yellow precipitate formed. The suspension was stirred overnight and the volatiles were evaporated in vacuo. The residue was triturated from MeOH (50 mL) and the pale yellow solid collected by filtration and washed with diethyl ether (50 mL) to give the title compound (70) (1.10 g, 93%): m/z 297 $(M+H)^+$ $(ES^+)$.

4-((4-Aminonaphthalen-1-yloxy)methyl)pyrimidin-2-amine (71)

A solution of the nitroarene (70) (1.10 g, 3.71 mmol) in a mixture of DCM (50 mL) and AcOH (40 mL) was passed through a Thales H-cube (1.0 mL·$min^{-1}$, 55 mm, 10% Pt/C, 40° C., full hydrogen mode). LC-MS analysis of the resulting solution showed a mixture comprising of mainly starting material and ca. 20% product. The DCM was removed by evaporation in vacuo and the solution re-subjected to reduction using the same conditions at RT. The volatiles were evaporated in vacuo to give the title compound (71) (ca. 70% by LC-MS) as a purple solid (0.90 g, 64% yield): m/z 267 $(M+H)^+$ $(ES^+)$.

Intermediate P
1-(4-((2-Aminopyrimidin-4-yl)methoxy)naphthalen-1-yl)-3-(3-tert-butyl-1-p-tolyl-1H-pyrazol-5-yl)urea A solution of 3-tert-butyl-1-p-tolyl-1H-pyrazol-5-amine (5) (0.98 g, 4.26 mmol) in DCM (4.0 mL) was added dropwise over 1 hr, to a suspension of CDI (0.69 g, 4.26 mmol) in DCM (3.0 mL) and the mixture was stirred at RT for 2 hr. This solution was then added dropwise to a solution of the naphthylamine (71) (0.90 g, 2.37 mmol) in DCM (10 mL), such that after each 1.0 mL aliquot was added, the reaction was stirred for 1 hr. The reaction was quenched with MeOH (20 mL), and silica was added (20 g) and the volatiles were evaporated in vacuo. The residue was subjected to purification by column chromatography (100 g, 50 to 100% EtOAc in isohexane, gradient elution). The resulting product was triturated from DCM (20 mL) and the solid collected, and washed with diethyl ether (50 mL) to give the title compound (Intermediate P) as a purple solid (0.48 g, 38%): m/z 523 $(M+H)^+$ $(ES^+)$.

Example 50
N-(4-((4-(3-(3-tert-Butyl-1-p-tolyl-1H-pyrazol-5-yl)ureido)naphthalen-1-yloxy)methyl)pyrimidin-2-yl)-2-methoxyacetamide

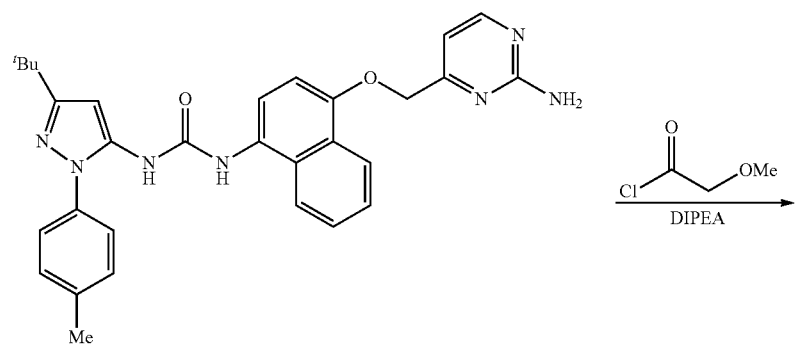

Intermediate P

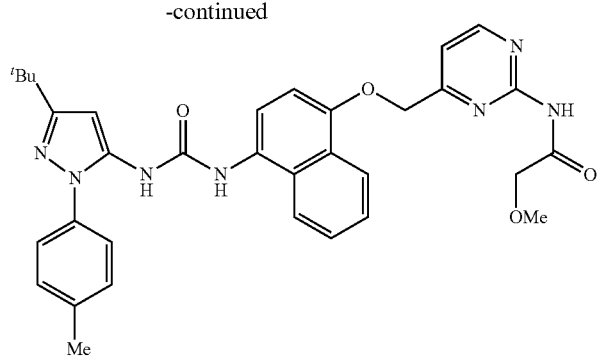

Example 50

A suspension of Intermediate P (52 mg, 0.10 mmol) in DCM (1.0 mL) and DMF (100 µL) was treated with methoxyacetyl chloride (27 µL, 0.30 mmol) followed by DIPEA (52 µL, 0.30 mmol) and the mixture stirred overnight at RT. The volatiles were evaporated in vacuo and the residue suspended in a mixture of MeOH (2.0 mL) and AcOH (2.0 mL). The suspension was subjected to SCX capture and release under standard conditions. As only a low recovery of material was obtained the SCX cartridge was extracted with MeOH (50 mL) and the solvent evaporated, to give an off white solid. This was triturated from MeOH (1.0 mL) and diethyl ether (5.0 mL) to give the title compound (Example 50) as a white solid (12 mg, 19%): m/z 594 (M+H)⁺ (ES⁺). $^1$H NMR (400 MHz, DMSO-$d_6$) δ: 1.27 (9H, s), 2.40 (3H, s), 3.34 (3H, s), 4.24 (2H, s), 5.34 (2H, s), 6.35 (1H, s), 7.02 (1H, d), 7.35 (2H, d), 7.44 (3H, m), 7.60 (3H, m), 7.95 (1H, m), 8.36 (1H, m), 8.59 (1H, br s), 8.68 (1H, d), 8.80 (1H, br s), 10.44 (1H, br s).

Intermediate Q 1-(4-(2-(2-Aminopyridin-4-yl)propan-2-yloxy)naphthalen-1-yl)-3-(3-tert-butyl-1-p-tolyl-1H-pyrazol-5-yl)urea

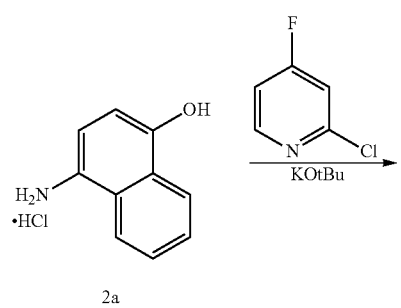

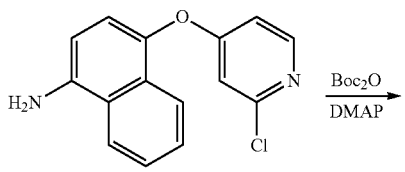

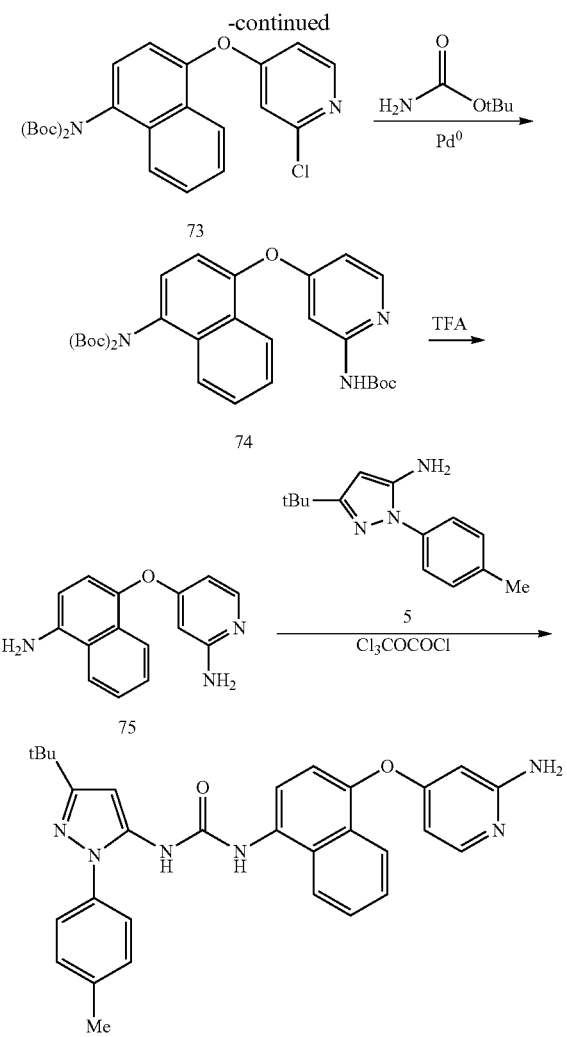

Intermediate Q 4-(2-Chloropyridin-4-yloxy)naphthalen-1-amine (72)

To a stirred solution of 2-chloro-4-fluoropyridine (1.26 g, 9.58 mmol) and 4-amino-1-naphthol hydrochloride (2a) (750 mg, 3.83 mmol) in NMP (40 mL), at −20° C., was added potassium tart-butoxide (1.290 g, 11.50 mmol). The reaction mixture was allowed to warm to RT and after 2.5 hr the reaction mixture was diluted with water (100 mL) and extracted with EtOAc (100 mL then 2×80 mL). The combined organic extracts were washed with brine (150 mL), dried and evaporated in vacuo. The crude product was subjected to SCX capture and release and the solvent was removed in vacuo to give the title compound (72) (1.02 g, 92%) as a brown solid: m/z 271 (M+H)$^+$ (ES$^+$).

4-(2-Chloropyridin-4-yloxy)naphthalen-1-N,N-di-tert-butylcarbamate (73)

To a stirred solution of 4-(2-chloropyridin-4-yloxy)naphthalen-1-amine (72) (1.02 g, 3.76 mmol) in THF (30 mL) at 0° C. was added DMAP (0.034 g, 0.282 mmol) and di-tert-butyl dicarbonate (0.904 g, 4.14 mmol) and the reaction mixture stirred at 0° C. for 30 min, and then at RT for 1.5 hr. The mixture was cooled to 0° C., and a further aliquot of di-tert-butyl dicarbonate (0.904 g, 4.14 mmol) was added and stirring continued at 0° C. for 15 min and then at RT for 16 hr. The reaction mixture was diluted with water (40 mL) and extracted with EtOAc (2×40 mL). The combined organic extracts were washed with brine (75 mL), dried and evaporated in vacuo. The crude material was purified by flash column chromatography (SiO$_2$; 80 g, 0-40% EtOAc in isohexane, gradient elution) to give the title compound (73) (892 mg, 48%) as a purple solid: m/z 471 (M+H)$^+$ (ES$^+$).

tert-Butyl 4-(4-(N,N-di-tert-butylcarbamyl)naphthalen-1-yloxy)pyridin-2-ylcarbamate (74)

A mixture of the chloropyridine (73) (892 mg, 1.89 mmol), tert-butyl carbamate (666 mg, 5.68 mmol), caesium carbonate (926 mg, 2.84 mmol), Pd$_2$(dba)$_3$ (43 mg, 0.047 mmol) and XantPhos (55 mg, 0.095 mmol) was suspended in THF (10 mL). The reaction mixture was purged with nitrogen, and was then heated at reflux for 15 hr. The mixture was cooled to RT, was diluted with water (35 mL) and extracted with EtOAc (35 mL, 25 mL). The combined organic extracts were washed with brine (50 mL), dried and evaporated in vacuo. The crude material was purified by flash column chromatography (SiO$_2$; 80 g, 0-30% EtOAc in isohexane, gradient elution) to give the title compound (74) (289 mg, 28%) as a white solid: m/z 552 (M+H)$^+$ (ES$^+$).

4-(4-Aminonaphthalen-1-yloxy)pyridin-2-amine (75)

To a stirred solution of the bis tert-butyl carbamate (74) (289 mg, 0.524 mmol) in DCM (8 mL), at 0° C., was added TFA (4.0 mL). The resulting mixture was stirred and allowed to warm to RT. After 5 hr, the volatiles were removed in vacuo and the residue was taken up in MeOH (5 mL) and subjected to SCX capture and release. The solvent was removed in vacuo to afford the title compound (75) (116 mg, 85%) as a brown-orange oil: m/z 252 (M+H)$^+$ (ES$^+$).

1-(4-(2-aminopyridin-4-yloxy)naphthalen-1-yl)-3-(3-tert-butyl-1-p-tolyl-1H-pyrazol-5-yl)urea (Intermediate Q)

A saturated aq. solution of NaHCO$_3$ (14 mL) was added to a solution of 3-tert-butyl-1-p-tolyl-1H-pyrazol-5-amine (5) (206 mg, 0.900 mmol) in DCM (20 mL). The mixture was stirred vigorously, was cooled to 0° C. and trichloromethylchloroformate (0.326 mL, 2.70 mmol) was added in one portion. The reaction mixture was stirred vigorously at 0° C. for a further 80 min. The layers were separated and the organic layer was dried, evaporated in vacuo and the resulting orange oil was dried further for 30 min under high vacuum. The resulting crude isocyanate was then taken up into THF (6 mL) and kept under nitrogen at 0° C.

To a stirred solution of 4-(4-aminonaphthalen-1-yloxy)pyridin-2-amine (75) (116 mg, 0.462 mmol) and DIPEA (241 µL, 1.385 mmol) in THF (3 mL), at 0° C., was added an aliquot of the isocyanate solution prepared above (2 mL, 0.300 mmol). The resulting mixture was vigorously stirred and allowed to warm to RT. Two additional aliquots of the isocyanate solution were added to the reaction mixture, the first after 1.5 hr, (1 mL, 0.150 mmol) and the second after 3.5 hr (0.5 mL, 0.075 mmol). After 20 hr water (30 mL) was added and the mixture was extracted with EtOAc (2×30 mL). The combined organic extracts were washed with brine (50 mL) then dried and evaporated in vacuo. The residue was purified by flash column chromatography (SiO$_2$; 12 g, 25-100% [5% MeOH in EtOAc] in isohexane, gradient elution) to furnish the title compound (Intermediate Q) (127 mg, 49%) as a brown oil: m/z 507 (M+H)$^+$ (ES$^+$).

Example 51

N-(4-(4-(3-(3-tert-Butyl-1-p-tolyl-1H-pyrazol-5-yl)ureido)naphthalen-1-yloxy)pyridin-2-yl)-2-(methylsulfonyl)acetamide

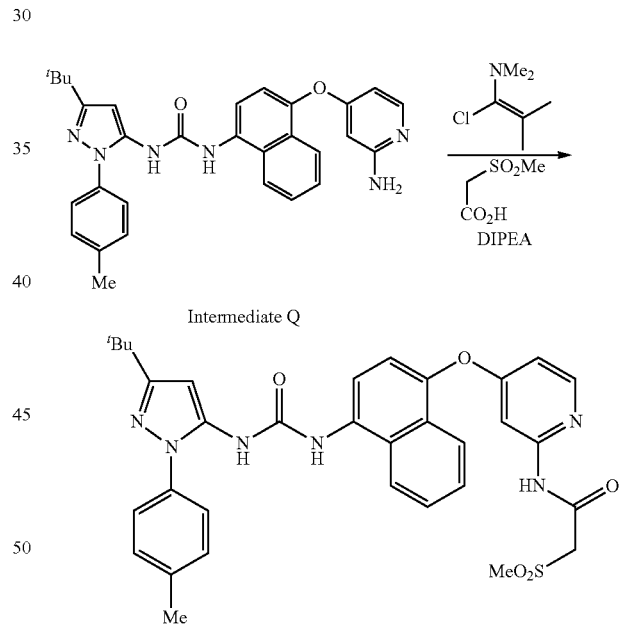

Example 51

To a suspension of methanesulfonylacetic acid (40 mg, 0.29 mmol) in DCM (2.0 mL) under nitrogen was added 1-chloro-N,N,2-trimethylpropenylamine (48 µL, 0.37 mmol), and the mixture was stirred at RT for 2 hr. The resulting mixture was added to a solution of (Intermediate Q) (37 mg, 0.07 mmol) and DIPEA (51 µL, 0.29 mmol) in DCM (2.0 mL) and stirring continued at RT for 3 hr. The reaction mixture was stirred with 1% NH$_3$ in MeOH (3.0 mL) for 45 min and then evaporated in vacuo. The residue was subjected to SCX capture and release and was then purified by flash column chromatography (SiO$_2$, 12 g, 0-70% [5% MeOH in EtOAc] in isohexane, gradient elution) to afford the title compound (Example 51) as a white powder (13 mg, 28%): m/z 627 (M+H)+ (ES+). $^1$H NMR (400 MHz, DMSO-$d_6$) δ: 1.29 (9H, s), 2.39 (3H, s), 3.10 (3H, s), 4.36 (2H, s), 6.40 (1H, s), 6.71 (1H, dd), 7.33-7.38 (3H, overlapping m), 7.47 (2H, m), 7.56 (1H, m), 7.65 (1H, m), 7.69 (1H, m), 7.85 (1H, d), 7.96 (1H, d), 8.11 (1H, d), 8.22 (1H, d), 8.91 (1H, br s), 9.23 (1H, br s), 10.96 (1H, br s).

Biological Testing

All exemplified compounds demonstrated $EC_{50}$ values of less than 1 µM versus LPS-induced TNFα release in differentiated U937 cells (see below for assay details).

| | $IC_{50}$ values | | $R$-$EC_{50}$ values[a] | $IC_{50}$ values[a] | | |
|---|---|---|---|---|---|---|
| Example No. | p38α enzyme[a] | P38γ enzyme[b] | d-U937 cells | THP-1 cells | MTT[c] 4 hr | 24 hr |
| 1 | ++ | ++ | ++ | ++ | − | − |
| 2 | ++ | ++ | + | + | − | − |
| 3 | ++ | ++ | ++ | ++ | − | + |
| 4 | + | ++ | ++ | ++ | − | − |
| 5 | ++ | + | ++ | ++ | − | + |
| 6 | ++ | ++ | ++ | + | − | + |
| 7 | ++ | ++ | ++ | ++ | − | + |
| 8 | + | + | ++ | ++ | − | + |
| 9 | ++ | ++ | ++ | ++ | − | + |
| 10 | + | + | ++ | ++ | − | − |
| 11 | ++ | + | ++ | ++ | − | − |
| 12 | ++ | ++ | ++ | ++ | − | − |
| 13 | ++ | ++ | ++ | + | − | − |
| 14 | ++ | ++ | ++ | ++ | − | − |
| 15 | + | ++ | + | ++ | − | − |
| 16 | + | ++ | ++ | ++ | + | + |
| 17 | ++ | ++ | ++ | ++ | − | − |
| 18 | + | − | + | ++ | − | − |
| 19 | ++ | ++ | ++ | ++ | − | − |
| 20 | ++ | ++ | ++ | ++ | − | + |
| 21 | ++ | ++ | ++ | ++ | − | − |
| 22 | ++ | ++ | ++ | ++ | − | − |
| 23 | ++ | ++ | ++ | ++ | + | + |
| 24 | ++ | ++ | ++ | ++ | − | − |
| 25 | ++ | ++ | ++ | ++ | − | − |
| 26 | ++ | ++ | ++ | + | − | − |
| 27 | + | ++ | ++ | ++ | − | − |
| 28 | + | + | ++ | ++ | − | − |
| 29 | + | ++ | ++ | ++ | − | − |
| 30 | + | ++ | ++ | ++ | − | − |
| 31 | + | ++ | ++ | ++ | − | + |
| 32 | ++ | ++ | ++ | + | − | − |
| 33 | ++ | + | ++ | ++ | − | − |
| 34 | ++ | + | + | + | + | − |
| 35 | ++ | − | + | + | − | − |
| 36 | + | − | ++ | + | − | − |
| 37 | + | − | + | + | − | − |
| 38 | + | − | ++ | + | − | − |
| 39 | + | − | + | + | − | − |
| 40 | ++ | + | + | + | − | − |
| 41 | ++ | ++ | + | ++ | − | − |
| 42 | + | + | ++ | + | + | − |
| 43 | + | + | + | + | − | − |
| 44 | ++ | + | + | ++ | − | − |
| 45 | + | + | + | ++ | − | − |
| 46 | + | − | + | + | − | − |
| 47 | + | − | ++ | ++ | − | − |
| 48 | + | − | + | + | − | − |
| 49 | ++ | ++ | ++ | + | − | + |
| 50 | ++ | − | ++ | + | − | − |
| 51 | ++ | ++ | ++ | ++ | − | + |

[a]++ $EC_{50}/IC_{50}$ value <10 nM; + $EC_{50}/IC_{50}$ value <500 nM
[b]++ $IC_{50}$ value <500 nM; + $IC_{50}$ value <5000 nM; − $IC_{50}$ value >5000 nM
[c]− <30%; + >30% at 10 ug/ml;

Summaries of the properties of Example 1 established using both in vitro and in vivo assays are presented below:

In Vitro Testing for Example 1

| Enzyme $IC_{50}$ (nM) | | Differentiated U937 cells LPS-induced TNFα release | | THP1 cells LPS-induced TNFα release |
|---|---|---|---|---|
| Alpha subtype | Gamma subtype | $EC_{50}$ (nM)[1] | MTT Assay | $IC_{50}$ (nM) |
| 5.3 | 402 | 0.88 | 4, 24 h (10 µg/ml) Negative[2] | 2.3 |

[1]50% effective concentration relative to the effect of 10 µg/mL BIRB796 (as 100%).
[2]no significant toxic effect observed in MTT assay A description of these assays is as follows:

Enzyme Inhibition Assay

The enzyme inhibitory activity of compound was determined by fluorescence resonance energy transfer (FRET) using synthetic peptides labelled with both donor and acceptor fluorophores (Z-LYTE, Invitrogen). Briefly, recombinant, phosphorylated p38 MAPK gamma (MAPK12:Millipore) was diluted in HEPES buffer, mixed with compound at desired final concentrations and incubated for two hours at room temperature. The FRET peptide (2 µM) and ATP (100 uM) were next added to the enzyme/compound mixture and incubated for one hour. Development reagent (protease) was added for one hour prior to detection in a fluorescence microplate reader. The site-specific protease only cleaves non-phosphorylated peptide and eliminates the FRET signal. Phosphorylation levels of each reaction were calculated using the ratio of coumarin emission (donor) over fluorescein emission (acceptor) with high ratios indicating high phosphorylation and low ratios, low phosphorylation levels. The percentage inhibition of each reaction was calculated relative to non-inhibited control, and the 50% inhibitory concentration ($IC_{50}$ value) then calculated from the concentration-response curve.

For p38 MAPK alpha (MAPK14: Invitrogen), enzyme activity was evaluated indirectly by determining activation/phosphorylation of the down-stream molecule, MAPKAP-K2. The p38 MAPK α protein was mixed with its inactive target MAPKAP-K2 (Invitrogen) and compound for two hours at room temperature. The FRET peptide (2 µM), which is a phosphorylation target for MAPKAP-K2, and ATP (10 µM) were then added to the enzymes/compound mixture and incubated for one hour. Development reagent was then added and the mixture incubated for one hour before detection by fluorescence completed the assay protocol.

LPS-induced TNF Alpha Release in U937 Cells: Potency

U937 cells, human monocytic cell line, were differentiated to macrophage-type cells by incubation with phorbol myristate acetate (PMA; 100 ng/ml) for 48 to 72 hours. Where appropriate, cells were pre-incubated with final concentrations of compound for 2 hrs. Cells were then stimulated with 0.1 µg/mL of LPS (from *E. coli*: O111:B4, Sigma) for 4 hrs, and the supernatant collected for determination of TNFα concentration by sandwich ELISA (Duo-set, R&D systems). THP-1, human monocytic cell line, was also used for this assay. THP-1 cells were stimulated with 1 µg/ml of LPS (from *E. coli*: O111:B4, Sigma) for 4 hrs, and the supernatant collected for determination of TNFα concentration. The inhibition of TNFα production was calculated as a percentage of that achieved by 10 µg/ml of BIRB796 at each concentration of test compound by comparison with vehicle control. The 50% effective concentration ($EC_{50}$) was determined from the resultant concentration-response curve.

LPS-induced TNF Alpha Release in THP-1 Cells: Potency

THP-1 cells, a human monocytic cell line, were stimulated with 1 µg/ml of LPS (from E. coli; O111:B4, Sigma) for 4 hr and the supernatant collected for determination of TNFα concentration by sandwich ELISA (Duo-set, R&D systems). The inhibition of TNFα production was calculated at each concentration by comparison with vehicle control. The 50% inhibitory concentration ($IC_{50}$) was determined from the resultant concentration-response curve.

MTT Assay

Differentiated U937 cells were pre-incubated with compound for 4 hrs in 5% FCS or 10% FCS for 24 hrs and 72 hr. The supernatant was replaced with 200 ul of new media and 10 µL of MTT stock solution (5 mg/mL) added to each well. After 1 hr incubation, the media were removed, 200 µL of DMSO added to each well and the plates were shaken lightly for 1 hr prior to reading the absorbance at 550 nm.

The percentage loss of cell viability was calculated for each well relative to vehicle (0.5% DMSO)-treatment. Consequently an apparent increase in cell viability for drug treatment relative to vehicle is tabulated as a negative percentage.

In Vivo Testing for Example 1

LPS-induced Neutrophilia in the Mouse: Duration of Action

Non-fasted mice were dosed by the intra tracheal route with either vehicle, or the test substance at the time points ("pre-dose") indicated with respect to the start of LPS treatment. At T=0, mice were placed into an exposure chamber and exposed to LPS. Eight hours after LPS challenge, animals were under anesthetized, the trachea cannulated and BALF extracted by infusing and withdrawing 1 ml of PBS into the lungs via a tracheal catheter. Total and differential white cell counts in the BALF samples were measured using a Neubaur haemocytometer. Cytospin smears of the BALF samples were prepared by centrifugation at 200 rpm for 5 min at room temperature and stained using a DiffQuik stain system (Dade Behring). Cells were counted using oil immersion microscopy.

Figure 2:
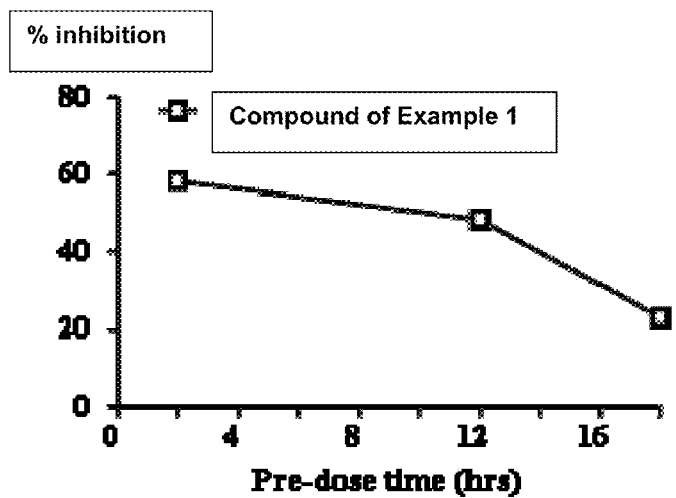
FIG. 2 shows a plot of the pre-dose time for the administration of the compound of Example 1 against the resulting % inhibition of neutrophilia in the LPS-induced neutrophil accumulation test.

The results are shown in FIGS. 1 and 2. Data for neutrophil numbers is reported as total and differential number (test substance relative to vehicle) of cells per mL of BALF, mean±S.E.M. (n=8).

Cigarette Smoke Model

A/J mice (males, 5 weeks old) were exposed to cigarette smoke (4% cigarette smoke, diluted with compressed air) for 30 min/day for 11 days using a Tobacco Smoke Inhalation Experiment System for small animals (Model SIS-CS; Sibata Scientific Technology, Tokyo, Japan). Test substances were given intra-nasally (35 µl of solution in 50% DMSO/PBS) and therapeutically twice daily for 3 days after the final cigarette smoke exposure. Twelve hours after the last dosing, animals were anesthetized, the trachea cannulated and bronchoalveolar lavage fluid (BALF) was collected. The numbers of alveolar macrophages and neutrophils were determined by FACS analysis (EPICS® ALTRA II, Beckman Coulter, Inc., Fullerton, Calif., USA) using anti-mouse MOMA2 antibody (macrophage) or anti-mouse 7/4 antibody (neutrophil). The results are shown in FIG. 3 for activated alveolar macrophages and in FIG. 4 for neutrophils. Data for cell numbers are shown as the mean±SEM. The cigarette smoke model used for this study is reported as a corticosteroid refractory system, (Medicherla S. et al., (2008); *J. Pharmacol. Exp. Ther.* 324 (3):921-9) and it was confirmed that fluticasone propionate did not inhibit either neutrophil or macrophage accumulation into airways at 50 µg/ml (35 µl, bid, in), the same dose that produced >80% inhibition of LPS-induced neutrophil accumulation.

Ovalbumin Challenge/Parainfluenza Infection Model

Figure 5:
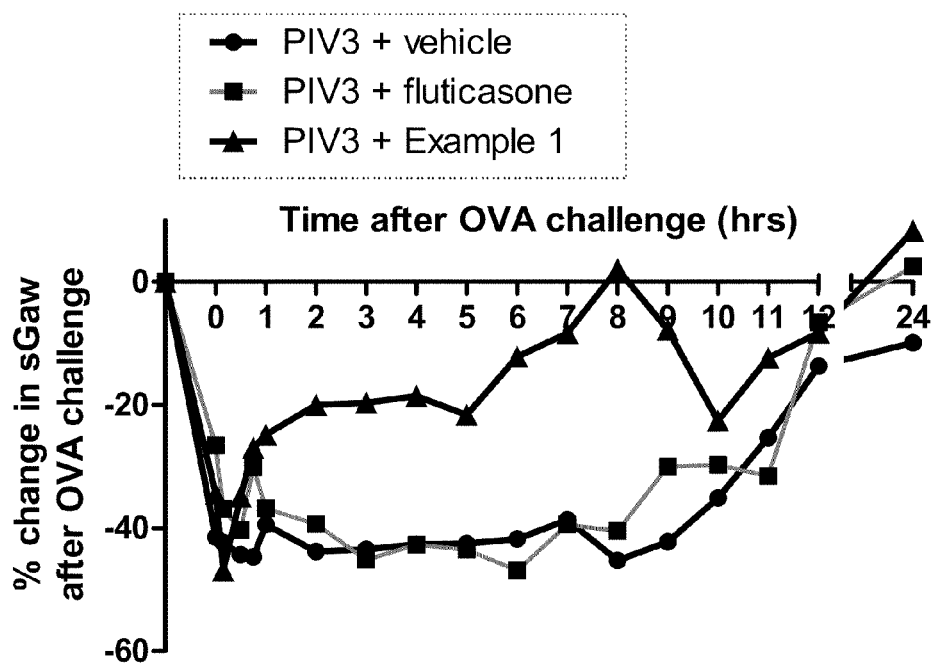
FIG. 5 shows the effect for the compound of Example 1 on lung function of ovalbumin-sensitised, para-influenza inoculated guinea pigs challenged with ovalbumin.

Male Dunkin-Hartley guinea-pigs (300-350 g, n=6/group) were sensitised with 100 µg ovalubumin (OVA)+100 mg $Al_2(OH)_3$ in 1 ml normal saline (i.p.) on days 2 and 6. Parainfluenza virus (PIV-3; $10^6$ infectious units) or media without virus was nasally instilled on days 11 and 12. Animals were treated with nebulised fluticasone propionate at a dose of 1.5 mg per day. Initial studies established that this dose of fluticasone propionate inhibited ovalbumin-mediated lung function changes in sensitized animals treated with PIV3 medium. Example 1 (4.5 mg per day) or the vehicle (DMSO:ethanol: saline, 30:30:40%) from days 10-15. All animals were challenged for 1 hr with nebulised OVA (10 µg/ml) on day 15 and repeated measurements of specific airways conductance ($sG_{aw}$) were made over a 24 hr period using whole body plethysmography. Measurements of $sG_{aw}$ after OVA challenge are plotted as % change from baseline. See FIG. 5.

Summary

The biological studies in vitro show that the compounds tested are potent inhibitor of p38 MAP kinase subtypes alpha and gamma with good efficacy in an in vitro model of anti-inflammatory activity (LPS-induced TNFalpha release from differentiated U937 cells and THP-1 cells). From the MTT results it may be concluded that the compounds tested do not exhibit overt cellular toxicity at the concentrations used.

The biological studies in vivo show that the compound tested is effective in inhibiting LPS-induced neutrophil accumulation in an animal model, with a long duration of effect as shown by the significant inhibition even at 12 or more hours of pre-dosing.

Throughout the specification and the claims which follow, unless the context requires otherwise, the word 'comprise', and variations such as 'comprises' and 'comprising', will be understood to imply the inclusion of a stated integer, step, group of integers or group of steps but not to the exclusion of any other integer, step, group of integers or group of steps.

All patents and patent applications referred to herein are incorporated by reference in their entirety.

Aspects of the disclosure comprising certain elements are also intended to extend to alternative embodiments "consisting" of or "consisting essentially" of the relevant elements.

Where technically appropriate embodiments may be combined and thus the disclosure extends to all permutations/combinations of the embodiments provided herein.

The application of which this description and claims forms part may be used as a basis for priority in respect of any subsequent application. The claims of such subsequent application may be directed to any feature or combination of features described herein. They may take the form of product, composition, process, or use claims and may include, by way of example and without limitation, the claims. It will be understood that one or more aspects or combinations thereof may serve as basis for disclaimers for excluding parts of the disclosure, as required.

The invention claimed is:

1. A compound of formula (I)

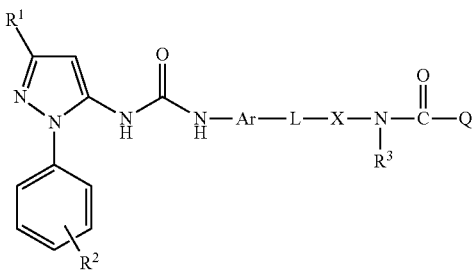

wherein R[1] is $C_{1-6}$ alkyl optionally substituted by a hydroxyl group;
R[2] is H or $C_{1-6}$ alkyl optionally substituted by a hydroxyl group;
R[3] is H, $C_{1-6}$ alkyl or $C_{0-3}$ alkyl$C_{3-6}$ cycloalkyl;
Ar is a naphthyl or a phenyl ring either of which may be optionally substituted by one or more groups (for example 1 to 3, such as 1, 2 or 3 groups) independently selected from $C_{1-6}$ alkyl, $C_{1-6}$ alkoxy, amino, $C_{1-4}$ mono or di-alkyl amino;
L is a saturated or unsaturated branched or unbranched $C_{1-8}$ alkylene chain, wherein one or more carbons (for example 1 to 3, such as 1, 2 or 3 carbons) are optionally replaced by —O— and the chain is optionally substituted by one or more halogen atoms (for example 1 to 6);
X is 5 or 6 membered heteroaryl group containing at least one nitrogen atom and optionally including 1 or 2 further heteroatoms selected from O, S and N;
Q is selected from:
a) a saturated or unsaturated, branched or unbranched $C_{1-10}$ alkyl chain, wherein at least one carbon (for example 1, 2 or 3 carbons, suitably 1 or 2, in particular 1 carbon) is replaced by a heteroatom selected from O, N, $S(O)_p$, wherein said chain is optionally, substituted by one or more groups (for example 1, 2 or 3 groups) independently selected from oxo, halogen, an aryl group, a heteroaryl group, a heterocyclyl group or a $C_{3-8}$ cycloalkyl group, each aryl, heteroaryl, heterocyclyl or $C_{3-8}$ cycloalkyl group bearing 0 to 3 substituents selected from halogen, hydroxyl, $C_{1-6}$ alkyl, $C_{1-6}$ alkoxy, $C_{1-6}$ haloalkyl, amino, $C_{1-4}$ mono or di-alkyl amino, $C_{1-4}$ mono or di-acyl amino, $S(O)_q C_{1-6}$ alkyl, $C_{0-6}$ alkylC(O) $C_{1-6}$ alkyl or $C_{0-6}$ alkylC(O)$C_{1-6}$ heteroalkyl, with the proviso that the atom linked directly to the carbonyl in —NR[3]C(O)— is not an oxygen or a sulfur atom; and
b) a $C_{0-8}$ alkyl-heterocycle said heterocyclyl group comprising at least one heteroatom (for example 1, 2 or 3, suitably 1 or 2, in particular 1 heteroatom) selected from O, N, and S, and which is optionally substituted by one, two or three groups independently selected from halogen, hydroxyl, $C_{1-6}$ alkyl, $C_{1-6}$ alkoxy, $C_{1-6}$ haloalkyl, amino, $C_{1-4}$ mono and di-alkyl amino, $C_{1-4}$ mono or di-acyl amino, $S(O)_q C_{1-6}$ alkyl, $C_{0-6}$ alkylC(O)$C_{1-6}$ alkyl, $C_{0-6}$ alkylC(O)N$C_{0-6}$ alkyl $C_{0-6}$ alkyl or $C_{0-6}$ alkylC(O)$C_{0-6}$ heteroalkyl; and
p is 0, 1 or 2;
q is 0, 1 or 2; or
a pharmaceutically acceptable salt thereof, including all stereoisomers, tautomers and deuterated compounds.

2. A compound of formula (I) according to claim 1, wherein Ar is napthyl.

3. A compound of formula (I) according to claim 1, wherein R[1] is tert-butyl.

4. A compound of formula (I) according to claim 1, wherein R[2] is methyl.

5. A compound of formula (I) according to claim 1, wherein R[2] is in the para position.

6. A compound of formula (I) according to claim 1, wherein L represents —$(CH_2)_nO(CH_2)_m$— wherein n and m are independently 0, 1, 2, 3, 4, 5, 6 or 7, with the proviso that n+m is zero or an integer from 1 to 7.

7. A compound of formula (I) according to claim 1, wherein R[3] is H.

8. A compound of formula (I) according to claim 1, wherein NR[3]C(O)Q is selected from: —NR[3]C(O)CH$_2$OC$_{1-6}$ alkyl, —NR[3]C(O)CH$_2$O(CH$_2$)$_2$OCH$_3$, —NR[3]C(O)CH(CH$_3$)OCH$_3$, —NR[3]C(O)CH$_2$NHCH$_3$, —NR[3]C(O)CH$_2$NH(CH$_2$)$_2$OCH$_3$, —NR[3]C(O)CH$_2$SCH$_3$, —NR[3]C(O)NH$_2$, —NR[3]C(O)CH$_2$S(O)$_2$CH$_3$, —NR[3]C(O)NHC$_{1-7}$ alkyl, —NR[3]C(O)N(C$_{1-4}$ alkyl)C$_{1-5}$ alkyl, and —NR[3]C(O)CHN[(CH$_2$)$_2$OCH$_3$]$_2$.

9. A compound of formula (I) according to claim 8, wherein NR[3]C(O)Q is selected from: —NHC(O)NHCH$_3$; —NHC(O)CH$_2$OCH$_3$; —NHC(O)CH$_2$O(CH$_2$)$_2$OCH$_3$; —NHC(O)CH(CH$_3$)OCH$_3$; —NHC(O)CH$_2$NHCH$_3$; —NHC(O)CH$_2$NH(CH$_2$)$_2$OCH$_3$, —NHC(O)CH$_2$SCH$_3$; —NHC(O)NH$_2$; —NHC(O)CH$_2$S(O)$_2$CH$_3$; —NHC(O)N(CH$_3$)$_2$; and —NHC(O)CHN[(CH$_2$)$_2$OCH$_3$]$_2$.

10. A compound of formula (I) according to claim 1, wherein the compound is of formula (IA)

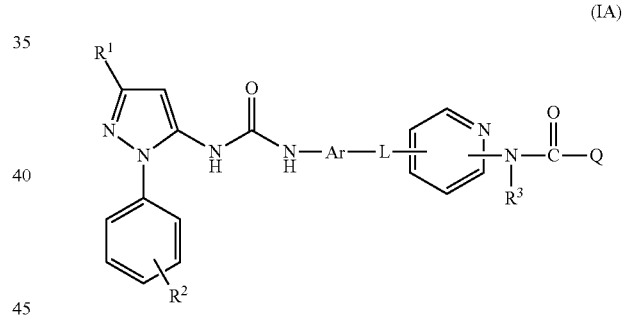

a pharmaceutically acceptable salt thereof, including all stereoisomers, tautomers and deuterated compounds.

11. A compound of formula (I) according to claim 10, wherein the compound is of formula (IB):

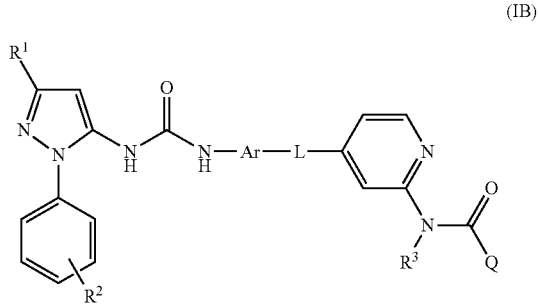

a pharmaceutically acceptable salt thereof, including all stereoisomers, tautomers and deuterated compounds.

12. A compound of formula (I) according to claim 1, wherein the compound is of formula (IC):

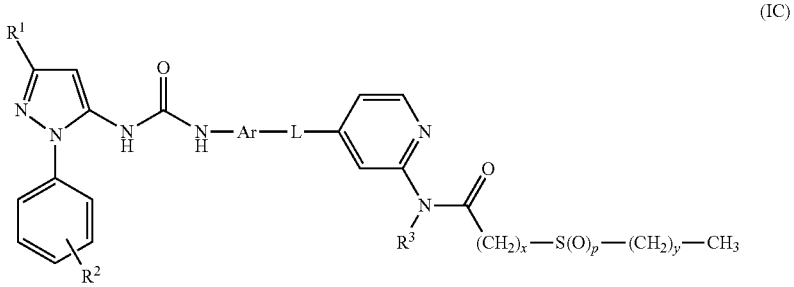

(IC)

wherein x is an integer from 1 to 6 and y is zero or an integer from 1 to 5 with proviso that x+y is an integer from 1 to 6, for example x is 1 and y is 1 or a pharmaceutically acceptable salt thereof, including all stereoisomers, tautomers and deuterated compounds.

13. A compound of formula (I) according to claim 1, wherein the compound is of formula (ID):

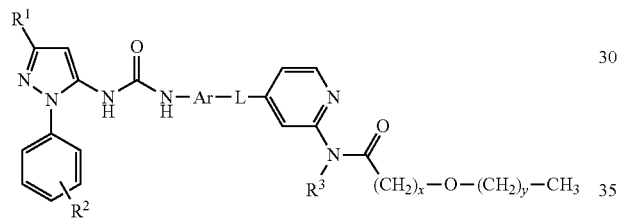

(ID)

wherein x is an integer from 1 to 6 and y is zero or an integer from 1 to 5, with the proviso that x+y is an integer from 1 to 6, for example x is 1 and y is 0 or a pharmaceutically acceptable salt thereof, including all stereoisomers, tautomers and deuterated compounds.

14. A compound of formula (I) according to claim 1, wherein the compound is of formula (IE):

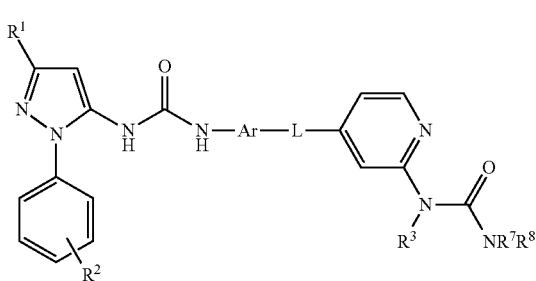

(IE)

wherein where $R^7$ and $R^8$ independently represent hydrogen or a $C_{1-9}$ saturated or unsaturated, branched or unbranched alkyl chain, wherein one or more carbons, such as 1, 2 or 3 are optionally replaced by a heteroatom selected from O, N or $S(O)_p$ or a pharmaceutically acceptable salt thereof, including all stereoisomers, tautomers and deuterated compounds.

15. A compound of formula (I) according to claim 1, wherein the compound is of formula (IF):

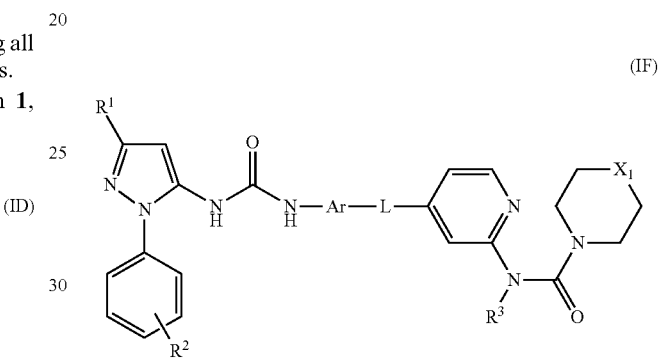

(IF)

wherein $X_1$ represents O, $CH_2$, NH, $NCH_3$ or $NCH_2CH_2OCH_3$.

16. A compound of formula (I) according to claim 1, which is:

Methyl 4-((4-(3-(3-tert-butyl-1-p-tolyl-1H-pyrazol-5-yl) ureido)naphthalen-1-yloxy)methyl)pyridin-2-ylurea;

N-(4-((4-(3-(3-tert-Butyl-1-p-tolyl-1H-pyrazol-5-yl)ureido)naphthalen-1-yloxy)methyl)pyridin-2-yl)tetrahydro-2H-pyran-4-carboxamide;

(S)-N-(4-((4-(3-(3-tert-Butyl-1-p-tolyl-1H-pyrazol-5-yl) ureido)naphthalen-1-yloxy)methyl)pyridin-2-yl)-2-methoxypropanamide;

(R)-N-(4-((4-(3-(3-tent-Butyl-1-p-tolyl-1H-pyrazol-5-yl) ureido)naphthalen-1-yloxy)methyl)pyridin-2-yl)-2-methoxypropanamide;

N-(4-((4-(3-(3-tert-Butyl-1-p-tolyl-1H-pyrazol-5-yl)ureido)naphthalen-1-yloxy)methyl)pyridin-2-yl)-2-(methylsulfonyl)acetamide N-(4-((4-(3-(3-tert-Butyl-1-p-tolyl-1H-pyrazol-5-yl)ureido)naphthalen-1-yloxy)methyl)pyridin-2-yl)-2-hydroxyacetamide;

N-(4-((4-(3-(3-tert-Butyl-1-p-tolyl-1H-pyrazol-5-yl)ureido)naphthalen-1-yloxy)methyl)pyridin-2-yl)-2-methyl-2-(methylamino)propanamide;

(S)-N-(4-((4-(3-(3-tent-Butyl-1-p-tolyl-1H-pyrazol-5-yl) ureido)naphthalen-1-yloxy)methyl)pyridin-2-yl)-2-(methylamino)propanamide;

(R)-N-(4-((4-(3-(3-tent-Butyl-1-p-tolyl-1H-pyrazol-5-yl) ureido)naphthalen-1-yloxy)methyl)pyridin-2-yl)morpholine-3-carboxamide;

(S)-N-(4-((4-(3-(3-tent-Butyl-1-p-tolyl-1H-pyrazol-5-yl) ureido)naphthalen-1-yloxy)methyl)pyridin-2-yl)morpholine-3-carboxamide;

N-(4-((4-(3-(3-tert-Butyl-1-p-tolyl-1H-pyrazol-5-yl)ureido)naphthalen-1-yloxy)methyl)pyridin-2-yl)-4-methylpiperazine-1-carboxamide;

N-(4-((4-(3-(3-tert-Butyl-1-p-tolyl-1H-pyrazol-5-yl)ureido)naphthalen-1-yloxy)methyl)pyridin-2-yl)morpholine-4-carboxamide;

N-(4-((4-(3-(3-tert-Butyl-1-p-tolyl-1H-pyrazol-5-yl)ureido)naphthalen-1-yloxy)methyl)pyridin-2-yl)-3-methoxypropanamide;

2-(3-(4-((4-(3-(3-tert-Butyl-1-p-tolyl-1H-pyrazol-5-yl)ureido)naphthalen-1-yloxy)methyl)pyridin-2-yl)ureido)-N-(2-methoxyethyl)acetamide;

N-(4-((4-(3-(3-tert-Butyl-1-p-tolyl-1H-pyrazol-5-yl)ureido)naphthalen-1-yloxy)methyl)pyridin-2-yl)-4-(dimethylamino)butanamide;

N-(4-((4-(3-(3-tert-Butyl-1-p-tolyl-1H-pyrazol-5-yl)ureido)naphthalen-1-yloxy)methyl)pyridin-2-yl)-3-(methylsulfonyl)propanamide;

N-(4-((4-(3-(3-tert-Butyl-1-p-tolyl-1H-pyrazol-5-yl)ureido)naphthalen-1-yloxy)methyl)pyridin-2-yl)-3-(methylsulfonyl)-2-oxoimidazolidine-1-carboxamide;

N-(4-((4-(3-(3-tert-Butyl-1-p-tolyl-1H-pyrazol-5-yl)ureido)naphthalen-1-yloxy)methyl)pyridin-2-yl)-2-(methylthio)acetamide;

N-(4-((4-(3-(3-tert-Butyl-1-p-tolyl-1H-pyrazol-5-yl)ureido)naphthalen-1-yloxy)methyl)pyridin-2-yl)-2-(methylsulfinyl)acetamide;

N-(4-((4-(3-(3-tert-Butyl-1-p-tolyl-1H-pyrazol-5-yl)ureido)naphthalen-1-yloxy)methyl)pyridin-2-yl)-2-morpholinoacetamide;

N-(4-((4-(3-(3-tert-Butyl-1-p-tolyl-1H-pyrazol-5-yl)ureido)naphthalen-1-yloxy)methyl)pyridin-2-yl)-2-(pyrrolidin-1-yl)acetamide;

N-(4-((4-(3-(3-tert-Butyl-1-p-tolyl-1H-pyrazol-5-yl)ureido)naphthalen-1-yloxy)methyl)pyridin-2-yl)-2-(4-methylpiperazin-1-yl)acetamide;

N-(4-((4-(3-(3-tert-Butyl-1-p-tolyl-1H-pyrazol-5-yl)ureido)naphthalen-1-yloxy)methyl)pyridin-2-yl)-2-(4-(2-methoxyethyl)piperazin-1-yl)acetamide;

N-(4-((4-(3-(3-tert-Butyl-1-p-tolyl-1H-pyrazol-5-yl)ureido)naphthalen-1-yloxy)methyl)pyridin-2-yl)-2-(2-methoxyethylamino)acetamide;

N-(4-((4-(3-(3-tert-Butyl-1-p-tolyl-1H-pyrazol-5-yl)ureido)naphthalen-1-yloxy)methyl)pyridin-2-yl)-2-(dimethylamino)acetamide;

N-(4-((4-(3-(3-tert-Butyl-1-p-tolyl-1H-pyrazol-5-yl)ureido)naphthalen-1-yloxy)methyl)pyridin-2-yl)-2-(methylamino)acetamide;

N-(4-((4-(3-(3-tert-Butyl-1-p-tolyl-1H-pyrazol-5-yl)ureido)naphthalen-1-yloxy)methyl)pyridin-2-yl)-2-((4-methoxybenzyl)(methyl)amino)acetamide;

N-(4-((4-(3-(3-tert-Butyl-1-p-tolyl-1H-pyrazol-5-yl)ureido)naphthalen-1-yloxy)methyl)pyridin-2-yl)-2-(2-methoxyethylthio)acetamide;

N-(4-((4-(3-(3-tent-Butyl-1-p-tolyl-1H-pyrazol-5-yl)ureido)naphthalen-1-yloxy)methyl)pyridin-2-yl) -2-(2-(2-methoxyethoxy)ethylthio)acetamide;

N-(4-((4-(3-(3-tert-Butyl-1-p-tolyl-1H-pyrazol-5-yl)ureido)naphthalen-1-yloxy)methyl)pyridin-2-yl)-2-(2-morpholinoethylthio)acetamide;

N-(4-((4-(3-(3-tert-Butyl-1-p-tolyl-1H-pyrazol-5-yl)ureido)naphthalen-1-yloxy)methyl)pyridin-2-yl)-2-(2-morpholinoethylsulfonyl)acetamide;

2-(Bis(2-methoxyethyl)amino)-N-(4-((4-(3-(3-tert-butyl-1-p-tolyl-1H-pyrazol-5-yl)ureido)naphthalen-1-yloxy)methyl)pyridin-2-yl)acetamide;

1-(4-((3-Methylureidopyridin-4-yl)methoxy)naphthalen-1-yl)-3-(3-tert-butyl-1-p-tolyl-1H-pyrazol-5-yl)urea;

N-(4-((4-(3-(3-tert-Butyl-1-p-tolyl-1H-pyrazol-5-yl)ureido)naphthalen-1-yloxy)methyl)pyridin-3-yl)-2-methoxyacetamide;

N-(4-((4-(3-(3-tert-Butyl-1-p-tolyl-1H-pyrazol-5-yl)ureido)naphthalen-1-yloxy)methyl)pyridin-3-yl)-2-(2-methoxyethoxy)acetamide;

N-(4-(2-(4-(3-(3-tent-Butyl-1-p-tolyl-1H-pyrazol-5-yl)ureido)naphthalen-1-yloxy)ethyl)pyridin-2-yl)-2-methoxyacetamide;

N-(4-(2-(4-(3-(3-tent-Butyl-1-p-tolyl-1H-pyrazol-5-yl)ureido)naphthalen-1-yloxy)ethyl)pyridin-2-yl)-2-(2-methoxyethoxy)acetamide;

4-(2-(4-(3-(3-tert-Butyl-1-p-tolyl-1H-pyrazol-5-yl)ureido)naphthalen-1-yloxy)ethyl)-1-methyl-3-(pyridin-2-yl)urea;

4-(2-(4-(3-(3-tert-Butyl-1-p-tolyl-1H-pyrazol-5-yl)ureido)naphthalen-1-yloxy)ethyl)-3-(pyridin-2-yl)urea;

N-(4-(2-(4-(3-(3-tert-Butyl-1-p-tolyl-1H-pyrazol-5-yl)ureido)naphthalen-1-yloxy)ethyl)pyridin-3-yl)-2-methoxyacetamide;

N-(4-(2-(4-(3-(3-tent-Butyl-1-p-tolyl-1H-pyrazol-5-yl)ureido)naphthalen-1-yloxy)ethyl)pyridin-3-yl)-2-(2-methoxyethoxy)acetamide;

N-(4-(2-(4-(3-(3-tert-butyl-1-p-tolyl-1H-pyrazol-5-yl)ureido)naphthalen-1-yl)ethoxy)pyridin-2-yl)-2-methoxyacetamide;

N-(4-(1-(4-(3-(3-tent-Butyl-1-p-tolyl-1H-pyrazol-5-yl)ureido)naphthalen-1-yloxy)ethyl)pyridin-2-yl)-2-methoxyacetamide;

N-(4-(2-(4-(3-(3-tent-Butyl-1-p-tolyl-1H-pyrazol-5-yl)ureido)naphthalen-1-yloxy)-2-methylpropyl)pyridin-2-yl)-2-methoxyacetamide;

N-(4-(2-(4-(3-(3-tent-Butyl-1-p-tolyl-1H-pyrazol-5-yl)ureido)naphthalen-1-yloxy)propyl)pyridin-2-yl)-2-methoxyacetamide;

N-(4-(1-(4-(3-(3-tent-Butyl-1-p-tolyl-1H-pyrazol-5-yl)ureido)naphthalen-1-yloxy)propan-2-yl)pyridin-2-yl)-2-methoxyacetamide;

N-(4-(1-(4-(3-(3-tent-Butyl-1-p-tolyl-1-pyrazol-5-yl)ureido)naphthalen-1-yloxy)-2-methylpropan-2-yl)pyridin-2-yl)-2-methoxyacetamide;

N-(4-((4-(3-(3-tert-Butyl-1-(4-(hydroxymethyl)phenyl)-1H-pyrazol-5-yl)ureido)naphthalen-1-yloxy)methyl)pyridin-2-yl)-2-methoxyacetamide;

N-(4-((4-(3-(3-tert-Butyl-1-p-tolyl-1H-pyrazol-5-yl)ureido)naphthalen-1-yloxy)methyl)pyrimidin-2-yl)-2-methoxyacetamide;

N-(4-(4-(3-(3-tert-Butyl-1-p-tolyl-1H-pyrazol-5-yl)ureido)naphthalen-1-yloxy)pyridin-2-yl)-2-(methylsulfonyl)acetamide N-(4-(4-(3-(3-tert-Butyl-1-p-tolyl-1H-pyrazol-5-yl)ureido)naphthalen-1-yloxy)pyridin-2-yl)-2-(2-methoxyethoxy)acetamide;

N-(4-(4-(3-(3-tert-Butyl-1-p-tolyl-1H-pyrazol-5-yl)ureido)naphthalen-1-yloxy)pyridin-2-yl)tetrahydro-2H-pyran-4-carboxamide;

N-(4-(4-(3-(3-tert-Butyl-1-p-tolyl-1H-pyrazol-5-yl)ureido)naphthalen-1-yloxy)pyridin-2-yl)-2-(methylthio)acetamide;

N-(4-(4-(3-(3-tert-Butyl-1-p-tolyl-1H-pyrazol-5-yl)ureido)naphthalen-1-yloxy)pyridin-2-yl)-3-methoxypropanamide;

N-(4-(4-(3-(3-tert-Butyl-1-p-tolyl-1H-pyrazol-5-yl)ureido)naphthalen-1-yloxy)pyridin-2-yl)-2-hydroxyacetamide;

N-(4-(4-(3-(3-Isopropyl-1-p-tolyl-1H-pyrazol-5-yl)ureido)naphthalen-1-yloxy)pyridin-2-yl)-2-methoxyacetamide;

N-(4-(4-(3-(3-Ethyl-1-p-tolyl-1H-pyrazol-5-yl)ureido)naphthalen-1-yloxy)pyridin-2-yl)-2-methoxyacetamide;

N-(4-(4-(3-(3-tert-Butyl-1-p-tolyl-1H-pyrazol-5-yl)ureido)naphthalen-1-yloxy)pyridin-2-yl)-2-methoxyacetamide;

N-(4-(4-(3-(3-(1-Hydroxy-2-methylpropan-2-yl)-1-p-tolyl-1H-pyrazol-5-yl)ureido)naphthalen-1-yloxy)pyridin-2-yl)-2-methoxyacetamide;

N-(4-(4-(3-(3-tert-butyl-1-(2,3,5,6-tetradeutero-4-(trideuteromethyl)phenyl)-1H-pyrazol-5-yl)ureido)naphthalen-1-yloxy)pyridin-2-yl)-2-methoxyacetamide;

N-(4-(4-(3-(3-tert-Butyl-1-p-tolyl-1H-pyrazol-5-yl)ureido)naphthalen-1-yloxy)pyridin-2-yl)-2-morpholinoacetamide;

N-(4-(4-(3-(3-tert-Butyl-1-p-tolyl-1H-pyrazol-5-yl)ureido)naphthalen-1-yloxy)pyridin-2-yl)-(dimethylamino)acetamide;

N-(4-(4-(3-(3-tert-Butyl-1-p-tolyl-1H-pyrazol-5-yl)ureido)naphthalen-1-yloxy)pyridin-2-yl)-2-(2-methoxyethylamino)acetamide;

N-(4-(4-(3-(3-tert-Butyl-1-p-tolyl-1H-pyrazol-5-yl)ureido)naphthalen-1-yloxy)pyridin-2-yl)-2-ureidoacetamide;

N-(4-(4-(3-(3-tert-Butyl-1-p-tolyl-1H-pyrazol-5-yl)ureido)naphthalen-1-yloxy)pyridin-2-yl)-2-(2-methoxyacetamido)acetamide;

N-(2-(4-(4-(3-(3-tert-Butyl-1-p-tolyl-1H-pyrazol-5-yl)ureido)naphthalen-1-yloxy)pyridin-2-ylamino)-2-oxoethyl)tetrahydro-2H-pyran-4-carboxamide;

N-(2-(4-(4-(3-(3-tert-Butyl-1-p-tolyl-1H-pyrazol-5-yl)ureido)naphthalen-1-yloxy)pyridin-2-ylamino)-2-oxoethyl)isonicotinamide;

N-(4-(4-(3-(3-tert-Butyl-1-p-tolyl-1H-pyrazol-5-yl)ureido)naphthalen-1-yloxy)pyridin-2-yl)-2-(2-(methylsulfonyl)acetamido)acetamide;

N-(2-(4-(4-(3-(3-tert-Butyl-1-p-tolyl-1H-pyrazol-5-yl)ureido)naphthalen-1-yloxy)pyridin-2-ylamino)-2-oxoethyl)-3-morpholinopropanamide;

N-(2-(4-(4-(3-(3-tert-Butyl-1-p-tolyl-1H-pyrazol-5-yl)ureido)naphthalen-1-yloxy)pyridin-2-ylamino)-2-oxoethyl)morpholine-4-carboxamide;

N-(2-(4-(4-(3-(3-tert-Butyl-1-p-tolyl-1H-pyrazol-5-yl)ureido)naphthalen-1-yloxy)pyridin-2-ylamino)-2-oxoethyl)-2,6-difluoro-3-(2-(2-methoxyethoxy)ethoxy)benzamide;

N-(4-(4-(3-(3-tert-Butyl-1-p-tolyl-1H-pyrazol-5-yl)ureido)phenoxy)pyridin-2-yl)-2-methoxyacetamide;

N-(4-(4-(3-(3-tert-Butyl-1-p-tolyl-1H-pyrazol-5-yl)ureido)-2-methylphenoxy)pyridin-2-yl)-2-methoxyacetamide;

N-(4-(4-(3-(3-tent-Butyl-1-p-tolyl-1H-pyrazol-5-yl)ureido)-3-methylphenoxy)pyridin-2-yl)-2-methoxyacetamide;

N-(4-(4-(3-(3-tert-Butyl-1-p-tolyl-1H-pyrazol-5-yl)ureido)-2-methoxyphenoxy)pyridin-2-yl)-2-methoxyacetamide;

N-(4-(4-(3-(3-tert-Butyl-1-p-tolyl-1H-pyrazol-5-yl)ureido)-2,3-dimethylphenoxy)pyridin-2-yl)-2-methoxyacetamide;

N-(4-(4-(3-(3-tert-Butyl-1-p-tolyl-1H-pyrazol-5-yl)ureido)-3-methoxyphenoxy)pyridin-2-yl)-2-methoxyacetamide;

N-Ethyl-N'-4-(4-(3-(3-tert-butyl-1-p-tolyl-1H-pyrazol-5-yl)ureido) naphthalen-1-yloxy)pyridin-2-ylurea;

4-(4-(3-(3-tert-Butyl-1-p-tolyl-1H-pyrazol-5-yl)ureido)naphthalen-1-yloxy)pyridin-2-ylurea;

N-Propan-2-yl-N'-4-(4-(3-(3-tert-butyl-1-p-tolyl-1H-pyrazol-5-yl)ureido)naphthalen-1-yloxy)pyridin-2-ylurea;

1-(3-(tert-Butyl)-1-(p-tolyl)-1H-pyrazol-5-yl)-3-(4-((2-(3-phenylureido)pyridin-4-yl)oxy)naphthalen-1-yl)urea;

1-(4-((2-(3-Benzylureido)pyridin-4-yl)oxy)naphthalen-1-yl)-3-(3-(tert-butyl)-1-(p-tolyl)-1H-pyrazol-5-yl)urea;

1-(4-((2-(3-Cyclopropylureido)pyridin-4-yl)oxy)naphthalen-1-yl)-3-(3-(tert-butyl)-1-(p-tolyl)-1H-pyrazol-5-yl)urea;

1-(3-(tert-Butyl)-1-(p-tolyl)-1H-pyrazol-5-yl)-3-(4-((2-(3-(2-methoxyethyl)ureido)pyridin-4-yl)oxy)naphthalen-1-yl)urea;

1-(3-(tert-Butyl)-1-(p-tolyl)-1H-pyrazol-5-yl)-3-(4-((2-(3-cyclopentyl)ureido)pyridin-4-yl)oxy)naphthalen-1-yl)urea;

1-(3-(tent-Butyl)-1-(p-tolyl)-1H-pyrazol-5-yl)-3-(4-((2-(3-methyl)ureido)pyridin-4-yl)oxy)naphthalen-1-yl)urea;

Ethyl 2-(3-(4-((4-(3-(3-(tert-butyl)-1-(p-tolyl)-1H-pyrazol-5-yl)ureido)naphthalen-1-yl)oxy)pyridin-2-yl)ureido)acetate;

4-(3-(4-(4-(3-(3-tert-Butyl-1-p-tolyl-1H-pyrazol-5-yl)ureido)naphthalen-1-yloxy)pyridin-2-yl)ureido)piperidine;

N-Acetyl 4-(3-(4-(4-(3-(3-tert-butyl-1-p-tolyl-1H-pyrazol-5-yl)ureido) naphthalen-1-yloxy)pyridin-2-yl)ureido)piperidine;

2-(2-Methoxyethoxy)-1-(4-(3-(4-(4-(3-(3-tert-butyl-1-p-tolyl-1H-pyrazol-5-yl)ureido)naphthalen-1-yloxy)pyridin-2-yl)ureido)piperidin-1-yl)ethanone;

N-Methylsulfonyl-4-(3-(4-(4-(3-(3-tert-butyl-1-p-tolyl-1H-pyrazol-5-yl)ureido)naphthalen-1-yloxy)pyridin-2-yl)ureido)piperidine;

N-(4-(4-(3-(3-tert-Butyl-1-p-tolyl-1H-pyrazol-5-yl)ureido)naphthalen-1-yloxy)pyridin-2-yl)morpholine-4-carboxamide;

N-(4-((4-(3-(3-(tert-butyl)-1-(p-tolyl)-1H-pyrazol-5-yl)ureido)naphthalen-1-yl)oxy)pyridin-2-yl)-4-methylpiperazine-1-carboxamide;

3-(4-((4-(3-(3-(tert-butyl)-1-(p-tolyl)-1H-pyrazol-5-yl)ureido)naphthalen-1-yl)oxy)pyridin-2-yl)-1,1-dimethylurea;

N-(4-((4-(3-(3-(tert-Butyl)-1-(p-tolyl)-1H-pyrazol-5-yl)ureido)naphthalen-1-yl)oxy)pyridin-2-yl)piperidine-1-carboxamide;

N-Methyl-N-(2-(morpholin-4-yl)ethyl)-N'-4-(4-(3-(3-tert-butyl-1-p-tolyl-1H-pyrazol-5-yl)ureido)naphthalen-1-yloxy)pyridin-2-ylurea;

N-(4-(morpholin-4-yl)butyl)-N'-4-(4-(3-(3-tert-butyl-1-p-tolyl-1H-pyrazol-5-yl)ureido)naphthalen-1-yloxy)pyridin-2-ylurea;

N-(2-(morpholin-4-yl)ethyl)-N'-4-(4-(3-(3-tert-butyl-1-p-tolyl-1H-pyrazol-5-yl)ureido)naphthalen-1-yloxy)pyridin-2-ylurea;

N-(3-methylisoxazol-5-yl)methyl-N'-4-(4-(3-(3-tert-butyl-1-p-tolyl-1H-pyrazol-5-yl)ureido)naphthalen-1-yloxy)pyridin-2-ylurea;

N-(1-methyl)piperidin-4-yl-N'-4-(4-(3-(3-tert-butyl-1-p-tolyl-1H-pyrazol-5-yl)ureido)naphthalen-1-yloxy)pyridin-2-ylurea;

N-(4-(4-(3-(3-tert-Butyl-1-p-tolyl-1H-pyrazol-5-yl)ureido)naphthalen-1-yloxy)pyridin-2-yl)-4-hydroxypiperidine-1-carboxamide;

N-(3-(imidazol-1-yl)propyl)-N'-4-(4-(3-(3-tert-butyl-1-p-tolyl-1H-pyrazol-5-yl)ureido)naphthalen-1-yloxy)pyridin-2-ylurea;

N-(2-(3-(4-(4-(3-(3-tert-Butyl-1-p-tolyl-1H-pyrazol-5-yl)ureido)naphthalen-1-yloxy)pyridin-2-yl)ureido)acetyl)pyrrolidine;

(R)-N-(4-(4-(3-(3-tert-Butyl-1-p-tolyl-1H-pyrazol-5-yl)ureido)naphthalen-1-yloxy)pyridin-2-yl)-3-(dimethylamino)pyrrolidine-1-carboxamide;

N-(4-(4-(3-(3-tert-Butyl-1-p-tolyl-1H-pyrazol-5-yl)ureido)naphthalen-1-yloxy)pyridin-2-yl)pyrrolidine-1-carboxamide;

2-(3-(4-(4-(3-(3-tert-Butyl-1-p-tolyl-1H-pyrazol-5-yl)ureido)naphthalen-1-yloxy)pyridin-2-yl)ureido)-N-methylacetamide;

2-(3-(4-(4-(3-(3-tert-Butyl-1-p-tolyl-1H-pyrazol-5-yl)ureido)naphthalen-1-yloxy)pyridin-2-yl)ureido) -N-(2-morpholinoethyl)acetamide;

2-(3-(4-(4-(3-(3-tert-Butyl-1-p-tolyl-1H-pyrazol-5-yl)ureido)naphthalen-1-yloxy)pyridin-2-yl)ureido)acetyl morpholine;

2-(3-(4-(4-(3-(3-tert-Butyl-1-p-tolyl-1H-pyrazol-5-yl)ureido)naphthalen-1-yloxy)pyridin-2-yl)ureido) -N-(2-(pyridin-4-yl)ethyl)acetamide;

N-(3-(1H-Imidazol-1-yl)propyl)-2-(3-(4-(4-(3-(3-tert-butyl-1-p-tolyl-1H-pyrazol-5-yl)ureido)naphthalen-1-yloxy)pyridin-2-yl)ureido)acetamide;

1-(2-(3-(4-(4-(3-(3-tert-Butyl-1-p-tolyl-1H-pyrazol-5-yl)ureido)naphthalen-1-yloxy)pyridin-2-yl)ureido)acetyl)-4-methylpiperazine;

N-(3-(1H-Imidazol-1-yl)propyl)-2-(3-(4-(4-(3-(3-tert-butyl-1-p-tolyl-1H-pyrazol-5-yl)ureido)naphthalen-1-yloxy)pyridin-2-yl)ureido)acetamide;

N-(6-(4-(3-(3-tent-Butyl-1-p-tolyl-1H-pyrazol-5-yl)ureido) naphthalen-1-yloxy)pyrimidin-4-yl)-2-methoxyacetamide;

N-(6-(4-(3-(3-tert-Butyl-1-p-tolyl-1H-pyrazol-5-yl)ureido)phenoxy)pyrimidin-4-yl)-2-methoxyacetamide;

N-(4-(4-(3-(3-tert-Butyl-1-p-tolyl-1H-pyrazol-5-yl)ureido)naphthalen-1-yloxy)pyrimidin-2-yl) -2-methoxyacetamide;

3-(4-(4-(3-(3-tert-Butyl-1-p-tolyl-1H-pyrazol-5-yl)ureido)naphthalen-1-yloxy)pyrimidin-2-yl)urea;

1-Methyl-3-(4-(4-(3-(3-tert-butyl-1-p-tolyl-1H-pyrazol-5-yl)ureido)naphthalen-1-yloxy)pyrimidin-2-yl)urea;

1,1-Dimethyl-3-(4-(4-(3-(3-tert-butyl-1-p-tolyl-1H-pyrazol-5-yl)ureido)naphthalen-1-yloxy)pyrimidin -2-yl)urea;

1-Cyclopropyl-3-(4-(4-(3-(3-tert-butyl-1-p-tolyl-1H-pyrazol-5-yl)ureido)naphthalen-1-yloxy)pyrimidin -2-yl)urea;

(4-(4-(3-(3-tert-butyl-1-p-tolyl-1H-pyrazol-5-yl)ureido)naphthalen-1-yloxy)pyrimidin-2-yl)morpholine -4-carboxamide;

3-(6-(4-(3-(3-tent-Butyl-1-p-tolyl-1H-pyrazol-5-yl)ureido)naphthalen-1-yloxy)pyrimidin-4-yl)urea; or 2-(3-(4-(4-(3-(3-tert-Butyl-1-p-tolyl-1H-pyrazol-5-yl)ureido)naphthalen-1-yloxy)pyridin-2-yl)ureido)acetic acid;

or a pharmaceutically acceptable salt thereof, including all stereoisomers, tautomers and deuterated compounds.

17. A pharmaceutical composition comprising a compound according to claim 1, in combination with one or more pharmaceutically acceptable diluents or carriers.

18. A method of treatment of a condition selected from the group consisting of COPD, asthma, paediatric asthma, cystic fibrosis, sarcoidosis, idiopathic pulmonary fibrosis, allergic rhinitis, rhinitis, sinusitis, allergic conjunctivitis, conjunctivitis, allergic dermatitis, contact dermatitis, psoriasis, ulcerative colitis, inflamed joints secondary to rheumatoid arthritis or osteoarthritis, rheumatoid arthritis, pancreatitis, and cachexia, which comprises administering to a subject an effective amount of a compound of formula (I) according to claim 1.

19. A method of treatment of a condition selected from the group consisting of COPD, asthma, paediatric asthma, cystic fibrosis, sarcoidosis, idiopathic pulmonary fibrosis, allergic rhinitis, rhinitis, sinusitis, allergic conjunctivitis, conjunctivitis, allergic dermatitis, contact dermatitis, psoriasis, ulcerative colitis, inflamed joints secondary to rheumatoid arthritis or osteoarthritis, rheumatoid arthritis, pancreatitis, and cachexia, which comprises administering to a subject an effective amount of a pharmaceutical composition according to claim 17.

\* \* \* \* \*